US006901159B2

(12) United States Patent
Baertsch et al.

(10) Patent No.: US 6,901,159 B2
(45) Date of Patent: May 31, 2005

(54) COMMUNICATION OF IMAGE DATA FROM IMAGE DETECTOR TO HOST COMPUTER

(75) Inventors: Richard Dudley Baertsch, Scotia, NY (US); Walter Vincent Dixon, Delanson, NY (US); Daniel Arthur Staver, Scotia, NY (US); Nick Andrew Van Stralen, Ballston Lake, NY (US); Robert Gideon Wodnicki, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 612 days.

(21) Appl. No.: 09/774,552

(22) Filed: Jan. 31, 2001

(65) Prior Publication Data

US 2003/0031353 A1 Feb. 13, 2003

(51) Int. Cl.[7] .................................................. G06K 9/00
(52) U.S. Cl. ...................... 382/132; 382/305; 378/98.6; 250/370.09
(58) Field of Search ................................. 382/128, 129, 382/130, 131, 133, 134, 168, 254, 274, 284, 286, 305, 132; 378/98.6, 98.8, 151, 92, 98.4, 40, 101; 250/208.1, 370.09, 370.1, 370; 348/195, 774; 345/1.1, 4, 5, 531, 60; 377/10

(56) References Cited

U.S. PATENT DOCUMENTS

| | | | | |
|---|---|---|---|---|
| 4,672,454 A | * | 6/1987 | Cannella et al. | 378/98.8 |
| 4,996,413 A | * | 2/1991 | McDaniel et al. | 250/208.1 |
| 5,079,426 A | | 1/1992 | Antonuk et al. | |
| 5,262,649 A | * | 11/1993 | Antonuk et al. | 250/370.09 |
| 5,949,848 A | | 9/1999 | Gilblom | |
| 6,055,295 A | * | 4/2000 | Murthy et al. | 378/151 |
| 6,205,199 B1 | * | 3/2001 | Polichar et al. | 378/98.8 |
| 6,243,441 B1 | * | 6/2001 | Zur | 378/98.8 |

OTHER PUBLICATIONS

Amorphous–Silicon, Image Sensors, dpix, 3406 Hillview Ave., Palo Alto, CA 94304, http://www.dpix.com/sensors/sensors.htm, Oct. 4, 2000.

PCI Local Bus, Chapter 1, Introduction, PCI Local Bus Applications, PCI Local Bus Overview, PCI Local Bus Features and Benefits, pp. 01–05.

Microsoft Computer Dictionary, Fourth Edition, 1999, Published by Microsoft Press A Division of Microsoft Corporation, One Microsoft Way, Redmond, Washington, 98052–6399, pp. 321,482,483,459.

Steven L. Garverick, et al., A 32–Channel Charge Readout IC for Programmable, Nonlinear Quantization of Multichannel Detector Data, IEEE Journal of Solid State Circuits, vol. 30, No. 5, May 1995, pp. 533–541.

L.E. Antonuk, et al., Strategies to Improve the Signal and Noise Performance of Active Matrix, Flat–Panel Imagers for Diagnostic x–ray Applications, Medical Physics, vol. 27, No. 2, Feb. 2000, pp. 289–306.

(Continued)

Primary Examiner—Bhavesh M. Mehta
Assistant Examiner—Seyed Azarian
(74) Attorney, Agent, or Firm—Jean K. Testa; Patrick K. Patnode

(57) ABSTRACT

An imaging system includes a programmable detector framing node controlling generation of radiation and controlling radioscopic image detection. Radioscopic image data is acquired by the detector framing node and communicated to a host memory of a host computer independently of a host computer operating system. Image data is received from a flat panel detector and is selectively reordered according to parameters of the selected flat panel detector before communication to the host memory. The detector framing node includes an image detection interface to receive the image data and a control unit to select a predetermined portion of the image data for storage into a detector memory unit before communication to the host memory.

47 Claims, 53 Drawing Sheets

OTHER PUBLICATIONS

McGraw–Hill Encyclopedia of Science & Technology, 1992, vol. 3, "Charge–coupled Devices", pp. 475–478.

McGraw–Hill Encyclopedia of Science & Technology, 1992, vol. 4, "Computerized Tomography", pp. 283–285.

McGraw–Hill Encyclopedia of Science & Technology, 1992, vol. 10, "Medical Imaging", pp. 591–594.

McGraw–Hill Encyclopedia of Science & Technology, 1992, vol. 12, "Optical Detectors", pp. 416–417.

McGraw–Hill Encyclopedia of Science & Technology, 1992, vol. 13, "Photodiode", p. 403, "Photoelectric Devices" p. 405, "Photomultiplier" pp. 435–437.

McGraw–Hill Encyclopedia of Science & Technology, 1992, vol. 15, "Radiography", pp. 136–143.

McGraw–Hill Encyclopedia of Science & Technology, 1992, vol. 19, "X–ray Tube", pp. 580–584.

Eugene Hecht, OPTICS, Third Edition, 1998, ADDISON-WESLEY, pp. 78–79.

Adrian Paskins, IEEE, The IEEE 1394 BUS 1997, pp. 1–6.

An Introduction to the Instrument and Industrial Control Protocol, IEEE 1394, IEEE 1394–1995 Specification.

Charles Severance, Linking Computers and Consumer Electronics, Standards, Feb. 1997, pp. 119–120.

Microelectronics Division of Lucent Technologies—About Universal Serial Bus, http://www.lucent.com/micro/usb/usbabout.html, Sep. 26, 2000.

Product Directory, Quality by Design, http://www.tte.thomson– csf.com:8200/Products_us/Xri/SO61_2.jsp, Oct. 4, 2000.

PaxScan 4030, Amorphous Silicon Digital X–Ray Detector, http://www.varian.com/prd/prd403.html (pp. 1–2); . . . prd401.html (pp. 1–2); . . . prd407.html (p. 1); . . . prd409.html (pp. 1–2); . . . prd410.html (pp. 1–3); . . . prd 411.html (p. 1); . . . prd 406.html (pp. 1–2); Feb. 2000.

Siemens Nuclear Web, http://www.sms.siemens.com/nmg/ew.html, Sep. 27, 2000, pp. 1–2.

High–Definition CCD Radiological Imagining Units, http://www.tte.thomson– csf.com:8200/Products_us/Xrt/TO17.jsp, Oct. 4, 2000, pp. 1–3.

* cited by examiner

| Panel Setup | (fm/sec) | length | latency | memory | offset | gbr |
|---|---|---|---|---|---|---|
| Single Frame | Real Time | 30 | unlimited | <5 frames | host | none | |
| Single Frame | Post Process | - | - | Delay ~.1 sec | host | " | y |
| Single Frame | Post Process | - | - | Delay ~.2 sec | " | y | y |
| Real Time | Real Time | R | unlimited | <5 frames | host | none | |
| Real Time | Real Time | R-X | unlimited | <5 frames | host | y | y |
| Real Time | Real Time | R-Y | unlimited | <5 frames | " | y | y |

*fig. 19*

| Modality | image size | Frames Stored host memory |
|---|---|---|
| Cardiac | 1024 X 1024 | 200 |
| Rad | 2048 X 2048 | 50 |
| Mammo | 2304 X 2048 | 44 |

*fig. 20*

Mapping of 16 MByte PCI Address Space

| Event Mnemonic | Event (showing size of arguments) | Op Code (hex) | Data (bytes) | Total (bytes) |
|---|---|---|---|---|
| Endq | Endq | 14 | 0 | 1 |
| Delay (T) | Delay (0xff ff ff ff) | 10 | 4 | 5 |
| Send (command, value) | Send (0xff ff ff ff, 0xff ff ff ff) | 04 | 8 | 9 |
| LoopKN (K, N) | LoopKN (0xff ff, 0xff) | 0C | 3 | 4 |
| LoopKF (K, F) | LoopKF (0xff ff, 0xff ff) | 0D | 5 | 6 |
| Wait (F) | Wait (0xff ff) | 09 | 3 | 4 |
| Flag (F) | Flag (0xff ff) | 08 | 3 | 4 |

660

SEND | HDR1(0) | HDR1(1) | HDR1(2) | HDR1(3) | HDR2(0) | HDR2(1) | HDR2(2) | HDR2(3)

S1 · S2

SEND

670

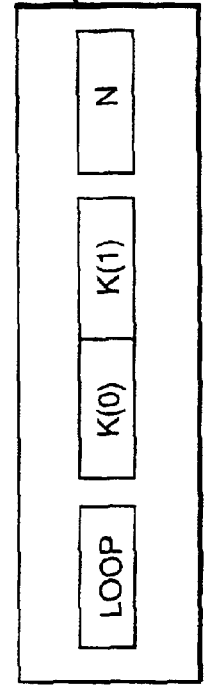

| Error Mnemonic | Description of Error |
|---|---|
| FC_TIMEOUT | Timeout Expired With No ACK Detected |
| FC_BAD_ACK | ACK Did Not Match Transmitted Command |
| FC_EXTRA_ACK | Unexpected ACK Received |
| FC_EXTRA_CMD | New Send Event While Waiting for ACK From Previous Send |
| SIG_DETN | No Input Signal Power on Fibre Channel (Cable Disconnected?) |
| RXERROR | Fibre Channel Receiver Detected Bad Data (Defective Chipset?) |
| WRDSYNCN | Fibre Channel Data Link Unsynchronized |
| CRXS(1) | Bad Received CRC Detected (Fiber-optic Cable Problem?) |
| CRXS(3) & CRXS(2) | Bad Order in Link State Machine (Defective Chipset?) | fig. 52

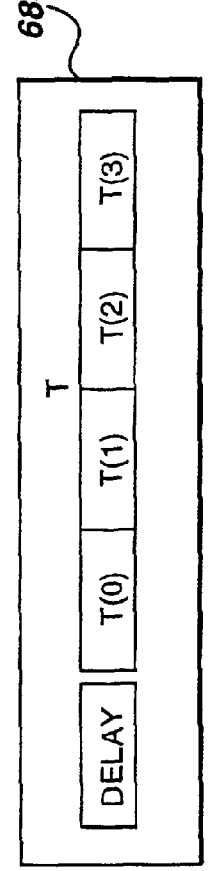

fig. 53 fig. 54

EVENT QUEUE

Constant Memory Format fig. 64

```
sequence_begin ();
# define qv defaults:
%qv1 =('delay_qv' => 5000);
# call frame with qv's
frame_type1(NULL, \%qv1, 1);
sequence_end ();
``` fig. 65

```
sub frame
{
 $QVf = 'frame' ;
 %qv = ('delay_qv' = > [10000]);
 %qp = ( );
 compile_init (@_,\%qp, \%qv, $QVf);
    Delay('Delay_qv1');
 compile_finit ( );
}
``` fig. 66

```
pDFN->DFNChangeQueueVariable
(
 (char *) SymName,            // variable name
 (char *) sndBuf,             // new value
 BufSize                      // num bytes to write
    (ULONG *) & Debug         // developer info
);
```

```
// load and run the event sequence
pDFNBeginSequenceNoMappingNoLog
    (snum,"d:\\HF.bin") ;
// assign data to be passed
sndBuf = 25000;
// change the queue variable
pDFN->DFNChange QueueVariable
(
    (char *) SymName,         // variable name
    (char *) sndBuf,          // new value
    (ULONG ) sizeof sndBuf    // num bytes to write
    (ULONG *) & debug         // developer info
);
``` fig. 67

```
sub frame_type1
{
    $HFfrm = 'frame_type1';
    %qv = ('delay_qv' = > [20000]);
    %qp = ( );
    $image_cmd = [0x800000,0x0];
    compile_init (@_,\%qp, \%qv, $HFfrm);
    Send ( $image_cmd);
    Delay('delay_qv');
    LoopKF(2, 0xAAFF01);
    compile_finit( ) ;
}
``` fig. 68

COMMUNICATION OF IMAGE DATA FROM IMAGE DETECTOR TO HOST COMPUTER

STATEMENT REGARDING FEDERALLY SPONSORED RESEARCH & DEVELOPMENT

The U.S. Government may have certain rights in this invention pursuant to the Portable Apollo X-Ray System for Military Applications Cooperative Agreement number DAMDD17-00-2-0009, awarded by the United States Army.

BACKGROUND OF THE INVENTION

The invention relates to a method, system, and apparatus for controlling, acquiring and processing digital radioscopic image data, and in particular to a method, system and apparatus for controlling and communicating acquired digital radioscopic x-ray image data to a computer running a non-real time operating system.

Medical imaging is a specialty that uses radiation, such as gamma rays, x-rays, high-frequency sound waves, magnetic fields, neutrons, or charged particles to produce images of internal body structures. In diagnostic radiology, radiation is used to detect and diagnose disease, while in interventional radiology, radiation is used to treat disease and bodily abnormalities.

Radiography is the technique of producing an image of any opaque specimen by the penetration of radiation, such as gamma rays, x-rays, neutrons, or charged particles. When a beam of radiation is transmitted through any heterogeneous object, the radiation is differentially absorbed depending upon varying object thickness, density, and chemical composition. The radiation emergent from the object forms a radiographic image, which may then be realized on an image detection medium, such as photographic film directly or by using a phosphor to first create a light image. Radiography is a non-destructive technique of testing a gross internal structure of an object, and is conventionally used in medical and industrial applications. Radiography is used to non-destructively detect medical conditions such as tuberculosis and bone fractures, as well as manufacturing imperfections in materials such as cracks, voids, and porosities.

X-ray radiography finds particular usefulness in medical and industrial applications. X-rays are a form of electromagnetic radiation, and were accidentally discovered in 1895 by Wilhelm Conrad Roentgen. X-rays are alternately referred to as roentgen rays. In circa 1895, Roentgen found that x-rays propagate through an internal object such as a hand and expose photographic film, thereby revealing an internal structure. X-rays exhibit different properties than visible light rays, and were designated by Roentgen as "x-rays," with "x" referring to the unknown. For example, x-rays are not focused with a traditional optical light lens, but rather use sophisticated focusing techniques. Today, x-rays are categorized as electromagnetic radiation having a frequency range extending between $2.4 \times 10^{16}$ Hz to $5 \times 10^{19}$ Hz. Most x-rays have a wavelength smaller than an atom and therefore interact with matter in a granular fashion, that is, like bullets of photon energy. X-rays are absorbed by materials according to the exponential absorption law $$I_x = I_O e^{-\mu x} = I_O e^{-(\mu/\rho)\rho x} \quad (1.0)$$

where $I_O$ is the initial intensity of the x-ray beam; $I_x$ is the intensity after passage through an object, the object having a thickness x, density $\rho$, linear absorption coefficient $\mu$, and mass absorption coefficient $\mu/\rho$.

X-rays are formed through celestial phenomenon, such as internal reactions of stars and quasars, and through electronic x-ray generation devices, such as x-ray tubes. X-ray tubes generally produce x-rays by accelerating a charged particle, such as an electron, through an electrostatic field and then suddenly stopping the x-ray through collision with a solid target. This collision ionizes the solid target by transporting closely held electrons to a higher energy state. As the electrons in the solid target return to their original energy state, x-rays are produced. X-rays are produced within x-ray tubes by accelerating electrons in a vacuum from a cathode toward an anode, with or without particle beam shaping and accelerating through placement of electrodes.

The electronic detection of x-rays is generally referred to as electronic radiography or radioscopy. Prior to electronic detection, radiographic images were captured on photographic film or displayed on a fluorescent screen. Real time visual observation of x-rays on a fluorescent screen is referred to as fluoroscopy. However, as early as the 1930s photo-multiplier tubes (a form of vacuum tube) were developed to produce an electrical signal in response to received light. Photo-multiplier tubes generally respond well to optical range light rays and are therefore often optically coupled with a scintillating material to detect non-optical electromagnetic radiation. The scintillating material converts non-optical radiation, such as gamma rays (emitted by radioactive isotopes used in nuclear medicine) and x-rays into optical radiation. Beginning circa 1980, photo-multiplier/scintillator detectors are generally being replaced by amorphous silicon based photo-cells.

Radioscopy includes one shot x-ray detection, also known as fluorography, and multiple shot x-ray detection, also known as fluoroscopy. Radio-mammography is a form of radioscopy in which the breast is vigorously compressed prior to exposure to maximize detail and minimize radiation exposure. Computed tomography ("CT"), also called computed axial tomography ("CAT"), is a form of radioscopy in which an x-ray tube is rotated around the body while emitting a narrow x-ray beam. The received x-ray beam information is then combined in a computer to produce a two or three dimensional anatomic medical image. Magnetic resonance imaging ("MRI") is a diagnostic procedure in which a high strength magnet aligns the spin of nuclei within cells of a body, such that each nuclei acts like a radio, both receiving and transmitting radio signals. External radio frequency signals are then applied to the body to disturb the spinning cellular nuclei. After the radio signal is stopped, the nuclei realign with the applied magnetic field while emitting faint radio signals. These faint radio signals correspond to different body tissues and are detected to produce an anatomical image.

Radioscopy and related medical diagnostic imaging technologies use precision control over penetrating radiation and well as precision timing for detection and processing of resultant image data. Medical diagnostic imaging generally acquires and controls a very large amount of image data, which in turn is communicated to computer processing equipment at a very high data rate. To provide control over the generation, detection, and processing of medical diagnostic imaging, computer workstations employ the use of a real time operating system ("RTOS") to control operation. A real time operating system, such as VXWORKS® by Wind River Systems, Inc. of Alameda, Calif., is an operating system that immediately responds to real time signaling events. On the other hand, non-real time operating systems, such as a WINDOWS® platform or a UNIX® platform, process operations in the form of tasks until the task is complete. Both WINDOWS® and UNIX® are non-real time, multi-task operating systems in which a processor or processors are continuously interrupted to respond to multiple task based system events. Due to the high speed of commercially available processors, multi-tasking operating systems may appear to control a number of simultaneous events. However, a multi-tasking operating system, by design, cannot respond in real time to the high through-put demands of real time processing equipment, such as used in medical diagnostic imaging.

BRIEF SUMMARY OF THE INVENTION

It is therefore desirable to provide an imaging system to control a radiation generation system and an image detection system in real time. The imaging system includes a host computer having a host memory and at least one host processor. The imaging system also includes a detector framing node, which is programmed to receive image data from a plurality of different flat panel detectors. The detector framing node communicates the image data to the at least one host processor over a communication bus independent of a host operating system.

It is further desirable to provide a detector framing node, including a computer communication interface to communicate image data with a host memory of a host computer over a computer communication bus. The host computer includes a host processor running an operating system. The image data is communicated from the computer communication interface to the host memory independently from control of the host processor. The detector framing node also includes a control unit to receive a plurality of event instructions from the host computer through the computer communication interface. The event instructions selectively control a radiation generation system and an image detection system. The event instructions are executed in real time and at predetermined timing intervals.

BRIEF DESCRIPTION OF THE DRAWINGS

FIG. 19 is a table illustrating estimated processing capability for a 1024×1024 cardiac/surgical digital x-ray image;

FIG. 20 is a table illustrating available frame storage for 400 MByte of PC RAM memory;

FIG. 52 is a table of reported Fiber Channel errors;

FIG. 53 is a block diagram of a Delay T event;

FIG. 54 is a block diagram of a Loop KN event;

FIG. 64 illustrates a top level Queue variable definition format;

FIG. 65 illustrates a frame level Queue variable definition format;

FIG. 66 is a format of a function call having defined ASCII names;

FIG. 67 is an example C++ user application explaining source code;

FIG. 68 is an example Perl script event sequence explaining source code;

DETAILED DESCRIPTION OF THE INVENTION

Figure 1:
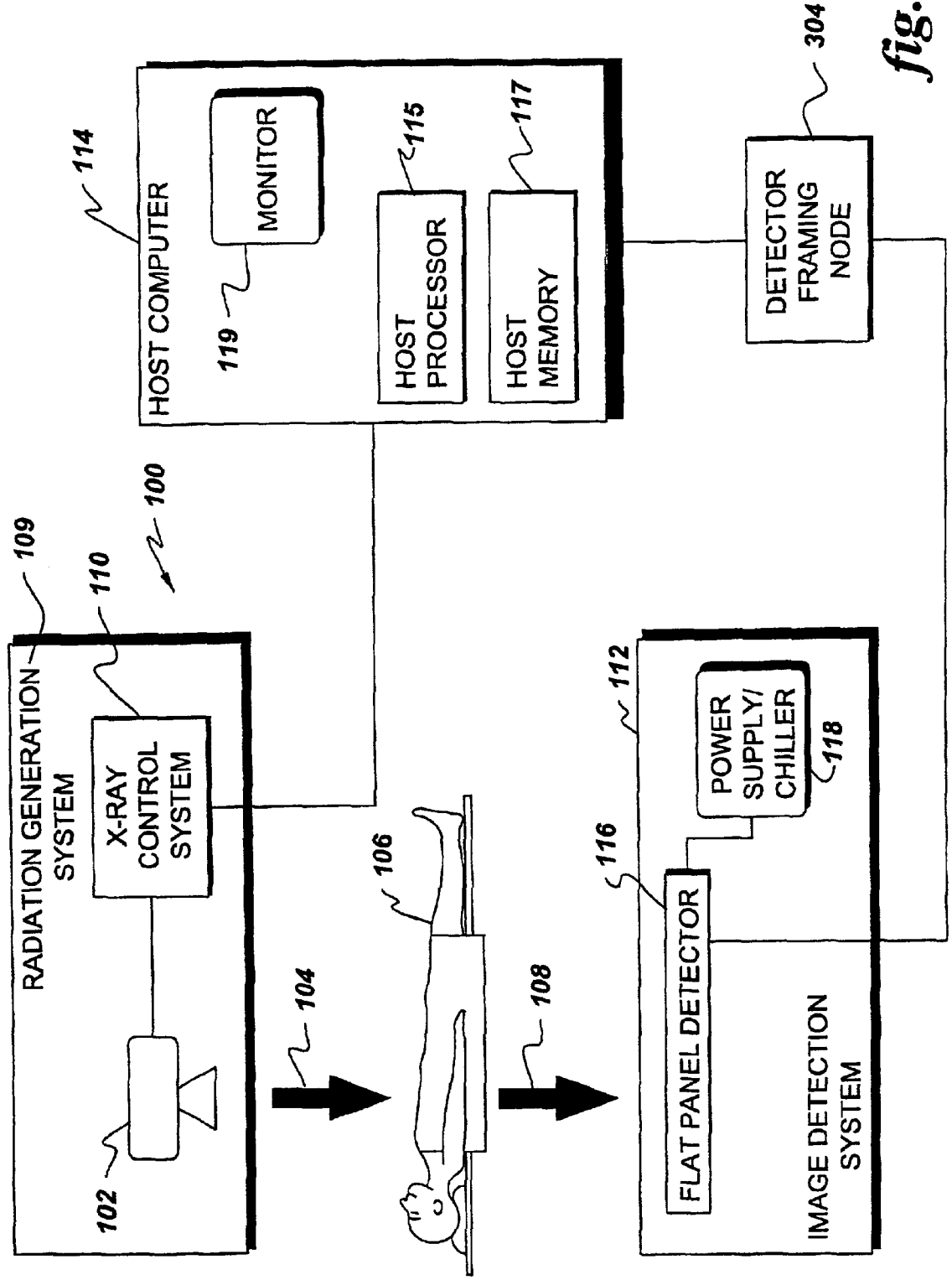
FIG. 1 is a block diagram of an imaging system including a host computer, radiation generation system, and an image detection system.

Referring to FIG. 1, a method, system, and apparatus are illustrated for controlling, acquiring and processing digital radioscopic image data. Imaging system 100 comprises radiation generation system 109, image detection system 112, host computer 114, and detector framing node 304. Host computer 114 includes monitor 119, host processor 115 and host memory 117. According to an embodiment of the present invention, imaging system 100 is an image detector monitoring system. According to another embodiment of the invention, the components of imaging system 100 function together as a single apparatus.

Radiation generation system 109 generates radiation to pass through object 106 and to be detected by image detection system 112. According to an embodiment of the present invention, radiation generation system 109 includes x-ray generation unit 102 to generate and focus radiation 104 toward object 106. According to an embodiment of the present invention, radiation 104 takes the form of x-rays. According to another embodiment of the present invention, radiation 104 takes the form of a plurality of sequentially generated radiation bursts. According to an embodiment of the present invention, object 106 is in the form of the human body. Upon passage through object 106, x-rays 104 form radiographic image 108 for later detection. In general, x-rays are generated by x-ray generation unit 102 in response to control signals output from x-ray control system 110. Radiographic image 108 is received by image detection system 112 and converted into a digital radiographic image. The digital radiographic image is then output from image detection system 112 and transmitted to host computer 114. Host computer 114 provides electronic control to radiation generation system 109 and to image detection system 112.

Image detection system 112 includes flat panel detector 116 for receiving radiographic image 108. Flat panel detector 116 becomes heated during operation, and is therefore connected to power supply/chiller 118 for supplying power and cooling thereto. A digital radiographic image is output from flat panel detector 116 to host computer 114.

Figure 2:
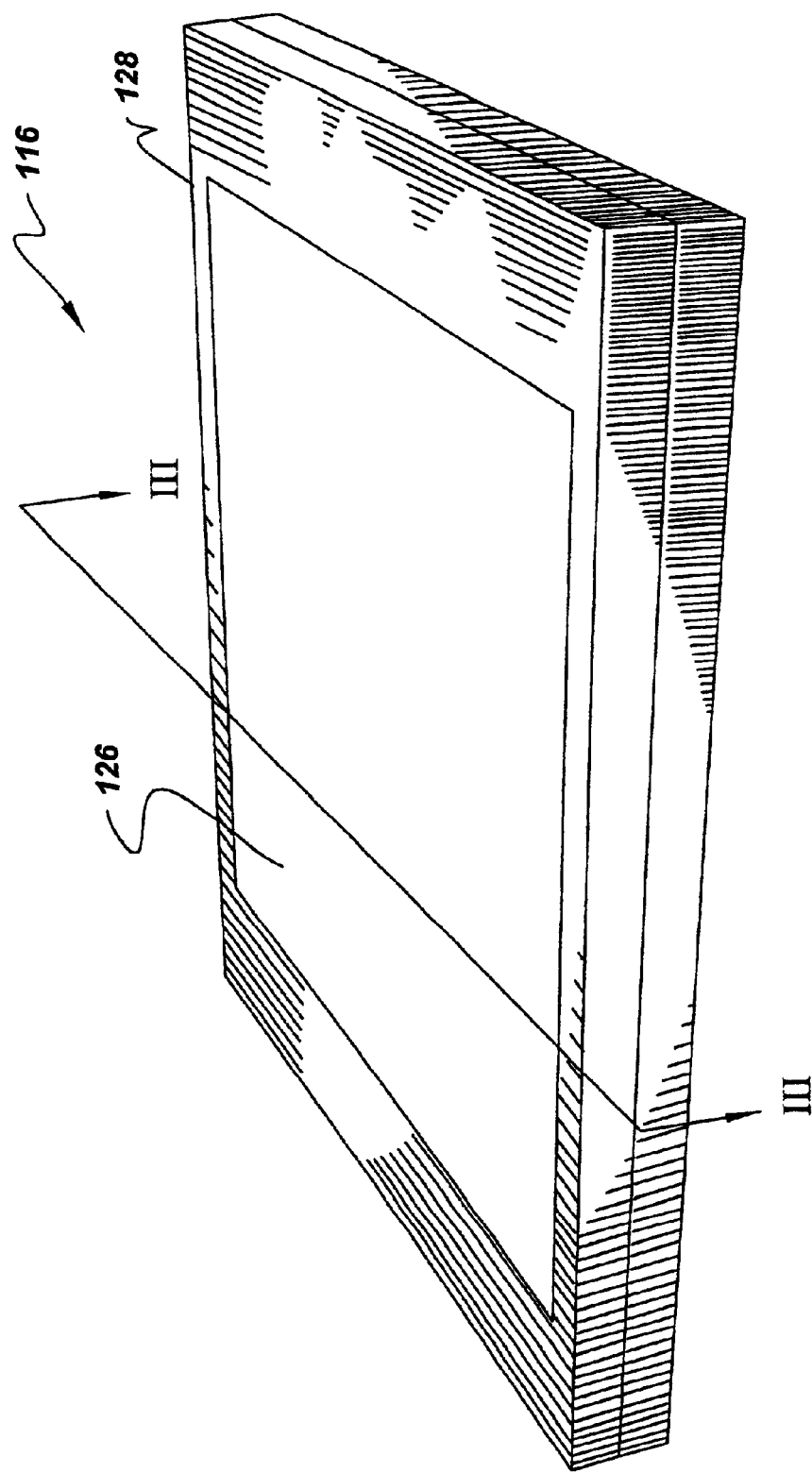
FIG. 2 (PRIOR ART) is an elevated perspective view of a flat panel detector.

FIG. 2 (PRIOR ART) is an elevated perspective view of flat panel detector 116. Flat panel detector 116 is a single detector technology that provides an image receptor in x-ray radiography. For example, flat panel detector 116 replaces existing x-ray imaging films, such as plain film and spot film, for radiographic applications. Moreover, due to thin packaging, flat panel detector 116 replaces imaging intensifiers, video cameras, cine cameras, and photo spot imaging, etc. for digital radiography; and also for digital fluorography and digital fluoroscopy. The area of a flat panel detector 116 is 26 cm×26 cm for a cardiac/surgical digital x-ray panel; 45 cm×56 cm for a radiography digital x-ray panel; and 29 cm×34 cm for a mammography digital x-ray panel. Glass plate 126 and metal casing 128 surround and protect the physical x-ray receptors, electronic detection equipment and associated electronics.

Figure 3:
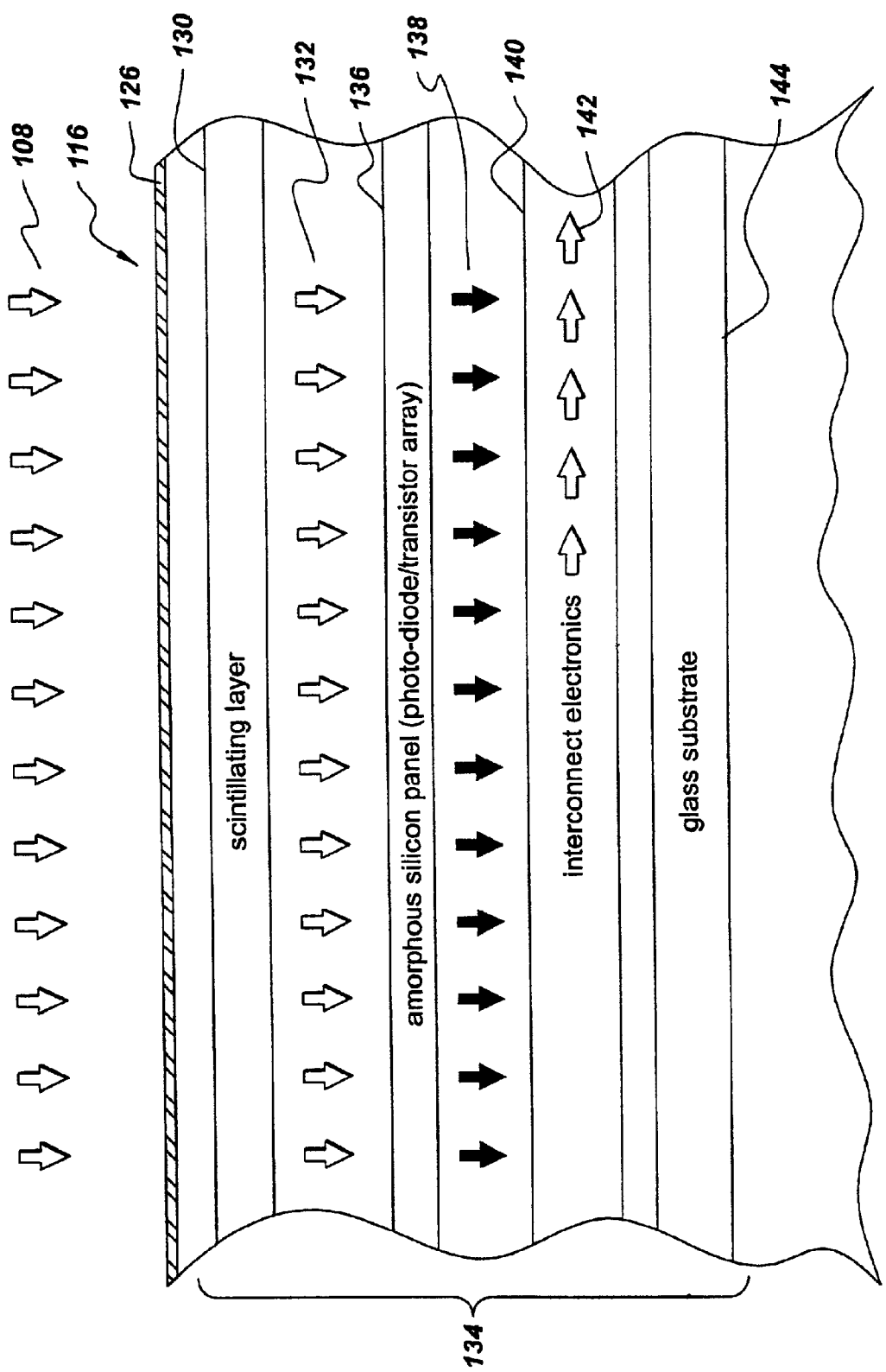
FIG. 3 (PRIOR ART) is an exploded sectional view of the flat panel detector of FIG. 2 taken along line III—III.

FIG. 3 (PRIOR ART) is an exploded sectional view of flat panel detector 116 taken along line III—III of FIG. 2. As illustrated, radiographic image 108 passes through glass plate 126 and is absorbed by x-ray detection panel 134. According to an embodiment of the present invention, x-ray detection panel 134 is a single panel x-ray detection panel. X-ray detection panel 134 is an amorphous silicon x-ray detection panel. X-ray detection panel 134 includes scintillating layer 130, which converts x-ray radiographic image 108 into optical radiographic image 132. Scintillating layer 130 is applied through vapor deposition onto x-ray detection panel 134, and in particular to amorphous silicon panel 136. Scintillating layer 130 takes the form of Gadolinium Oxysulfide, $Gd_2O_2S:Tb$; or Cesium Iodide, CsI(Tl). To receive high energy x-rays, the Cesium Iodide scintillating layer is used.

Amorphous silicon panel 136 is a photo-diode/transistor array that receives and converts optical radiographic image 132 into a plurality of representative image data values 138. Image data values 138 are received in analog form by interconnect electronics 140, and output from panel 136 as analog image data. Scintillating layer 130, amorphous silicon panel 136, and interconnect electronics 140 are formed on silicon glass substrate 144 through semiconductor technology known in the art. Together, scintillating layer 130, amorphous silicon panel 136, interconnect electronics 140, and glass substrate 144 form x-ray detection panel 134.

Figure 4:
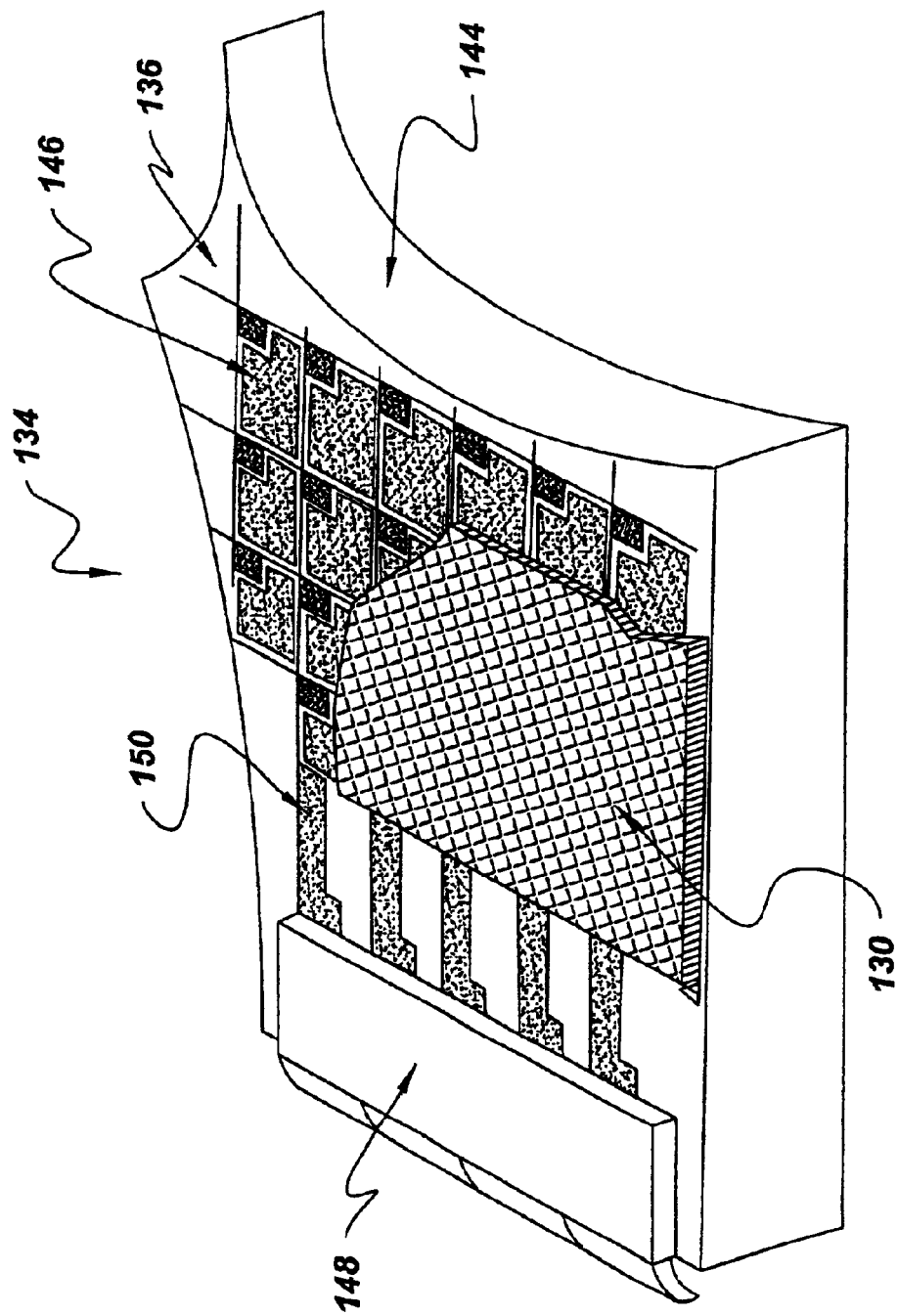
FIG. 4 (PRIOR ART) is an elevated prospective view of an x-ray detection panel removed from a protective metal casing.

FIG. 4 (PRIOR ART) is an elevated prospective view of x-ray detection panel 134 removed from metal casing 128. As illustrated in FIG. 4 (PRIOR ART), amorphous silicon panel 136 forms a plurality of photo cells 146. Electrical information output from each photo cell 146 is transmitted to contact leads 148 by way of a plurality of corresponding contact fingers 150. Contact fingers 150 provide connection between contact leads 148 and amorphous silicon panel 136. As illustrated, scintillating layer 130 is formed on top of amorphous silicon panel 136.

X-ray detection panel 134 provides an array of light sensors with a small spacing between elements, and a large number of elements to adequately receive and detect projected x-ray radiographic images. Amorphous silicon panel 136 is a thin film technology formed on a relatively large glass substrate 144. Eleven layers of amorphous silicon, various metals, and insulators are deposited by plasma enhanced chemical vapor deposition ("PECVD"), sputtering and meniscus coating to form field effect transistors ("FETs"), diodes, interconnects, and contacts. X-ray detection panel 134 forms panels for industrial and medical applications, and in particular, a cardiac/surgical digital x-ray panel, 20×20 cm; a radiography digital x-ray panel, 41×41 cm; and a mammography digital x-ray panel, 19×23 cm. The cardiac/surgical digital x-ray panel has 1024 columns×1024 rows at 200 $\mu$m pitch; the radiography digital x-ray panel has 2048 columns×2048 rows at 200 $\mu$m pitch; and the mammography digital x-ray panel has 1920 columns×2304 rows at 100 $\mu$m pitch.

Amorphous silicon provides a number of advantages over single crystal silicon for the formation of flat panel detectors, and is particularly distinguishable from single-crystal silicon. Amorphous silicon is characterized by having no definite form, and having no real or apparent crystalline structure. On the other hand, single-crystal silicon is grown as a single crystal, sliced into wafers, then polished for further refinement into integrated circuits. Amorphous silicon allows the formation of much larger panels than single crystal silicon because the formation of a single crystal is not used. However, amorphous silicon finds a 100 to 1000 times increase in defects, and a significant reduction in switching speed, which effect signal lag and signal offset characteristics. Scintillating layer 130, CsI(Tl), converts x-rays into optical rays and is evaporated onto amorphous silicon panel 136 to provide intimate contact therewith. CsI(Tl) forms a needle-like structure, which acts like a plurality of light pipes to prevent lateral spread of the light. Moreover, CsI(Tl) provides a transmission spectrum which is well matched to the quantum efficiency of amorphous silicon layer 136.

Figure 5:
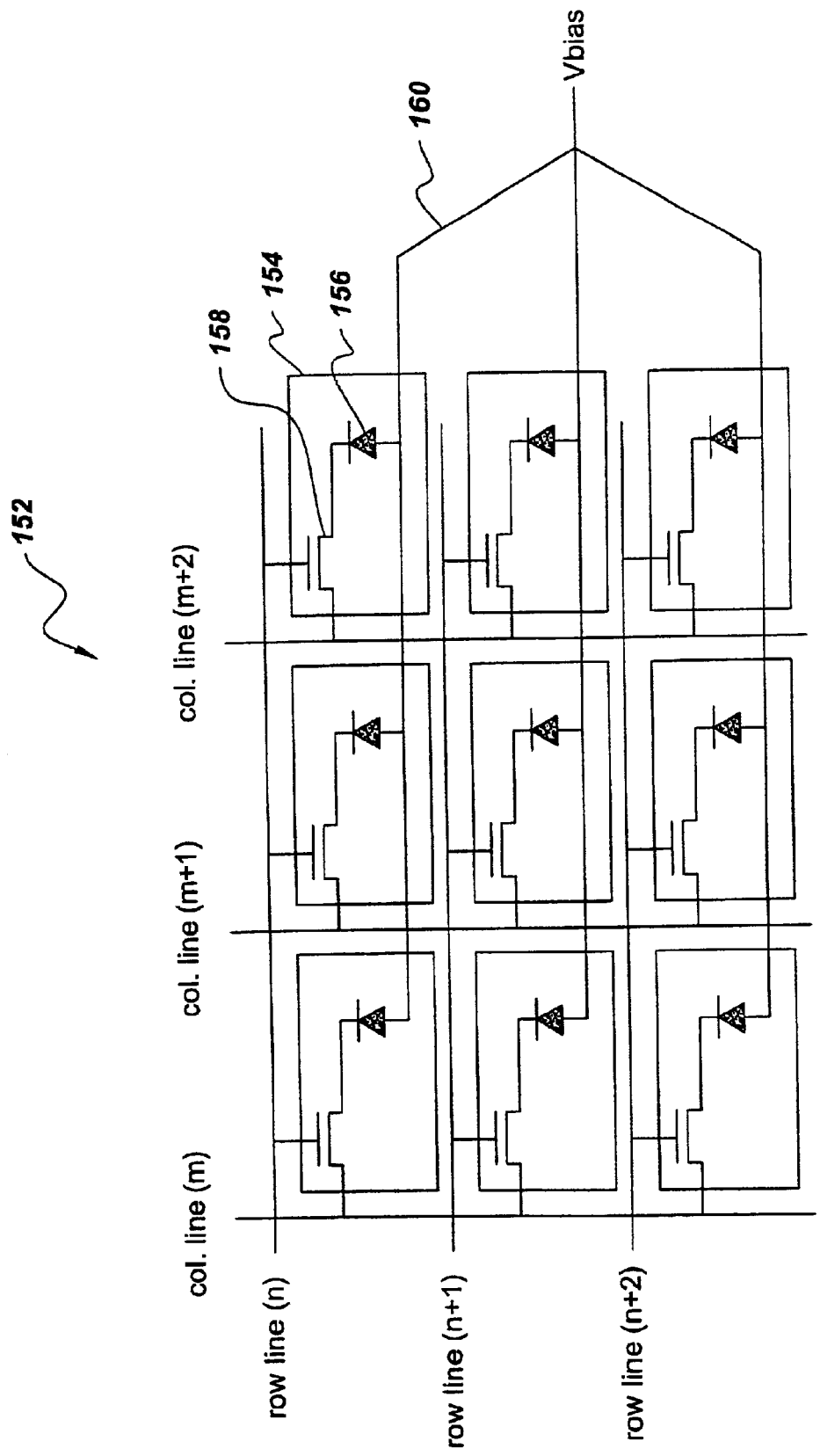
FIG. 5 (PRIOR ART) is a schematic view of a photo cell array formed on an amorphous silicon panel.

FIG. 5 (PRIOR ART) is a schematic view of photo cell array 152 formed on amorphous silicon panel 136. As illustrated, a plurality of photo cells 154 are sequentially triggered in response to a scan from row lines (n), (n+1), (n+2), . . . , etc. Accordingly, corresponding outputs are read out along column lines (m), (m+1), (m+2), . . . , etc. Each photo cell 154 includes a photo diode 156 and a field effect transistor 158. Photo diode 156 is biased by way of bias lines 160 and discharged at the appropriate time by way of field effect transistors 158. The field effect transistors 158 control electrical discharge from the appropriate corresponding column lines. During operation, field effect transistors 158 are turned on by pulsing the appropriate row line to a high voltage, which is pulsed on the order of +11 V. Field effect transistors 158 are turned off by pulling the appropriate row line low, which is on the order of −11 V.

X-ray exposure creates electron-hole pairs in photo diodes 156 of amorphous silicon, x-ray detection panel 134 causing partial discharge. When field effect transistors 158 are then turned on, photo diodes 156 are recharged, and the amount of charge needed to recharge photo diodes 156 is measured. During operation, all row lines are turned off, i.e. to −11 V, during x-ray exposure. The row lines are then sequentially turned on, i.e. to +11 V. Analog to digital conversion of the signals on the appropriate column lines are pipe lined such that the outputs from row "n" are converted from analog information to digital information while row "n+1" is read out. The time period used for analog to digital conversion is on the order of the time used to read out each row line.

Figure 6:
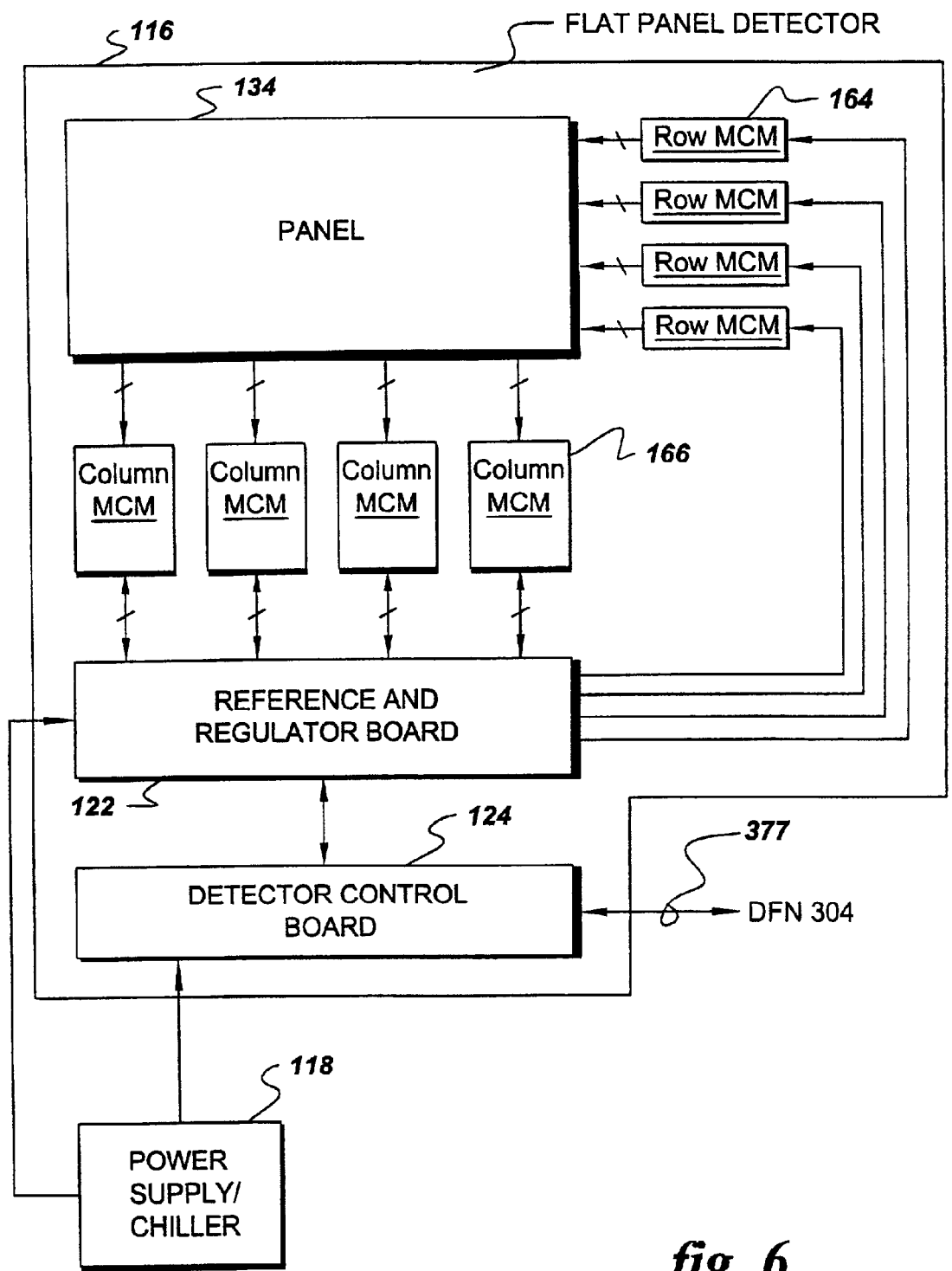
FIG. 6 (PRIOR ART) is a block diagram of an electrical connection in an amorphous silicon single panel detector system.

FIG. 6 (PRIOR ART) is a schematic diagram of electrical connections in flat panel detector 116 according to an embodiment of the present invention. Flat panel detector 116 includes a single amorphous silicon, x-ray detection panel 134, electrically coupled to a plurality of row multi-chip modules 164 and a plurality of column multi-chip modules 166. In response to sequential trigger signals from row multi-chip modules 164, all columns are simultaneously read out onto column multi-chip modules 166. Column multi-chip modules 166 convert analog readout signals from detection panel 134 into digital signals, which are in turn received by reference and regulator board 122.

Reference and regulator board 122 combines data output from column multi-chip modules 166 and outputs the same to detector control board 124. In summary, row multi-chip modules 164 turn field effect transistors 158 on and off while column multi-chip modules 166 read out respective column signals. Reference and regulator board 122 supplies voltages to the row and column modules, while communicating control and data signals with respect to detector control board 124.

Figure 7:
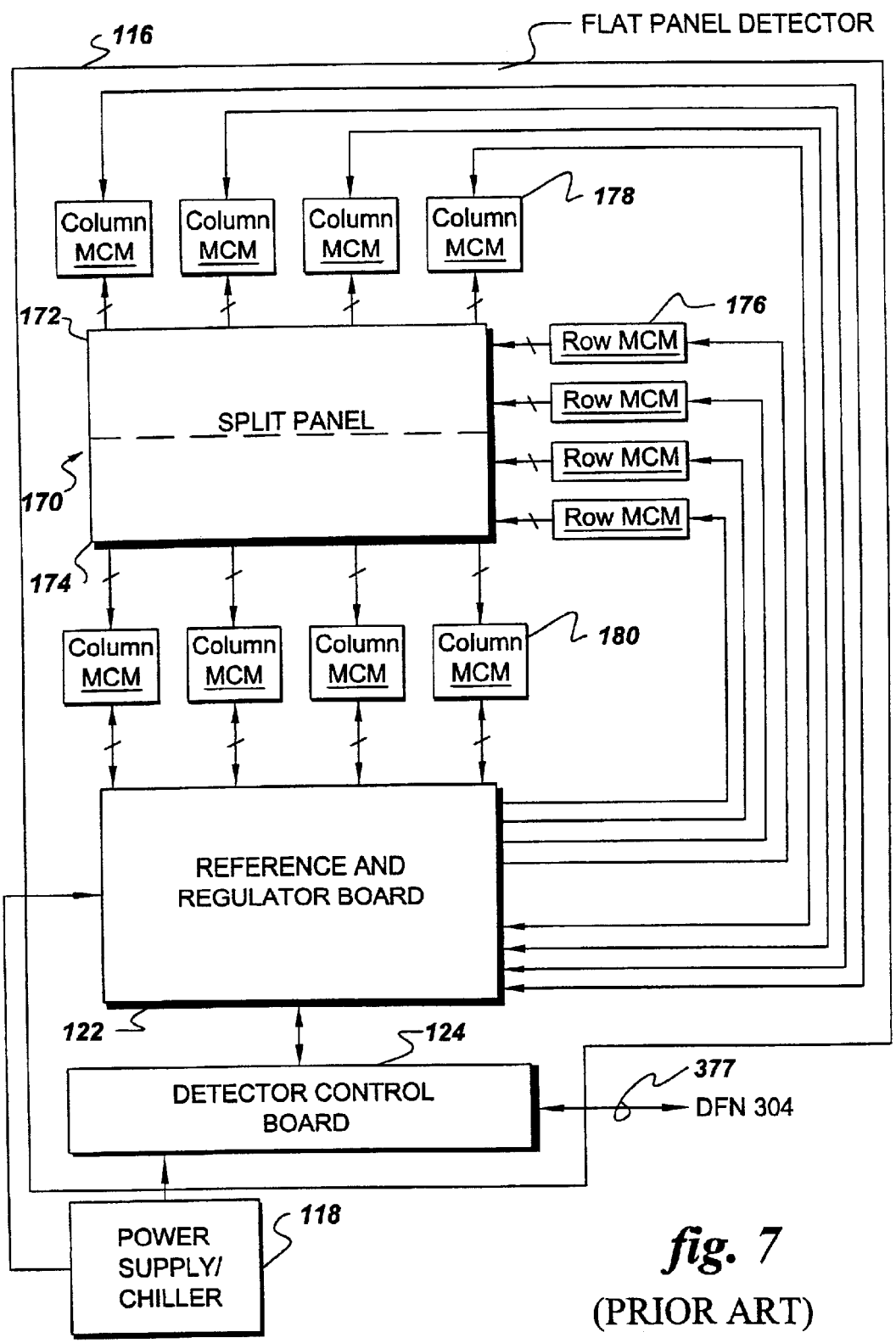
FIG. 7 (PRIOR ART) is a block diagram of electrical connection in an amorphous silicon split panel detector system.

FIG. 7 (PRIOR ART) is a block diagram of electrical connection in flat panel detector 116 according to another embodiment of the present invention. Flat panel detector 116 schematically represents electrical connections, such as found in cardiac/surgical digital x-ray panels and radiography digital x-ray panels. As illustrated, flat panel detector 116 includes cardiac/surgical split panel x-ray detection panel 170 having a first panel portion 172 and a second panel portion 174. According to an embodiment of the present invention, split panel x-ray detection panel 170 is a cardiac/surgical split panel x-ray detection panel. First and second panel portions 172 and 174 are respectively triggered by row multi-chip modules 176. The output from first panel portion 172 is received by first column multi-chip modules 178 while the output from second panel portion 174 is respectively received by second column multi-chip modules 180.

Figure 8:
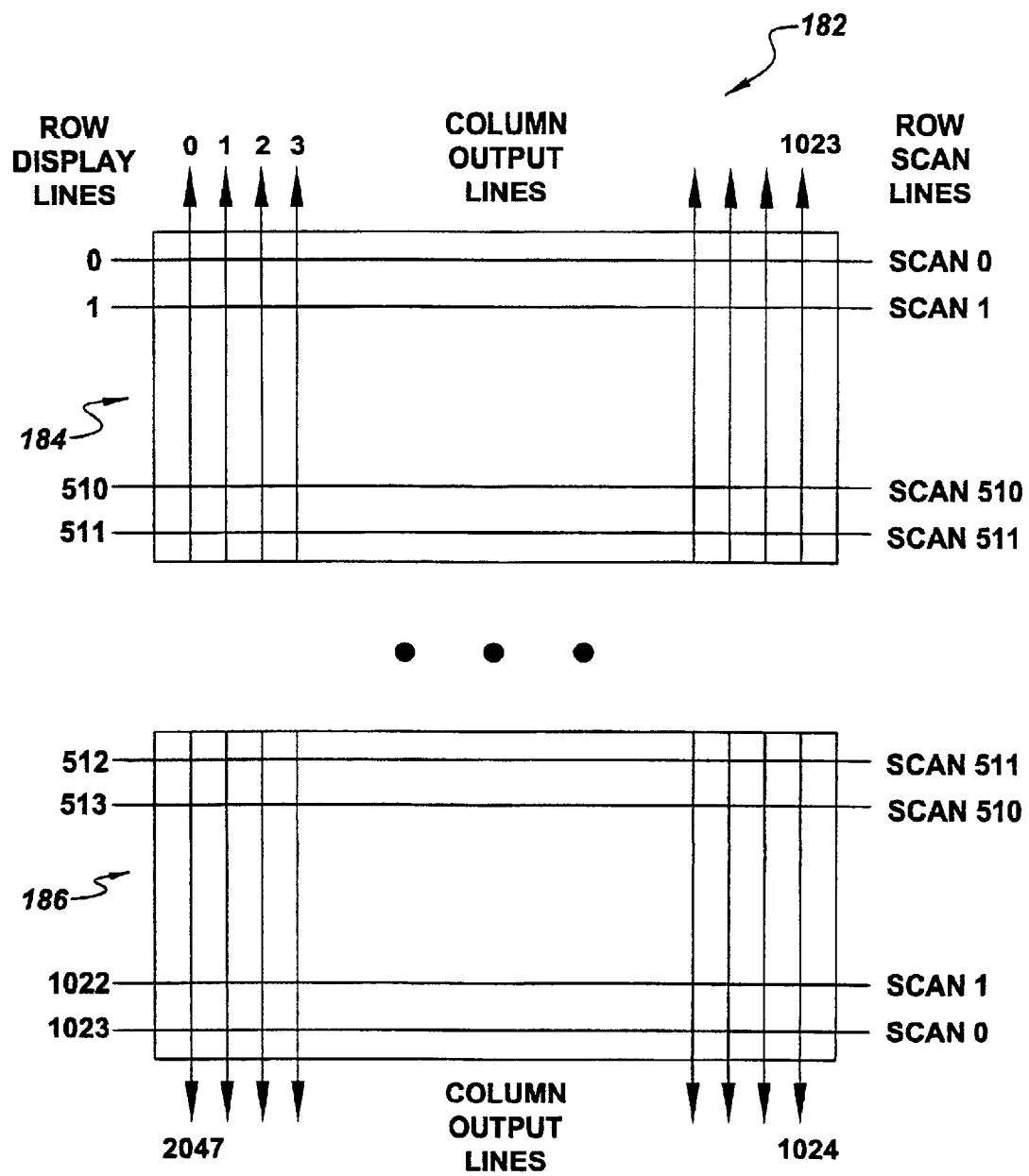
FIG. 8 (PRIOR ART) is a schematic diagram of a split panel, cardiac/surgical digital x-ray panel.

FIG. 8 (PRIOR ART) schematically represents an embodiment of a split panel, such as split panel 170, as a cardiac/surgical digital x-ray panel 182. Cardiac/surgical digital x-ray panel 182 is formed from a first panel portion 184 and a second panel portion 186. Scan lines 0 to 511 appear in first panel portion 184 and also in second panel portion 186. Accordingly, as row scan line 0 is triggered, two row display lines, namely 0 and 1023, are simultaneously activated, and corresponding column output lines are output from first panel portion 184 and second panel portion 186.

Likewise, as row scan line 1 is simultaneously activated in first panel portion 184 and second panel portion 186, corresponding column output lines are output from first panel portion 184 and second panel portion 186. As each scan line from each corresponding panel portion is activated, all column output lines from each panel portion output their respective values. Accordingly, as row scan line 0 is activated, column output lines 0 through 1023 are simultaneously output from first panel portion 184 while column output lines 1024 through 2047 are simultaneously output from second panel portion 186.

Figure 9:
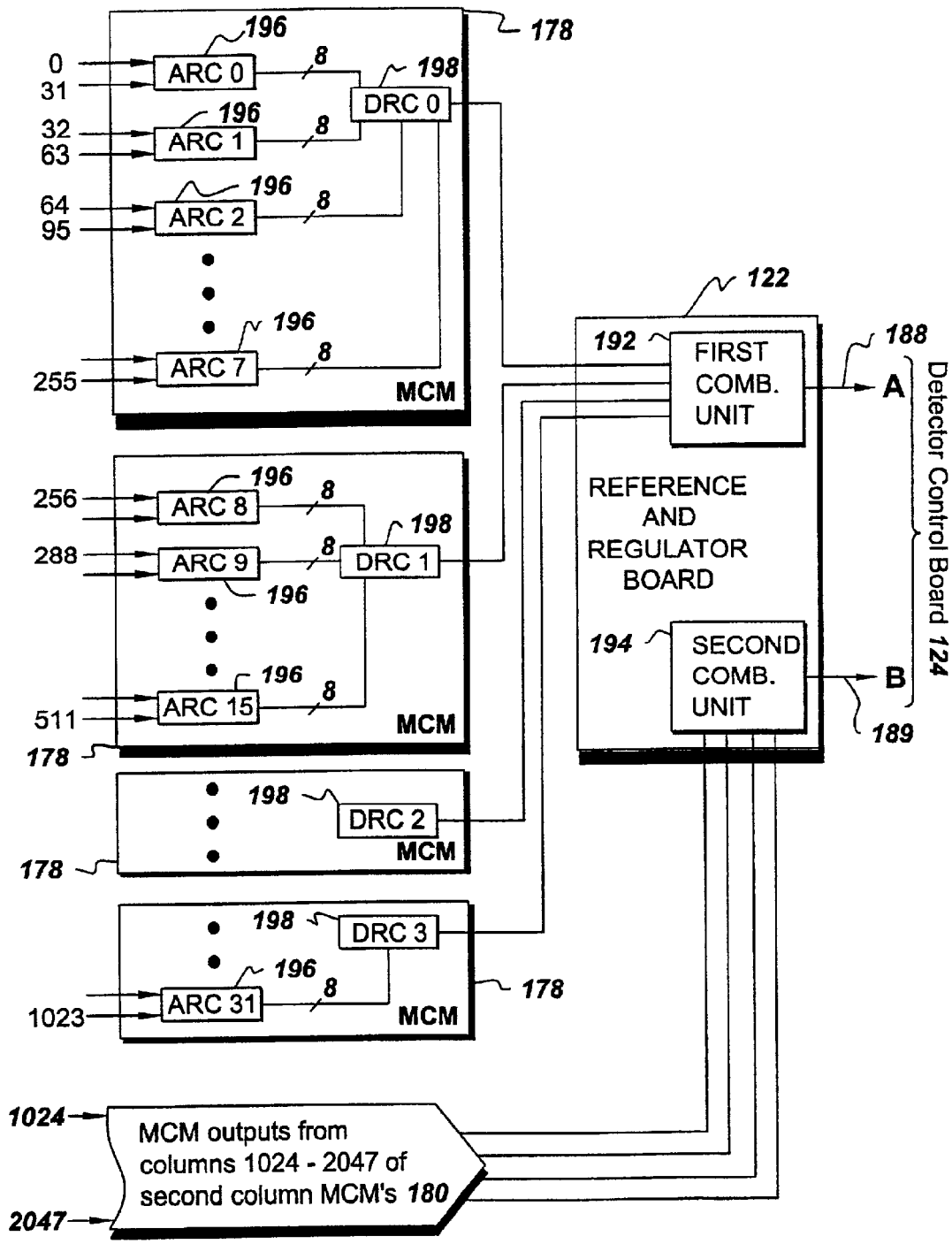
FIG. 9 (PRIOR ART) is a block diagram of column multi-chip modules and a reference and regulator board in a split panel detector system.

FIG. 9 (PRIOR ART) is a block diagram of column multi-chip modules 178 and 180 in conjunction with reference and regulator board 122. Column multi-chip modules 178 receive column signals output from first panel portion 172 while second column multi-chip modules 180 receive the column output signals from second panel portion 174. Accordingly, output from first column multi-chip modules 178 are combined by way of reference and regulator board 122 into combined signal output 188 to be received by detector control board 124. Likewise, column multi-chip modules receive column signals output from columns 1024 through 2047, which are then combined, and transferred to reference and regulator board 122. Reference and regulator board 122 combines the received signals then outputs the combined signal output 189. Collectively, the combined output signals from reference and regulator board, including output 188 and output 189, is output 195.

Reference and regulator board 122 includes first combination unit 192 for combining the outputs from multi-chip modules 178, and also second combination unit 194 for combining the outputs from multi-chip modules 180 corresponding to columns 1024–2047. Each multi-chip module 178 includes eight analog read out chips ("ARCs") 196, which provide a corresponding output to digital read out chips ("DRCs") 198. Thus, the output from the DRCs 198 are received by reference and regulator board 122.

Each ARC chip 196 utilizes a non-linear ramp-compare type analog digital converter. Each ARC chip 196 also receives 32 analog inputs and converts the data into eight channels of multiplexed twelve bit serial, grey scale encoded, data. Each DRC chip 198 then receives the multiplexed twelve bit serial grey encoded data from four ARC chips 196, performs serial to parallel conversion, and converts the grey code into twelve bit binary code. Each ARC chip 196 performs analog to digital conversion on the received data by comparing the signal from each data line in a comparator with a square root encoded ramp generated by a digital to analog converter in common to all channels of all ARCs 196. The ramp voltage is increased in steps at a regular clock rate. When a ramp voltage matches a held voltage, a comparator trips, and a ramp counter value is latched. A time to convert each line of data is at least as great as the clock period times the minimum number of clocks used to convert all received column data lines. A voltage step of the ramp is increased as the signal increases. Quantum noise increases as the square root of each signal, and accordingly the step is increased quadratically so that the step size is a fixed proportion of the noise. By way of the foregoing, interface conditioning of control signals bound for row and column modules use a clock signal on the order of 32.5 MHz, for buffering data output between column modules 178 and 180 and detector control board 124.

Figure 10:
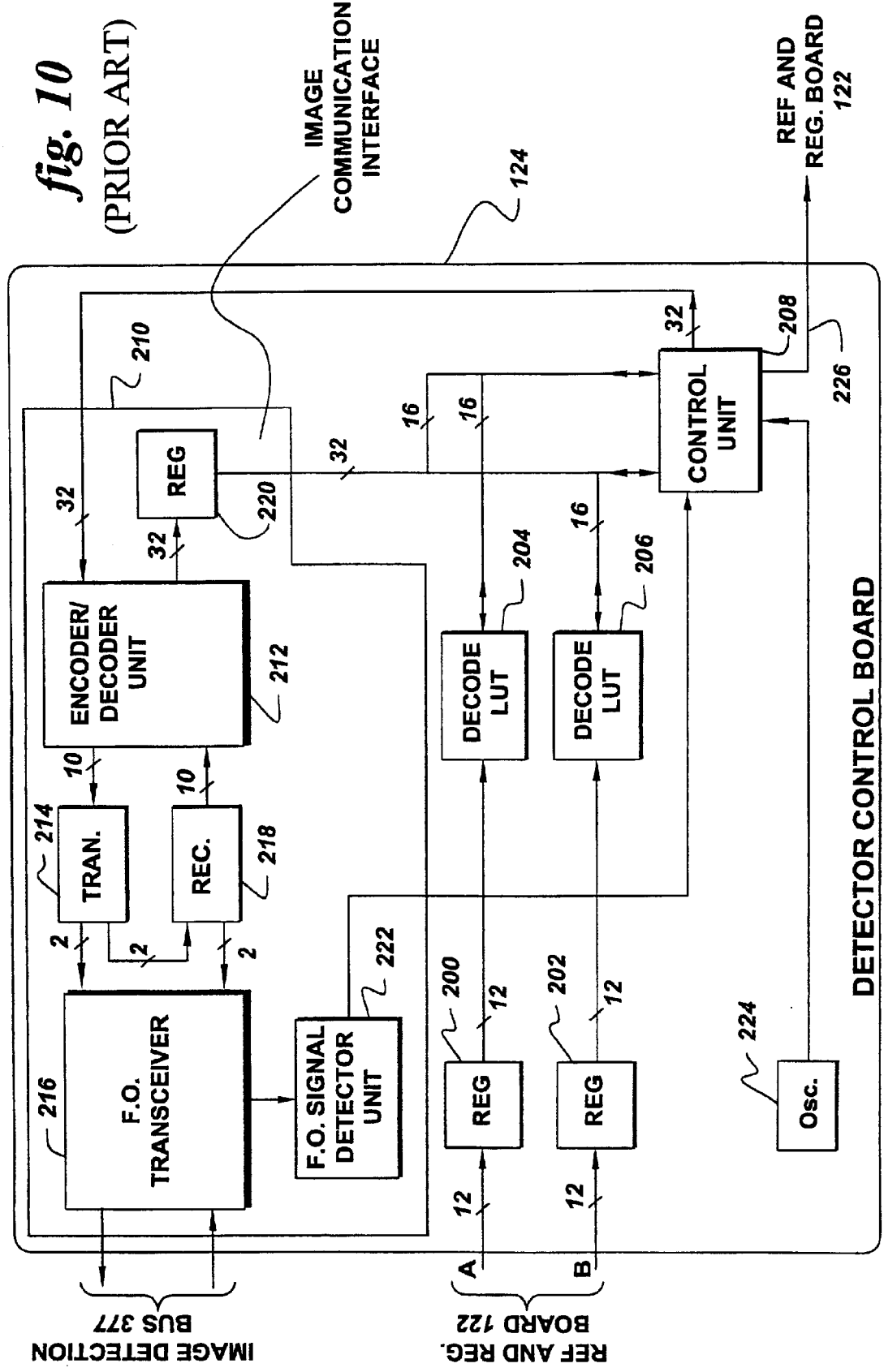
FIG. 10 (PRIOR ART) is a block diagram of a detector control board.

FIG. 10 (PRIOR ART) is a block diagram of detector control board 124. In general, detector control board 124 receives twelve bit binary encoded data "A," corresponding to the output 188 from first column multi-chip modules 178. Detector control board 124 also receives twelve bit binary encoded data "B," corresponding to the output from second column multi-chip modules 180. Each of binary encoded inputs A and B are respectively received by registers 200 and 202. The outputs from registers 200 and 202 are then respectively transferred to decode look up tables ("LUTs") 204 and 206. Decode LUTs 204 and 206 are random access memories that perform a conversion from twelve bit binary quadratically encoded data into 16 bit binary linearly encoded data.

Operation of detector control board 124 is controlled by control unit 208. Control unit 208 is formed as a field programmable gate array ("FPGA"). Control unit 208 receives 16 bit pixel data from decode LUT 204 and 16 bit pixel data from decode LUT 206, then combines the pixel data into a 32 bit word. The 32 bit word is then output to image communication interface 210. According to an embodiment of the invention, image communication interface 210 is a fiber optic interface. Each 32 bit word is a combination of two 16 bit pixels, which were output separately from detector control board 124. The two pixels included in each 32 bit word may be side by side, as in a mammography single digital x-ray panel 224 (set forth in detail below and in reference to FIG. 13 (PRIOR ART)) or may be received from two separate panels, such as output from first panel portion 184 and second panel portion 186 of cardiac/surgical digital x-ray panel 182. Radiography digital x-ray panel 228, set forth below and in reference to FIG. 11 (PRIOR ART), also includes two panel portions 230 and 232, and therefore follows the pixel format of cardiac/surgical digital x-ray panel 182. Split panel detector systems, corresponding to cardiac/surgical digital x-ray panel 182 and radiography digital x-ray panel 228, utilize data "reordering" before display on a conventional computer monitor. Data reordering is set forth in more detail below with regard to detector framing node 304.

Image communication interface 210 clocks 32 bit words received from control unit 208 into encoder/decoder unit 212. Encoder/decoder unit 212 converts each received 32 bit word into four ten bit words, each having error correction. The ten bit words are in turn received by transmitter 214. Transmitter 214 converts the received ten bit words into serial data having two bits, namely a clock bit and a signal bit. Transmitter 214 outputs the two bit data to fiber optic transceiver 216 for conversion into a fiber optic signal. The fiber optic signal is then transmitted on image detection bus 377 to a detector framing node, set forth in detail below. According to an embodiment of the present invention, image detection bus 377 is an optical fiber data link. Likewise, fiber optic transceiver 216 receives fiber optic signals from the image detection bus 377 and converts the received optical signals into a two bit data signal for reception by receiver 218. Receiver 218, in turn, converts the received two bit data, including a clock and a data signal, into ten bit words having error correction. The ten bit words are then received by encoder/decoder unit 212 for conversion into 32 bit words, which are stored in register 220 before transmission to control unit 208. An output from fiber optic transceiver 216 is also received by fiber optic signal detection unit 222 to maintain timing and protocol in cooperation with control unit 208. Control unit 208 is clocked by oscillator 224. Control unit 224 provides a control signal to reference and regulator board 122 by way of control line 226. Control unit 208 is a FPGA, Flex 10k50 manufactured by Altec, Inc. of San Jose, Calif.

Figure 11:
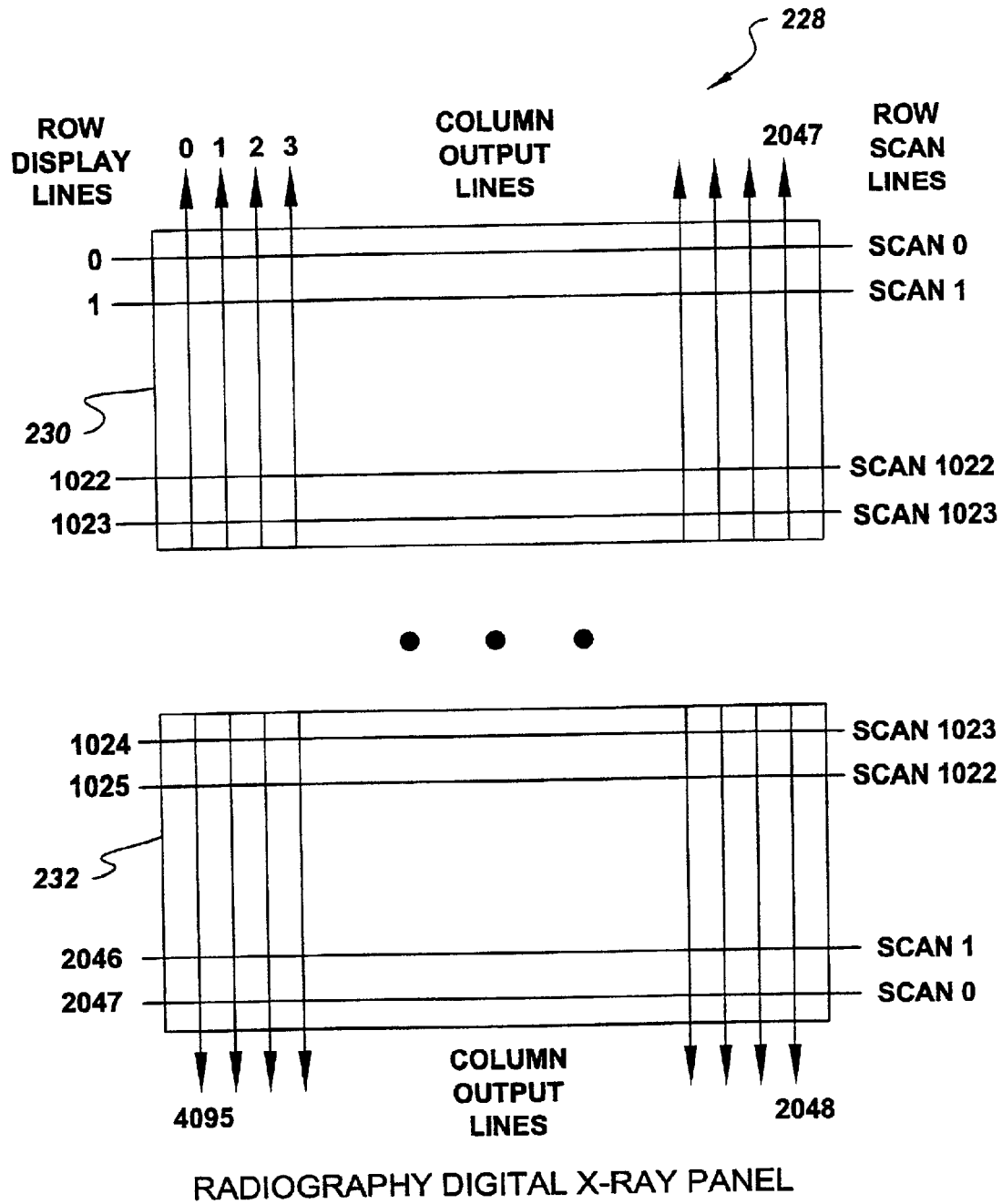
FIG. 11 (PRIOR ART) is a schematic diagram of a split panel radiography digital x-ray panel.

FIG. 11 (PRIOR ART) schematically represents a split panel detector, such as split panel 170, as radiography digital x-ray panel 228. Radiography digital x-ray panel 228 is formed from first panel portion 230 and second panel portion 232. Radiography digital x-ray panel 228 is 41×41 cm and has a total of 2048 columns×2048 rows at 200 μm pitch. The illustrated embodiment of flat panel detector 116 has twice as many row multi-chip modules 176 and twice as many column multi-chip modules 180 as the embodiment of FIG. 7. As each scan line is sequentially triggered, all column output lines 0 through 2047 simultaneously release pixel information from first panel portion 230, while column output lines 2048 through 4095 simultaneously release pixel information from second panel portion 232. Radiography digital x-ray panel 228 occupies approximately four times the surface area of cardiac/surgical digital x-ray panel 182. Radiography digital x-ray panel 228 is used for applications requiring a large surface area, such as a chest x-ray, while cardiac/surgical digital x-ray panel 182 finds application in procedures requiring a smaller surface area, such as cardiac fluoroscopy during surgical procedures.

Figure 12:
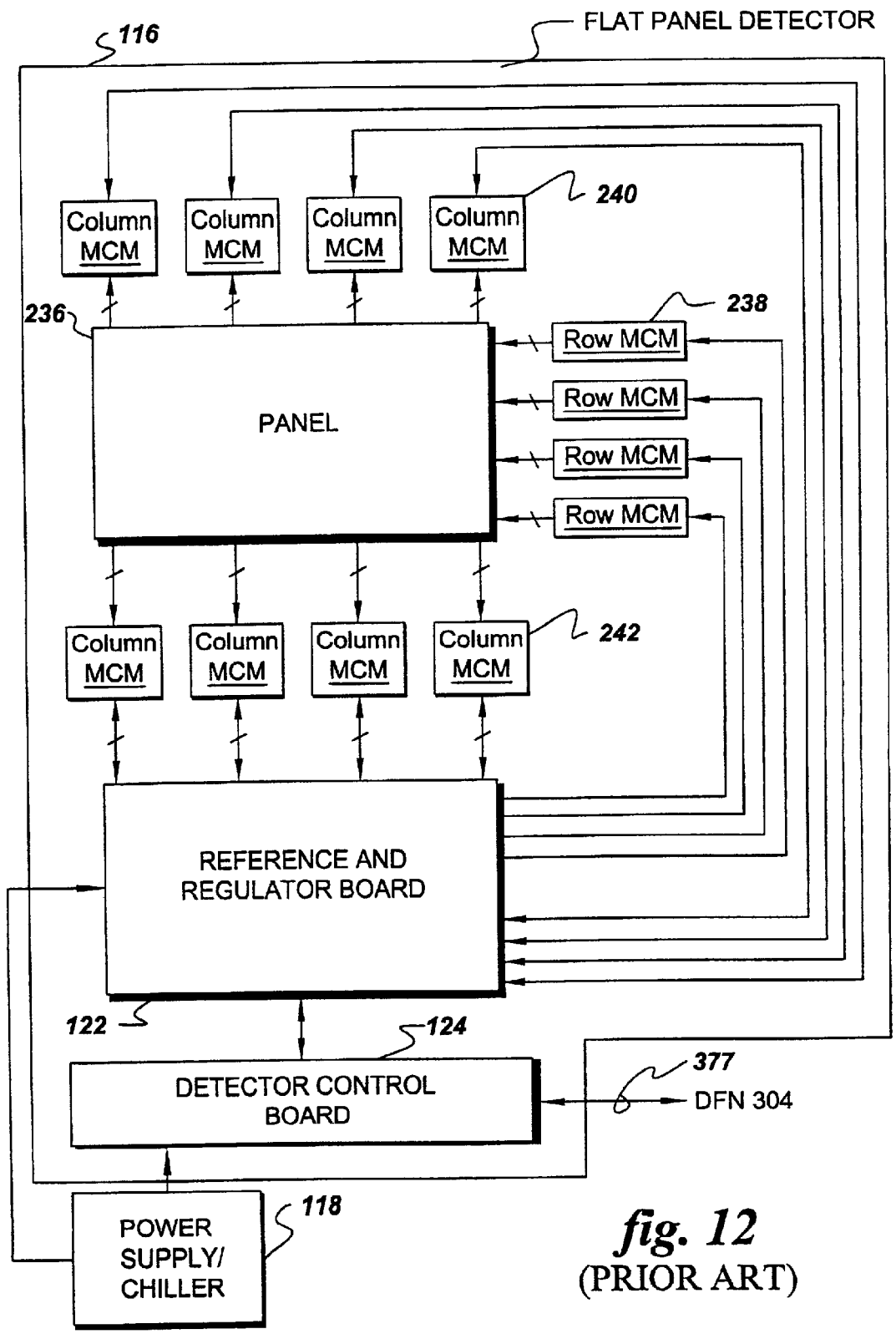
FIG. 12 (PRIOR ART) is a block diagram of electrical connection in an amorphous silicon single panel detector system.

FIG. 12 (PRIOR ART) is a block diagram of electrical connections in flat panel detector 116 according to another embodiment of the present invention. Flat panel detector 116 includes single panel 236, which is triggered by row multi-chip modules 238. Single panel 236 is read out by way of column multi-chip modules 240 and 242. Column multi-chip modules 240 and 242 are placed at opposite ends of single panel 236 such that even numbered columns are read out by column multi-chip modules 240 and odd numbered columns are read out by column multi-chip modules 224. Alternate read out of columns from opposite sides of single panel 236 enhances column density by allowing extra physical space for connection of single panel 236 to connecting hardware.

Figure 13:
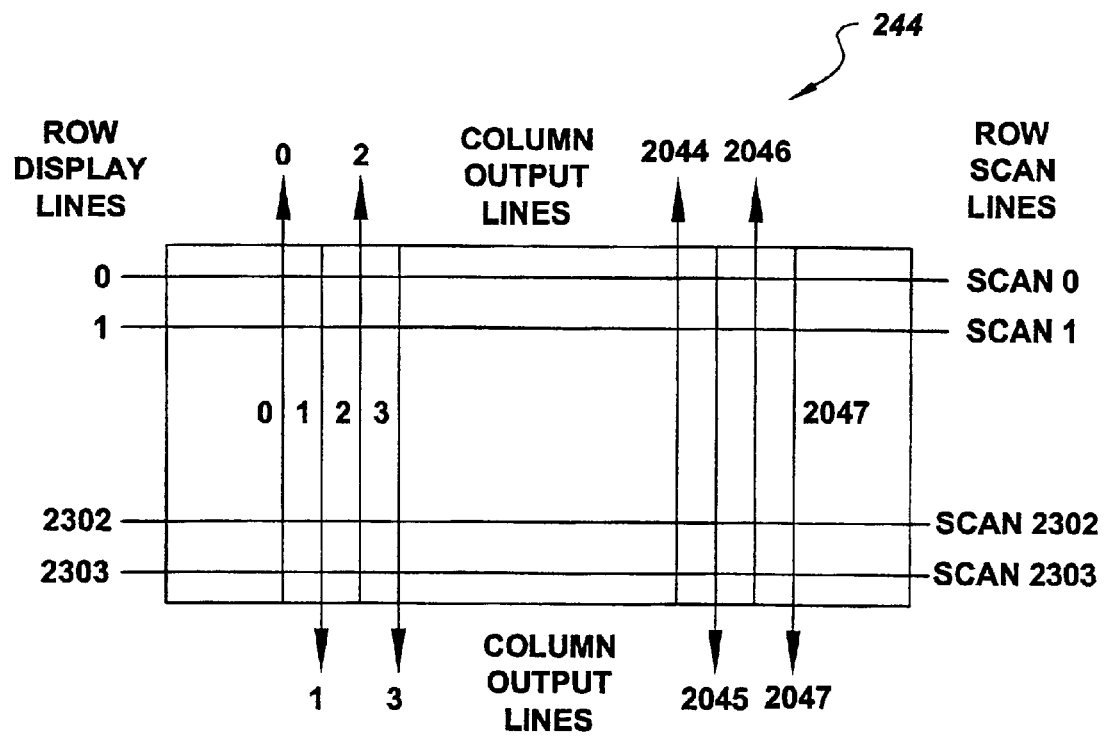
FIG. 13 (PRIOR ART) is a schematic diagram of a single panel mammography digital x-ray panel.

FIG. 13 (PRIOR ART) schematically represents an embodiment of a single panel detector, such as single panel 236, as a mammography digital x-ray panel 244. Mammography digital x-ray panel 244 is 19×23, cm having 1920 columns×2304 rows at 100 μm pitch. Mammography digital x-ray panel 244 has a total of 2048 columns. However, 1920 of the available 2048 columns are actual used. The remaining 128 columns are spaced throughout the columns in digital x-ray panel 244 to facilitate repair. Column output lines are alternately output from alternate sides of mammography digital x-ray panel 244. This configuration allows ease in manufacture and simplifies assembly of connecting hardware to the mammography digital x-ray panel 244.

The 128 repair lines included in mammography digital x-ray panel 244 are used to repair open column address lines caused by manufacturing defects. The repair lines cross over both ends of the address lines and are separated by an insulating layer. A repair connection is facilitated by using a laser to weld an address line to a repair line through the insulating layer. In the case of row address lines, the row address lines are fully repaired using spare lines on flat panel detector 116, and therefore the readout system is does not account for the repair. In the case of column repairs, data from repair lines is output in a different sequence from flat panel detector 116 such that the data is sorted by way of post processing.

Figure 14:
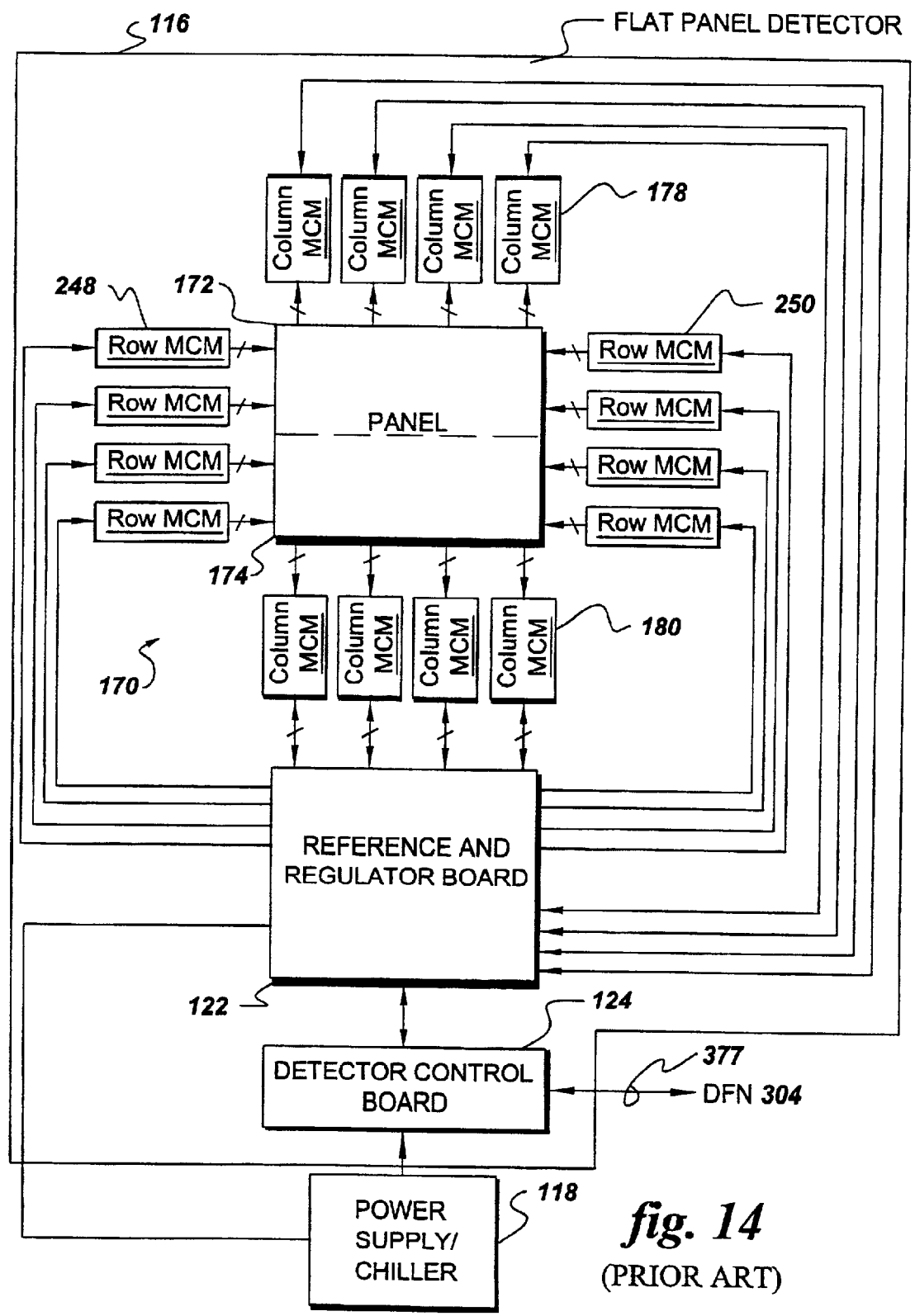
FIG. 14 (PRIOR ART) is a block diagram of electrode connections in a split panel detector system having redundant row multi-chip modules.

FIG. 14 (PRIOR ART) is a block view of electrode connections in flat panel detector 116 according to another embodiment of the present invention. Flat panel detector 116 includes two sets of row multi-chip modules, namely first row multi-chip modules 248 and second row multi-chip modules 250. Unlike first and second column multi-chip modules 178 and 180, first and second row multi-chip modules 248 and 250 provide redundant connections across panel rows. Accordingly, if first or second panel portions 172 or 174 develop a defect, each row is optionally triggered from alternate sides thereof, such that data integrity of the row is preserved.

Each embodiment of flat panel detector 116 set forth above may be formed with redundant row multi-chip modules 250 to preserve data integrity in case of defects in panel formation.

Figure 15:
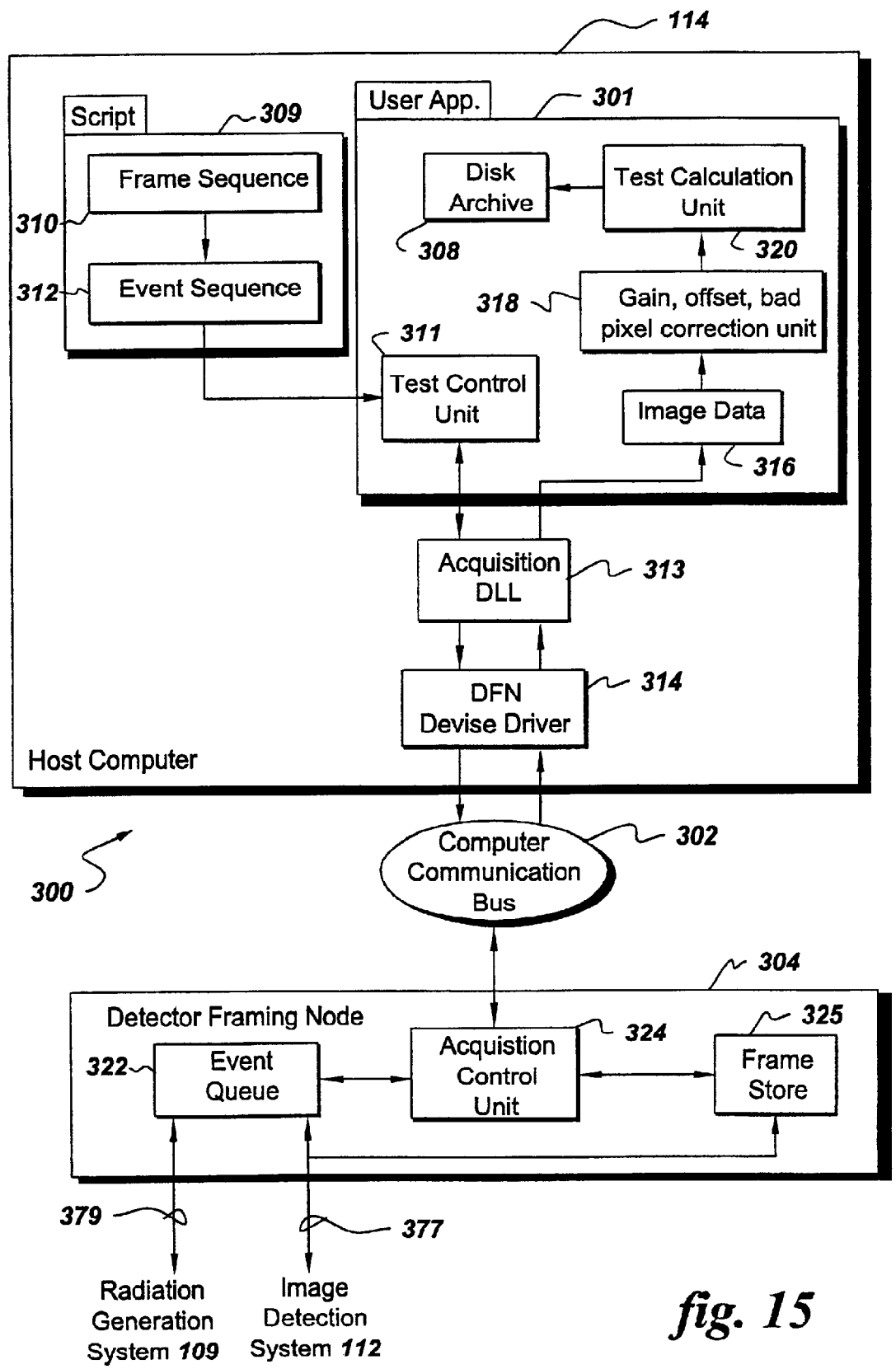
FIG. 15 is a block diagram of control and data flow in an imaging system.

FIG. 15 is a block diagram of real time radioscopic imaging system 300. System 300 is used in a variety of different medical applications and is also used in engineering, manufacturing, device test and repair. System 300 supports a plurality of different detector panels and particularly supports three different families of detector panel designs, namely for cardiac/surgical, radiography, and mammography applications. System 300 includes host computer 114 running user application 301 from script 309. The user application 301 communication with detector framing node 304 by way of acquisition DLL 313 and DFN device driver 314.

System 300 replaces a prior Image Detection Controller subsystem ("IDC"), which was based upon a TMS320-C80 processor and PC using real time operating system, VXWORKS®. System 300 achieves 30 frames/sec acquisition and processing of 1024×1024 pixel images for fluoroscopy. Image detection bus 377 provides a 1.25 Gbit/sec fiber optic communication link between host computer 114 and detector control board 124. Image detection bus 377 particularly communicates between detector control board 124 of image detection system 112 and detector framing node ("DFN") 304, which is embodied as a peripheral component interconnect ("PCI") card suitable for connection to computer communication bus 302. According to an embodiment of the present invention, computer communication bus 302 is a PCI bus, and more particularly, a PCI bus operating at 33 MHz. According to another embodiment of the present invention, computer communication bus 302 is a PCI bus operating at 66 MHz. Detector control board 124 itself is embodied in a prior Apollo Common Detector Control Printed Wiring Assembly ("PWA"), manufactured by General Electric Medical Systems of Milwaukee, Wis. The Apollo Common Detector Control PWA is used in a variety of applications including full field digital mammography ("FFDM"). Use of detector framing node 304 facilitates use of non-real time host computer 114 for image processing after image acquisition.

System 300 provides acquisition and control based on a commercial single or multiple processor PC hardware, such as the PENTIUM® class processors manufactured by Intel, Inc., of Santa Clara, Calif. System 300 is a single data acquisition and control system for present and anticipated x-ray modalities, and supports application of the system to both engineering and manufacturing. A flexible architecture is provided to address needs of improved or future technology.

System 300 supports single and multiple frame acquisition of images with frame to frame control of supported detector parameters. A number of rows and a number of columns in an acquired image are supported as input parameters, while providing control of data acquisition timing from an external frame trigger. System 300 acquires and views gain and offset corrected images at 30 frames/sec for a 1024×1024 array or 7.5 frames/sec for a 2048×2048 image. System 300 supports a non-real time operating system to test system functionality. According to an operative embodiment, the non-real time operating system is WINDOWS NT 4.0® supporting C++ language based applications. Modular software is structured to support a combination of applications and more direct hardware access for advanced users and programmers. User-coded test applications and generalized data acquisition routines are provided in separate modules.

System 300 provides archive capability for both raw, and gain and offset corrected data for single and multiple frames, including regions of single and multiple frames. A high resolution display of single and multiple frames and for regions of single and multiple frames is supported for both freshly acquired and archived data. Control of radiation generation system 109 or a grid controlled x-ray tube is supported through a real time bus interface. Real time triggering of the x-ray generator with 2 μsec timing resolution is supported along with programmable time delays of up to 16 seconds.

System 300 is a real time image data acquisition system in which the image data is acquired at a predetermined frame rate and the number of image frames to be acquired is determined at the time of acquisition. Before acquisition, the event compiler 408 sets up the frame rate by setting a time for executing a repetitive trigger over the real time bus 379. Likewise, the event compiler 408 sets up image acquisition by delaying the image request command to the image detection system 112 from the repetitive trigger. There is an integration period before scanning of the flat panel detector 116 is allowed to account for delays in the phosphor and collection of electron-hole pairs in the photodiode array. For real time data acquisition, there is minimal buffering during transfer of the image data from the image detection system 112 to the detector framing node 304, such that the image detection system 112 and the detector framing node 304 operate in synchronism.

According to an embodiment of the present invention, system 300 is configured as follows:

| | |
|---|---|
| Computer: | Single/multiple PENTIUM ® class with PCI back-plane |
| Operating System: | WINDOWS NT 4.0 ® |
| Panel Designs: Apollo20: | 1024 × 1024 - Data Reordered |
| | Apollo40: 2048 × 2048 - Data Reordered |
| | Mammo3: 2304 × 2048 - Bad column corrected |
| | Smaller regions of interest |
| Acquisition Modes: | Radiographic (isolated frames) |
| | Real Time (30 frames/sec for 1024 × 1024 image) |
| | Cine Loop (30 frames/sec for 1024 × 1024 image) Hardware debug |
| Image processing: | Offset, Gain, Bad pixel, Mammography bad column |
| Display Req.: | 8 bit gray scale including gamma correction |
| | Real time window and level |
| | Xia type display applications including zoom and pan |
| X-ray support: | Simple 8 bit parallel real time bus |
| Archive support: | Hard drive and writable CD ROM drive |

System 300 provides an improvement over the above prior IDC test system. Real time parameters, which were previously addressed in prior art VXWORKS® operating system ("OS"), are now captured in detector framing node 304 operatively embodied as a single PCI card. Detector framing node ("DFN") 304 contains fiber channel communication circuitry, a buffer memory, a PCI communications controller, a real time bus to control the x-ray generator and a set of firmware programmable FPGAs for control of all circuits on DFN 304. An external PCI memory card is used in conjunction with DFN 304 to expand computer memory and provide storage for raw pixel x-ray image data. Operation of data acquisition and subsequent data processing is through user written applications. A library of functions access hardware functionality and facilitate disparate needs of users in engineering, device repair and manufacturing areas.

FIG. 15 particularly illustrates operation of system 300 according to an embodiment of the present invention. An exact sequence of image frames and associated acquisition parameters is needed in advance for a particular image acquisition. Accordingly, one can specify, for each frame, the readout delay relative to x-ray pulse, the detector parameters, etc. A description of such attributes is captured in a frame sequence 310 of script 309. Program applications configure the data acquisition system through the frame sequence structure and then trigger the system to initiate acquisition of the frames. The frame sequence 310 will vary depending on the type of experiment being performed for each test. At a hardware level, the acquisition itself responds to a sequence of instructions from host computer 114. According to an embodiment of the present invention, the instructions are event instructions, known collectively as an event sequence 312. Each event instruction is executed at well-timed intervals. Event instructions trigger events that control external devices, such as through commands communicated over bus interfaces. For example, event instructions include 32 bit control words that are sent over image detection bus 377 to image detection system 112, and x-ray pulse trigger commands sent over real-time bus 379 to radiation generation system 109. Based on frame sequence 310, a complete list of such event instructions to be performed is constructed. The event sequence 312 need not be constructed in real-time and is therefore easily executed on host computer 114 running a non-real time operating system to support an event compiler. Once the event sequence 312 is known, the details are transmitted to DFN 304 for execution in real-time.

FIG. 15 is a block diagram showing the flow of control information and data through system 300 during image acquisition. As illustrated, frame sequence 310 is created by way of script 309. Frame sequence 310 is then translated into event sequence 312 using a compiler, which knows the details of the target control hardware. Event sequence 312 is received by test control unit 311, then sent to DFN device driver 314, over computer communication bus 302, and finally to detector framing node 304. The event sequence 312 is then stored in preparation for execution. Event sequence 312 is initiated by sending a Begin Sequence command over computer communication bus 302. The extent of real-time control allotted to host computer 114 is confined to a determination of when event sequence 312 will begin. Subsequently, host computer 114 is completely removed from image acquisition.

Once event sequence 312 is complete, host computer 114 retrieves the acquired data in addition to various diagnostics and responses, which were recorded during execution of the event sequence. Therefore, host computer 114 is involved in pre- and post processing roles, and is therefore entirely removed from real-time operation.

As illustrated, detector framing node 304 communicates commands and responses with computer communication bus 302 by way of acquisition control unit 324. Event sequence 312 is communicated to event queue 322 by way of acquisition control unit 324. Event instructions are then transmitted to radiation generation system 109 from event queue 322. During application of the radiation, event instructions are transmitted to event queue 322 from image detection system 112. Radioscopic image data is also received by frame store 325 from image detection system 112, then transmitted to acquisition control unit 324 for transmission to host computer 114. In host computer 114, image data 316 is transferred through DFN device driver 314 and acquisition dynamic link library ("acquisition DLL") 313 before being subject to gain, offset, and bad pixel correction by gain, offset, and bad pixel correction unit 318. After completion of the correction, the image data is interfaced with test calculation unit 320 before being sent to disk archive 308.

Figure 16:
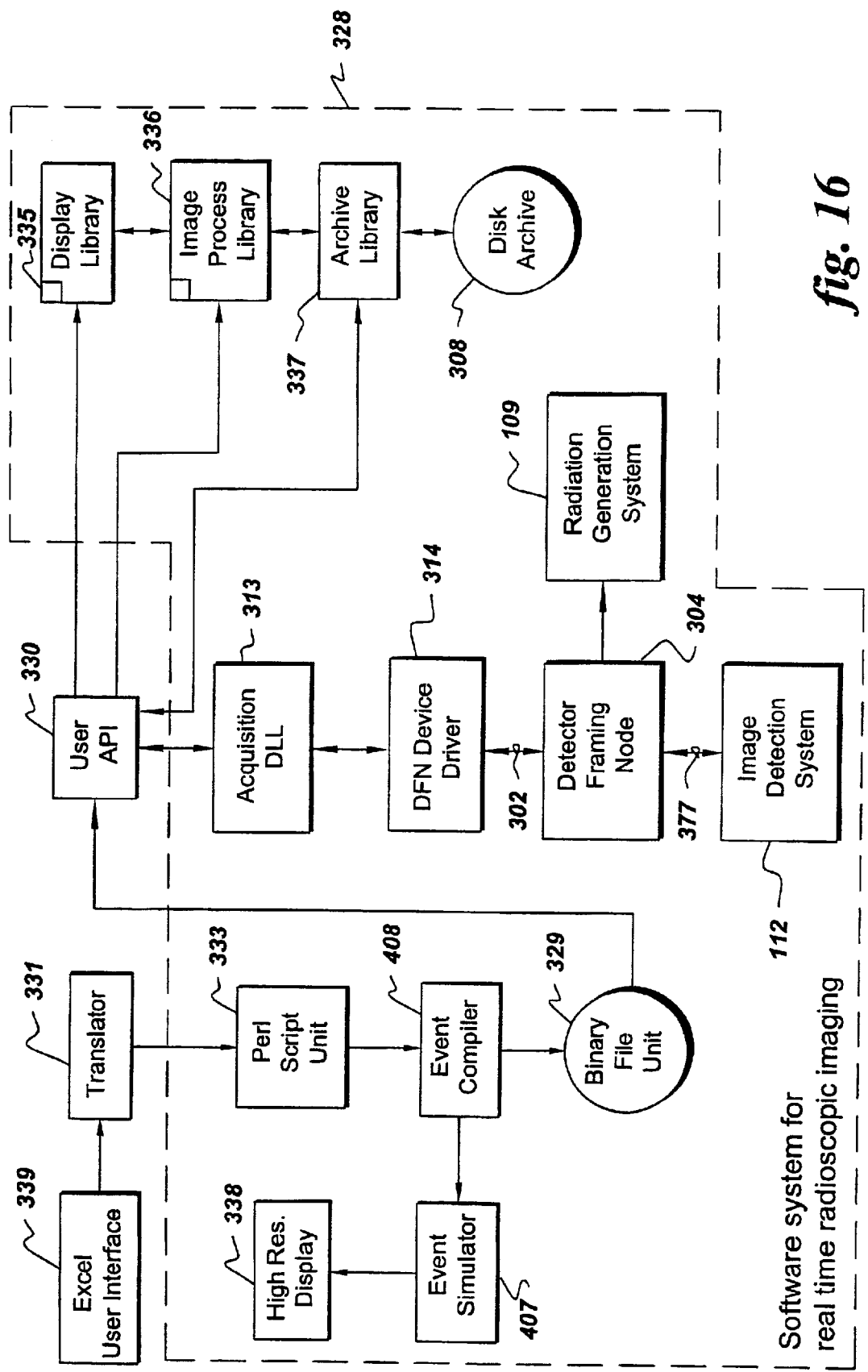
FIG. 16 is a block diagram of a software system for real time radioscopic imaging.

FIG. 16 is a block diagram of a software system 328 for real time radioscopic imaging. User application interface ("API") 330 is software, which runs on host computer 114 and links acquisition hardware to user application 301. Acquisition DLL 313 is software communicating with elements within software system 328. Acquisition DLL 313 communicates bi-directionally with user API 330 and DFN device driver 314. As illustrated, DFN device driver 314 communicates bi-directionally with detector framing node 304, which in turn communicates with radiation generation system 109 and image detection system 112. User API 330 also communicates with display library 335, image process library 336 and archive library 337.

For communication with software system 328, instructions are prepared in excel user interface 339, and then translated by translator 331 before being received by Perl script unit 333. Event compiler 408 also outputs information to binary file unit 329. The output from binary file unit 329 is then loaded into EAB memory 474 on EP 374 under control of user API 330, Acquisition DLL 313, and DFN device driver 314. The binary file contains information to control event sequence 312. Event sequence 312 can be debugged on the high resolution display 338 be creating the timing information in the event simulator 407.

Figure 17:
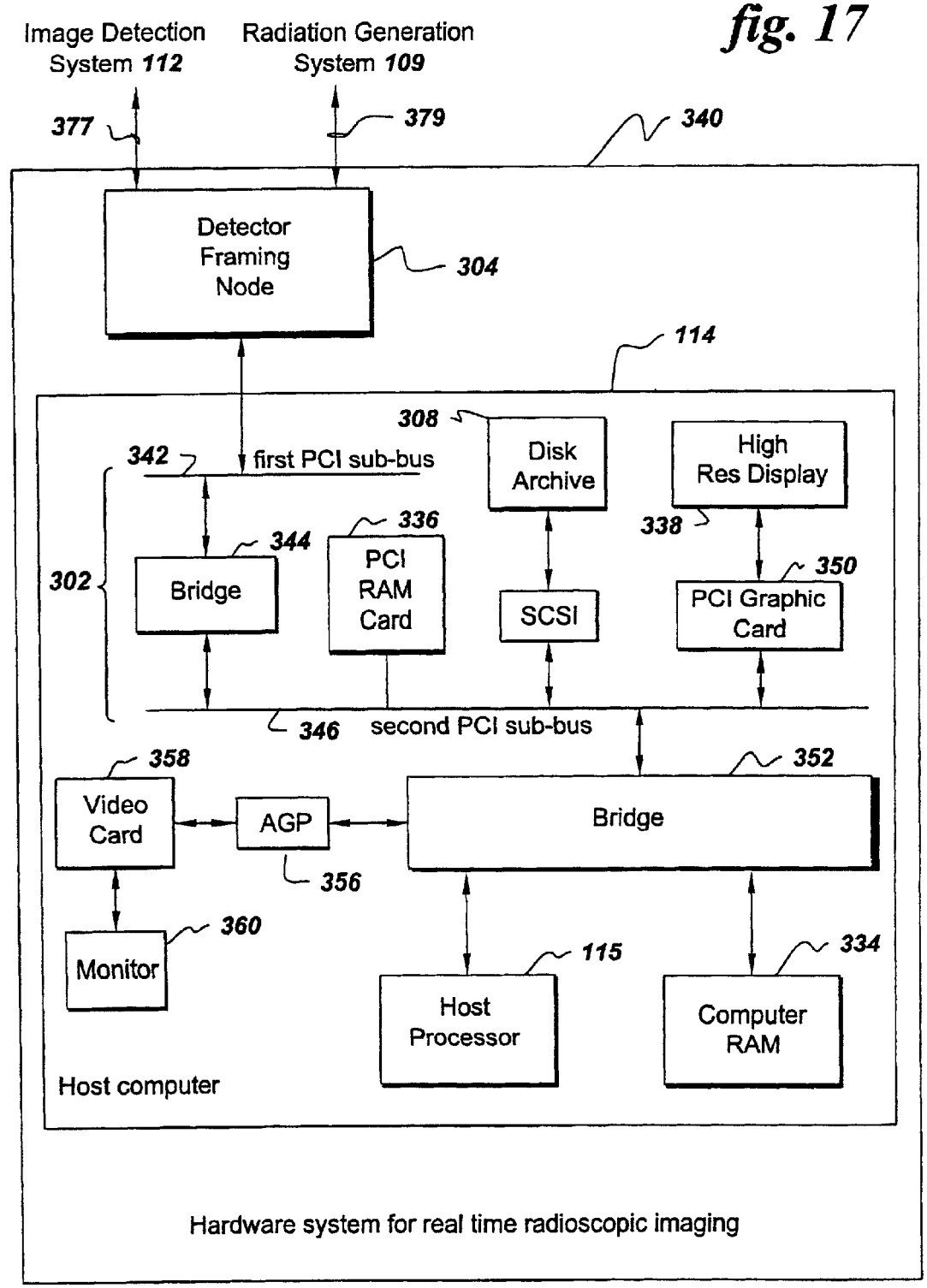
FIG. 17 is a block diagram of a hardware system for real time radioscopic imaging.

FIG. 17 is a block diagram of a hardware system 340 for real time radioscopic imaging. Hardware system 340 includes data acquisition and control hardware. Hardware system 340 is also a block diagram of tester hardware. Except for detector framing node 304, remaining hardware components are commercial off-the-shelf ("COTS"). Host computer 114 is controlled by host processor 115. According to another embodiment of the present invention, host processor 115 is formed as a pair of processors operating together. According to yet another embodiment of the present invention, host processor 115 is formed as a plurality of interconnected processors. Host memory 117 is formed by computer RAM 334 and PCI RAM card 336 set forth in greater detail below. Hardware system 340 receives data of 1024×1024 images (2 MByte) at 30 frames/sec, which corresponds to a data transfer rate of 60 MBytes/sec. Computer communication bus 302 has a transfer rate of 132 MByte/sec. Because of arbitration of first PCI sub bus 342, the transfer rate across computer communication bus 302 is less than 132 MByte/sec.

Hardware system 340 includes DFN 304, which is connected to computer communication bus 302. Computer communication bus 302 is comprised of first PCI sub bus 342 and second PCI sub bus 346, connected by bridge 344. Second PCI sub bus 346 interconnects with disk archive 308 by way of small computer systems interface ("SCSI") 348. Second PCI sub bus 346 also connects to high resolution display 338 by way of PCI graphics card 350. Second PCI sub bus 346 connects to host processor 115, accelerated graphics port ("AGP") 356 and computer RAM 334 by way of bridge 352. AGP 356 is a high speed graphics port for connection of monitor 119 by way of video card 358.

In a real time mode, PCI 302 bus arbitration will slow the data transfer rates on first PCI sub bus 342 and second PCI sub bus 346 such that the continuous display rate of 30 frames/sec will likely be determined by arbitration conflicts. In hardware debug mode, a test of DFN hardware is started from host processor 115 by sending a Command to DFN 304. The results of this test (i.e. bad, good) are returned to host computer 114. This hardware debug mode is used to run the Built-in-self test ("BIST") described later in the specification. In real time mode, data is sent directly from a buffer memory on the DFN 304 to computer RAM 334 and displayed almost simultaneously.

Figure 18:
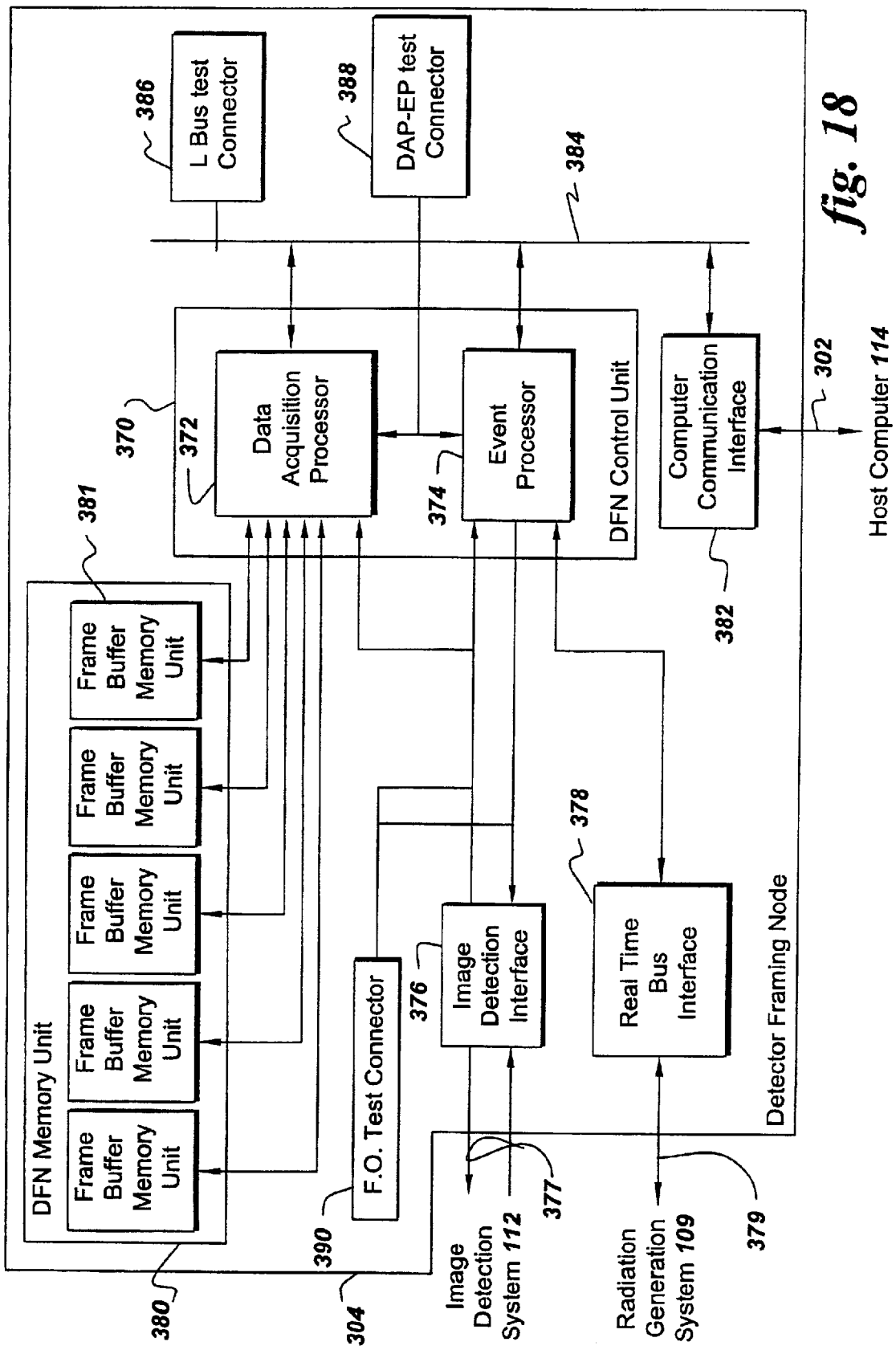
FIG. 18 is a block diagram of a detector framing node.

FIG. 18 is a block diagram of detector framing node 304. Image detection interface 376 communicates with detector control board 124 (described above with reference to FIG. 10 (PRIOR ART)) to receive image data therefrom. According to an embodiment of the present invention, image detection interface 376 is a fiber optic interface. DFN memory unit 380 includes a total of ten 8 Megabit SRAMs. DFN memory unit 380 includes five frame buffer memory units 381, with each frame buffer memory unit 381 comprising two 8 Megabit SRAMs. When one frame buffer memory unit 381 becomes full the data is read out of that unit to computer communication bus 302 and data is then written to another frame buffer memory unit 381. A large image, such as 2048×2048, is read directly into DFN memory unit 380 with data reordering occurring during a data write under control of data acquisition processor ("DAP") 372. DAP 372 and event processor ("EP") 374 are FPGAs, which are used to control real-time bus interface 378. Real time bus interface 378 is connected to real time bus 379. EP 374 also controls read and write of data with respect to image detection bus 377 by way of image detection interface 376. Computer communication interface 382 is embodied as a PCI interface in the form of an application specific integrated circuit ("ASIC") to control bus communications between local bus 384 and computer communication bus 302. As illustrated, fiber optic test connector 390 interfaces with the bus connecting image detection interface 376 and DFN control unit 370.

Imaging system 100 provides support for several different users, including support for different x-ray image panel designs and applications. Accordingly, flexible testing is provided to support different image acquisition modes. The acquisition modes used by imaging system 100 are described in terms of the target applications and users. For example, support for, at least, four specific modes is presented: Hardware Debug, Panel Setup, Single Frame, and Real Time. However, modal capability of imaging system 100 is more generically specified in terms of data management and bandwidth considerations.

FIG. 19 is a table illustrating estimated processing capability for a 1024×1024 cardiac/surgical digital x-ray image. The various modes of operation are shown with a preliminary estimate of performance. Two cases of interest are distinguished. One is a real time case, where the bandwidth of the hardware acquires, corrects and displays a single pipe-lined sequence within an intended frame rate. In a second case, called Post Process, bandwidth of the hardware is insufficient given the complexity of the algorithm and/or the panel size. As a result, the data is acquired and stored in real time, processed during a delay period, and finally displayed at an intended frame rate.

As illustrated in FIG. 19, "gbr" refers to the three particularly supported correction algorithms, namely corresponding to cardiac/surgical digital x-ray, radiography digital x-ray, and mammography digital x-ray, other than offset correction. These are: gain correction (g), bad-pixel correction (b), and repair line correction (r).

FIG. 20 is a table illustrating available frame storage for 400 MByte of either PC RAM memory or memory on a separate PCI memory card. Test modes include a hardware test mode to access status and functional information of PCI hardware cards and external devices connected through DFN 304. This includes tests of the DFN 304 card itself, an external PCI memory card, image detection bus 377, detector control board 124, and real time bus 379 (for communications with radiation generation system 109).

Panel setup mode is used at the beginning of panel test, during panel alignment, where near real time visualization is valuable to ensure proper flex contacts to image detection system 112. Here, data acquisition occurs with reordering in DFN 304 as a single processing operation. There is direct transfer of the data to computer RAM 334, bypassing PCI RAM card 336. In other applications data is passed to PCI RAM card 336 or another commercially available image processing card rather than computer RAM 334. Once the data is in the PCI RAM card 336, the data is accessible by host processor 115 at a later time for processing. In the case of a commercially available image processing card, the data is further processed in that card before delivery to host processor 115 via computer communication bus 302. As a result, data is displayed at 30 frames/sec for a 1024×1024 image, or 7.5 frames/sec for a 2048×2048 image. There is a one or two frame delay between acquisition and display of the image. For those applications where the data is transferred directly to host computer 114, the available computer RAM 334 limits the number of frames stored.

A single frame mode provides a typical application including mammography digital x-ray and radiography digital x-ray testers where a relatively small number of frames are acquired. One or more frames are captured and reordered in DFN memory block 380 on the DFN 304, transferred to computer RAM 334, and processed in host processor 115 to correct gain, offset, bad columns, channels of ARCs 196 and bad pixels. Corrections to channels of ARCs 196 include gain and offset correction to correct ARC gain, which varies from channel to channel. After correction, the frames are displayed on high resolution display 338. The delay between the completion of data acquisition and display is expected to be less than 0.25 sec for a single 2048×2048 image. After acquisition, the small number of frames would still be in computer RAM 334 and would be available to the application after display.

An embodiment of a real time mode is a cardiac/surgical digital x-ray tester or a radiography digital x-ray tester having a real time display, such that data is acquired, reordered, processed and displayed sequentially. The delay between data acquisition and display is on the order of 0.03–0.06 secs for a 1024×1024 image. A 1024×1024 image is supported at 30 frames/sec. In this mode every nth frame is stored and displayed, where n=1 to 10, while having an ability to store the last 60 frames of 1024×1024 data under operator control.

Figure 21:
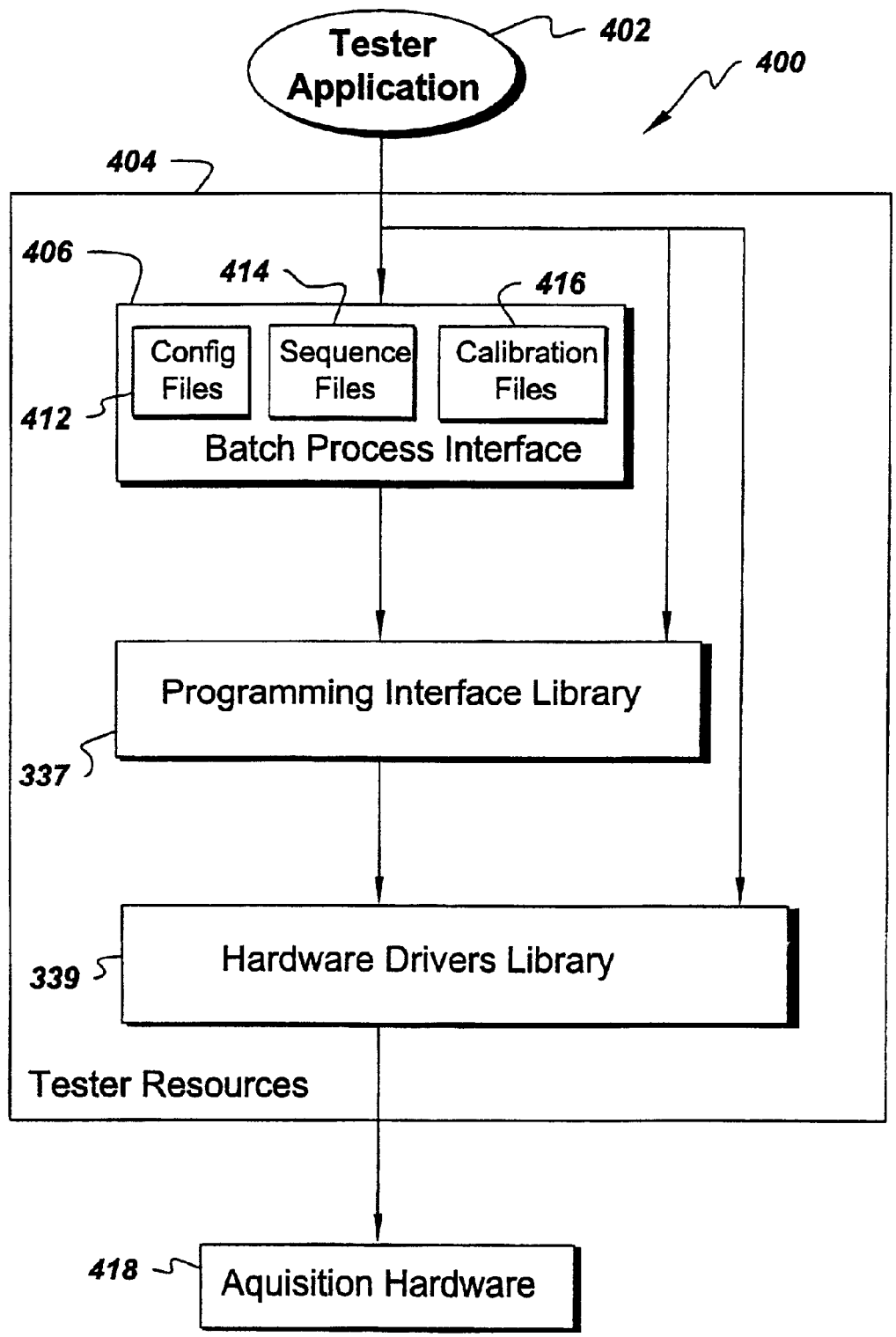
FIG. 21 is a schematic illustration of a software tester interface executing a data acquisition and control software tester interface operation.

FIG. 21 is a schematic illustration of software tester interface 400 executing a data acquisition and control software tester interface operation. Software tester interface 400 includes a tester application 402 to access acquisition hardware 418 through tester resources 404. Tester resources 404 include a batch process interface 406, a programming interface library 337 and a hardware drivers library 339. Batch process interface 406 includes configuration files 412, sequence files 414, and calibration files 416. The software tester interface 400 is a direct interface to the hardware drivers library 339 and programming interface library 337, which provides a convenient set of high level C-calls for sequence acquisition. The hardware driver library 339 is also a software library and contains an event compiler, which provides the translation of a user-defined frame sequence to detailed event instructions on detector framing node 304 to handle real time events.

Programming interface library 337 is a programming interface to assist the writing of a tester application with respect to image acquisition. The programming interface has a well defined subset of functionality whereas the hardware interface accesses the full functionality of the tester. The programming interface library 337 contains high level functions, which interface between the hardware drivers and the user application, i.e. tester application 402. This layer contains functions to poll the hardware devices and report back status information. This layer also enables the user to configure the acquisition hardware in a particular acquisition mode and to initiate the acquisition sequence.

The details of the image acquisition are specified by a structure defining the frame sequence. This structure is passed by a user program to an acquisition subroutine provided in the programming interface. The returned object is a pointer to a data and header, which is then available to the user program. Alternatively, the data is directly archived to disk. Convenient interfaces to various possible corrections and options for display are available at this level. Header translation from device specific to descriptive values occur in this layer.

Examples of library functions available for a user programs include:

1-Get hardware status

2-Configure acquisition system

3-Acquire and display data sequence (raw)

4-Acquire and display data sequence (corrected)

5-Store data sequence to disk

Batch process interface 406 is a subset of a programming interface from programming interface library 337, which provides a text based mechanism for image acquisition. Configuration files 412 and sequence files 414 are text files, which define all information to carry out acquisition of a sequence of frames. The separation of this information into two files ensures that there is no misunderstanding on which frame-to-frame parameter variation will be supported. In the simplest mode of operation, the user is authorized to alter these files in a common text editor and then initiate the acquisition with a command. The returned header will reflect the acquisition parameters as defined in the configuration and sequence files.

Information which is constant across a sequence is contained in configuration files 412. Examples include firmware revision numbers, serial numbers, panel type and process stage, tester location. In addition, the information contained in the configuration files 412 includes reordering, correction, archive, and display options. Calibration files 416 contain all information to correct data for gain, offset, bad pixel and channel gain of ARCs 196 on a pixel by pixel basis. In contrast, sequence files 414 contain the specific acquisition parameters of each frame in the sequence. These specific acquisition parameters include all the detector parameters and event timing.

Figure 22:
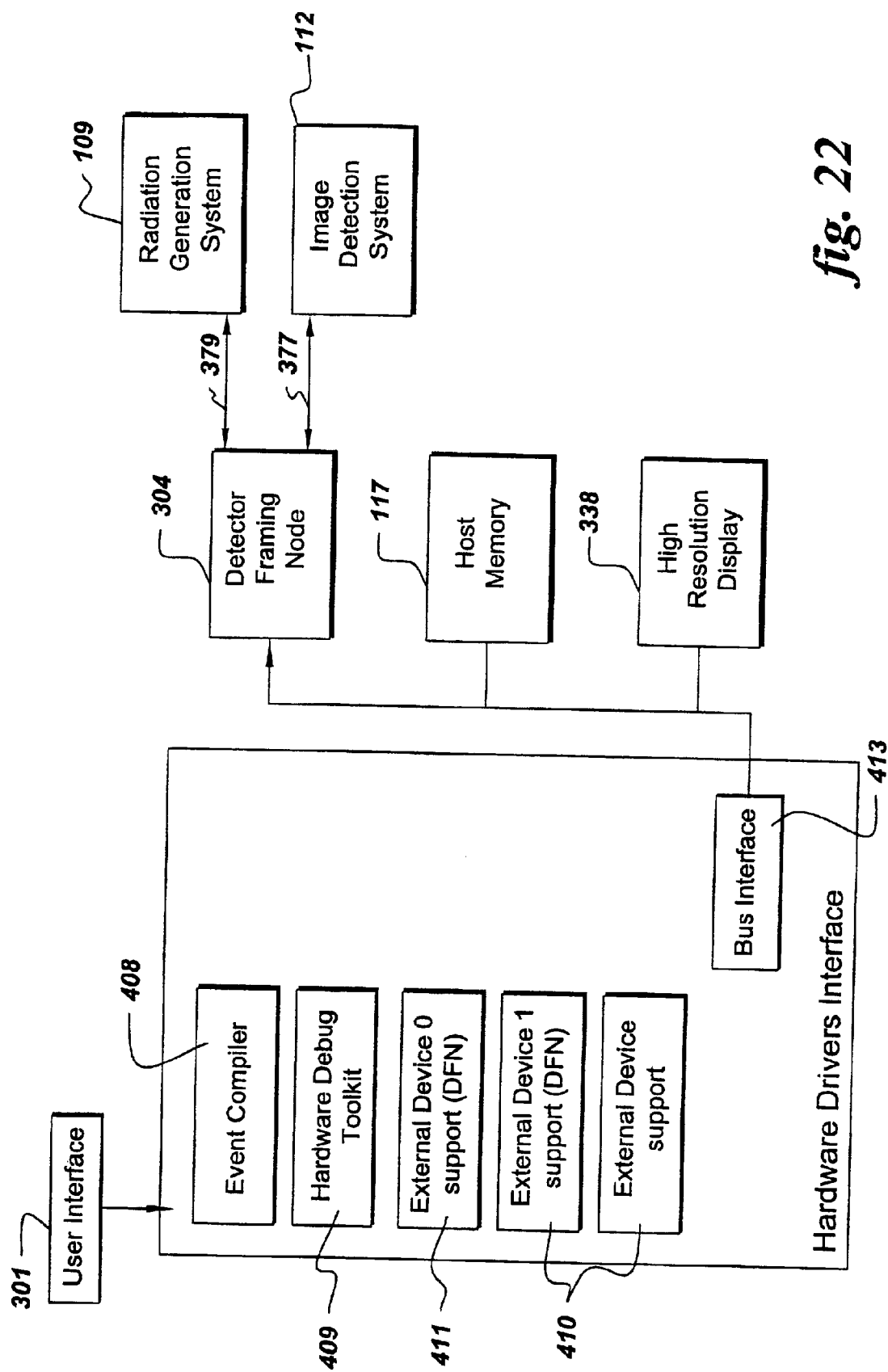
FIG. 22 is a block diagram of a hardware interface interacting with system components by way of a computer communication bus.

FIG. 22 is a block diagram of hardware drivers interface 410 interacting with system components by way of computer communication bus 302. Hardware drivers interface 410 includes commands as a main element in an event compiler 408, which translate a structure describing the frame sequence to a detailed set of event instructions, which are loaded into a queue on event processor 374 of detector framing node 304. Hardware drivers interface 410 includes event compiler 408, hardware debug toolkit 409, and a plurality of external device supports 411 for external devices. The external device supports support a plurality of external devices, such as detector framing node 304, high resolution display 338, etc. The hardware drivers interface 410 communicates with the external devices by way of bus interface Commands are available to send elemental messages to the external devices and pass back reply messages to the user application, e.g. detector messages and x-ray status messages. The development of the test system involves a set of software to debug and validate the individual pieces of hardware. This software is formalized and documented, and provided as part of the tester product as a tool kit to assist the support of the system by the user and maintenance personnel. Event compiler 408 is a software package that takes a frame sequence file and generates a set of control words to be loaded into DFN control unit 370 in DFN 304 to achieve the desired control functionality.

As illustrated in FIG. 17, hardware system 340 provides hardware and software with window level control for driving a commercial display driver card to view data acquisition results. The display displays both raw and processed archived images. The displayed data is 8 bits including gamma correction for display phosphor non-linearity. At a lowest magnification there is a one to one correlation between the display least significant bit ("LSB") and the least significant bit received from image detection system 112. A second monitor 368 is used to provide a user interface. Image display supports Xia functionality, such as pan, zoom and pixel amplitude display. Row and column numbers of a selected pixel are optionally displayed along with calculation of statistics for a region of interest.

Disk archive 308 is used for short term storage and is embodied as either a removable disc drive or writable 650 MByte CD ROM. Capability for archiving both raw and processed images along with a header of descriptive information is supported.

Host computer 114 includes network support and is configured with an 10/100 Mbit/sec Ethernet card and software for data transfers via the Ethernet. Other devices are supported, such as LEDs used in panel test or collimators. Such support includes an additional PCI card and driver in the C program to collect or send data to the additional PCI card.

An 8 bit real time parallel I/O bus 379 is used to control or receive control from radiation generation system 109. Timing is provided by DFN control unit 370. Delays between the x-ray generation and data acquisition on Detector Control Board 124 are provided under software control. Synchronization of data acquisition with x-ray generation is therefore provided. X-ray generator voltage and current may be set under software control as well as operations to turn the x-ray generation unit 102 on and off via the tester hardware and software. Pulsed control of x-ray generation unit 102 with a control grid is provided. Control of current and voltage from pulse to pulse is provided with a 200 msec time resolution. Alternatively a separate interface to x-ray generator 102 is provided.

The 8 bit real time parallel I/O bus 379 is also used to control x-ray generator 102 of radiation generation system 109. Timing is provided by DFN control unit 370 on DFN 304. Delays between the x-ray generation and data acquisition on Detector Control Board 124 are provided under software control. The x-ray generator 102 is triggered as an on/off signal. Alternatively, generator voltage, current and exposure time are set and measured. Likewise, the 8 bit real time parallel I/O bus 379 is used to control an x-ray generator for radiography digital x-ray.

Figure 23:
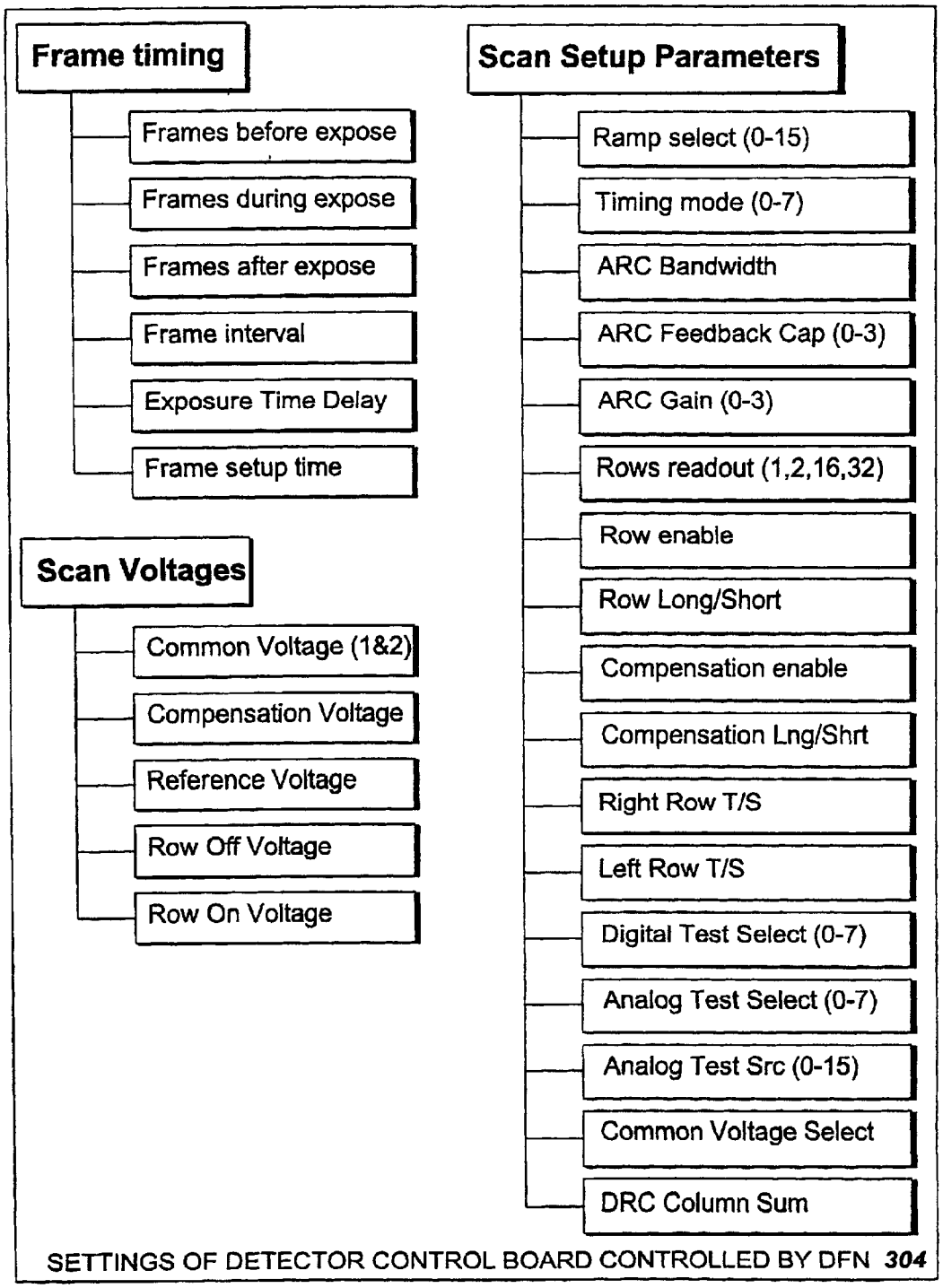
FIG. 23 is a block diagram illustrating settings of a detector control board.

FIG. 23 is a block diagram illustrating configuration settings of detector control board 124. Detector framing node 304 interfaces with detector control board 124 through fiber channel interface hardware and supports a communication rate of 1.25 GHz. The user is able to control data acquisition by controlling the configuration settings of FIG. 23.

Referring to FIG. 1 and FIG. 18, detector framing node 304 allows host computer 114 to interface to radiation generation system 109 and image detection system 112. Accordingly, detector framing node 304 supports a fiber channel interface for communication to detector control board 124, the RS-485 real time bus interface 378 for communication to radiation generation system 109, and the computer communication interface 382 for communication to host computer 114. A block diagram of DFN 304 architecture is shown in FIG. 18 and illustrates the interfaces just described. In addition to the hardware for interface communication, two FPGAs control the flow of data through the card. The EP 374 contains a sequencer, which orchestrates detector and x-ray event instructions in real time. EP 374 also contains a command interpreter which communicates with host computer 114. The DAP 372 controls the routing of image data during frame readout and acts as a bridge chip between image detection bus 377, and local bus 384 and DFN memory unit 380.

Detector Framing Node 304 supports an architecture based upon programmable logic, in the form of DFN control unit 370. The DFN control unit 370 is formed from a pair of FPGAs, which are preferable over embedded processors. First, firmware for the FPGAs is written in VHDL hardware description language, which remains largely platform independent, for integration into a single ASIC. Secondly, VHDL simulation of detector framing node 304 reduces hardware development time. Third, the use of programmable logic devices helps to simplify design of DFN 304 and allows for custom routing of signals between the various client buses on DFN 304, namely image detection bus 377, computer communication bus 302 and real time bus 379. Use of configurable logic simplifies design, simulation, and programming.

Detector framing node 304 uses a 32 bit, 33 MHz computer communication interface 382 to support a transfer rate of 60 MBytes/sec. According to an alternate embodiment, computer communication interface 382 is a 64 bit PCI interface. DFN memory unit 380 includes five frame buffer memory units 381 embodied as 2 MByte frame buffers. Each frame buffer memory unit 381 facilitates sustained (transfer may occur in bursts) data transfer from image detection bus 377 to computer communication bus 302 without loss or data interruption. The use of five buffers provides a margin for capture of a single mammography digital x-ray image without loss or data interruption. Real time bus 379 is an 8 channel full duplex real-time bus interface (RS-485).

Detector framing node 304 controls radiation generation system 109 through serial connection. In other words, detector framing node 304 is in series with external control of the x-ray generation. Detector framing node 304 supports the following: image detection interface 376 operating at 1.25 GBaud rate; 32 bit, 33 MHz computer communication interface 382; 8 bit RS-485 real-time bus interface 378; real-time sequencing of detector and x-ray event instructions; built in self test ("BIST"); field reconfiguration;

power-down capability; sustained data throughput of 60 MBytes/sec; software reset; and monitoring of key signals. BIST is provided on all five frame buffer memory units 381, i.e. 10 SRAMs; electrical loopback test on image detection bus 377; and electrical loopback test on real time bus 379.

Major components of detector framing node 304 are embodied according to Table 1 set forth below:

TABLE 1

| Name | Part Number | Manufacturer |
|---|---|---|
| Computer 382 | PCI 9054 | PLX Tech. |
| EP 374 | EPF10K200EFC600-1 | Altera |
| DAP 372 | EPF10K200EFC600-1 | Altera |
| EEPROM 530, 532 | EPC-2 | Altera |
| 10 SRAM chips | K7M803625M-QC90000 | Samsung |
| F.O. transceiver 560 | MDX-19-4-1 | Methode |
| F.O. transmit unit 562 | TQ9501 | Tri-Quint |
| F.O. receive unit 564 | TQ9502 | Tri-Quint |
| Encoder/decoder unit 566 | TQ9303 | Tri-Quint |
| PCI eeprom 606 | NM93CS66LEN | Fairchild |
| Real time bus interface 378 | SN75ALS171DW | Texas Instruments |
| clock buffer 576 | 49CT3805PYI | IDT |
| power on reset unit 534, 536 | MAX6306UK29D3-T | Maxim |

For testing and monitoring, detector framing node 304 supports self temperature monitoring, unique board ID, layout revision number, JTAG port 542 for reconfiguration of DFN control unit 370, JTAG port 544 for reprogramming of FPGA eeproms, visual diagnostic indicators, connector for access to local bus, connector for access to image detection bus 377, and a connector for access to DAP/EP test bus 384.

EP 374 is an FPGA 200 K gate Altera Flex family, −1 speed grade, supporting a 32 bit local data bus with bus master capability. EP 374 also supports a 20 bit local address bus, a 32 bit test bus, a 32 bit direct link to DAP 372, a 32 bit fiber channel receive bus, a 32 bit fiber channel transmit bus, a twelve bit fiber channel control bus, a fiber channel reference clock input −31.25 MHz, a local bus clock input −36/33 MHz, a 2.5 V core for low power operation, and a 3.3 V TTL compatible interface. EP 374 drives eight visual diagnostic indicators, and also interfaces to on-board temperature sensors. Likewise, EP 374 reads an available 5 bit layout revision code and interfaces to a board ID chip.

DAP 372 is a 200 K gate Altera Flex family, −1 speed grade, supporting a 32 bit local bus, a 20 bit address bus with bus master capability, a 32 bit fiber channel receive bus, fiber channel reference clock input −31.25 MHz, local bus clock input −36/33 MHz, local bus arbitration logic, SRAM address bus, SRAM data bus, SRAM control lines, SRAM clocks, JTAG bus controller, 32 bit test bus, 2.5 V core for low power, and 3.3 V I/O for TTL compatibility.

FIG. 18 is a block diagram of detector framing node 304. DFN 304 allows host computer 114 to interface to radiation generation system 109 and x-ray image detection system 112 in order to control x-ray digital image acquisition. DFN 304 includes image detection interface 376 and real time bus interface 378. DFN control unit 370 is comprised of two FPGAs to control the flow of data through DFN 304. EP 374 contains a sequencer to orchestrate detector and x-ray event instructions in real time. EP 374 also contains a command interpreter to communicate with host computer 114 over computer communication bus 302. DAP 372 controls routing of image data during frame readout and acts as a bridge chip between image detection bus 377, and local bus 384 and DFN memory unit 380.

Figure 24:
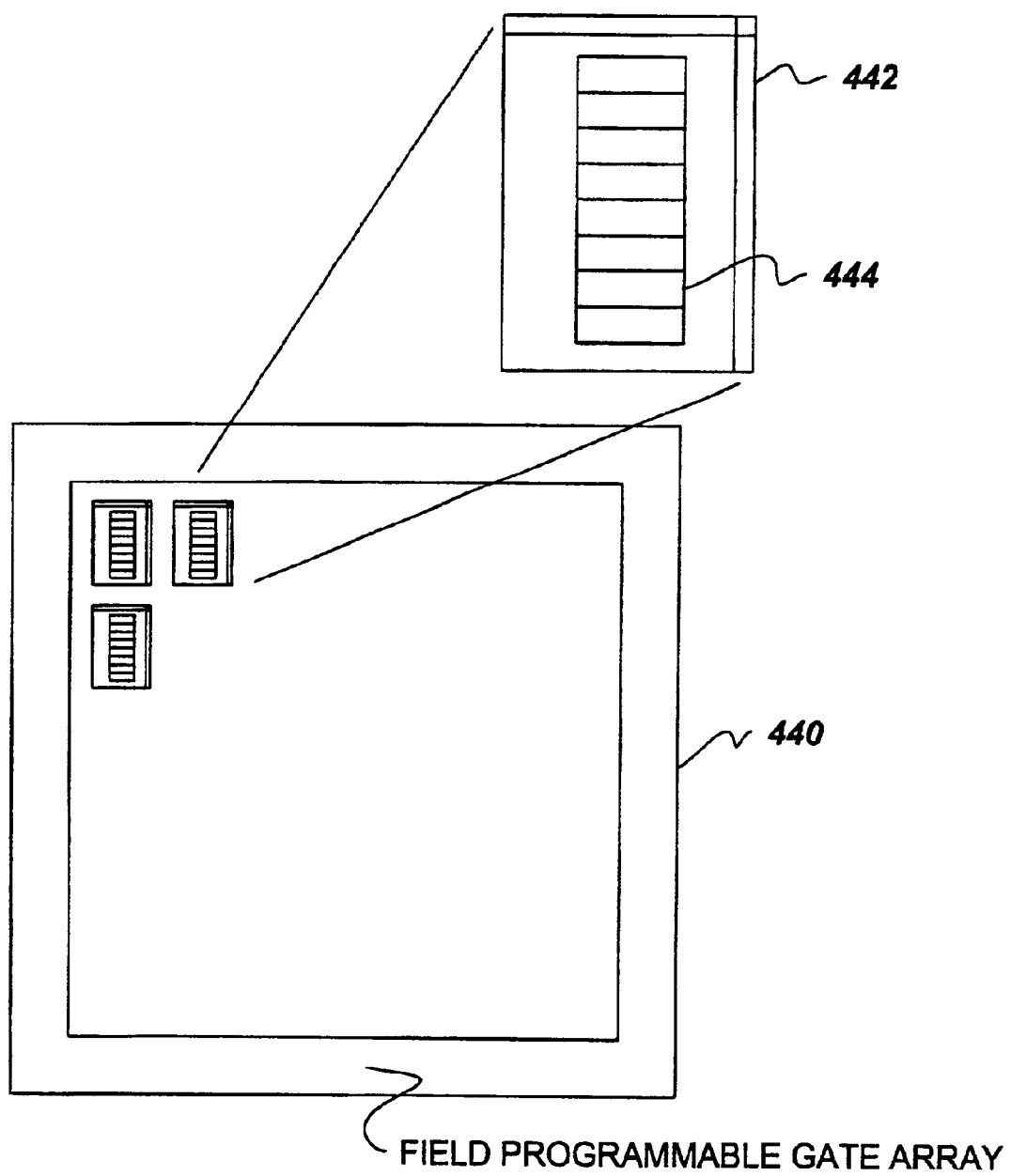
FIG. 24 is a schematic diagram of a field programmable gate array.

FIG. 24 is a schematic diagram of a field programmable gate array ("FPGA") 440. The majority of functionality incorporated into DFN 304 is realized using two FPGAs 440 as DFN control unit 370. FPGAs 440 provide fast custom logic and a large number of user I/O, which are used for bus intensive applications. All logic on DFN 304 is described using the VHDL hardware description language, and is highly portable across different FPGA architectures. The specific FPGAs used for DFN 304 include a matrix of logic array blocks ("LABs") 442 with a large amount of configurable interconnect. As illustrated in FIG. 24, each LAB 442 is further divided into eight logic elements ("LE") 444 with associated local interconnect resources. Each LE 444 contains a four input SRAM based look up table for realizing combinatorial logic functions and is coupled to a single flip-flop. Signals are routed into and out of user I/O pad cells, which are themselves configurable to change parameters, such as output rise time and open-collector output. FPGAs 440 are selected for logic density and speed of operation.

Figure 25:
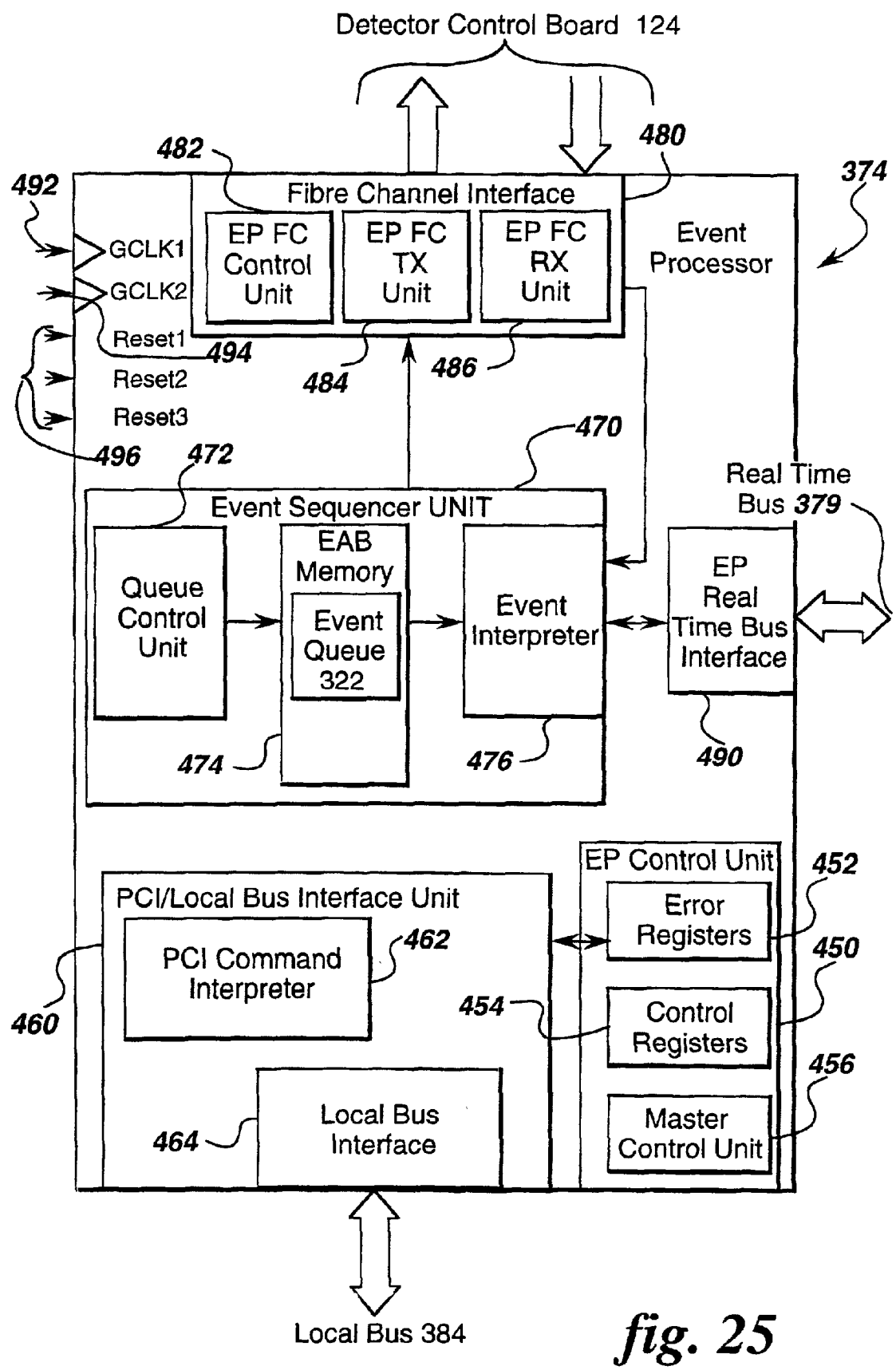
FIG. 25 is a block diagram of an event processor.

FIG. 25 is a block diagram of EP 374. EP 374 is used as a control device on DFN 304. As illustrated in FIG. 25, EP 374 is comprised of a number of sub units, which communicate with one another to control various aspects of DFN 304 functionality. Each of these sub units is discussed in turn.

EP control unit 450 is responsible for overseeing operation of EP 374 and in coordinating interactions between local bus 384, fiber channel interface 480 and event sequencer unit 470. EP control unit 450 maintains a plurality of control registers 454, which parameterize the various operations taking place in EP 374. EP control unit 450 also maintains a plurality of error registers 452, which are used to report any problems in execution to host computer 114. EP control unit 450 coordinates interaction between error registers 452 and control registers 454 by way of master control unit 456.

PCI/local bus interface unit 460 is responsible for hosting communication between EP 374 and local bus 384. Through the local bus connection to computer communication interface 382, PCI/local bus interface unit 460 functions as a main respondent to commands sent over computer communication bus 302 to DFN 304. PCI/local bus interface unit 460 includes a PCI command interpreter 462, which processes commands from host computer 114. Example commands include loading the event queue into EAB memory 474 in event sequencer unit 470 with data for an upcoming sequence or processing a begin sequence command.

Event sequencer unit 470 houses an event queue in EAB memory 474 and is responsible for decoding and executing event instructions during sequence operation. The event queue is embodied using available on chip EAB memory 474 on EP 374. The event queue in EAB memory 474 is organized byte-wise for most efficient use of memory resources. Sequencing of events and read/write of the event queue in EAB memory 474 is controlled by queue control unit 472. Interpretation of event instructions is performed by event interpreter 476. As event instructions are read out of the event queue during sequence execution, data to be sent out to the various interfaces is transferred by the event interpreter 476 to other units on EP 374 for further processing.

Fiber channel interface 480 is responsible for maintaining communications with image detection interface 376. Data is transmitted by the FC EP transmit unit 484 and received by the EP FC receive unit 486. The status of the link is monitored by the EP FC control unit 482, which notifies host computer 114 if communication is lost or when anomalous conditions occur. Unlike most of EP 374, which runs off of the 36.0 MHz local bus clock, the EP FC transmit unit 484 runs off of the 31.25 MHz fiber channel transmit clock 584. Similarly, the EP FC receive unit 486 runs off of the fiber channel receive clock 585. This asynchronous operation is used in order to effect a rate change between image detection bus 377 and local bus 384. The units within fiber channel interface 480 communicate asynchronously with the remainder of EP 374 using flags for handshaking and double buffered registers.

EP real time bus interface 490 handles requests for changing the state of real time bus 379 from the event queue in EAB memory 474. EP real time bus interface 490 is also responsible for notifying the event queue and host computer 114 when external devices (e.g. radiation generation system 109) force the state of real time bus 379.

There are two global clock inputs to EP 374, namely GCLK1 input 492 and GCLK2 input 494. These inputs are optimally distributed to all logic on the devices using two dedicated clock trees. On EP 374, GCLK1 492 and GCLK2 494 are driven by the 36.0 MHz local clock 574 and the 31.25 MHz fiber channel transmit clock 584 respectively.

There are also four additional dedicated global signal lines, which are not optimized for timing. On EP 374 these are connected to three reset signal triggers 496. Two reset triggers are generated by computer communication interface 382 (USERo and LCL_rst), and the third signal comes from a power on reset circuit, set forth in greater detail below.

Figure 26:
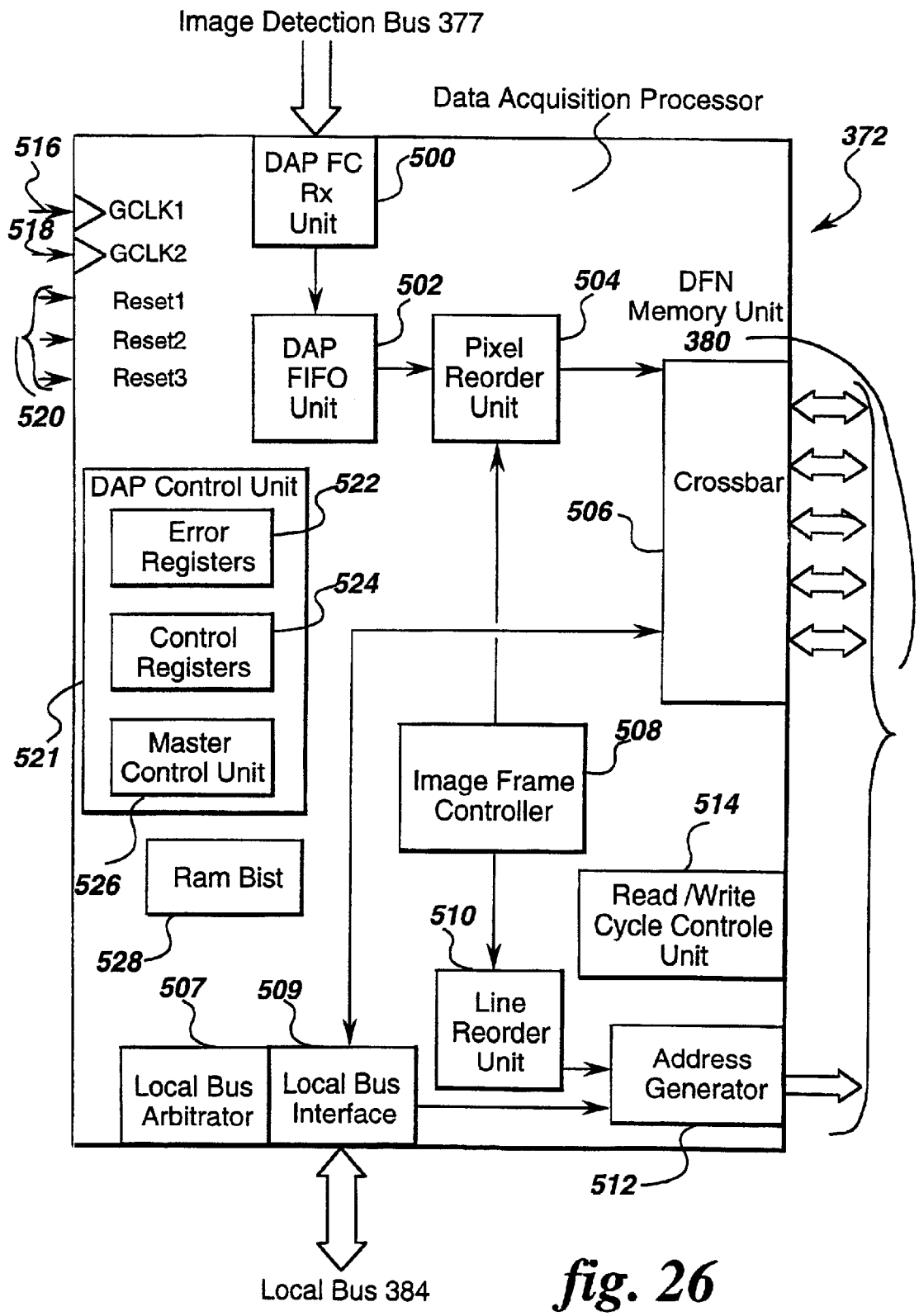
FIG. 26 is a block diagram of a data address processor.

FIG. 26 is a block diagram of DAP 372, which is the second FPGA to be used in DFN control unit 370. DAP 372 is mainly concerned with accomplishing the rate change between data received from image detection bus 377, effectively operating at 31.25 MHz, and computer communication bus 302, operating at 36.0 MHz. DAP 372 performs the rate change by storing data received from image detection bus 377 in one frame buffer memory unit 381, while simultaneously reading previously stored data out of a second frame buffer memory unit 381 to computer communication bus 302 through computer communication interface 382.

As illustrated in FIG. 26, DAP 372 is comprised of a number of sub units, which are responsible for orchestrating the flow of image data on DFN 304. Starting with the DAP FC receive unit 500, 32 bit image data is received at the 31.25 MHz fiber channel receive clock rate. Each 32 bit word comprises two 16 bit pixel values, each read out in parallel by detector control board 124. The combined 32 bit word is written into DAP first in first out ("FIFO") unit 502 using the fiber channel receive clock. At the same time, data is being read asynchronously out of DAP FIFO unit 502 and into the pixel reorder unit 504. The reorder function performed by pixel reorder unit 504 is set forth in greater detail below. This data is now processed at the 36.0 MHz local bus clock rate. From the pixel reorder unit, pixels move to crossbar 506, which routes the pixels to the currently active frame buffer memory unit 381.

At the same time that receive data is being stored in the currently active receive frame buffer memory unit 381, previously stored image data is being read out of the currently active stored frame buffer memory unit 381 to computer communication bus 302. Data is again routed through cross bar 506, but this time is passed on to computer communication interface 382, then to computer communication bus 302. The five available frame buffer memory units 381 in DFN 304 each provide an incremental timing safe guard against the possibility of dropping communication on computer communication bus 302. If communication is interrupted, the receive circuitry continues to store the incoming data from image detection system 112, which might otherwise be lost. Once computer communication bus 302 is picked up again, transfer of data continues at the local bus clock rate of 36.0 MHz. This provides uninterrupted data transfer and rate translation between image detection bus 377 and computer communication bus 302.

As part of the data flow architecture, DAP 372 also contains a local bus arbitrator 507, which is responsible for coordinating access to local bus 384 between EP 374, computer communication interface 382 and DAP 372. The connection between crossbar 506 and computer communication interface 382 is in fact bi-directional. This bi-directionality, combined with control of address generator 512 directly by computer communication bus 302 allows host computer 114 to read/write the frame buffer memory units 381 directly.

As illustrated in FIG. 26, DAP 372 is responsible for controlling the address bus and read/write signals for the frame buffer memory units 381. Image frame controller 508 is configured with the details of the type of detector panel being accessed (line length, lines/image) and keeps track of the incoming pixel data to ensure that proper framing is maintained. In the event of inconsistent line length or frame size, an error is generated and reported to host computer 114. Line reorder unit 510 feeds into address generator 512 to generate proper addresses for the currently active receive and store frame buffer memory units 381. At the same time, precise timing of the various memory unit control signals is maintained by the read/write cycle control unit 514. Detailed information regarding frame buffer memory units 381 is set forth below.

There are two global clock inputs to DAP 372, GCLK1 516 and GCKL2 518. These inputs are optimally distributed to all logic on the devices using two dedicated clock trees. On DAP 372, GCLK1 516 and GCLK2 518 are driven by 36.0 MHz local bus clock and the 31.25 MHz fiber channel receive clock, respectively. There are also four additional dedicated global signal lines. On DAP 372 the dedicated global signal lines are connected to three reset triggers 520. Two of the reset triggers are generated by computer communication interface 382 (USERo and LCL_rst) and the third signal is generated from a power on reset circuit, set forth in greater detail below.

DAP control unit 521 is responsible for overseeing operation of DAP 372. DAP control unit 521 maintains control registers 524 which parameterize the various operations taking place in the DAP 372. DAP control unit 521 also maintains error registers 522, which are used to report any problems in execution to host computer 114. RAM BIST 528 performs a built in self test of the frame buffer memory units 381 on initial power up and during normal operation on command from host computer 114. Detailed information is set forth below.

Figure 27:
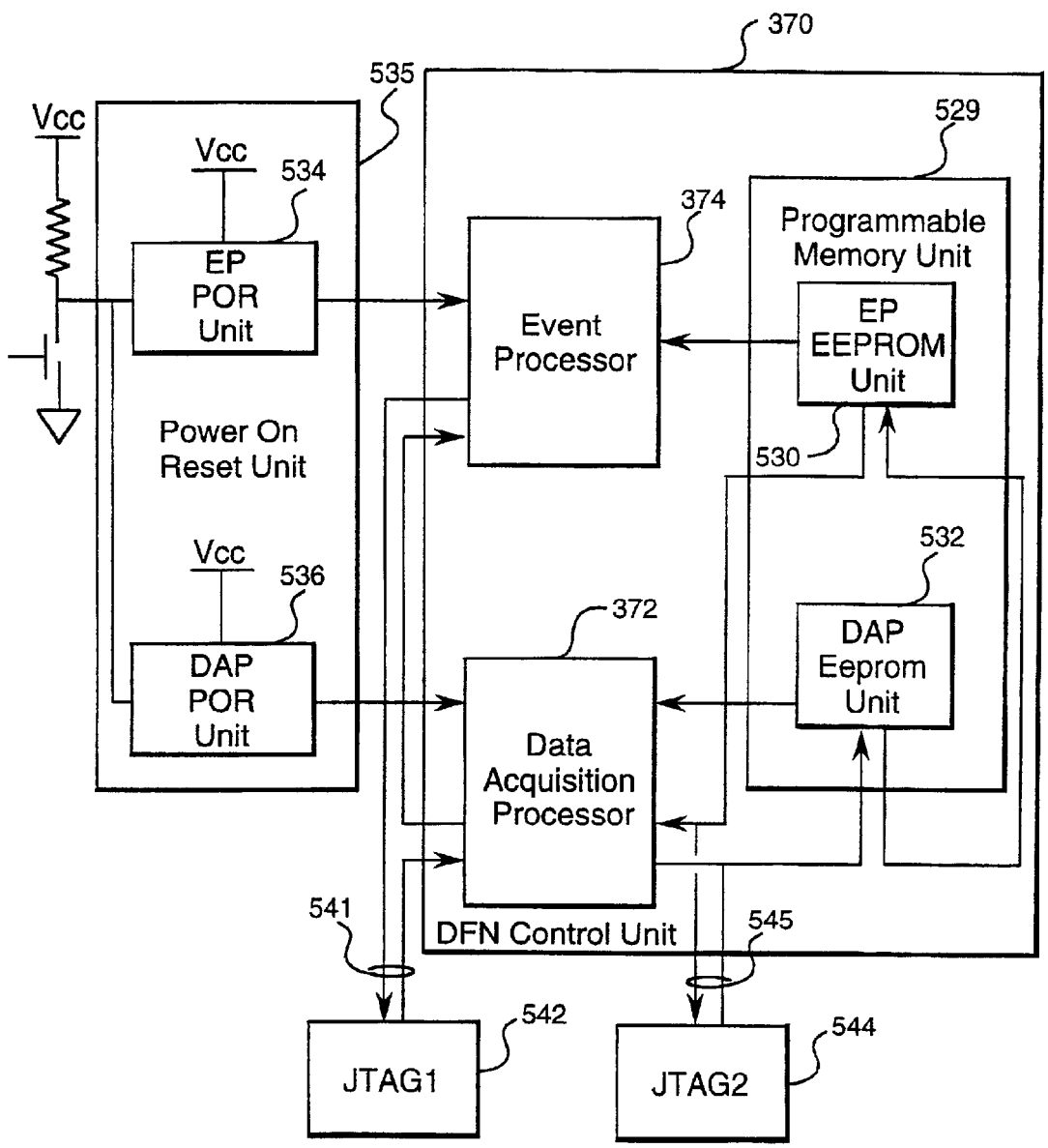
FIG. 27 is a block diagram of a detector framing node control unit in conjunction with a power on reset unit.

FIG. 27 is a block diagram of DFN control unit 370 in conjunction with power on reset unit 535. To facilitate test and debug, as well as for firmware updates in the field, DAP 372 and EP 374 are configurable through programmable memory unit 329. Programmable memory unit 329 includes DAP eeprom unit 532 and EP eeprom unit 530. Alternatively, DAP 372 and EP 374 are programmable JTAG ports JTAG1 542 and JTAG2 544. In typical operation, power is applied to DFN 304 when host computer 114 is first turned on. At this stage each of DAP 372 and EP 374 boot from their respective eeproms and therefore become operational by loading the data from the respective eeprom. FIG. 27 illustrates configuration circuitry on DFN 304. Each of DAP 372 and EP 374 has an associated eeprom unit comprised of two EPC2 chips that are daisy-chained to provide storage for programming. One eeprom unit per each of DAP 372 and EP 374 is shown for simplicity. Each EPC2 chip is a socketed 20 pin PLCC package, which is easily removed for reprogramming. As illustrated, configuration, i.e. loading data, is in passive serial mode in which a single line provides serial data to configure the devices.

The programmable control unit 529 stores initial boot sequence instructions for controlling the detector framing node control unit 370. The programmable control unit 529 loads the initial boot sequence instructions for execution by control unit 570 upon reset or initial application of power to detector framing node 304. According to an embodiment of the present invention, the initial boot sequence instructions are updated by communicating update instructions from host computer 114 through the computer communication interface 382 and into detector framing node memory unit 380. The update instructions are then communicated from detector framing node memory unit 380 to the programmable memory unit 529. The JTAG loop 545 communicates the update instructions from local bus 384 and programmable memory unit 529.

As illustrated in FIG. 27, DAP power on reset ("POR") unit 536 and EP POR unit 534 are used to hold a reconfig line low for an additional 140 msec after power comes up on DFN 304 and configuration is complete. This ensures that DAP 372 and EP 374 configure in case the power supply rise time of 100 msec is violated. Alternatively, a push button switch is used to force a manual override of each POR circuit and reconfigure the FPGAs without cycling power to the board. All signal lines involved with FPGA configuration are made available on the top layer of the board to facilitate debug of FPGA configuration if a problem is detected during initial test of the board. In addition, jumpers are provided to selectively disable reboot of DAP 372 or EP 374 in order to help debug problems during configuration or due to specific devices.

During test and debug of DFN 304, configuration of the FPGAs and programming of eeprom units 530 and 532 are accomplished through the illustrated JTAG ports 542 and 544. JTAG1 542 is provided for the loop including EP 374 and DAP 372. No-populate 0-Ohm resistors are used to allow for either of EP 374 or DAP 372 to be taken out of the loop in case a problem arises during debug or firmware development.

JTAG2 544 is provided for the loop including the two eeprom units 530 and 532, and is used for programming the eeprom units 530 and 532. The eeprom units 530 and 532 are programmable over their respective JTAG ports using a Byte Blaster cable and MaxPlusII software, by Altera, Inc. of San Jose, Calif. As illustrated in FIG. 27, JTAG2 544 is also provided for second JTAG loop 545, including DAP eeprom unit 532 and EP eeprom unit 530, used to program the EP 374 and DAP 372.

When DFN 304 is in the field, the firmware is optionally updated to a different version. For convenience, these updates are performed directly without opening host computer 114 and swapping eeprom devices for a later revision. The capability for in-system programming of the eeprom units is supported through respective JTAG ports as mentioned above. DFN 304 allows host computer 114 to access the JTAG1 542 or JTAG2 544 directly over computer communication bus 302 without using the Byte Blaster cable and MaxPlusII software.

As illustrated in FIG. 27, second JTAG loop 545, which allows eeprom units 530 and 532 to be programmed from JTAG2 port 544 is also connected to DAP 372 through user I/O pins. Once the board FPGAs configure properly with the old version of the firmware, the eeprom units are reprogrammable using a firmware application resident in DAP 372. Data for the eeprom units is transferred to the frame buffer memory units 381 over computer communication bus 302. From the frame buffer memory units 381, the data is read out by DAP firmware, serialized, and transferred over the respective JTAG bus along with format and command information.

After DAP 372 has reprogrammed the eeprom units over the corresponding JTAG bus, DAP 372 issues a JTAG command to cause the eeprom units to automatically reconfigure both of DAP 372 and EP 374. There is one try allowed for reprogramming of the EPC2 chips forming EP eeprom unit 530 and DAP eeprom unit 532. Error checking is used to ensure that the devices have been programmed correctly, however this will not prevent a user from programming the wrong firmware into the EPC2s. This situation is mitigated using software interlocks and through general precaution. The eeprom units may always be physically replaced on DFN 304.

DFN 304 uses ten 9.4 Megabit SRAMs, grouped into five frame buffer memory units 381. Address and data buses for the SRAMs are connected to DAP 372, which is responsible for control of these devices and for effecting a pixel data reordering algorithm, set forth in greater detail below. Data reordering for each flat panel detector is achieved by writing data from each row of the detector panel into the SRAM in an order such that when the SRAM is read out sequentially, the data is reordered for correct display on a memory mapped high resolution display 338. The data is transferred from the SRAMs into computer RAM 334 of host computer 114 using computer communication bus 302 for direct memory access ("DMA").

Each SRAM is in a 100 pin thin quad flat pack ("TQFP") packaging. The part is organized as 256K×36 and has a 12 nsec cycle time. Address, data inputs, and all control signals, except output enable and linear burst enable, are true on the rising edge of the clock. Operation of the SRAMs are at 36 MHz, which allows head room. Since the data is typically two 16 bit words, the low order 4 bits of each SRAM are unused and the effective memory capacity is 8.4 Mbits. The TQFP package allows debug since all pins are available for probing. However, the use of a BGA package improves manufacturing yield. Five SRAMs are placed on each physical side of the board on which DFN 304 is formed to minimize address and data line length. Pairs of SRAMs forming each frame buffer memory unit 381 are placed on alternate sides of the physical board.

Writing data to frame buffer memory unit 381, formed as a pair of SRAMs, and reading data from a second frame buffer memory unit 381, also a pair of SRAMs, occurs in parallel. This is achieved by providing five 32 bit data buses and five 18 bit address buses in DAP 372, which address and read or write data to the five pairs of 8.4 Mbit SRAMs. Thus, 250 pins of the 600 pin DAP 372 are used for address and data for the SRAMs.

In addition to the 18 bit address bus and the 32 bit data bus, the SRAM control pins used are write enable (WE#), three chip selects (CS1#, CS2, CS2#) and sleep mode (ZZ). CS1# is used to select SRAMs for read or write. CS2 and CS2# are used to implement the data reordering scheme set forth below for the cardiac/surgical digital x-ray flat panel and the radiography digital x-ray flat panel. Sleep mode may be used for power down. Note that the # indicates the pin is active low.

Figures 28, 29, 30:
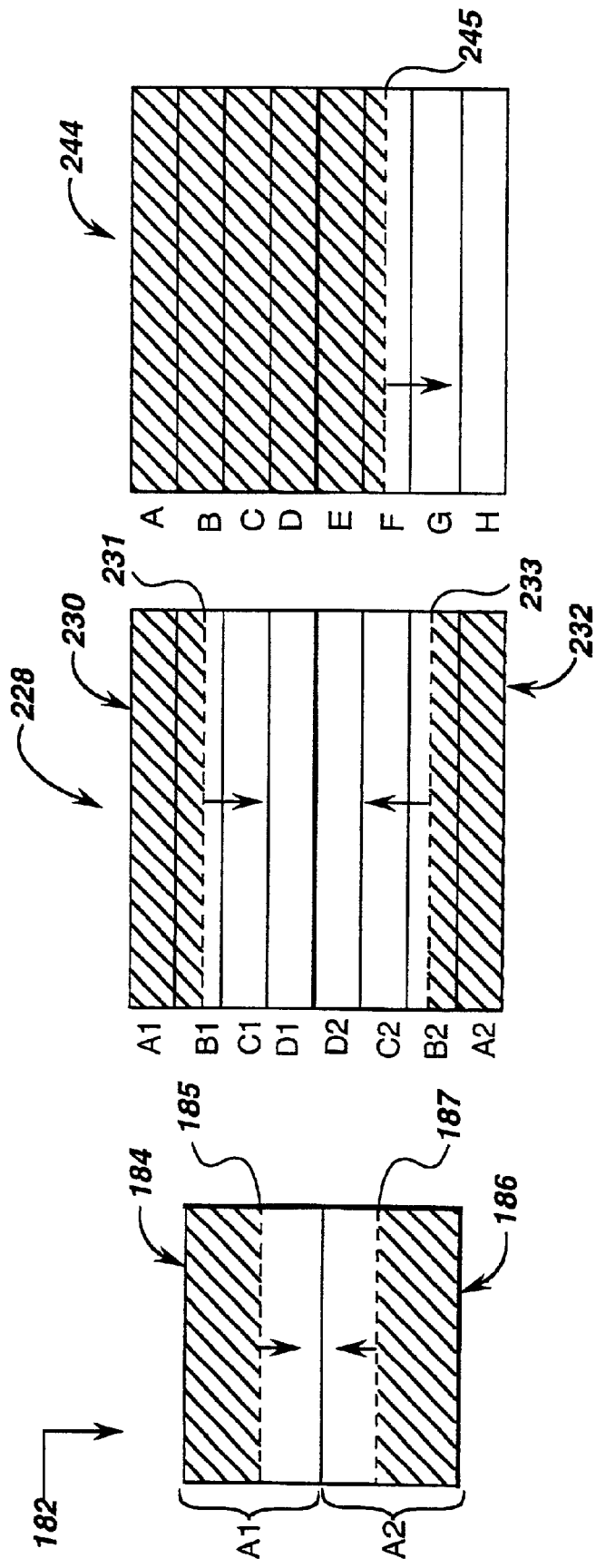
FIG. 28 is a schematic diagram of data being read out of a cardiac/surgical digital x-ray panel.
FIG. 29 is a schematic diagram of data being read out of a radiography digital x-ray panel.
FIG. 30 is a schematic diagram of data being read out of a mammography digital x-ray panel.

FIG. 28 is a schematic diagram of data being read out of a cardiac/surgical digital x-ray panel 182. As illustrated, first cardiac scan line 185 is the line of data being read out of first panel portion 184, and second cardiac scan line 187 is the line of data being read out of second panel portion 186. Each scan line 185 and 187 is moving in a direction toward the center between split panels 184 and 186. The data is read out of each of the split panels by reading out pixels from the top row of the top panel and the bottom row of the bottom panel in parallel. The data from the first four pixels (two from the top row and two from the bottom row), are stored in the DAP 372 in preparation for writing data into the active frame buffer memory unit 381.

In the case of cardiac/surgical digital x-ray, the data being read out of the cardiac/surgical digital x-ray panel 182 is being stored in SRAMs A1 and A2 of DFN memory unit 380 in DFN 304. SRAMs A1 and A2 comprise a single frame buffer memory unit 381. FIG. 28 represents the correspondence of SRAMs to the data actually being read out, namely into 2 SRAMs. DFN memory unit 380 has 10 SRAMs.

FIG. 29 is a schematic diagram of data being read out of a radiography digital x-ray panel 228. As illustrated, first radiography scan line 231 is the line of data being read out of first panel portion 230, and second radiography scan line 233 is the line of data being read out of second panel portion 232. Each scan line 231 and 233 is moving in a direction toward the center line between split panels 230 and 232. In the case of radiography digital x-ray, the data being read out of the radiography digital x-ray panel 228 is being stored in SRAMs A1, B1, C1, D1 and A2, B2, C2, D2 of DFN memory unit 380 in DFN 304. Each respective pair of SRAMs A1 and A2, B1 and B2, C1 and C2, and D1 and D2 comprise a single frame buffer memory unit 381. FIG. 29 represents the correspondence of SRAMs to the data actually being read out, namely into 8 SRAMs. DFN memory unit 380 has 10 SRAMs.

FIG. 30 is a schematic diagram of data being read out of a mammography digital x-ray panel 244. As illustrated, mammography scan line 245 is the line of data being read out of mammography digital x-ray panel 244. Scan line 245 is moving in a downward direction across panel 244. In the case of mammography digital x-ray, the data being read out of panel 244 is being stored in SRAMs A, B, C, D, E, F, G, and H of DFN memory unit 380 in DFN 304. The physical SRAMs are the same as SRAMs A1 and A2, B1 and B2, C1 and C2, and D1 and D2 set forth above. However, the designation is changed to reflect sequential data storage in the SRAMs of frame buffer memory unit 381. FIG. 30 represents the correspondence of SRAMs to the data actually being read out, namely into 8 SRAMs. DFN memory unit 380 has 10 SRAMs.

Figure 31:
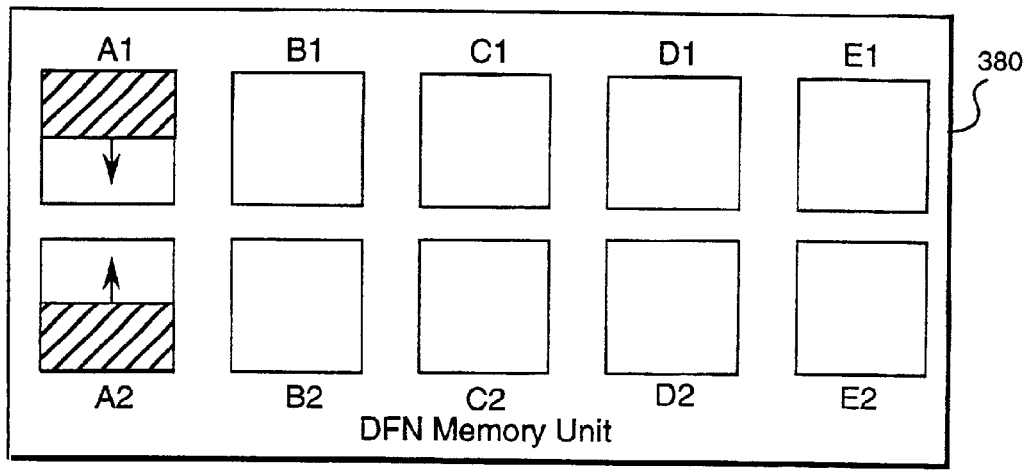
FIG. 31 is a schematic diagram of cardiac/surgical digital image data being read into a plurality of static random access memories.

FIG. 31 is a schematic diagram of digital radioscopic image data being read into a plurality of SRAMs A1, A2, B1, B2, C1, C2, D1, D2, E1, E2, which form DFN memory unit 380, in a cardiac/surgical application. The data being read into DFN memory unit 380 is the same data as being read out from cardiac/surgical digital x-ray panel 182 in FIG. 28. The plurality of SRAMs are designated as pairs A1, A2; B1, B2; C1, C2; D1, D2; and E1, E2, to denote that each pair of SRAMs is store data simultaneously. As illustrated, as data is read out from cardiac/surgical digital x-ray panel 182, the data is stored in real time into DFN memory unit 380. Because the amount of data used by cardiac/surgical digital x-ray panel 182 is on the order of 2 MBytes, 2 SRAMs, namely SRAM A1 and SRAM A2 are used for each image.

When cardiac/surgical digital x-ray panel 182 is used in a fluoroscopy application, to acquire real time moving images of 30 frames/second, each SRAM pair stores a single frame of the real time moving image. With reference to FIG. 18, each SRAM pair is denoted as a frame buffer memory unit 381. DFN 304 allows one frame buffer memory unit 381 to acquire data simultaneously while a second frame buffer memory unit 381 reads out data. Each SRAM illustrated in FIGS. 31, 32, and 33 has a pin labeled chip select #1, i.e. CS#1, which is used to select a pair of the SRAM chips at any one time.

Figure 32:
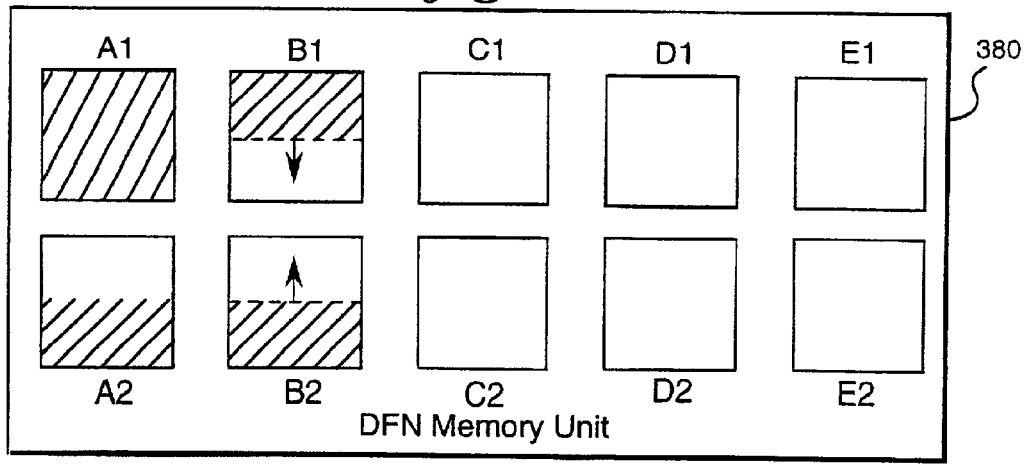
FIG. 32 is a schematic diagram of radiography digital image data being read into a plurality of static random access memories.

FIG. 32 is a schematic diagram of digital radiography image data being read into a plurality of SRAMs A1, A2, B1, B2, C1, C2, D1, D2, E1, E2, which form DFN memory unit 380, in a radiography digital x-ray application. The data being read into DFN memory unit 380 is the same data as being read out from radiography digital x-ray panel 228 in FIG. 29. The plurality of SRAMs are designated as pairs A1, A2; B1, B2; C1, C2; D1, D2; and E1, E2, to denote that each SRAM forming a pair is stored with data simultaneously. As illustrated, as data is read out from radiography digital x-ray panel 228, the data is stored in real time into DFN memory unit 380. Because the amount of data used by radiography digital x-ray panel 228 is on the order of 8 MBytes, 8 SRAMs, namely SRAMs A1, A2, B1, B2, C1, C2, D1, and D2 are used for each image. FIG. 32 illustrates a single radiography digital x-ray image being acquired into DFN memory unit 380, and in particular, the pair of SRAMs B1, B2.

Figure 33:
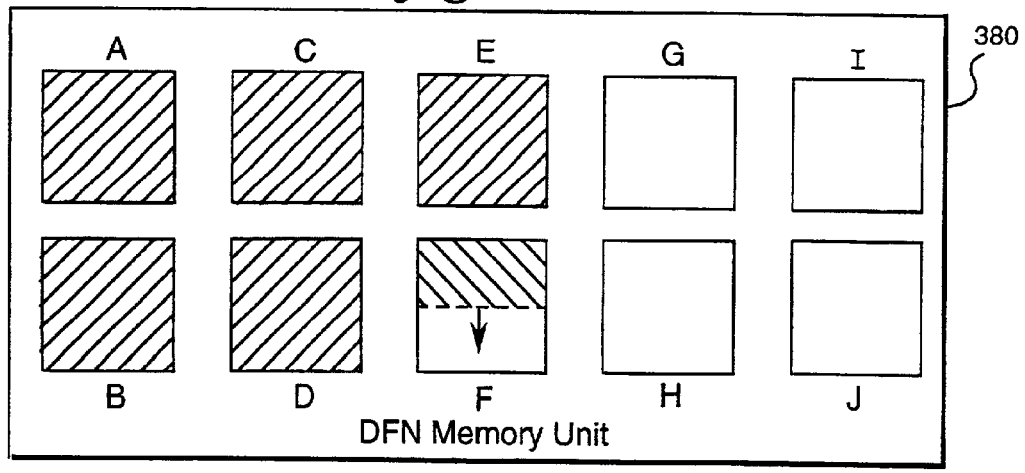
FIG. 33 is a schematic diagram of mammography digital image data being read into a plurality of static random access memories.

FIG. 33 is a schematic diagram of digital mammography image data being read into a plurality of SRAMs A1, A2, B1, B2, C1, C2, D1, D2, E1, E2, which form DFN memory unit 380, in a mammography digital x-ray application. The data being read into DFN memory unit 380 is the same data as being read out from mammography digital x-ray panel 244 in FIG. 30. The plurality of SRAMs are designated singularly A, B, C, D, E, F, G, H, I, and J, to denote that each SRAM acquires data individually, rather than in pairs. Data is stored in this fashion because the mammography digital x-ray panel 244 is a single panel, rather than a "split panel," as in the other cases set forth above. As data is read out from radiography digital x-ray panel 228, the data is stored in real time into DFN memory unit 380. Because the amount of data used by mammography digital x-ray panel 244 is on the order of 8 MBytes, 8 SRAMs, namely SRAMs A, B, C, D, E, F, G, and H are used for each image. FIG. 33 illustrates a single mammography digital x-ray image being acquired into DFN memory unit 380.

Figure 34:
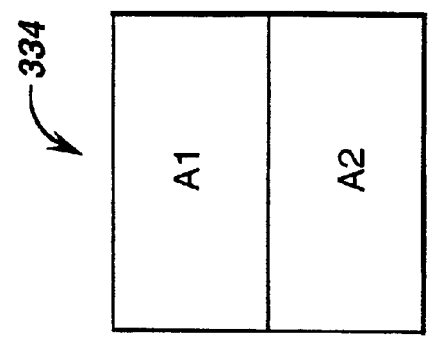
FIG. 34 is a schematic diagram of memory allocation of a single cardiac/surgical digital x-ray image in a PC random access memory.

FIG. 34 is a schematic diagram of memory allocation of a single cardiac/surgical digital x-ray image in computer RAM 334. Alternatively, the cardiac/surgical digital x-ray image may be stored in PCI RAM card 336. Once in computer controlled memory, the digital x-ray image may be processed and viewed under control of host computer 114.

Figure 35:
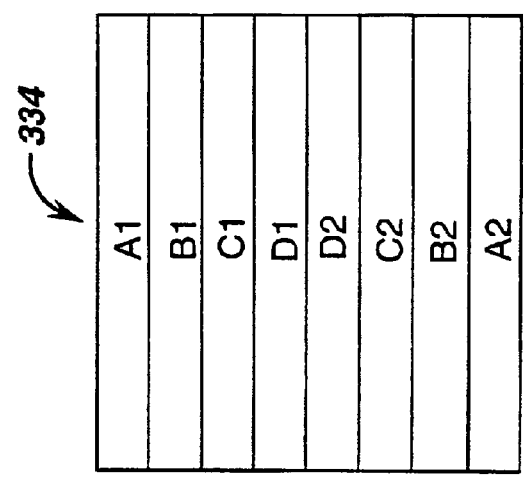
FIG. 35 is a schematic diagram of memory allocation of a single radiography digital x-ray image in a PC random access memory.

FIG. 35 is a schematic diagram of memory allocation of a single radiography digital x-ray image in computer RAM 334. Alternatively, the radiography digital x-ray image may be stored in PCI RAM card 336. Once in computer controlled memory, the digital x-ray image may be processed and viewed under the control of host computer 114.

Figure 36:
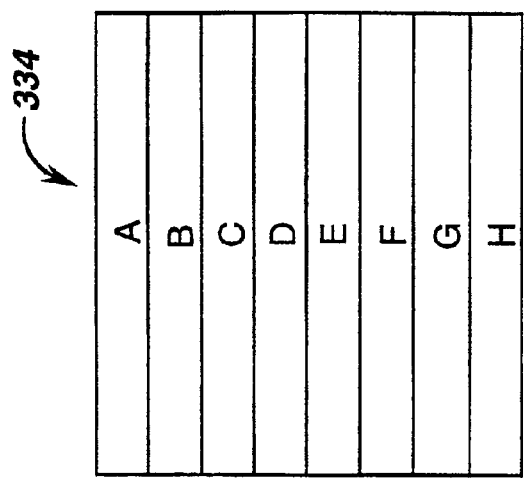
FIG. 36 is a schematic diagram of memory allocation of a single mammography digital x-ray image in a PC random access memory.

FIG. 36 is a schematic diagram of memory allocation of a single mammography digital x-ray image in computer RAM 334. Alternatively, the mammography digital x-ray image may be stored in PCI RAM card 336. Once in computer controlled memory, the digital x-ray image may be processed and viewed under the control of host computer 114.

FIGS. 31–33 illustrate data being written into DFN memory unit 380. In general, during initial readout from a flat panel detector, the first two pixels from the top row of the flat panel detector are written to the top left most SRAM A1 by pulling the corresponding chip select control pin line CS2# line low. An address line trigger A18 (not shown), which is controlled by firmware on DFN 304, is low on this write cycle. The first two pixels from the bottom row from the flat panel detector are next stored in bottom left most SRAM A2 by pulling a CS2 line high. Address line trigger A18 is high on this write cycle. In practice, two 16 bit pixels, initially from the top row of the flat panel detector are written as a single 32 bit long word in SRAM A1. Likewise, two 16 bit pixels, initially from the bottom row of the flat panel detector are written as a single 32 bit word in SRAM A2.

Data readout from the flat panel detector continues in the above fashion, such that pixel pairs from the top of the flat panel detector are alternately transmitted with respect to pixel pairs from the bottom flat panel across image detection bus. When the SRAM A1 and SRAM A2 are full, data is then stored in SRAM B1 and SRAM B2, and so on. By way of example, for image acquisition from cardiac/surgical digital x-ray panel 182, when SRAM A1 and SRAM A2 are full, the top of the image is stored in SRAM A1 and the bottom of the image is stored in SRAM A2. Data is then stored in the next pair of SRAMs, namely SRAM B1 and SRAM B2. Data is sequentially read out from the SRAMs to accomplish the reordering in traditional left-to-right fashion, such that data is first read out sequentially from SRAM A1, and then sequentially read out from SRAM A2. Upon readout, the data has been reformatted for display on a monitor.

A pair of SRAMs hold 2 MBytes of data, which corresponds to a single cardiac/surgical digital x-ray image. For radiography digital x-ray, the image is stored in 4 pairs of memory chips, i.e. 8 MBytes of data. Each pair of SRAM memory chips is viewed as storing a 2 MByte stripe of data from the panel. As a pair of SRAM memory chips fill with data, they are available to be readout over PCI bus 383. A portion of an entire image frame output from a flat panel detector may be stored on DFN 304 while another portion is being transferred to host computer 114. Thus, 4048×4048 or larger panels are supported.

In a configuration for mammography digital x-ray having a single flat panel, no reordering is provided. Data is read out from the single flat panel in sequential pixel order, two bits at a time, and likewise written sequentially to SRAMs A1, A2, B1, . . . , etc. The firmware in DAP 372 handles mammography digital x-ray without reordering.

As set forth above, digital x-ray image data does not go directly from each flat panel detector into SRAM memory, but rather goes through ARC chips 196 and through DRC chip 198 (see FIG. 9), is converted to a serial format on detector control board 124, and is transmitted over image detection bus 377 serially to DFN 304, for conversion back to a 32 bit parallel word. The fiber channel clock is set at 31.25 MHz and the 32 bit words are stored in a DAP 372 register at this rate. One 32 bit word contains two 16 bit pixels, one from the top panel of a split panel detector and one from the bottom panel, for cardiac/surgical and radiography digital x-ray. Data is written to or read from memory using the 36 MHz clock of computer communication bus 302. The data transfer over computer communication bus 302 occurs at the 33 MHz clock rate of computer communication bus 302. The buffering used to convert the clock rate from image detection bus 377 to local bus 384 to computer communication bus 302 occurs within FIFOs on computer communication interface 382 or optionally in DAP 372.

Figure 37:
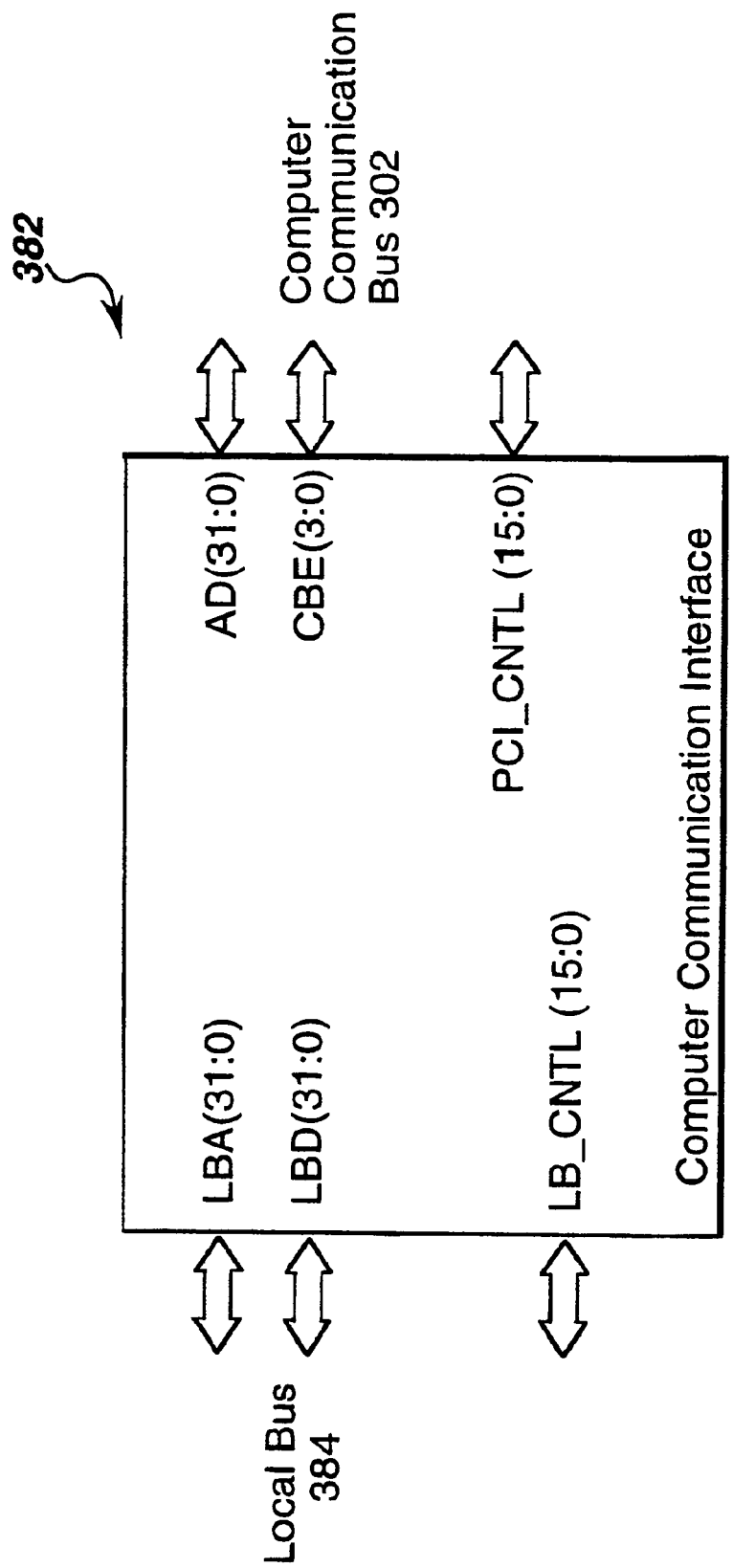
FIG. 37 is a schematic view of a PCI interface.

FIG. 37 is a schematic view of computer communication interface 382, which is a 32 bit, 33 MHz PCI bus master I/O accelerator chip. Computer communication interface 382 implements PCI class specifications and operates in burst mode at transfer rates up to 132 MByte/second. Computer communication interface 382 interfaces with computer communication bus 302 operating at 33 MHz to DFN local bus 384 operating at 36 MHz and above. Internally Computer communication interface 382 contains a first in first out ("FIFO") memory to perform data rate conversion between the two busses. Features of computer communication interface 382 include DMA engines, direct slave and direct master capability, and PCI messaging using mailbox and doorbell registers.

DMA is used to transfer images from 2 MByte memory buffers on DFN 304 directly to computer RAM 334. Using the DMA engines on computer communication interface 382 relieves the burden of managing the data transfer from both the computer application and from the processors on DFN 304. DMA setup has four 32-bit words of data to be written to computer communication interface 382. The 32-bit words of data include a local base address, a PCI base address, a size of transfer, and a command to initiate the transfer. These four 32 bit words are written by EP 374 when a memory buffer needs to be transferred to computer RAM 334.

Direct slave mode of operation is used for all direct computer accesses to DFN 304. Computer communication interface 382 is programmed to recognize the address on computer communication bus 302 where DFN 304 resides. When a memory access within defined memory space of DFN 304 is accessed, computer communication interface 382 responds on computer communication bus 302 and performs a memory access on the local bus side of DFN 304. This mode of operation is used to read and write registers on DAP 372 and EP 374, to access memory within the memory buffers on DFN 304, and to send commands to DFN 304.

Direct master mode of operation is used for sending detector information to host computer 114. When DFN 304 receives an acknowledgement from an issued command, DFN 304 sends this information to a pre-designated buffer in computer RAM 334. Host computer 114 sets up the buffer space and authorizes DFN 304 to transfer data into computer ram 334 before this mode of communication is used.

Computer communication interface 382 has a number of mailbox registers, and two doorbell registers used for messaging between DFN 304 and the computer application. There is a 32-bit outgoing and a 32-bit incoming doorbell register. The mailbox registers are used to buffer the results of commands to DFN 304. The outgoing doorbell register is used to send interrupts to the host computer 114. Interrupts originate from a number of sources, including command completion signals and errors.

Computer communication interface 382 PCI bus side signals are generally set forth in Table 2 below:

TABLE 2

| Name | Pin Function |
| --- | --- |
| AD(31:0) | PCI side multiplexed Address/Data Bus |
| C_BE(3:0) | PCI side byte enables |
| DEVSEL | Device Select |
| ENUM | Enumeration; Hot-swap related |
| FRAME | Cycle Frame; Defines a frame of data |
| GNT | Grant; PCI bus granted to card |
| RST | Reset; PCI reset will reset the computer communication interface 382 |
| IDSEL | Initialization Device Select |
| INTA | Interrupt A; PCI interrupt request by DFN to computer |
| IRDY | Initiator Ready |
| LOCK | Lock; Lock computer communication bus 302 |

TABLE 2-continued

| Name | Pin Function |
| --- | --- |
| PAR | Parity; Even parity on AD and CBE |
| PERR | Parity Error; Report data parity errors |
| PME | Power Management Event |
| REQ | Request; Request for computer communication bus 302 |
| SERR | System Error; Report Address parity errors |
| STOP | Stop; Request to stop current transaction |
| TRDY | Target Ready |
| PCLK | PCI Clock; 33 MHz |

Table 3 sets forth computer communication interface 382 local bus side signals.

TABLE 3

| Name | Pin Function |
| --- | --- |
| LBA(31:0) | Local Address Bus |
| LBD(31:0) | Local Data Bus |
| ADS | Address Strobe; Indicates start of address cycle |
| BIGEND | Big Endian Select; Unused |
| BLAST | Burst Last; Indicate last transfer in bus access |
| BREQI | Bus Request In; EP uses the bus |
| BREQO | Bus Request Out; computer communication interface 382 uses the bus |
| BTERM | Burst Terminate |
| EOT | End Of Transfer; Terminate current DMA |
| DP(3:0) | Data Parity; Unused |
| LBE(3:0) | Byte Enables |
| LHOLD | Local Bus Request; Request the bus from local arbitrator |
| LHOLDA | Local Bus Grant; Local arbitrator grants the bus |
| LSERR | System Error PCI System error interrupt |
| LW_R | Local Write/Read; Low for reads |
| READY | Ready; Bus Master prepared for transaction |
| L_WAIT | Wait; Inserts wait states |

Table 4 sets forth computer communication interface 382 general signals.

TABLE 4

| Name | Pin Function |
| --- | --- |
| CCS | Config Register Select |
| LCLK | Local Bus Clock; 36.0 MHz (max = 50 MHz) |
| LED | Hot-Swap LED, monitor; Unused |
| LINT | Local Bus Interrupt; Used by EP to interrupt PCI Bus |
| LRESET | Local Bus Reset; Reset FPGAs on PCI reset |
| MODE(1:0) | Bus mode; Set to "00" = C Mode |
| USERI | FPGA controllable input signal; Unused |
| USERO | Computer controllable output signal; software reset and pwrdwn mode |
| TEST | Initiate NANDTREE boundary test; Pulled high for test |

Figure 38:
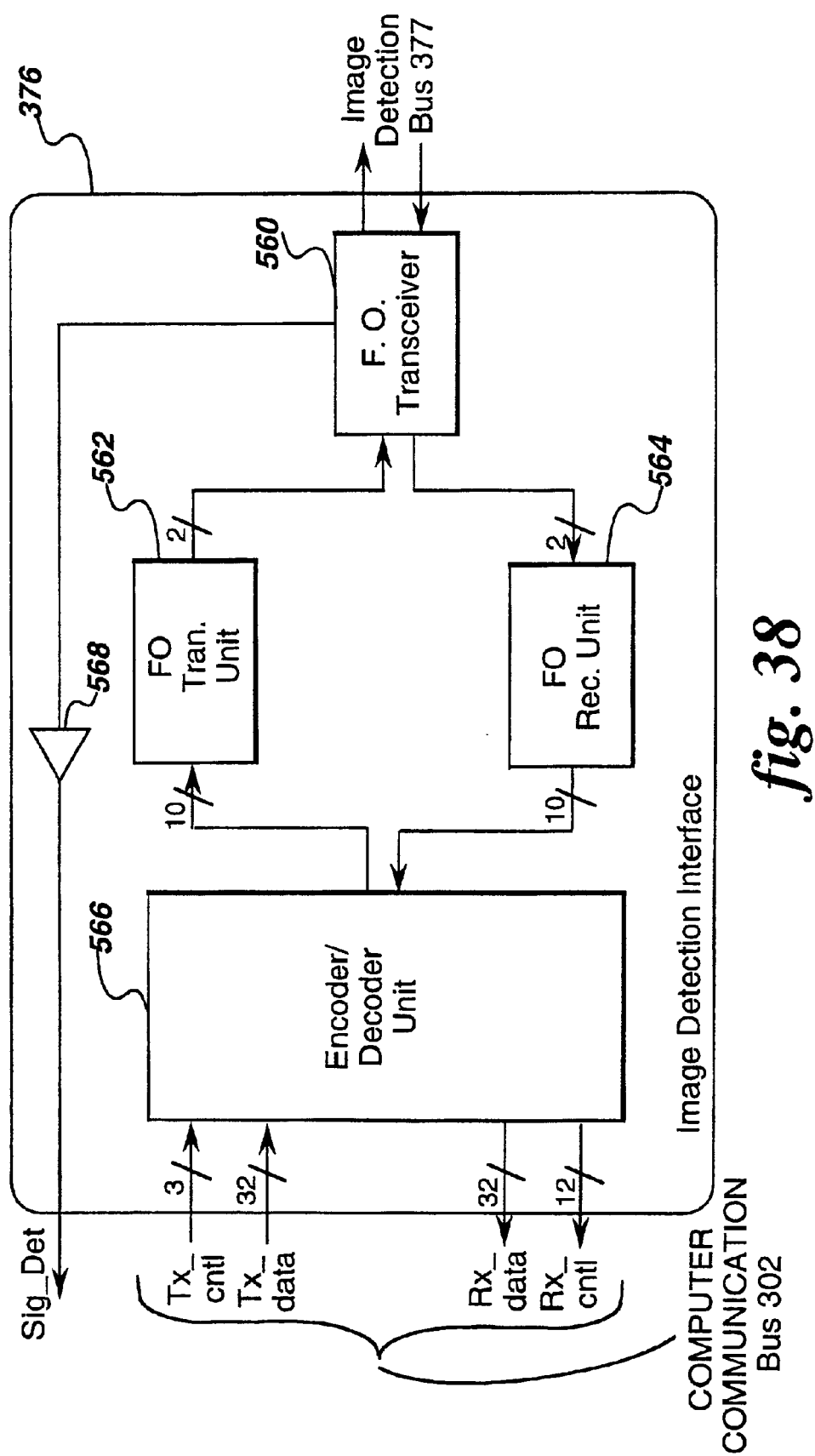
FIG. 38 is a block diagram of a image detection interface.

FIG. 38 is a block diagram of image detection interface 376. DFN 304 supports image detection interface 376, which is capable of transferring data at a rate of 1.25 Gbps from image detection system 112 to EP 374. This interface is a modification of the fiber channel standard (ANSI standard X3T11), which is widely used in commercial high speed RAID disc arrays products. The system clock rate has increased over the prior IDC system, which uses a real time operating system, from 1.0625 GHz up to 1.25 GHz. This change supports an increased image data transfer rate.

Transmission over image detection bus 377 is divided into a hierarchy of layer abstractions, each handling key aspects of a complete Gbit communications system. However, the physical and transmission protocol layers (FC-0 and FC-1 respectively) are relevant because these layers are the layers that have been implemented by image detection system 112. Electronics in image detection system 112 implement the FC-0 and FC-1 standards using a set of three custom ICs and a fiber optic transceiver module.

FIG. 38 is a block diagram of image detection interface 376 on DFN 304. Image detection interface 376 includes encoder/decoder unit 566, fiber optic transmit unit 562, fiber optic receive unit 564, and fiber optic transceiver 560. Buffer unit 568 is connected to fiber optic transceiver 560 and outputs signal detection signal sig_det therefrom. The FC-0 layer defines a full duplex serial communications link operating at 1.0625 GHz. Image detection system 112 deviates slightly from this standard and instead operates at 1.25 GHz.

As illustrated in FIG. 38, the physical layer is comprised of the fiber optic transmit unit 562 chip, fiber optic receive unit 564 and fiber optic transceiver 560. The fiber optic transmit unit 562 accepts a ten bit input at 125 MHz and serializes the input up to a 1.25 GHz transmit rate. The transmitter 562 drives the F/O module over a differential positive emitter-coupled logic ("PECL") interface. Similarly, receiver unit 564 is driven by the PECL outputs of the fiber optic transceiver 560 at the 1.25 GHz rate. The receiver deserializes the input data stream and produces ten bit data at a rate of 125 MHz. The 1.25 GHz transmit clock is generated by fiber optic transmit unit 562 by multiplying a 31.25 MHz reference clock by 40 times using an onboard phase lock loop ("PLL"). Similarly, the deserializer recovers the 1.25 GHz clock from the incoming serial data and divides the 1.25 GHz clock by 40 to generate the 31.25 MHz receive clock.

The fiber channel standard is quite strict concerning the need for precise timing of the reference clock to avoid problems related to jitter noise. A high quality crystal oscillator is therefore used on DFN 304 to ensure a stable a reference clock. Signal integrity for the 1.25 GHz transmit and receive channels is also a potential concern. Transmit and receive chips are placed as close as possible to the fiber optic transceiver module. In addition, these signals are routed on the top layer of the board as micro strip lines to minimize capacitive loading.

The FC-1 layer defines a communications protocol by which packets of data are transmitted and received in 32 bit words at a rate of 31.25 MHz. The FC-1 layer incorporates 8 bit/10 bit encoding as well as cyclic redundancy check ("CRC") processing to ensure data integrity. This layer is also responsible for establishing and maintaining coherent data communication with the device on the other end of image detection bus 377. Each of these functions is discussed further below.

As shown in FIG. 38, the transmission protocol layer in the fiber channel subsystem is comprised of encoder/decoder unit 566. Encoder/decoder unit 566 interfaces to EP 374 over two independent 32 bit data buses: one for transmit and one for receive. Both the transmit and receive data buses operate at the 31.25 MHz word rate. Encoder/decoder unit 566 takes the input data, performs 8 bit/10 bit encoding, then outputs ten bit words to the fiber optic transmit unit 562. Encoder/decoder unit 566 also receives ten bit words from fiber optic receive unit 564 and performs reverse 8 bit/10 bit encoding to output 32 bit receive data to EP 374. In addition to these functions, encoder/decoder unit 566 monitors the state of image detection bus 377 and provides status information to EP 374.

The FC-0 layer transmits and receives data in ten bit words at a rate of 125 MHz. These ten bit words are in fact special characters which are mapped to the 8 bit data that is transmitted and received by EP 374. The reason for this 8-bit/10-bit encoding is to mitigate the effects of PLL wander. Each of the ten bit characters contain a number of high to low transitions such that the PLL in the receive circuit continues to accurately recover the 1.25 GHz transmit clock from the incoming serial data. Encoder/decoder unit 566 takes the incoming 32 bit word, parses the word to successive bytes, and then performs 8 bit/10 bit mapping to generate the output for fiber optic transmit unit 562. Similarly, encoder/decoder unit 566 takes the input from fiber optic receive unit 564, performs decoding, and assembles the resulting bytes into 32 bit words. In addition to the 256 characters that map the 8 bit transmit data, there are a number of utility characters that provide link, framing, and status information. These are discussed in further detail below. In order to further ensure the integrity of the transmitted data, encoder/decoder unit 566 performs CRC processing on the incoming and outgoing 32 bit data.

According to protocol of image detection bus 377, data from EP 374 is transmitted in packets of 4 or more 32 bit words called data frames. Data frames are comprised of data words and special command words called ordered sets. There are typically three types of data frames encountered when communicating with image detection system 112.

FIGS. 33, 34, and 35 are block diagrams of each of three types of data frames. EP 374 and DAP 372 accept and transmit the indicated data frames. An ordered set has a unique 32 bit word defined by a fiber channel standard and is used to communicate specific information to EP 374. Ordered sets are detected by encoder/decoder unit 566 during 8 bit/10 bit encoding and flagged to EP 374 using the CRXCO signal line. When this line goes low, the data presented to EP 374 constitutes ordered sets. Image detection system 112 makes use of a handful of the ordered sets which have been defined by the fiber channel standard. Start of data frame is indicated using either SOFn1, SOFn2, or SOFn3 and end of data frame is indicated using EOFn. When not transmitting useful data, the IDLE ordered set is transmitted.

Figure 39:
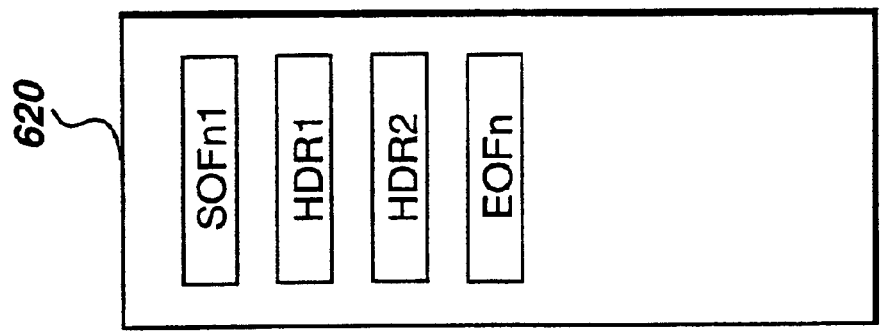
FIG. 39 is a block diagram of a fiber channel command data frame.

FIG. 39 is a block diagram of command data frame 620, which is the simplest type of data frame used. Command data frame 620 is used to send commands over image detection bus 377 to image detection system 112. Once command data frame 620 is received and processed, an acknowledge is returned. This acknowledge is also in the form of a command data frame. The command data frame begins with an SOFn1 and is followed by two 32 bit data words. The first word, HDR1 defines the type of command transmitted. The second word HDR2 provides the argument for the particular command. The data frame ends with the EOFn ordered set character.

Figure 40:
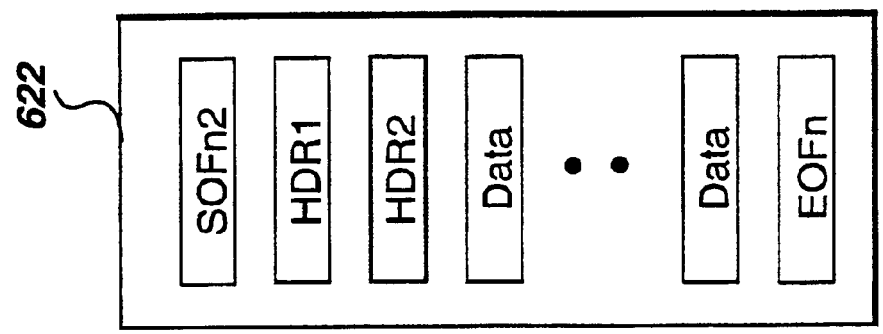
FIG. 40 is a block diagram of a fiber channel image detection data frame.

FIG. 40 is a block diagram of image detection data frame 622. Image detection data frame 622 is similar to command data frame 620 but differs in that the start of the data frame character is now SOFn2, and HDR1 and HDR2 are replaced by a series of 32 bit data words comprising pixel value data such that 528 words are transmitted in a single data frame. When the data frame is complete, the EOFn character is transmitted.

Figure 41:
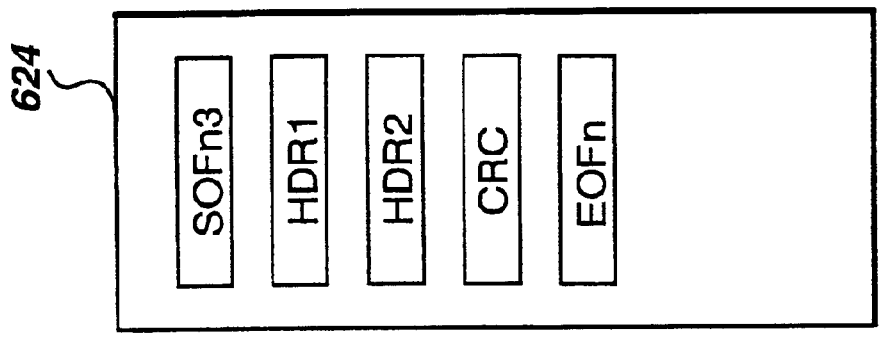
FIG. 41 is a block diagram of a fiber channel image done data frame.

FIG. 41 is a block diagram of image done data frame 624. Image done data frame 622 is used to indicate the end of a complete image and is identical to command data frame 582, except for the start of data frame being replaced by SOFn3 instead of SOFn1.

When power is applied to image detection interface 376, the transmitter and receiver chips begin communicating with the system on the other end of image detection bus 377. Before useful data is transferred across the link, however, synchronization is first established between the two systems. The first step in link synchronization is to properly frame the serial data that is being received by fiber optic receive unit 564. After encoder/decoder unit 566 comes out of reset, encoder/decoder unit 566 asserts the SYNCEN line on the fiber optic receive unit 564, which forces search for a special K28.5 fiber channel "comma" character, which is being transmitted by the system on the other end of the link. Once this character is located, the fiber optic receive unit 564 will word align the incoming serial data to the ten bit boundary and notify encoder/decoder unit 566 using the SYNC line.

Encoder/decoder unit 566 will then monitor the incoming 8 bit data words for known framing characters to determine whether proper communication with the other system has been established. Once the link is good, encoder/decoder unit 566 will deassert SYNCEN. In the current system, SYNCEN is connected to a WRDSYNC line. The WRDSYNC line is also connected to EP 374 and notifies same that link synchronization has been established.

If during typical operation of image detection bus 377, link synchronization is somehow lost (e.g. image detection bus 377 becomes unplugged), encoder/decoder unit 566 will detect that an anomalous situation exists. In this case, encoder/decoder unit 566 will reassert the WRDSYNC lien ("SYNCEN") simultaneously notifying computer 114 that there is a problem and will force the receiver to search for word alignment. Image detection interface 376 will then continue to search for good ten bit characters until synchronization is reestablished.

During the time that the system is attempting to achieve synchronization, EP 374 monitors progress on receive status lines. EP 374 also observes unframed data on the receive data bus to look for special data words (such as the IDLE ordered set), which provide status information on the state of image detection bus 377. If synchronization is not achieved, the control block resets encoder/decoder unit 566 and attempts to lock once more. After two tries if synchronization is not established, an error is reported to computer 114.

Fiber optic transceiver 560 provides media transition for DFN 304 and also outputs a SIGDET signal, which goes low when the receive photo diode in fiber optic transceiver 560 fails to detect optical power for reliable operation. This signal is then output by fiber optic transceiver 560 to buffer 568. This situation typically means that the system on the other side of the link is turned off or the cable of image detection bus 377 has been unplugged. If SIGDET goes low an error is reported to computer 114 so that the operator optionally reconnects the fiber cable or investigates the problem further.

Image detection interface 376 includes a number of control transmit signals set forth in Table 5, setting forth transmit signal assignments below:

TABLE 5

| Name | Pin Function |
| --- | --- |
| CTXD0 | Transmit data bus |
| CTXCLK | Transmit clock; 31.25 MHz |
| CTXC0 | Ordered Set; Low = data; high = control word |
| CTXC1 | CRC; Low = check CRC; high = generate CRC |
| CTXCERR | CRC Error; High = CRC error detected |
| CTXWREF | Reference word clock |
| RESETN | Reset Endec; Active low |
| LOOPEN | Loop Enable; Loop the Transmitter to the Receiver |
| REFCLK | Reference Clock; Used to lock local PLL |
| SIGDET | Signal Detect; When low indicates no laser input |

Table 6 below sets forth receive signal assignments.

TABLE 6

| Name | Pin Function |
| --- | --- |
| CRXD0 | Receive data bus |
| CRXCLK | Receive clock; Recovered 31.25 MHz clock |
| CRXS0 | Ordered Set; Low = data; high = control word |
| CRXS1 | CRC error flag; High indicates CRC error detected |
| CRXS2,3 | Line Status |
| CRXS4,5 | Line State ID bits |
| RXERROR | Receive Error; High indicates bad receiver data |
| WRDSYNC | Word Synchronization; Low indicates sync acquired |

Figure 42:
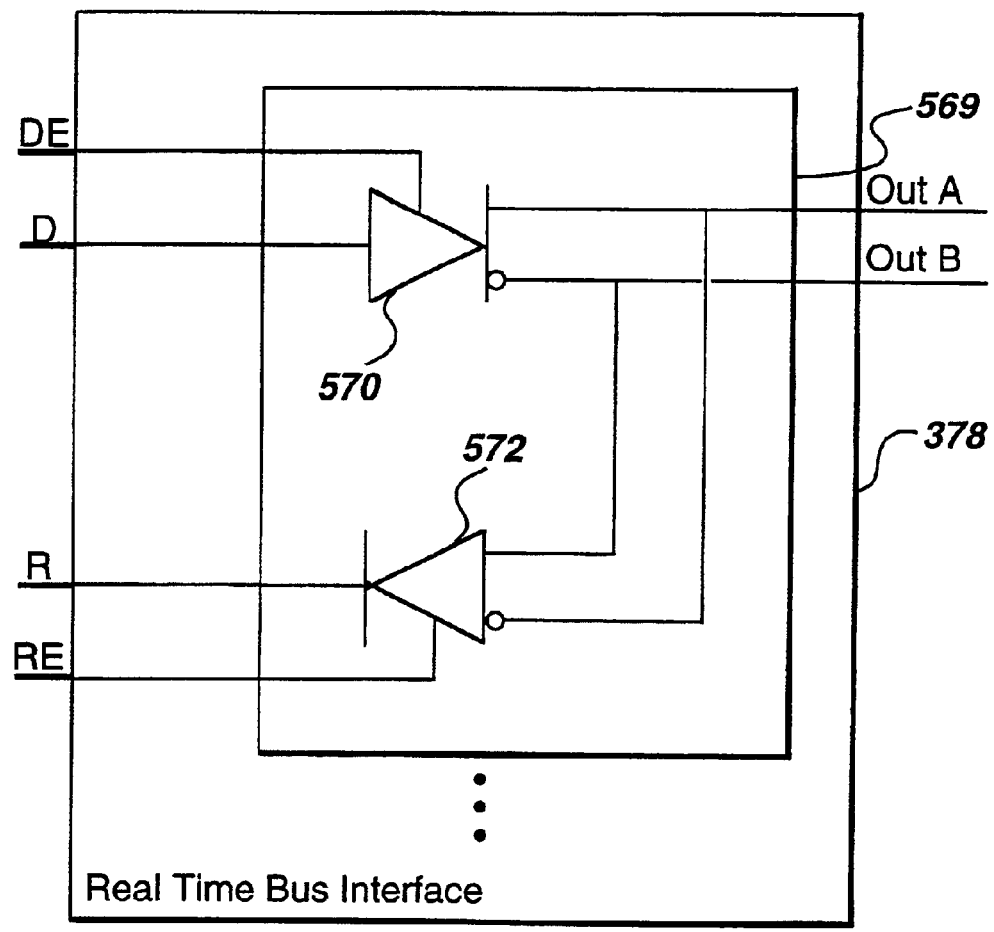
FIG. 42 is a schematic view of a single channel of a real time bus interface.

FIG. 42 is a schematic view of a single channel of real time bus interface 378. DFN 304 communicates with the radiation generation system 109 over a GE Medical Systems ("GEMS") standard through real time bus interface 378. This standard includes of a group of full duplex differential signal lines operating at 0 and 5 V levels. There are twelve channels on real time bus 379, with more channels being optionally added. The Institute of Electrical and Electronics Engineers ("IEEE") maintains a standard known as RS-485, which is typically used for high speed SCSI interface products. Real time bus interface 378 implements a subset of IEEE RS-485 and uses transceiver chips which have been designed to meet RS-485. One channel 569 of a RS-485 transceiver for real time bus interface 378 is particularly illustrated. Data is input on the D line and buffered by way of transmit buffer 570 to a differential output on out A and out B. Unlike emitter coupled logic ("ECL"), these outputs have a large signal differential where for example, if out A is 5 V then out B will be 0 V (and visa versa). The output drivers are enabled using the DE line. Data is received by receive buffer 572 driving the R output line, which also effects differential to single-ended conversion. The receiver is disabled using the RE line. Monitoring the driver output with the receiver provides useful redundancy for self test.

Real time bus interface 378 has three RS-485 channels on one device. Individual control of the transmit output enable line is provided while control of the receive output enable line are ganged together on one pin. The part therefore has a three channel input, output and control bus for a total of 9 basic signals, which is routed to EP 374. Each channel is capable of driving 60 mA and operates at up to a 10 MHz (30 nsec pulse). Real time bus interface 378 includes a total of 36 basic signal lines, which are routed from EP 374 to the transceiver chips to control all 12 channels. Real time bus 379 is made available external to the DFN 304 card using a 31 pin female micro miniature D type connector. Voltage suppressors are also included as part of the real time bus interface 378 to ensure that the transceivers will not be damaged if a connecting cable to radiation generation system 109 is unplugged with power being applied to DFN 304 or when undesired transients are generated by radiation generation system 109.

Figure 43:
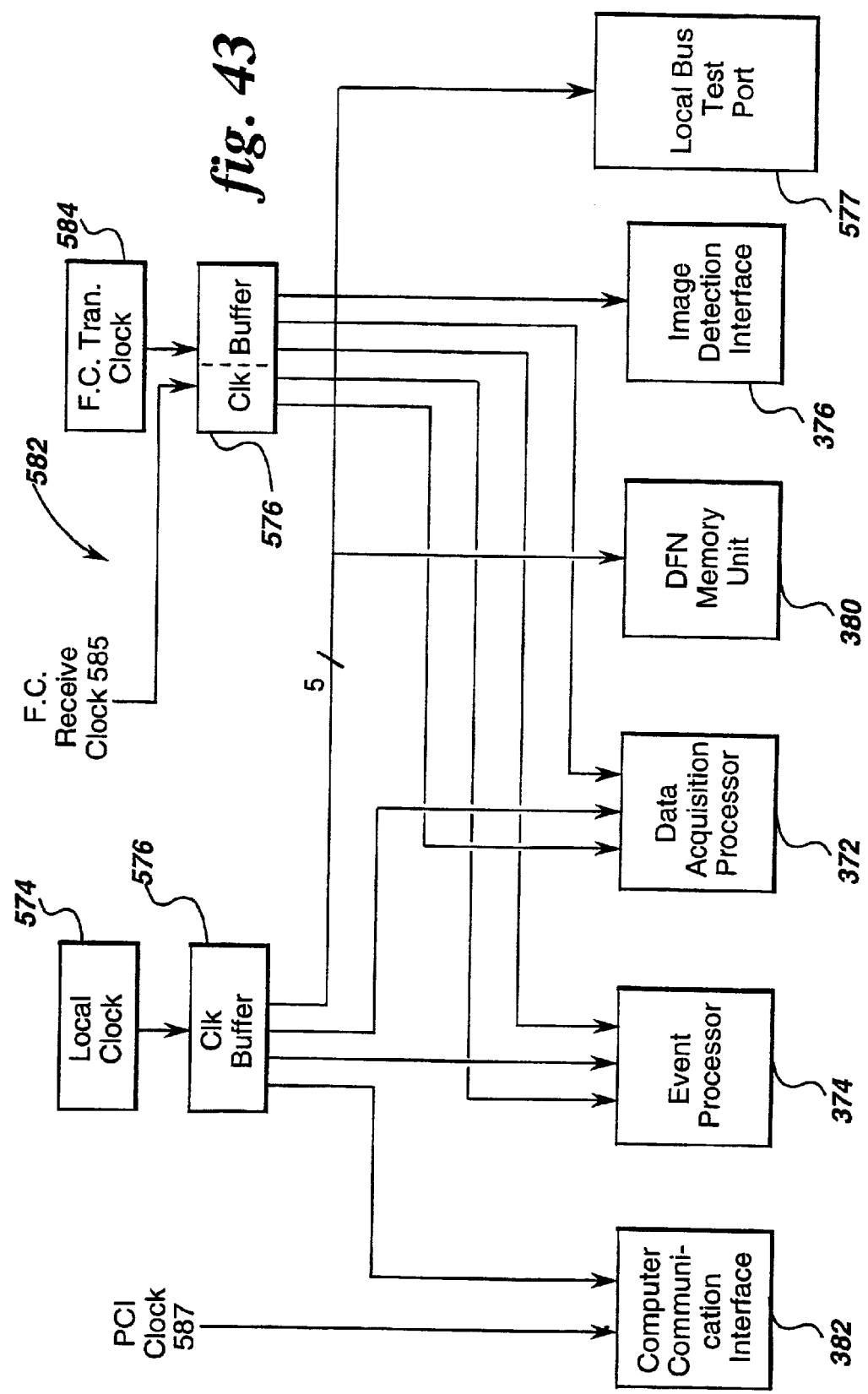
FIG. 43 is a block diagram of a DFN clocking system.

FIG. 43 is a block diagram of DFN clocking system 582. Clocking system 582 is designed to interface between a number of different modes of communication. In order to accommodate these interfaces, four different clocks are used. Distribution and generation of these clocks is particularly illustrated.

As illustrated in FIG. 43, fiber channel transmit clock provides image detection bus 377 with transmit communication at 31.25 MHz. Fiber channel transmit clock 584 is used as a reference clock for fiber channel receive and transmit circuit PLLs. A crystal oscillator on DFN 304 generates fiber channel transmit clock 584. This clock has a 50% duty cycle with no greater than 10% deviation. The jitter noise on this clock is less than 40 ppm.

Fiber channel transmit clock 584 is buffered using clock buffer 576 and is distributed to image detection bus 377 circuitry as well as to EP 374, DAP 372 and a FC test port (not shown). Fiber channel transmit clock 584 is used in EP 374 to drive the FC transmit logic directly. Clock 384 is routed to one of the two available global clock pins on EP 374. On DAP 372, fiber channel transmit clock 584 is routed to one of the dedicated global input signals.

Fiber channel receive clock 585 is recovered from the incoming fiber channel signal data by a phase lock loop located in fiber optic receive unit 564. This clock has been generated on the other side of image detection bus 377 and is a 31.25 MHz clock that is asynchronous to the 31.25 MHz transmit clock. Fiber channel receive clock 585 is buffered by one of the two clock buffer chips and is then distributed to DAP 372, EP 374 and a FC test port. On DAP 372, fiber channel receive clock 585 is routed to one of the available global clock inputs. This configuration allows the clock to be used for the on-chip FIFO which facilitates a rate change from image detection bus 377 to local bus 384 for storage of data in DFN memory unit 380.

The local clock 574 is generated using a crystal oscillator on DFN 304 and provides a main clock for all devices interacting through the local bus 384. This clock operates at 36.0 MHz. Computer communication interface 382 operates up to 50 MHz, and therefore sets an upper limit on local bus clock speed. The local bus clock speed is selected to be slightly higher than computer communication bus 302 clock speed to improve PCI bus utilization.

The local clock 574 is buffered by one of the two clock buffer chips and is routed to computer communication interface 382, DAP 372, EP 374 and a local bus test port 577. Local clock 574 is routed to one of the two dedicated clock inputs on DAP 372 and EP 374 for optimum timing performance. In addition to all of the local bus devices, this clock is buffered and routed to all of SRAM chips on DFN memory unit 380.

PCI clock 587 is generated by a PCI bus arbitrator on computer 114 and is made available to DFN 304 on the PCI card edge connector. This clock is used exclusively by computer communication interface 382 and is not buffered for distribution. Each of the above described 31.25 MHz and 36.0 MHz clocks is buffered through one of two clock buffer chips, namely clock buffers 576.

Figure 44:
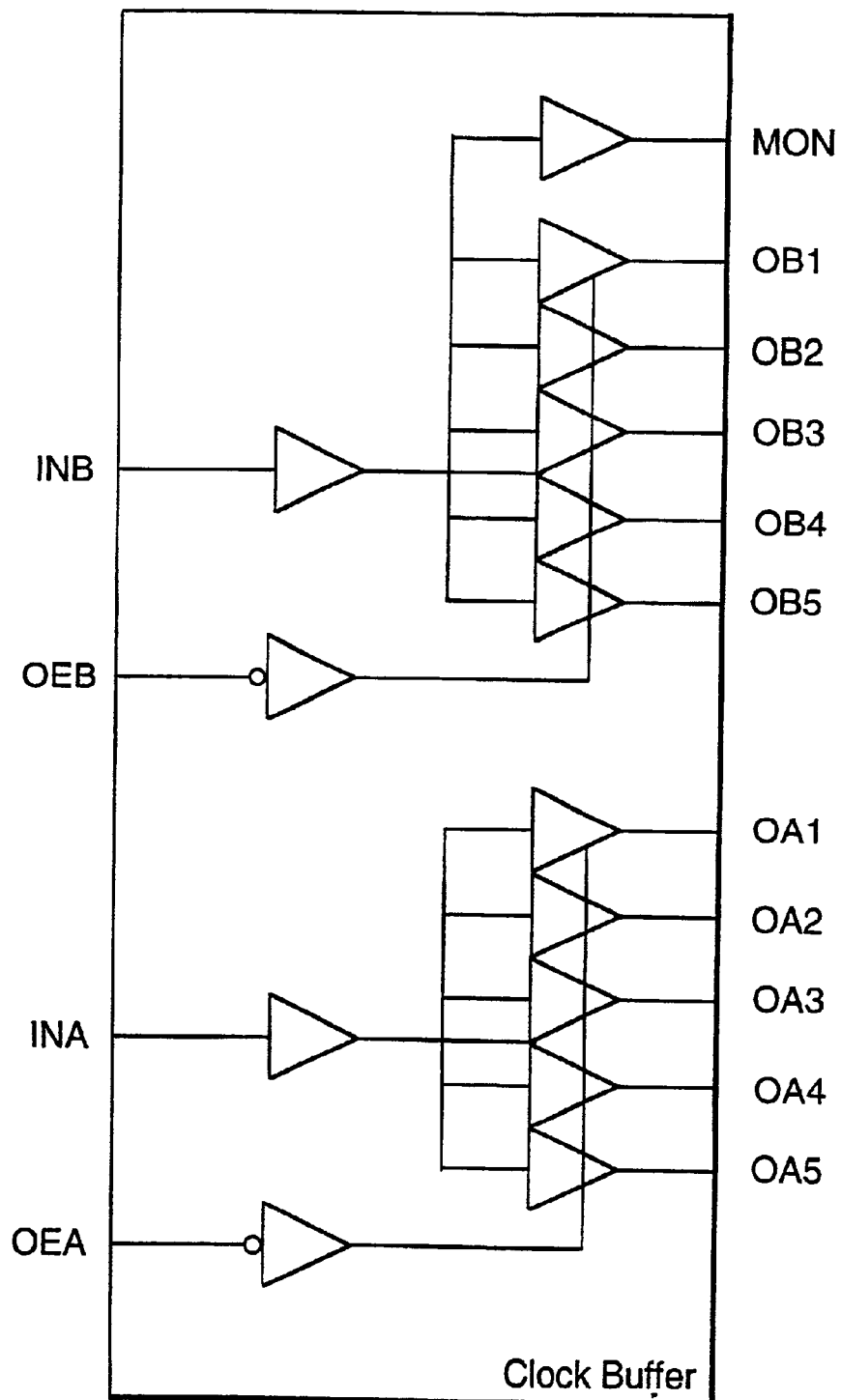
FIG. 44 is a block diagram of a clock buffer.

FIG. 44 is a block diagram of clock buffer 576. Clock buffer 576 includes two banks of five buffers with separate output enable controls on each. When disabled, the outputs of the clock buffer chips are driven to high impedance. Controls for these outputs are routed from the USERo signal, from computer communication interface 382, to disable the local clock 574 through software and from EP 374 to disable the FC clocks through firmware. Local clock 574 is buffered directly through a driver which cannot be disabled. This configuration allows the chip to operate in standby mode while the rest of the board is unclocked and therefore powered down.

Reset of DAP 372 and EP 374 of DFN 304 into a known state occurs on power up, during debug, and during normal operation if anomalous behavior occurs. Although some devices are designed to boot to a known state on reconfiguration, there is no way to guarantee that this is the desired initial state for proper operation of DFN 304. Moreover, initial reset of DFN 304 over computer communication bus 302 potentially produces undesirable results because DFN 304 will most likely configure well ahead of the computer operating system, and also has control of both image detection system 112 and radiation generation system 109. Thus, on-board reset circuitry is provided to bring DFN 304 to a well defined state. DFN 304 is reset on power-up and through software or hardware as described in this section.

Figure 45:
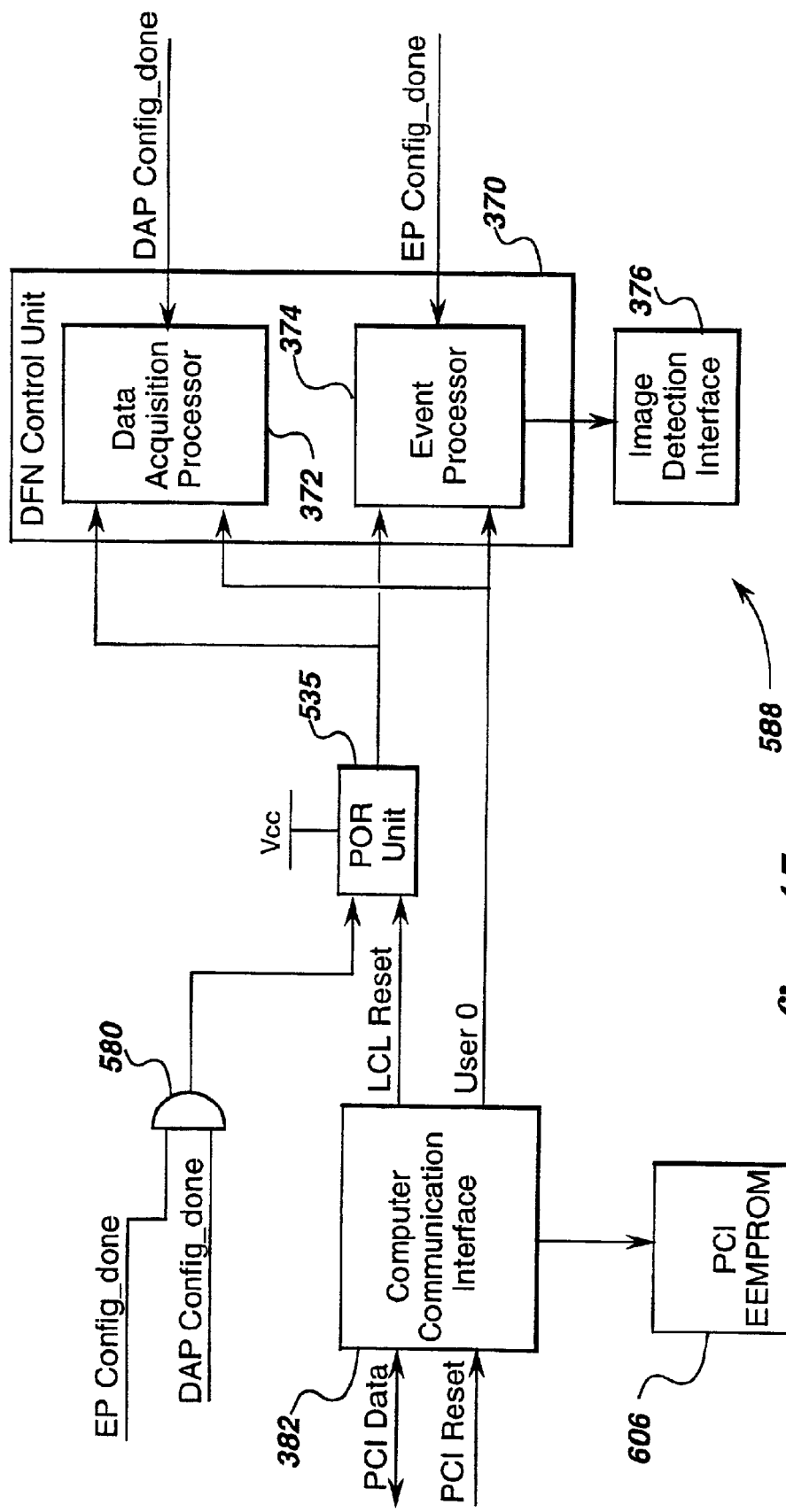
FIG. 45 is a schematic diagram of a power on reset system.

FIG. 45 is a schematic diagram of power on reset system 588. On power-up, DFN 304 is brought to a known state using active circuitry. As illustrated in FIG. 45, a power on reset unit 535 that DAP 372 and EP 374 are held in reset for at least 140 msec after power has stabilized, and such that the FPGAs have been successfully configured (data loaded from eeprom into FPGA memory). The outputs of the FPGA configuration circuitry (EP_config and DAP_config) are used to determine that both FPGAs have configured successfully before reset to the devices is released. Reset is held low an additional 140 msec after power has stabilized and both FPGAs have configured successfully. This also ensures that both FPGAs begin functioning simultaneously since they may come out of configuration at different times.

The reset signal from POR unit 535 is routed to DAP 372 and EP 374, and is connected to one of the four dedicated input lines. These dedicated input lines are accessible to all logic on each FPGA device. The firmware is coded for asynchronous reset based on the state of this global input line.

In addition to reset on power-up, DFN 304 resets when a computer reset button is pushed. As shown in FIG. 45, this functionality is provided through computer communication interface 382 using the local bus reset output pin. This pin is held low whenever the PCI RST# line is asserted. When PCI RST# is asserted, computer communication interface 382 resets to a default configuration as specified by PCI eeprom 606. In addition, the reset signal propagates out to all devices on local bus 384 through the local bus reset pin. This signal is routed to EP 374 and DAP 372 and is connected to the second of four available dedicated inputs to these devices. As in power on reset, these global inputs are used for asynchronous reset in the firmware for the two devices. These signals are also logically ORed in firmware with the power on reset signal.

Software (USERo) reset is used for debug of DFN 304 and firmware. Software (USERo) is useful to be able to reset DAP 372 and EP 374 circuitry independent of computer communication interface 382. This capability is provided through the software reset function. Computer communication interface 382 is programmable to change the state of the USERo dedicated line by writing a bit to a register location. As illustrated in FIG. 45, this line is connected to the third available global input line on DAP 372 and EP 374, and is optionally used to reset these devices without resetting computer communication interface 382. The issuing of a "PCI reset" resets both computer communication interface 382 and the FPGAs and is undesirable when attempting to debug a complex problem involving both computer communication interface 382 and the FPGA devices. Additionally, the ability to reset DFN 304 through software directly is useful if anomalous operation occurs. For test and debug on the bench, any of a number of Test Bus signals are used to reset the FPGA devices together or separately. This functionality is coded into the firmware as asynchronous reset on a user I/O pin input signal.

There are three different power supply domains on DFN 304: 5 V, 3.3 V, and 2.5 V. Power for the 5 V devices is taken directly off of the PCI connector. There is one 5 V power plane. The major devices operating off of this supply are the real time bus interface 378 and fiber channel interface 376. The supply is decoupled using two 10 V 47 $\mu$F Tantulum and one 0.1 $\mu$F surface mount capacitors at the connector. Power to the fiber optic transceiver module is decoupled using two pi network type filters in order to prevent extraneous coupling from the module back into the supply. Power for the 3.3 V devices on the card is taken directly off of the PCI connector. There is one 3.3 V power plane. The major devices operating off of this supply are computer communication interface 382, the SRAM Buffer memories, and the two FPGA devices. The supply is decoupled using two 10 V 47 $\mu$F Tantulum and one 0.1 $\mu$F surface mount capacitors at the connector. Power for the 2.5 V devices on DFN 304 is generated locally using a 2.5 V regulator. There is one 2.5 V power plane. The major devices operating off of this supply are the FPGAs (core logic). The supply is decoupled using two 10 V 47 $\mu$F Tantulum capacitors at the output of the regulator. The sense line on the regulator is connected to the 2.5 V power plane near the center of the FPGA devices in order to accurately monitor the supply voltage. For applications using multiple detector framing nodes in a single chassis or for applications having strict power budgets (e.g. a battery operated PC), DFN 304 supports a power down mode of operation.

In reset power down mode, the FPGA and image detection bus 377 devices are held in reset by computer communication interface 382 USERo signal until such time as computer 114 updates this signal using a PCI write to computer communication interface 382. With this method, clock lines to all devices are left toggling, however dynamic logic on these chips is not switching. Computer communication interface 382 does not contribute significantly to the overall power budget on the card. Thus, computer communication interface 382 is left fully operational during power down mode. In clock power down mode, the local bus and fiber channel clocks are disabled by asserting the output enable control lines on the clock buffer chips. There are currently unpopulated jumpers on the board that connect these control lines to the USERo signal from computer communication interface 382. Populating these jumpers selects the clock power down mode as the preferred method for power savings for the card.

In order to verify proper function of key systems on DFN 304, Built In Self Test ("BIST") firmware routines are included. These routines are run automatically on power-up and report any errors detected to computer 114 once communication is established. The tests will also be available to be run through direct commands from computer communication bus 302.

The fiber channel loopback test is designed to test image detection interface 376. The test is initiated by EP 374 by asserting the LOOPEN signal line. This signal line shorts fiber optic transmit unit 562 outputs to fiber optic receive unit 564. This closes the loop through encoder/decoder unit 566 back to EP 374. EP 374 then attempts to send an FC command over the link and monitors the return bus for an expected echo. The format of the command words includes alternating 1 and 0 patterns and is designed to test the transmit and receive bus lines for shorts and opens. If the correct pattern is received, the test passes. The results are reported to computer 114. This test is does not verify the fiber optic transceiver module but is optionally qualified with a setting that causes the test to run without asserting LOOPEN. In this case, a short length of fiber cable is looped from the module output back to its input to close the loop. This test is available for debugging of DFN 304.

The real time bus interface 378 is also tested for integrity of the transceiver chip set electronics. This test is performed by EP 374 by writing data out to the devices on the transmit bus and then monitoring the receive bus for the same data. Since the chips have their receivers and transmitters for each channel wired together, anything transmitted will automatically be received. The test includes a series of words of alternating 1 and 0 patterns which are designed to check for opens and shorts on the transmit and receive data bus traces and chip pins. If this test is successful, it will also show that the chips themselves are functioning correctly. This test is further augmented to test the traces out to a 31 pin miniature D connector as well as the connector solder joints. A special external test connector shorts all even channels to all odd channels. Data is transmitted on the even channels and monitored on the odd channels and visa versa. This test shows that the entire communication chain out to the connector is working. This test is generally not run automatically and is available for debug of real time bus interface 378.

A RAM Built In Self Test ("BIST") is also provided for DFN 304. DFN memory unit 380 includes ten 8 Megabit SRAM devices, which together contribute the majority of connections to DAP 372. There is the possibility that these devices might have been damaged during board handling and therefore they need to be tested using an exhaustive RAM BIST test. RAM BIST includes three related tests, all of which are conducted by firmware in DAP 372. In the first test, odd and even memory locations are filled with alternating 1 and 0 patterns and then read out and checked. In the second test the odd and even values are reversed. In the third test, the value of the address of a particular location is written into that location. Once the entire DFN memory unit 380 has been filled, the data is read out and compared to the original. These three tests verify that every bit of SRAM on the card is good and will also check for shorts on traces and between pins on the SRAM chips and on the majority of pins on DAP 372.

DFN 304 has built in test and monitoring features. Dedicated test ports, jumpers, test points and temperature monitoring are used for observeability. Test ports facilitate test and debug of DFN 304, and a large number of test points are routed to miniature test ports for direct access. In particular the local bus 384, the internal bus connected to image detection bus 377, and the bus that connects DAP 372 and EP 374 have been brought to test ports. Daughter boards, with bus transceivers on them, provide high speed monitoring of signals on these lines without significantly loading them. These buses are used when testing EP 374 and DAP 372, which are FPGA devices and therefore not probed directly. The same is true for computer communication interface 382, which is a fineline surface mount part and difficult to probe. Test clips do exist for some of the devices on the board, but dedicated test ports simplify access.

Figure 46:
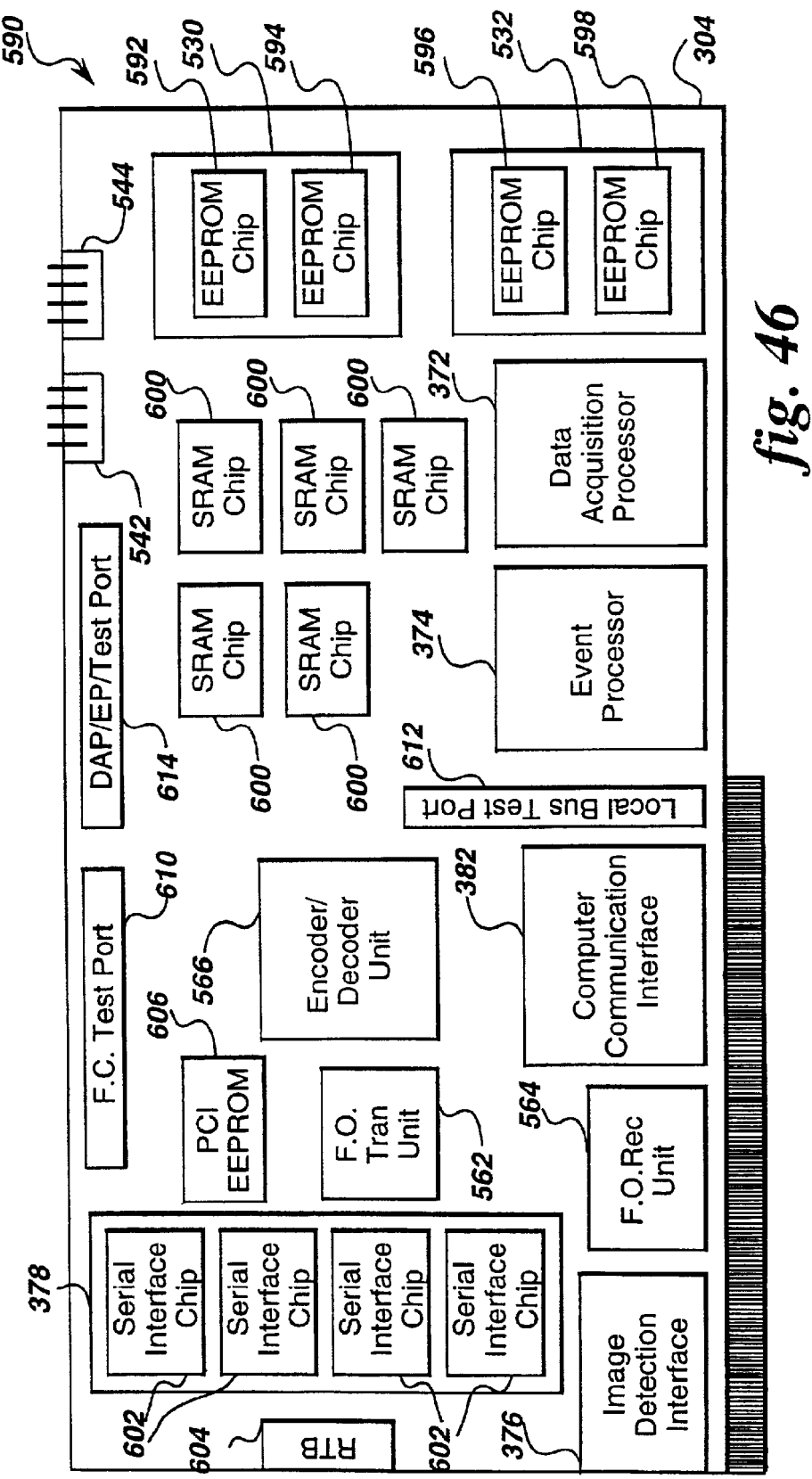
FIG. 46 is a block diagram illustrating chip placement on a physical PCI card of a detector framing node.

FIG. 46 is a block diagram illustrating chip placement on the physical PCI card 590 of detector framing node 304. Due to the complex electrical layout, and limited board space available for PCI cards, physical placement of chipset electronics on physical PCI card 590 is considered. Placement of test ports, with respect to other devices on physical PCI card 590 is also incorporated as shown.

As illustrated in FIG. 46, five SRAM chips 600 are placed on a single side of physical PCI card 590. As set forth above, a pair of SRAM chips 600 are used to form each frame buffer memory unit 380 (see FIG. 18). Thus, for each frame buffer memory unit 380, one SRAM chip 600 is placed on a first side of physical PCI card 590, while another SRAM chip 600 is placed on a second side. In this manner, most address and data lines are shared thereby minimizing routing on the physical PCI card 590. Furthermore, DAP eeprom unit 530 is physically comprised of eeprom chips 592 and 594, while EP eeprom unit 532 is comprised of eeprom chips 596 and 598. As illustrated, JTAG1 port 542 and JTAG2 port 544 are physically located on an edge of physical PCI card 590. Real time bus interface 378 is comprised of four interface chips 602 to implement protocol with the real time bus 379 through real time bus connector 604. Computer communication interface 382 is programmed by PCI eeprom 606, which is a separate circuit element. As illustrated, each of fiber optic transmit unit 562 and fiber optic receive unit 564 are separate circuit elements on physical PCI card 590.

Fiber channel test port 610 is placed on physical PCI card 590 for signal monitoring. All fiber channel transmit and receive data bus signals, as well as the status signals and send and receive clocks, are routed to fiber channel test port 610. Local bus test port 612 receives all local data and address bus signals. In addition, all control signals for local bus 384 have been routed to local bus test port 612. DAP/EP/Test port 614 includes a total of 50 lines, including dedicated user I/O pins on DAP 372 and an additional 50 lines on EP 374. The lines from DAP 372 and EP 374 have been tied together and routed to DAP/EP/Test port 614. These signals provide monitoring of signals internal to the FPGA devices. They also constitute an additional dedicated communications bus between DAP 372 and EP for integrating additional functionality.

For convenience in board test, a group of test points are also brought out to be readily accessible. These points are identified in this section. These are isolated points which are not related to the test bus ports, and not particularly illustrated.

Temperature monitoring is provided to prevent thermal runaway and for statistical tracking of card operation. Three temperature monitoring devices are incorporated on physical PCI card 590. These devices sit underneath the FPGAs, image detection bus 377 and the SRAM memory buffers. The devices are read over an I2C bus and their outputs are available to computer 114 by way of read out from temperature monitor registers on DFN 304. Additionally, these devices are monitored directly by the FPGAs themselves at regular intervals. If the temperature is observed to rise above a prescribed limit, DFN 304 is automatically placed in powerdown mode after a temperature overflow error is communicated to computer 114.

A board revision code is provided on DFN 304 for tracking purposes. The board revision code is embedded in the physical board artwork. The code includes 8 user I/O pins routed to EP 374 which are either tied high or low directly to yield a revision number. This revision number is then be read directly by computer 114 by interrogating a board revision number register, which is mapped to revision code pins.

A unique board serial number is also provided for tracking. Every board produced will have a unique serial number. This serial number is generated using a Si Serial Number IC, by Dallas Semi.: DS2401Z. The serial number IC is interrogated on a single line, which is connected to EP 374. The resulting serial number is stored in a register EP 374, which is readable directly by computer 114.

Figure 47:
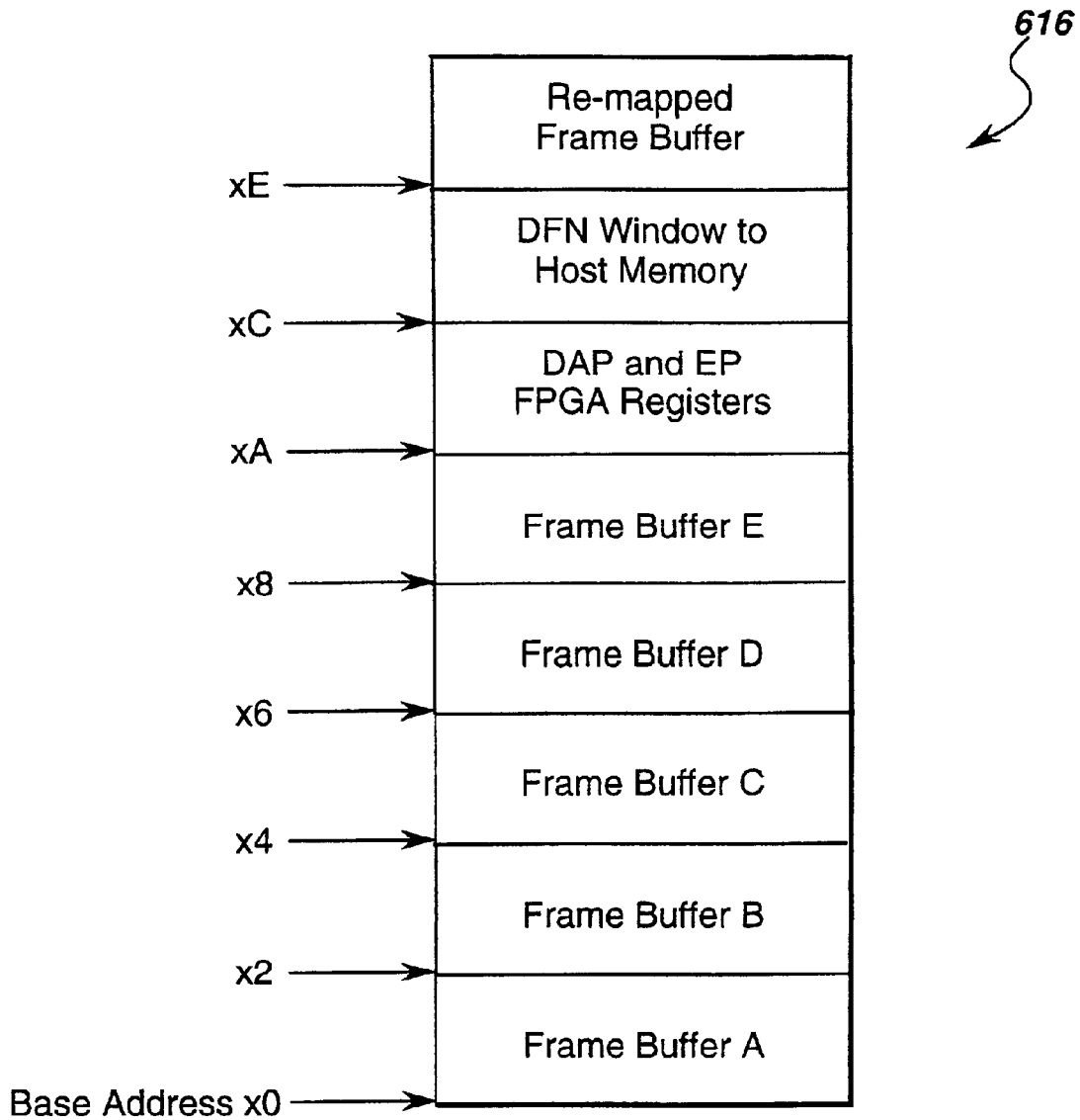
FIG. 47 is a block diagram of a mapping of 16 MByte PCI address space.

FIG. 47 is a block diagram of a mapping 616 of 16 MByte address space. DFN 304 is included in physical PCI card 590, which in turn is placed in a PCI slot in computer 114. DFN 304 occupies 16 MByte of address pace on PCI buss 302. The PCI controller in computer 114 determines the base address of DFN 304. The 16 MBytes in the PCI address window are organized shown in FIG. 47. Frame buffers A–E are the 2 MByte memories on DFN 304. The location of registers on the EP 374 and the DAP 372 begin at 24 bit hexadecimal address xA00000 and xB00000, respectively. DFN 304 is controlled by two mechanisms: 1) writing to registers in the EP 374 or DAP 372 or, 2) by sending commands to the EP 374. The registers on the EP 374 and DAP 372 can be accessed by the user program through the acquisition DLL 313. EP firmware registers are shown in Table 7 below.

TABLE 7

| Name | Description |
| --- | --- |
| EP_REV_ID | Current revision level of EP 374 |
| EP_STATE | Current state of EP state machine (and DFN) |
| DFN_REV | Current revision level of DFN 304 |
| EAB_SIZE | EAB memory block size in bytes |
| RT_BUS | Current state of RTB (state of each bit and direction of each bit) |
| STAT05R | RESERVED STATUS REGISTER |
| CUR_QUEUE | Currently executing detector queue command |
| LOOP INDEX | Current state of first nested loop index in event queue |
| SSN_NUM1 | Silicon serial number of DFN board (most significant bytes) |
| SSN_NUM2 | Silicon serial number of DFN board (least significant bytes) |
| ACK1 HDR1 | returned from detector |
| ACK2 HDR2 | returned from detector |
| ERRORQUEUE | Errors relating to queue execution (set by DFN cleared by computer) |
| HOST_FLAGS_REG | Queue register to send interrupts to computer (set by DFN learned by computer) |
| ERROR_FC_EP | Fiber channel error register (set by DFN cleared by computer) |
| EP_ENABLE_REG | Enable bit mask for circuits in EP (set by DFN cleared by computer) |
| Cmd_0Par | First DFN command parameter |
| Cmd_1Par | Second DFN command parameter |
| Cmd_2Par | Third DFN command parameter |
| Cmd_3Par | Fourth DFN command parameter |
| RT_BUS_CONFIG | Real time buss configuration |
| RT_BUS_SER_OUT | Data to be serialized and put out on real time bus serial bit |
| HOST_FLAGS_IN | Used to send flags between application and queue |
| AUTOSCRUB_DELAY | Autoscrub delay (2 μsec intervals) |
| PARAM_BASE | Base address of queue variables in EAB memory |
| DBELL_MASK | Specification of which doorbell types are allowed |
| LED_STATE | Register to control LEDs on DFN |
| CMD_TIMEOUT | Timeout for command executions (2 μsec intervals) |
| DET_TIMEOUT | Timeout for detector responses (2 μsec intervals) |
| WAITF_TIMEOUT | Timeout for wait on flag commands in queue (2 μsec intervals) |
| DMA_CMD | Used to specify some of the parameters for DMA |
| DMA_MODE | Used to specify some of the parameters for DMA |
| CMD_REG | Command register (register on EP for commands) |

The DAP 372 includes the DAP control unit 521 for maintaining control over the DFN 304 and also has a plurality of error registers for reporting error conditions to host computer 114. Table 8 shows the DAP registers and their accompanying description.

TABLE 8

| Name | Description |
| --- | --- |
| DAP_REV_ID | Current revision of the DAP processor FPGA code |
| DAP_STATE | Current state of the DAP finite state machine |
| RES_LOG_STAT_A | Status register for response log buffer A |
| RES_LOG_STAT_B | Status register for response log buffer A |
| LAST_WRTN_DFN | Ordinal position pointer of the last buffer written by DFN 304 |
| DFN_IMG_STAT | Number of images and detector syncs trapped by firmware |
| IMAGE_NUMBER | 32 bit image counter |
| TIMER_COUNT | 2 μsec timer counter |
| NUM_WRAPS | Number of wraps of timer count |
| SEQUENCE_ID | Current sequence (set by computer) |
| DAP_STAT0AR | RESERVED STATUS REGISTER |
| DAP_STAT0BR | RESERVED STATUS REGISTER |
| DAP_ERR0R | Error register (set by DFN, cleared by computer) |
| BIST_ERR BIST | Error register (set by DFN, cleared by computer) |
| RES_LOG_FULL | Response log has been filled by DFN (set by DFN cleared by computer) |
| DAP_ENABLE_REG | Enable bit mask for circuits in DAP 372 (set by DFN 304 cleared by host computer 114) |
| SIZE_RES_LOG | Response log buffer memory size in computer memory |
| BASE_LOG_A | Physical address of response log buffer A in computer memory |
| BASE_LOG_B | Physical address of response log buffer B in computer memory |
| TOT_IMG_SIZE | Specifies the size of the detector panel |
| NUM_BUFFERS | Number of entries in image buffer list |
| IMG_BUF_BAS_ADR | Physical address of image buffer address list |
| END_QUEUE_PTR | End of queue pointer (circular queue of image buffers on computer) |
| ROI_ORIGIN | Specifies the upper right hand corner of region of interest |
| ROI_SIZE | Specifies the size of region of interest |
| DMA_CHK | Sets window of allowed DMA addresses |
| PANEL_SIZE | Specifies the panel size |
| GEN_DATA | Specifies the pattern if the system is in generate data mode |
| READOUT_SIZE | Specifies the size of the detector panel |
| RL_GEN_FLAGS | Flags which enable various response log types |
| DMA_CONFIG | DMA configuration register |
| DAP_PARAM15R | RESERVED STATUS REGISTER |

Host computer 114 issues a plurality of commands to DFN 304, which are received and interpreted by PCI command interpreter 462 in EP 374. All commands to DFN 304 are executed by writing a 32 bit longword to the single hexadecimal address location xA00200. The command issued is specified by the 8 most significant bits ("MSBs") of the longword. Supported commands are listed in Table 9 below. Each command has up to 24 bits of parameter space to specify operation of the command. Additionally, four registers on DFN 304 are reserved for extra parameter space (command parameter registers). If the command parameter registers are used, these parameters are loaded before command execution. The number of parameters used for a specific command is dependent on the command issued. Each command is described hereinafter.

Upon issuance of a command, DFN 304 will attempt to execute the command. The steps that command interpreter 462 will take are:

1. The command will be decoded and determined if it is a recognized command.
2. The command will be tested for validity depending on the top-level state of DFN 304.
3. The command will be issued to the sub-block on either the DAP or the EP responsible for the function.
4. A command timeout counter will be set and started.
5. Command interpreter 462 will wait until either the executing sub-block executed the command or until the command timeout signal is asserted.

6. The command issued will be copied into mailbox register 0 on computer communication interface 382.

7. Results of the command are copied into mailbox registers 1 through 4 on computer communication interface 382.

8. At least one bit in the doorbell register on computer communication interface 382 will be set indicating that the command execution is complete and the DFN 304 can be issued another command.

Commands recognized are listed in Table 9 as follows:

TABLE 9

| Command | Description |
| --- | --- |
| Get status | Take a snapshot of certain status variables |
| Run BIST | Execute one or more of the Built in self tests |
| Restart DFN | Issue a soft reset to selected functional blocks |
| Download EAB memory | Write between 1 and 16 Bytes to the EAB memory |
| Read back EAB memory | Read between 1 and 16 Bytes of EAB memory |
| Start queue | Begin executing the detector and x-ray event queues |
| Abort queue | Abort the execution of detector and x-ray event queues |
| DIAGNOSTIC mode | Make a state transition to top level state DIAGNOSTIC |
| NORMAL mode | Make a state transition to top level state NORMAL |
| TEST mode | Make a state transition to top level state TEST |
| Reset timer | Reset the timer |
| Abort DMA | Abort currently executing DMA |
| Setup DMA | Setup DMA on DFN 304 |
| Access Local Bus | Perform a read or write on DFN 304s local bus |
| Send Command | Send a command directly to the detector control board |
| FC RCV Snapshot | Take a snapshot of the fiber channel receive bus |
| Switch RL buffer | Switch between response log buffer A and B |
| Disable Function | Disable one or more explicitly enabled functions of DFN 304 |
| Generate Error | Generate an error to test command processor and driver |
| Host Flag | Computer processor sends a flag to event queue |
| Unimplemented | A dummy command that will not be implemented in DFN 304 to test the command processor |

Each command has a unique command code. They are listed for the individual commands in the tables below. All commands are executed in one or more states of DFN 304.

Figure 48:
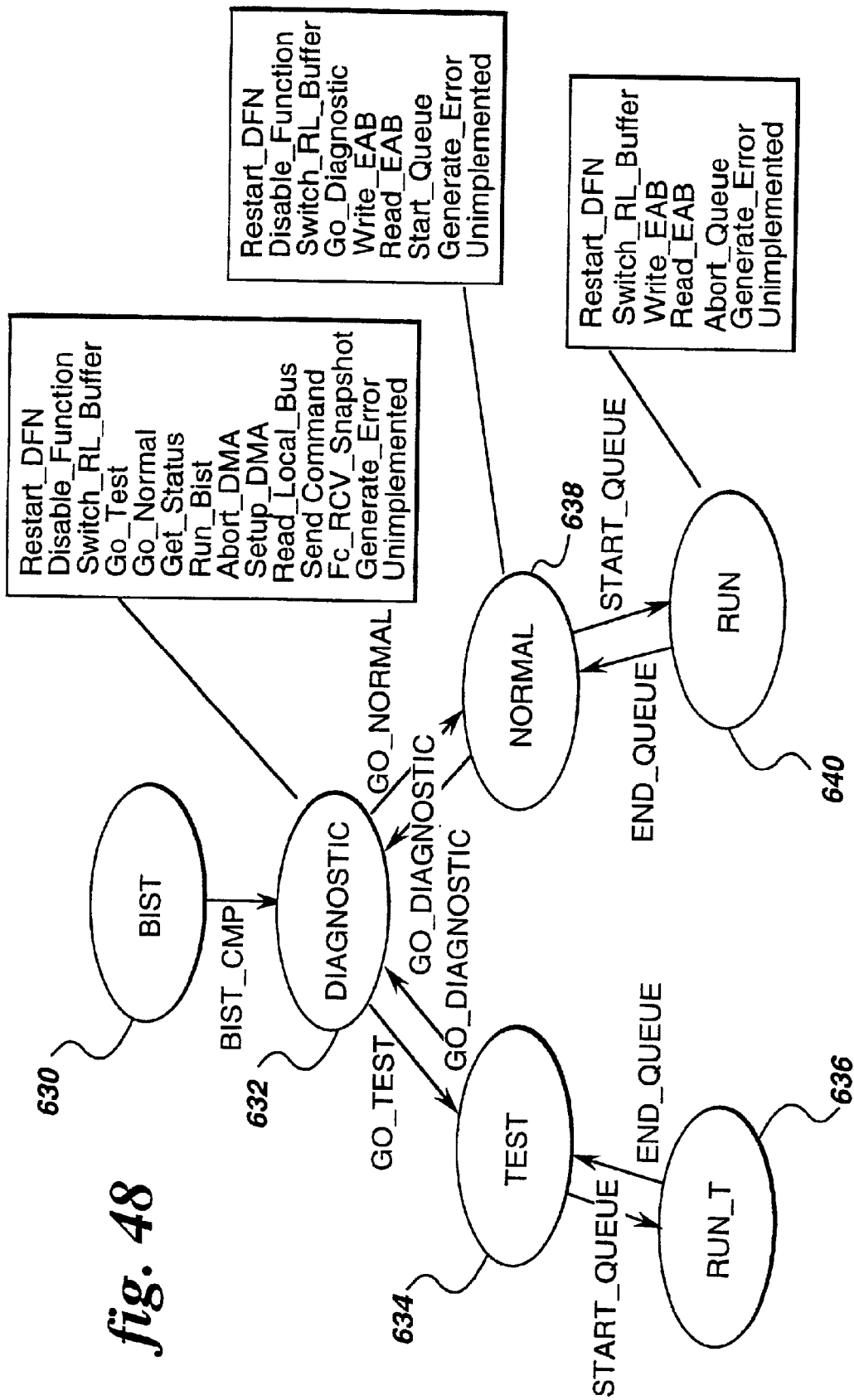
FIG. 48 is a block diagram depicting top level states of a detector framing node and commands available for those states.

FIG. 48 is a block diagram depicting the top level states of DFN 304 and the commands available for those states. As illustrated, BIST operation 630 communicates command BIST_CMP to DIAGNOSTIC operation 632. In turn, DIAGNOSTIC operation 632 communicates bi-directionally with TEST operation 634 and NORMAL operation 638. TEST operation 634 bi-directionally communicates with RUN_T operation 636 and NORMAL operation 638 communicates bi-directionally with RUN operation 640.

While DFN control unit 370 is executing the above operation, other operations are not issued to DFN 304. When DFN control unit 370 has completed executing the power up sequence, it transitions to a DIAGNOSTIC state. At this time the card will respond to commands. Normally, a command is issued to DFN 304 if the issued command is valid for the current state, such that DFN 304 will execute commands that are valid for that state. If a command is issued to DFN 304 which is not valid for the state that it is currently in, it will respond with an interrupt message indicating that the command was received and understood, but not executed because of a state error. If a command is issued to DFN 304 that is not understood, then DFN 304 responds with an interrupt indicating that a command was received but not understood.

Some commands need to be further specified using one or more of the 24 bits of parameter space argument field and others do not use additional arguments, as set forth below.

GET STATUS: TAKE A SNAPSHOT OF ONE OR ALL OF STATUS FUNCTIONS.

| | |
| --- | --- |
| Command Code | 0000 0001 |
| States where command are executable | DIAGNOSTIC |
| Parameter Space arguments | bits 2 down to 0 |
| Command Parameter registers | NONE |

RUN BIST

| | |
| --- | --- |
| Command Code | 0000 0010 |
| States where command are executable | DIAGNOSTIC |
| Parameter Space arguments | bits 3 down to 0 |
| Command Parameter registers | NONE |

RESTART DFN

| | |
| --- | --- |
| Command Code | 0000 0011 |
| States where command are executable | DIAGNOSTIC |
| Parameter Space arguments | NONE |
| Command Parameter registers | NONE |

DOWNLOAD EAB MEMORY

| | |
| --- | --- |
| Command Code | 0000 0101 |
| States where command are executable | NORMAL, TEST, RUN, RUN_TEST |
| Parameter Space arguments | bits 3 down to 0 |
| Command Parameter registers | CMD_0_PAR[,CMD_1_PAR CMD_2_PAR CMD_3_PAR] |

READ BACK EAB MEMORY

| | |
| --- | --- |
| Command Code | 0000 0100 |
| States where command are executable | NORMAL, TEST, RUN, RUN_TEST |
| Parameter Space arguments | bits 2 down to 0 |
| Command Parameter registers | NONE |

START QUEUE

| | |
| --- | --- |
| Command Code | 0000 0110 |
| States where command are executable | NORMAL, TEST |
| Parameter Space arguments | bit 23 down to 0 |
| Command Parameter registers | NONE |

ABORT QUEUE

| | |
| --- | --- |
| Command Code | 0000 0111 |
| States where command are executable | NORMAL, TEST, RUN, RUN_TEST |
| Parameter Space arguments | NONE |
| Command Parameter registers | NONE |

DIAGNOSTIC MODE

| | |
| --- | --- |
| Command Code | 0000 1000 |
| States where command are executable | NORMAL, TEST |
| Parameter Space arguments | NONE |
| Command Parameter registers | NONE |

NORMAL MODE

| | |
| --- | --- |
| Command Code | 0000 1001 |
| States where command are executable | DIAGNOSTIC |
| Parameter Space arguments | NONE |
| Command Parameter registers | NONE |

TEST MODE

| | |
| --- | --- |
| Command Code | 0000 1010 |
| States where command are executable | DIAGNOSTIC |
| Parameter Space arguments | NONE |
| Command Parameter registers | NONE |

RESET TIMER

| | |
| --- | --- |
| Command Code | 0000 1011 |
| States where command are executable | DIAGNOSTIC, NORMAL, TEST |
| Parameter Space arguments | bits 23 down to 0 |
| Command Parameter registers | NONE |

-continued

ABORT DMA

| | |
|---|---|
| Command Code | 0000 1100 |
| States where command are executable | DIAGNOSTIC, NORMAL, TEST |
| Parameter Space arguments | NONE |
| Command Parameter registers | NONE |

SETUP DMA

| | |
|---|---|
| Command Code | 0000 1101 |
| States where command are executable | DIAGNOSTIC |
| Parameter Space arguments | NONE |
| Command Parameter registers | CMD_0_PAR, CMD_1_PAR, CMD_2_PAR, CMD_3_PAR |

ACCESS LOCAL BUS

| | |
|---|---|
| Command Code | 0000 1110 |
| States where command are executable | DIAGNOSTIC |
| Parameter Space arguments | bit 23 down to 22 |
| Command Parameter registers | CMD_0_PAR, [CMD_1_PAR] |

SEND COMMAND

| | |
|---|---|
| Command Code | 0000 1111 |
| States where command are executable | DIAGNOSTIC |
| Parameter Space arguments | bit 23 |
| Command Parameter registers | CMD_0_PAR, CMD_1_PAR |

FC RCV SNAPSHOT

| | |
|---|---|
| Command Code | 0001 0000 |
| States where command are executable | DIAGNOSTIC |
| Parameter Space arguments | NONE |
| Command Parameter registers | NONE |

SWITCH RL BUFFER

| | |
|---|---|
| Command Code | 0001 0001 |
| States where command are executable | DIAGNOSTIC, NORMAL, TEST, RUN, RUN_TEST |
| Parameter Space arguments | NONE |
| Command Parameter registers | NONE |

DISABLE FUNCTION

| | |
|---|---|
| Command Code | 0001 0010 |
| States where command are executable | DIAGNOSTIC, NORMAL, TEST, RUN, RUN_TEST |
| Parameter Space arguments | bits 1 down to 0 |
| Command Parameter registers | NONE |

GENERATE ERROR

| | |
|---|---|
| Command Code | 0001 0011 |
| States where command are executable | DIAGNOSTIC, NORMAL, TEST, RUN, RUN_TEST |
| Parameter Space arguments | bit 5 down to 0 |
| Command Parameter registers | NONE |

UNIMPLEMENTED

| | |
|---|---|
| Command Code | 0001 0100 |
| States where command are executable | DIAGNOSTIC, NORMAL, TEST, RUN, RUN_TEST |
| Parameter Space arguments | NONE |
| Command Parameter registers | NONE |

HOST FLAG

| | |
|---|---|
| Command Code | 0001 0101 |
| States where command are executable | NORMAL, RUN |
| Parameter Space arguments | bit 7 down to 0 |
| Command Parameter registers | NONE |

PC buffer management is provided by a plurality of image buffer control registers. The registers on DAP 372 are used for image buffer control, and are set forth in Table 10 below.

TABLE 10

| Register Name | Description |
|---|---|
| IMG_BUF_BAS_ADR | Base address of list in PC memory (bits 31 to 0) |
| NUM_BUFFERS | Number of entries in the list (bits 15 to 0) |

TABLE 10-continued

| Register Name | Description |
|---|---|
| END_QUEUE_PTR | Last buffer (ordinal) that the computer has processed. (bits 15 to 0) |
| LAST_WRTN_DFN | Last buffer (ordinal) that DFN 304 has transferred Bit 31 flag to indicate that a wrap has occurred. Bits 15 to 0 ordinal of last frame written by DFN. |
| DAP_ENABLE_REG | Bit "2" when cleared enables the buffer management circuit (set on power up, and on error) |

In the following discussion, the flag bFULL (a bit in LAST_WRTN_DFN) indicates that the buffers are full and the flag bAllowWrap (a bit in END_QUEUE_PTR) indicates that wrapping is enabled.

The host computer 114 will allocate memory for the frame buffers and manage them. The number of buffers will be dependent on the X-RAY application and on the amount of memory available to host computer 114. The buffers are large enough to contain at least 1 frame of image data. The actual size of the image buffer is dependent on the application. (i.e. 2 MByte for cardiac/surgical digital x-ray, 8 MBytes for radiography digital x-ray, and 9 MByte for mammography digital x-ray). When the computer wants to capture data, it creates a list of base addresses that are read by DFN 304. This list includes all or a subset of the N buffers that host computer 114 is managing.

For continuous operation, the list will wrap. To indicate whether a wrap has occurred, register LAST_WRTN_DFN listed above also has a flag which indicates the occurrence of a wrap. This list is set before the Begin Sequence command or any command where a frame of data will be transferred from DFN 304. The three registers (IMG_BUF_BAS_ADR, NUM_BUFFERS and END_QUEUE_PTR) listed above are initialized before the "begin sequence" command. If the number of entries in the list is "N," then the normal setting for register END_QUEUE_PTR will be "N" indicating that all buffers from 1 to N−1 are free to be used by DFN 304.

The DFN initializes bFull=FALSE and LAST_WRTN_DFN=0, and the driver initializes END_QUEUE_PTR=0. Before acquisition, the Driver sets a "END_QUUE_PTR" bit to 0 (no wrap) or 1 (wrap).

For the operations below, that flag bit is called "bAllowWrap".

By way of example, when the DFN 304 determines that an image is in the DFN memory and needs to be transferred to the host computer 114, DFN 304 executes the following operations:

1. if (bAllowWrap = TRUE)
   if (LAST_WRTN_DFN = END_QUEUE_PTR)
   if (bFull = TRUE)
       ERROR and stop
   else /* bAllowWrap = FALSE */
   if (LAST_WRTN_DFN = 0)
   if (bFull = TRUE)
       ERROR and stop
2. do DMA
3. increment LAST_WRTN_DFN (modulo)
4. if (bAllowWrap = TRUE)
   if (LAST_WRTN_DFN = END_QUEUE_PTR)
       bFull = TRUE
   else /* bAllowWrap = FALSE */
   if (LAST_WRTN_DFN = 0)

```
    bFull = TRUE
 5. send DMA done interrupt to PC
 6. return
```

Host computer 114 will map, then umnap the image(s) and update END_QUEUE_PTR. The firmware takes this action whenever END_QUEUE_PTR is written by host computer 114:

```
if (bAllowWrap = TRUE)
    write to END_QUEUE_PTR sets bFull = FALSE
else /* bAllowWrap = FALSE */
    write to END_QUEUE_PTR does nothing to bFull
```

The host computer 114 processes and displays frames after DFN 304 has transferred data into them. If host computer 114 is waiting for a frame to be filled by DFN 304, host computer 114 does not need to continuously poll DFN 304. The doorbell message from DFN 304 optionally indicates that DFN 304 has filled a buffer because there may be more types of doorbell messages. The doorbell is set after the whole image has been transferred, not after each DMA transfer, if more than one DMA is performed to transfer the entire image. After the doorbell message has been received, the host computer 114 reads DFN 304 last buffer count (register 3). If the buffer that it wants to process has been filled, it processes and displays that buffer. After host computer 114 is finished processing the buffer, and it is authorizing wraps, it increments the number in the "host last buffer" count (register 4). Upon error in DFN 304, the buffer management circuit disables itself by setting bit "2" in the DAP_ENABLE_REG register. The error condition identified that disables the buffer management circuit occurs when DFN 304 has a image buffer using transfer to host computer 114, such that DFN 304 reads if VAL(register 4)=(VAL (register 3)+1) mod N.

The response log acquires image data information. According to an embodiment of the present invention, the image data information includes commands and errors as they occur such that the image data information can be associated with a corresponding captured image. For response log management, response log packets are sent to host computer 114 as they are generated on DFN 304. A command sent to the detector while executing the event queue generates a response log packet if enabled. Any command sent to the detector is enabled or disabled from generating a response log packet.

Definition of Response Log ("RL") Entry Format

Figure 61:
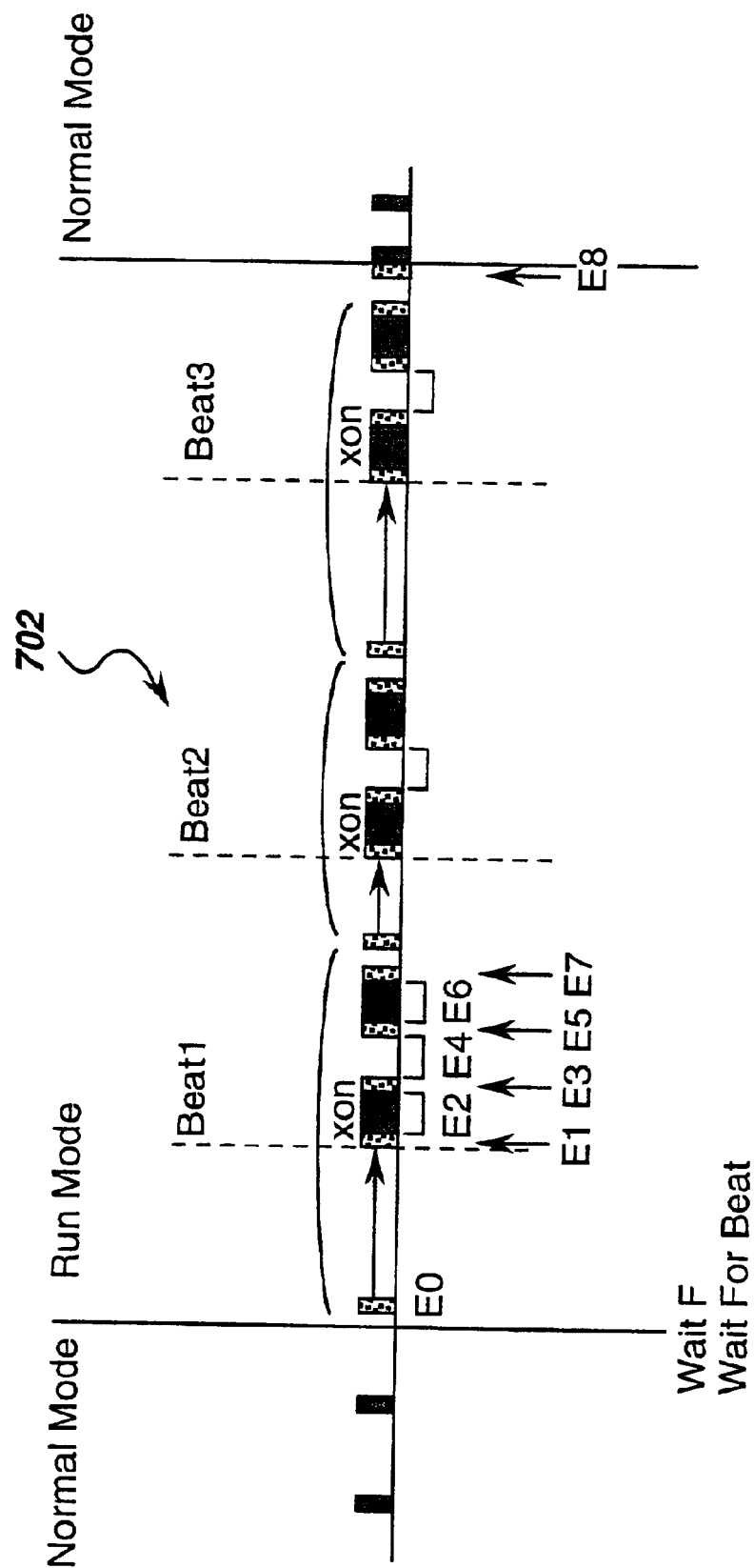
FIG. 61 is an event graph of a Gated Cardiac Sequence.

The format incorporates a unique Type identifier for each response log ("RL") entry. This format is to make it easier for applications to sift through RL data for particular types of information. The Type identifier is divided into Class and Subclass sections and includes 4 bits that are reserved for chaining. Chaining is used to create a single RL entry with up to 128 Bytes of data available. The RL entry format includes a 32 bit time stamp which is the elapsed time since the beginning of the sequence. The Sequence ID has a 24 bit unique identifier which is written by a DFN driver using the either the Begin Sequence command or the Reset Timer command; DFN mode reflects the current mode of operation of the card (e.g. Diagnostic, Run, etc . . . ). There are five 32 bit fields which store the data for the entry. Their use is defined depending on the type of the response log entry. A predefined separator to make it easier to sift through a corrupted RL buffer terminates the structure. A response log entry is organized in little Endian format; that is the least significant byte of a field or object occupies the lower address in the response log 737 (FIG. 61). For example, the response log entry will begin with the Type field bits 7:0, the subclass and reserved chaining information.

Table 11 below sets forth a structure of the response log ("RL") entry format.

TABLE 11

| Object | Bytes | Description |
|---|---|---|
| Type | 2 | Class(7:0); subclass(11:8) |
| Timestamp | 4 | Time when data generated |
| Sequence ID | 4 | Unique identifier(23:0); DFN mode(27:24) |
| Field 1 | 4 | 32 bit Data Word 1 |
| Field 2 | 4 | 32 bit Data Word 2 |
| Field 3 | 4 | 32 bit Data Word 3 |
| Field 4 | 4 | 32 bit Data Word 4 |
| Field 5 | 4 | 32 bit Data Word 5 |
| Terminator | 2 | Separator word ("0xFAFA") |

Classes of Response Log ("RL") Entry

A number of specific classes of RL entry are defined to make it easier to sort through the data when looking for particular information. Currently defined classes are shown in the Table 12 and discussed in this section. RL entry reporting for class 0x03 is individually disabled using a bit field in the respective event code. Reporting for classes 0x02, 0x04, and 0x06 is individually disabled using bits in registers on DFN 304. The class field "-S-" is a 4 bit Subclass place holder; the class field "-N-" is a 4 bit place holder reserved for chaining of RL entries.

Table 12 sets forth currently defined RL entry classes.

TABLE 12

| CLASS | CLASS CODE | Sub-class |
|---|---|---|
| Image Tag | 0x01 | -x0 |
| Detector Command | 0x02 | -x0, x1, x2 |
| Queue Event | 0x03 | -x0 |
| Image Readout | 0x04 | -x0, x1 |
| Real time bus State | 0x05 | -x0 |
| DMA Information | 0x06 | -x0 |
| Sequence Transition | 0x07 | -x0, x1, x2, x3 |
| Error | 0x0E | -x0 |

Image Tag

An image tag is generated when the end of frame (SOFn3) is received on the image detection bus 377 for the respective image. The tag records the exact time at the end beginning of the frame sequence in ticks of the 2 μsec Frame Sequence counter. It also records the Ordinal Image Number for the particular frame. In addition, it records the image specific register settings which were active when the image data was received. This setting includes the image and block size as well as any additional frame options that control readout of the image. This entry also records data read from the SOFn3 which provides details on the formatting of the image data from the detector.

Table 13 below sets forth a format of image tag RL entry.

TABLE 13

| Object | Description | Format |
|---|---|---|
| Identifier | Image Tag | Class(7:0) = 0x01, subclass(11:8) = 0x0 |
| Timestamp | Time data generated | 32 bit count in 2 μsec clk tics |
| Sequence ID | Unique identifier | RESERVED(31:28), DFN Mode(27:24); Sequence ID(23:0) |
| Field 1 | Ordinal Image # | 32 bit count of current image |
| Field 2 | Image Size | — |
| Field 3 | Block Size | — |
| Field 4 | SOFn3 - HDR1 | (B3: Number of bits per pixel) |
| Field 5 | SOFn3 - HDR2 | (B0-1: Pixels per line) (B2-3: Lines per image) |
| Terminator | Unique separator | 0xFAFA |

Detector Commands

Detector Command RL entry is generated when a command is sent and executed on the detector. The entry is not generated until either the acknowledgment is received from the detector or the fiber channel timeout is exceeded. The entry contains the original command, and the detector response. RL entries are also created for spontaneous detector acknowledgment without DFN initiation for debugging purposes. In this case, fields 1 and 2 will be 0xFFFFFFFF indicating an anomalous condition and Fields 3 and 4 will hold the detector response.

Table 14 sets forth a format of detector command RL Entry.

TABLE 14

| Object | Description | Format |
|---|---|---|
| Identifier | Detector Command | Class(7:0) = 0x02 subclass(11:8)= 0x0 : normal 0x1 : Unexpected detector ack received 0x2 : Timeout: Detector did not respond |
| Timestamp | Time data generated | 32 bit count in 2 μsec clk tics |
| Sequence ID | Unique identifier | RESERVED(31:28) DFN Mode(27:24); Sequence ID(23:0) |
| Field 1 | CMD - HDR1 | Type of Detector command |
| Field 2 | CMD - HDR2 | Argument of command |
| Field 3 | ACK - HDR1 | Detector response - type |
| Field 4 | ACK - HDR2 | Detector response - argument |
| Field 5 | Reserved | — |
| Terminator | Unique separator | 0xFAFA |

Event Queue Information

The Event Queue RL entry is generated whenever a Detector queue event is executed. The entry contains an Event Descriptor which gives the byte code for the event type as well as the current value of the queue pointer into EAB memory for the respective event instruction. The arguments of the event instruction are stored in Fields 2 and 3. Additional information, like the current value of the loop pointer on a Loop instruction is stored in Field 4. Loop entries generate an entry each time through the loop.

Table 15 sets forth a format of event queue response log ("RL") entry.

TABLE 15

| Object | Description | Format |
|---|---|---|
| Identifier | Queue Event | Class(7:0) = 0x03 subclass(11:8) = 0x0 |
| Timestamp | Time when data generated | 32 bit count in 2 μsec clk tics |
| Sequence ID | Unique identifier | RESERVED(31:28) DFN Mode(27:24); Sequence ID(23:0) |
| Field 1 | Event Descriptor | Event Byte code(7:0); Queue Pointer(15:8) |
| Field 2 | Event Arguments 1 | Event arguments B0(7:0); B1(15:8); B2(23:16); B3(31:24) |
| Field 3 | Event Arguments 2 | Event arguments B4(7:0); B5(15:8); B6(23:16); B7(31:24) |
| Field 4 | Ancillary Information | Loop event: Current value of the loop counters loop2_index(31:16); loop1_index(15:0) |
| Field 5 | Reserved | — |
| Terminator | Unique separator | 0xFAFA |

Image Readout Information

Image readout related information is recorded using these RL entries. This information is embedded in the data received from the detector during image readout and is used for debugging detector readout firmware. This data corresponds to the SOFn2 and SOFn3 commands received during image acquisition. Data for the SOFn1 command is stored in the image tag and discussed above.

Table 16 sets forth a format of image readout RL entry.

TABLE 16

| Object | Description | Format |
|---|---|---|
| Identifier | Image Readout | Class(7:0) = 0x04 subclass(11:8) = 0x0 : Image Packet (SOFn2) 0x1 : Image Done (SOFn3) |
| Timestamp | Time data generated | 32 bit count in 2 μsec clk tics |
| Sequence ID | Unique identifier | RESERVED(31:28) DFN Mode(27:24); Sequence ID(23:0) |
| Field 1 | Line number | Hdr11 (Image Packet) |
| Field 2 | Reserved | — |
| Field 3 | Reserved | — |
| Field 4 | Reserved | — |
| Field 5 | Reserved | — |
| Terminator | Unique separator | 0xFAFA |

Real Time Bus State

The Real Time Bus State RL entry is generated when a state change is detected on real time bus 379. This information will be useful for tracking the actual state of the lines of real time bus 379 during acquisition.

Table 17 sets forth a format of real time bus state RL entry.

TABLE 17

| Object | Description | Format |
|---|---|---|
| Identifier | Real Time Bus State | Class(7:0) = 0x05 subclass(11:8) = 0x0 |
| Timestamp | Time data generated | 32 bit count in 2 μsec clk tics |
| Sequence ID | Unique identifier | RESERVED(31:28) DFN Mode(27:24); Sequence ID(23:0) |
| Field 1 | New State | RESERVED(31:28) State after the change: Read state(11:0); Drive state (27:16) |

TABLE 17-continued

| Object | Description | Format |
|---|---|---|
| Field 2 | Previous State | RESERVED(31:28) State before the change: Read state(11:0); Drive state (27:16) |
| Field 3 | Reserved | — |
| Field 4 | Reserved | — |
| Field 5 | Reserved | — |
| Terminator | Unique separator | 0xFAFA |

DMA Information

The DMA Information RL entry is generated when DMA of the current image buffer is initiated. This information will be useful for debugging DMA problems including situations in which third party PCI cards are reducing the available bandwidth on the bus.

Table 18 sets forth a format of DMA RL entry.

TABLE 18

| Object | Description | Format |
|---|---|---|
| Identifier | DMA Information | Class(7:0) = 0x06 subclass(11:8) = 0x0 |
| Timestamp | Time data generated | 32 bit count in 2 μsec clk tics |
| Sequence ID | Unique identifier | RESERVED(31:28) DFN Mode(27:24); Sequence ID(23:0) |
| Field 1 | Image Number | Ordinal image number (31:0) |
| Field 2 | Current Buffer | Ordinal buffer number (31:16); Current DFN buffer number (15:0) |
| Field 3 | Buffer Address | Address of current buffer in computer RAM |
| Field 4 | DMA Size | Size of the DMA packet (31:0) |
| Field 5 | Reserved | — |
| Terminator | Unique separator | 0xFAFA |

Sequence Transition

The Sequence Transition RL entry is generated whenever a sequence related transition takes place. Note that the sequence timer is reset whenever an RL entry of this type is generated. When the user mode program begins interaction with the detector outside of an event sequence ("Chit-Chat" mode), the driver resets the sequence timer and passes a sequence ID to DFN 304 to be used for subsequent RL entries. The archive DLL is responsible for keeping track of the absolute time in the system as all RL entries supply relative timing information.

Table 19 sets forth a format of sequence transition RL entry.

TABLE 19

| Object | Description | Format |
|---|---|---|
| Identifier | Sequence Transition | Class(7:0)=0x07 subclass(11:8)=0x0 0x0:Begin Sequence 0x1:End Sequence 0x2:Sequence Timer Wrapped 0x3:Sequence Timer Reset |
| Timestamp | Time data generated | 32 bit count in 2 μsec clk tics |
| Sequence ID | Unique identifier | RESERVED(31:28) DFN Mode(27:24); Sequence ID(23:0) |
| Field 1 | Last Timer Count | State of the sequence timer when transition occurred (31:0) |
| Field 2 | Wraps since reset | Number of wraps (15:0) |
| Field 3 | Reserved | — |
| Field 4 | Reserved | — |
| Field 5 | Reserved | — |
| Terminator | Unique separator | 0xFAFA |

Errors

The Error RL entry records errors which were generated due to problems on DFN 304 or on the fiber channel link.

Table 20 sets forth a format of error RL entry.

TABLE 20

TABLE 20 sets forth a format of error RL entry.

| Object | Description | Format |
|---|---|---|
| Identifier | Error | Class(7:0)=0x0E subclass(11:8)=0x0 |
| Timestamp | Time data generated | 32 bit count in 2 μsec clk tics |
| Sequence ID | Unique identifier | RESERVED(31:28) DFN Mode(27:24); Sequence ID(23:0) |
| Field 1 | EP Error | 32 bit error word |
| Field 2 | DAP Error | 32 bit error word |
| Field 3 | Queue Error | 32 bit error word |
| Field 4 | Fiber Channel Error | 32 bit error word |
| Field 5 | Reserved | — |
| Terminator | Unique separator | 0xFAFA |

Table 21 sets forth registers on DFN 304 used for response log control.

TABLE 21

| Register | Description |
|---|---|
| SIZE_RES_LOG | Size of response log buffers |
| BASE_LOG_A | Base address of response log buffer A, bits(31-12) are used for base address. |
| BASE_LOG_B | Base address of response log buffer B, bits(31-12) are used for base address. |
| RES_LOG_FULL | Bit YY indicates that response buffer A is filled. Bit YZ indicates that response buffer B is filled. Bit E1 indicates that both response buffers are full and response log circuit is deactivated. |
| EP_ENABLE_REG | Bit "Y" when cleared enables the response log circuit (set on power up, and on error) |

TABLE 21-continued

| Register | Description |
| --- | --- |
| RESP_LOG_STAT_A | Status of response log buffer A bits(31-5) contain last written address. Bit(1) indicates if buffer has any data in it. Cleared when response log circuit Enabled, set when first entry is made. Bit(0) when set indicates that last data were transferred to buffer A. |
| RESP_LOG_STAT_B | Status of response log buffer B bits(31-5) contain last written address. Bit(1) indicates if buffer has any data in it. Cleared when response log circuit Enabled, set when first entry is made. Bit(0) when set indicates that last data were transferred to buffer B. |

DFN 304 is initially (on power up and after an error) disabled from sending response log packets. To enable transfer, host computer 114 configures the response log circuit and then enables the circuit. The computer configures the two response log buffers by writing the size of the response log buffers and the base addresses of the two buffers into the SIZE_RES_LOG register the BASE_LOG_A register and the BASE_LOG_B register. The size of the two response log buffers is identical and is an integral multiple of 32 Bytes. The response log buffers start on a 4K page boundary (i.e. bits 11–0 are 0).

Host computer 114 next enables the response log 737 by clearing bit Y of the EP_ENABLE_REG. Upon startup, DFN 304 will use the base address of response buffer A for the first response log entry. The second response log entry will be sent to the base address of response buffer offset by 32 Bytes (10000). Subsequent response log entries will be transferred to the base address of response buffer A offset by 32 (Bytes) times the number of response log entries. When the response buffer A is full (address is beyond BASE_LOG_A+SIZE), DFN 304 will set bit YY in the RES_LOG_FULL indicating that buffer A is full. Bit ZZ in the doorbell register on the PCI 9054 will also be set, sending an interrupt to the host computer 114. If bit YZ in the RES_LOG_FULL register is not set, DFN 304 will then start writing response log entries into response buffer B, starting at the base address and continuing until response log buffer B is filled. When buffer B is filled, DFN 304 will set bit YZ in the RES_LOG_FUiLL indicating that buffer B is full and set bit ZZ of the doorbell register on the PCI 9054 sending another interrupt to the computer. Then DFN 304 will check if bit YY in the RES_LOG_FULL register has been cleared. If this bit has been cleared, then DFN 304 will reuse response log buffer A. When DFN 304 switches response log buffers from either A to B or from B to A, it will expect that the response log full flags for the next buffers (either YY or YZ of register RES_LOG_FLL) are cleared. An error condition will have occurred if the computer has not cleared the bit. If this error condition occurs, bits YY and YZ and Bit E1 of the RES_LOG_FULL register will be set, and DFN 304 will set bit Y of the EP_ENABLE_REG register, which will disable and reset the response log circuit. Clearing this bit restarts the response log circuit. If the circuit is restarted, DFN 304 will begin transferring response log entries into the base address of response log buffer A.

Host computer 114 forces a switch between the two response log buffers by issuing the command Switch RL buffer. If this occurs, then DFN 304 will immediately switch between buffers A and B. If the switch is forced while response log buffer A is the current active buffer, then bit YY of the register RES_LOG_FULL will be set and a doorbell interrupt will be set to the computer. DFN 304 will begin sending response log entries to the base address of response log buffer B. If bit YZ of RES_LOG_FULL is set, then an error has occurred and DFN 304 will set bit Y of the EP_ENABLE_REG register, disabling the response log circuit.

At any time the host computer 114 reads the two registers RESP_LOG_STAT_A or RESP_LOG_STAT_B to determine the status of the response log circuit. The contents of these status registers contain address of the last response log entry written to response log buffer A and B respectively. They also contain a flag indicating whether response log buffer A or B was the target of the last response log entry. After a forced switch, they are read to determine the number of response log entries that occurred before the switch. They are read after both response-log buffers are filled to determine which buffer contains the older response log entries.

Fiber Channel Loopback

The Fiber channel loopback test is designed to test the Fiber channel chip set. The test is initiated by EP 374 device by asserting the LOOPEN signal line. This signal line shorts the outputs of the fiber optic transmit unit 562 to the receive inputs of the fiber optic receive unit 564. This closes the loop through the encoder/decoder unit 566 back to EP 374. Next, EP 374 attempts to send a FC command over the link and monitors the return bus for the expected echo. The format of the command words has alternating 1 and 0 patterns and is designed to test the transmit and receive bus lines for shorts and opens. If the correct pattern is received, the test passes. The results are reported to the computer.

This test is incapable of verifying the fiber optic transceiver module but is also qualifiable with a setting that causes the test to run without asserting LOOPEN. In this case, a short length of fiber cable is looped from the module output back to its input to close the loop. The test is generally available for debugging of DFN 304.

Real Time Bus Loopback

The real time bus 379 is testable for integrity of the transceiver chip set electronics. The real time bus loopback test is performed by EP 374 by writing data out to the devices on the transmit bus and then monitoring the receive bus for the same data. Since the chips have their receivers and transmitters for each channel wired together, anything transmitted will automatically be received. The real time bus loopback test has a series of words of alternating 1 and 0 patterns which are designed to check for opens and shorts on the transmit and receive data bus traces and chip pins. A successful real time bus loopback test indicates that the chips themselves are functioning correctly.

The real time bus loopback test is further augmented to test the traces out to the 31 pin miniature D connector as well as the connector solder joints. An external test connector is made up to short all even channels to all odd channels. Data is then transmitted on the even channels and monitored on the odd channels and vise versa. The real time bus loopback test indicates that the entire communication chain out to the connector is working order and is generally not run automatically. The real time bus loopback test is available for debug of real time bus 379.

RAM Built in Self Test ("BIST")

DFN 304 has ten 8 Megabit SRAM devices which together contribute the majority of connections to DAP 372. There is the possibility that these devices might have been damaged during board handling and therefore they need to be tested using an exhaustive RAM BIST test.

The RAM BIST has three related tests all of which are conducted by firmware in DAP 372. In the first test, odd and even memory locations are filled with alternating 1 and 0 patterns and then read out and checked. In the second test the odd and even values are reversed. In the third test, the value of the address of a particular location is written into that location. Once the entire RAM has been filled, the data is read out and compared to the original.

These three tests will verify that every bit of RAM on the card is good and will also check for shorts on traces and between pins on the SRAM devices and on the majority of pins on DAP 372.

Interrupts

DFN 304 supports generation of interrupts but does not respond to interrupts. The procedure for handing interrupts generated by DFN 304 is defined here. Interrupts generated on DFN 304 are not directly issued to the PCI interrupt pin. The computer communication interface 382 is responsible for issuing and clearing the interrupt on computer communication bus 302.

The computer communication interface 382 contains two doorbell registers whose purpose is to generate interrupts on DFN 304 and on computer communication bus 302. The doorbell register used to generate interrupts on computer communication bus 302 is the Local-to-PCI Doorbell Register (L2PDBELL). This register is accessed from the PCI side (i.e. host computer 114) at offset x64 from the computer communication interface 382 base address. The host computer 114 reads this register to determine which doorbell bit was set. DFN 304 sets the doorbell by writing a 1 to a particular bit. The host computer 114 clears a doorbell bit by writing a "1" to that bit position.

The host computer 114 enables DFN 304 generated interrupts by setting two bits in the Interrupt Control/Status Register (INTSCR) on computer communication interface 382. This register is accessed from the PCI side at offset x68 from the computer communication interface 382 base address. DFN generated interrupts are enabled by setting both bit 8, the PCI Interrupt Enable Bit, and bit 9, the PCI Doorbell Interrupt Enable bit.

The L2PDBELL register is a 32 bit register. A particular type of doorbell denotes a unique interrupt messages. The general method of handling interrupts generated by DFN 304 is:

Read the L2PDBELL register;

Determine the source(s) of the interrupt by examining the bits which generated the interrupt;

Perform action(s);

Clear the source(s) of the interrupt on DFN 304;

Clear the bit in the L2PDBELL register which generated the interrupt; and

Read back the L2PDBELL register to determine that the PCI interrupt has been cleared.

In some cases, depending on the cause of the interrupt, steps 3 and 4 above may not be used.

The specific bit which each specific interrupt type sets in the L2PDBELL register is shown in the following Table 22.

TABLE 22

| Cause | Bit in L2PDBELL |
|---|---|
| Command received and executed normally | 0 |
| Command received and not understood | 1 |
| Command received and executed with error | 2 |
| Command received and not executed (wrong state) | 3 |
| Command received and not executed (not implemented) | 4 |
| Command received and executed but timed out | 5 |
| End of queue reached with no images pending | 6 |
| End of queue reached with images pending | 7 |
| Image transfer to computer complete, others are pending | 8 |
| Image transfer to computer complete and non are pending | 9 |
| Interrupt to computer generated in queue | 10 |
| Queue is waiting on signal from computer | 11 |
| Response Log buffer has been switched | 12 |
| RESERVED | 13 |
| RESERVED | 14 |
| RESERVED | 15 |
| Error (Read ERR0R to determine source) | 16 |
| Error (Read ERR1R to determine source) | 17 |
| Error (Read ERR2R to determine source) | 18 |
| Error (Read ERR3R to determine source) | 19 |
| Error (Read DAP_ERR0R determine source) | 20 |
| Error (Read DAP_ERR1R determine source) | 21 |
| Error (Read DAP_ERR2R determine source) | 22 |
| Error (Read DAP_ERR3R determine source) | 23 |
| RESERVED | 24 |
| RESERVED | 25 |
| RESERVED | 26 |
| RESERVED | 27 |
| RESERVED | 28 |
| RESERVED | 29 |
| RESERVED | 30 |
| RESERVED | 31 |

The bits marked "RESERVED" are for future use and will not normally be set by DFN 304. The bits marked "Error" indicate that an error has been trapped in either the DAP or the EP FPGAs on DFN 304. If DFN 304 sets one of these bits, the actual source of the error is determinable by reading the appropriate error register as indicated in Table 22. Under normal circumstances, the error is cleared in DFN 304 before it is cleared in computer communication interface 382.

The interrupts caused by setting bits 0 through 12 on the L2PDBELL register are interrupts that are generated during normal execution.

DAP/EP Interaction

Information that is sent from EP 374 to DAP 372 used for assembly of response logs is communicated to DAP 372 using bits (49:34) of the FPGA bus connecting DAP 372 and EP 374.

The entire set of information that DAP 372 needs to assemble response log entries is communicated once for each 2 $\mu$sec interval. Much of the information originates from the event queue within EP 374. The data is then serialized out of EP 374 immediately after EP 374 receives the 2 $\mu$sec pulse. The first word out of the event queue is an instruction word, indicating which response log entries need to be generated corresponding to the current event instruction.

The format of the instruction word is set forth in the following Table 23.

TABLE 23

| Name | Description |
| --- | --- |
| bits(15) | Reserved |
| bit (14) | Make a Detector Command class response entry flag. |
| bits(13:10) | Detector Command sub-class code |
| bit(9) | Make a Event Queue Information class response entry flag. |
| bits(8:5) | Event Queue Information sub-class code |
| bit(4) | Real Time Bus State class response entry flag |
| bits(3:0) | Real Time Bus State sub-class code |

The next 20 words (words 1 through 20) that will be transferred to DAP 372 also originate from the event queue and will be serialized out in 16 bit words.

The order is as follows in Table 24.

TABLE 24

| Name | Description |
| --- | --- |
| word 1 | Detector Commands-field 1 (bits 15:0) |
| word 2 | Detector Commands-field 1 (bits 31:16) |
| word 3 | Detector Commands-field 2 (bits 15:0) |
| word 4 | Detector Commands-field 2 (bits 31:16) |
| word 5 | Detector Commands-field 3 (bits 15:0) |
| word 6 | Detector Commands-field 3 (bits 31:16) |
| word 7 | Detector Commands-field 4 (bits 15:0) |
| word 8 | Detector Commands-field 4 (bits 31:16) |
| word 9 | Event Queue Information-field 1 (bits 15:0) |
| word 10 | Event Queue Information-field 1 (bits 31:16) |
| word 11 | Event Queue Information-field 2 (bits 15:0) |
| word 12 | Event Queue Information-field 2 (bits 31:16) |
| word 13 | Event Queue Information-field 3 (bits 15:0) |
| word 14 | Event Queue Information-field 3 (bits 31:16) |
| word 15 | Event Queue Information-field 4 (bits 15:0) |
| word 16 | Event Queue Information-field 4 (bits 31:16) |
| word 17 | RT Bus State-field 1 (bits 15:0) |
| word 18 | RT Bus State-field 1 (bits 31:16) |
| word 19 | RT Bus State-field 2 (bits 15:0) |
| word 20 | RT Bus State-field 2 (bits 31:16) |

The next 6 words (21 through 26) transferred to DAP 372 are error signals. The next 6 words are transferred in the following order, as set forth in Table 25.

TABLE 25

| Name | Description |
| --- | --- |
| word 21 | EP Error-(bits 15:0) |
| word 22 | EP Error-(bits 31:16) |
| word 23 | Queue Error - (bits 15:0) |
| word 24 | Queue Error - (bits 31:16) |
| word 25 | Fiber Channel Error - (bits 15:0) |
| word 26 | Fiber Channel Error - (bits 31:16) |

System Overview

As shown in FIG. 1, imaging system 100 provides an upgradeable digital x-ray system, which takes advantage of widely available PC technology for a computer platform. Imaging system 100 runs under a task based, non-real time operating system. At the same time, imaging system 100 provides control of the low level events occurring during image acquisition. High level and low level functions are partitioned for best utilization of resources. In particular, all functions which occur in real-time are pushed down into hardware to remove the burden of real-time operation on the computer operating system. These functions are often better suited to hardware implementation because complex data processing operations are not performed. In contrast, image processing functions such as gain and offset correction are often relatively costly to implement in custom purpose hardware.

Therefore, imaging system 100 uses simple and special purpose hardware for real-time control, and processes image data on host computer 114.

The Event Sequence

Image acquisition includes a sequence of events, which occur at precisely-timed intervals and involve control of radiation generation system 109 and image detection system 112. In most cases, the user knows an exact order in which these events need to occur well in advance of the image acquisition. This sequence will vary from acquisition to acquisition depending on the type of experiment being performed and the type of information the user is seeking to learn through the image acquisition. Therefore, a list or description of the sequence of event instructions to be performed is constructed. This list is not constructed in real-time and is therefore performed on host computer 114. Once the Event Sequence is known, the details are transmitted to special purpose hardware for execution in real-time.

Returning to FIG. 15, described in greater detail above, a high level description of the image acquisition is generated by acquisition control software, such as test control application 306. This description includes a sequence of frames to be acquired and optionally includes details such as frame time or amplifier gain to be used during acquisition. This Frame Sequence is then translated to an Event Sequence using a compiler which knows the details of the target control hardware. This event sequence is then sent over computer communication bus 302 to detector framing node 304, where it is stored in preparation for execution. Execution of the sequence is initiated by sending a Begin Sequence command over computer communication bus 302. The extent of real-time control allotted to host computer 114 is determining when the sequence will begin. Once the Event Sequence is complete, host computer 114 retrieves the acquired data, in addition to various diagnostics and responses, which were recorded during execution of the event sequence. Therefore, host computer 114 is involved in pre- and post-processing roles and is entirely relieved of the burden of real-time operation.

The Event Graph

Figure 49:
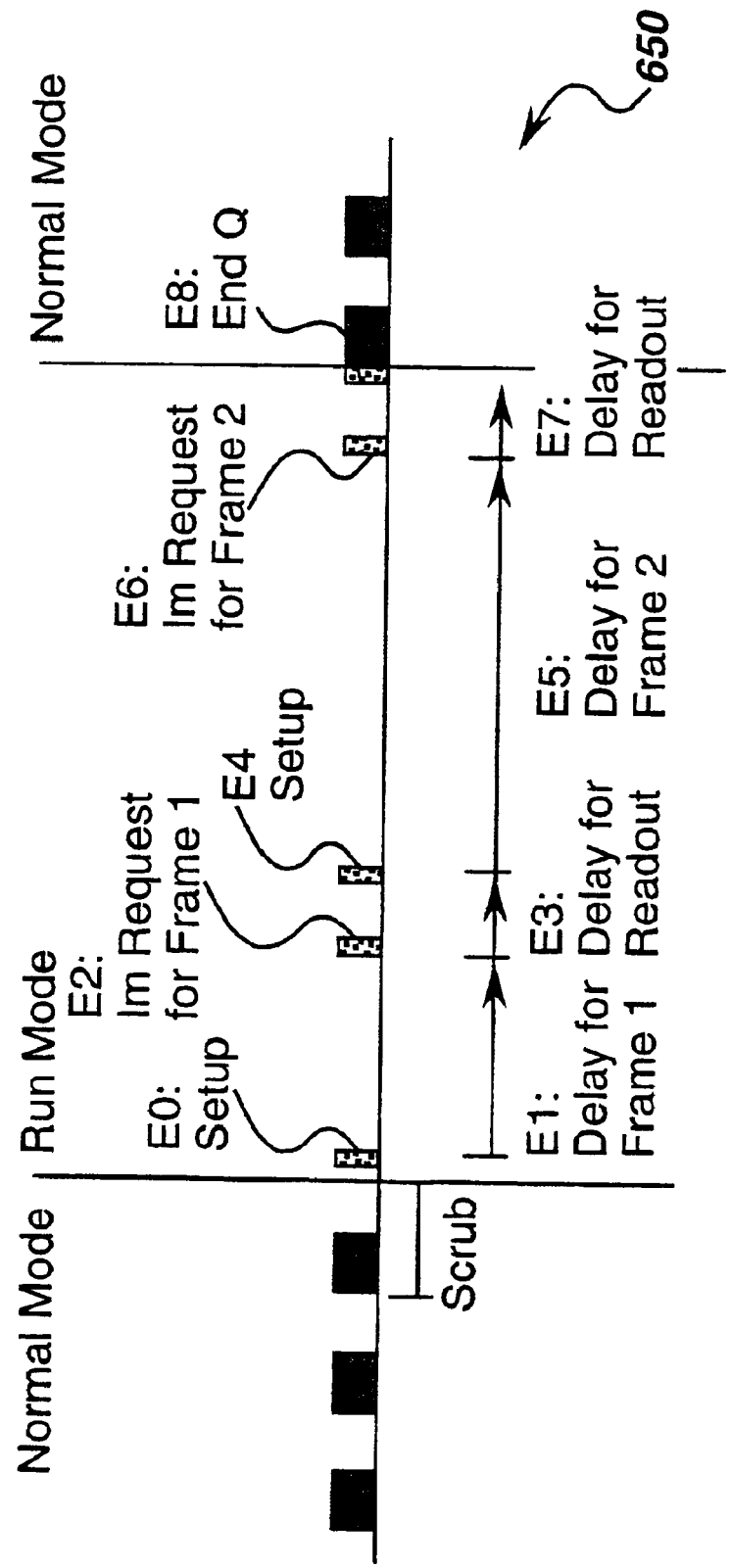
FIG. 49 is an event graph illustrating a typical sequence for image capture.

FIG. 49 is an example event graph 650 illustrating a typical sequence for image capture. Example event graph 650 includes a series of isolated events, each of which is planned to take place at a predetermined point in time. With reference to example event graph 650 and beginning on the left hand side, a series of scrub frames (panel scans with no data returned) are shown. These represent the scrub frames which are taken while detector framing node 304 is sitting idle prior to the event sequence. This idle state is referred to as DFN Normal mode and is the default state of operation. The event sequence is triggered and begins as the system leaves Normal mode and enters Run mode (event sequence execution). The first event instruction in the event sequence, E0, sets up detector framing node 304 for the frame. E1 is the delay time from the start of the first frame until the beginning of readout of the first frame. This is followed immediately by E2, which is an image request, and E3, which is a delay accounting for the image readout time. Once E3 is complete, E4 sets up the next frame and E5—the delay for the second frame—begins. The frame is readout on E6–E7, and the EndQ event instruction E8 corresponds to the end of the event sequence. When this point is reached, the execution is completed, and the system leaves Run mode to return to Normal mode.

During execution of the sequence shown in FIG. 49, two frames of data are acquired. These frames are transferred directly to computer RAM 334. In addition, commands sent to detector framing node 304 to initiate the readout each result in an acknowledgment being returned from detector framing node 304. This acknowledgment is recorded for each event and stored in computer RAM 334 in the response log buffer 737 (set forth in greater detail below). All of this information along with pointers to the frame data in computer RAM 334 are passed to the top level computer application immediately following completion of the event sequence. The sequence is repeated again by sending another begin sequence command to detector framing node 304 over computer communication bus 302.

Standard Event Set

The Standard Event Set for the firmware of detector framing node 304 contains a minimal number of event instructions to support features of imaging system 100. These event instructions are grouped roughly by functionality. Each event instruction includes a single Op-Code byte specifying the event, followed by the argument bytes to be used when applicable. All op-code words are one byte long and their arguments are multiple bytes long as indicated. Op-code and argument bytes are packed for optimum utilization of the EAB memory 474 on detector framing node 304 in EP 374. Diagrams illustrating the format of control and data words for each event are set forth below. The diagrams show the exact byte order of data in EAB memory 474 beginning with the op-code. Multi-byte words show the byte ordering with "(0)" being the most significant byte.

Figures 50, 51:
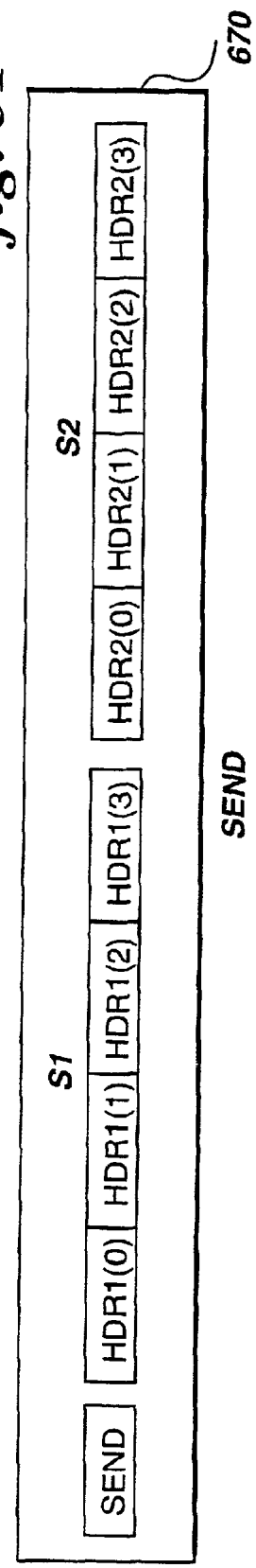
FIG. 50 is a table of a standard event set.
FIG. 51 is a block diagram of a Send event.

FIG. 50 is a table of a standard event set 660. All event instructions take one cycle of the 2 $\mu$sec event clock to be read from EAB memory 474 and processed.

FIG. 51 is a block diagram of Send event 670. This event instruction sends the command words S1 and S2 to a device. The response from detector framing node 304 is recorded in the response log 737 on host computer 114. A Perl Script example to execute Send event 670 follows:

Send(0x2001, 1x2);

The above example has the format Send("command", "argument") such that different numbers may be used. In this example, a DFN Signature Request command is sent to detector control board 124 in image detection system 112. The reply from detector control board 124 is recorded in the response log 737, and has the exemplary form:

ACK1=0x20021
ACK2=0x40300100

As set forth above, ACK1="command" and ACK2= "signature". The detector control board 124 responds with a signature indicating that it is running Cardiac H20 firmware. The send event 670 is used to send a Store Scan Setup Parameters command to detector control board 124. In this case S1 will have the format of the command, "0x00004020" and S2 will be the 32 bit parameter word to be stored. The send event 670 is also used for the Read Temperature command. In this case, S1 is "0x00004100" and S2 has no effect. After processing this command, detector control board 124 replies with an acknowledge having two 32 bit words, which are recorded in the response log 737. The first of these is a copy of the original S1 word unless the command was not recognized in which case it would be "0x0000FFFF." The second word will be the requested temperature. Send is executed in a single 2 $\mu$sec tick of the Event Sequence clock. A FC timeout is set with a user programmed register on the card. If this timeout is exceeded without a reply from the device, an error is generated. The timeout for return of Fiber Channel ACKs is set in 28 nsec increments with a timeout of 1024*28 nsec=28.672 msec. The timeout is set to a nominal value (e.g. 256 counts) by the DFN driver. Fiber Channel error conditions are detected by detector framing node 304 and passed on to host computer 114 using a PCI interrupt. They are also recorded in response log 737. The send event 670 has a time-out on its execution. The return information is monitored by detector framing node 304 to determine whether the information has been received and processed correctly.

FIG. 52 is a table of reported Fiber Channel errors 672.

FIG. 53 is a block diagram of Delay T event 680. This event instruction provides a delay in execution given by T, where T is a 32 bit binary word representing the number of ticks of the 2 $\mu$sec event sequence clock. Timing of frame readout is not regulated implicitly by an interrupt system which counts off 30 Hz increments in the background. In DFN Run mode, precise timing of frame readout is maintained entirely by event instruction in the event queue. A Perl Script example follows:

Delay(16500);

In the Perl script, the argument to this event instruction is provided in ticks of the 2 $\mu$sec event clock. Therefore the above example measures out a delay of 33 msec which is the frame time for a cardiac image. The Delay event is useful for generating the delay between successive readouts of detector control board 124. This delay would then constitute part of the entire frame time for the given frame with the remainder of the delay being taken up by the readout operation. This event instruction is also used to account for the delay due to readout of the image data. The Delay T event 680 is used to insert a delay between the beginning of a light frame and the point at which radiation generation system 109 is turned on.

FIG. 54 is a block diagram of Loop KN event 684. This event instruction decrements the event queue pointer to allow looping on sections of the event queue. Looping is performed on instructions which occur before the loop event. The distance the pointer is moved is given by K, and the number of times the loop is performed is given by N+2. Note that the loop pointer is zero-based and the loop instruction is not reached until the first time through the loop. These two conventions account for the additional two counts which are added to the counter. Note that looping is performed on the event instructions prior to the Loop event, therefore all loops are executed at least once (N=0). Currently, N is one byte long and therefore 257 loops (255+2) are allowed. A Perl Script example follows:

Send(0x007000, 0x1);
Delay(16500);
LoopKN(2, 20);

In this example, detector framing node 304 is read 22 times at a frame rate of 33 msec per frame. This is accomplished by sending the above image request command, e.g. Send("image request"), followed by a delay of 16500 2 $\mu$sec counts, and a LoopKN statement. In the Perl file, the jump distance "K" is provided in terms of number of event instructions, whereas in the binary event compiler output COFF file, the jump distance "K" is specified in terms of actual bytes. The compiler takes care of performing the mapping between these two ways of specifying the event instruction. The Loop KN event is useful for taking a prescribed number of data frames from detector framing node 304. The loop KN event can encompass a section of the event sequence which includes both dark and light frames. In this way a long series of images may be captured using a relatively short sequence of event instructions.

Figure 55:
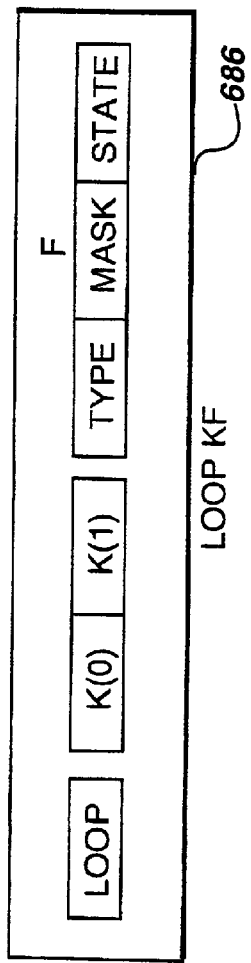
FIG. 55 is a block diagram of a Loop KF event.

FIG. 55 is a block diagram of Loop KF event 686. Loop KF event has a binary format. FIG. 686 shows the order of bytes in EAB memory 474. This order is reversed in the Perl script such that ("TYPE,MASK,STATE" becomes "STATE, MASK,TYPE") due to differences in Endian ordering. This event instruction decrements the event queue pointer to allow looping on sections of the event queue. The distance the pointer is moved is given by K. Looping continues until the F flag is received. F is described by the Type (RT bus="00", Host Flag="01"), the Mask and the State. One layer of nested looping is allowed. See Wait F for a description of Flags. A Perl Script example follows:

Send("image request");
Delay(16500);
LoopKF(2, 0xAAFF01);

In this example, detector framing node 304 is read indefinitely at a frame rate of 33 msec per frame until a Host Flag is received from the user application (see Wait F for Flag definition). This is accomplished by sending the image request command ("image request"), followed by a delay of 16500 2 µsec counts, and a LoopKF statement. In the Perl file, the jump distance "K" is provided in terms of number of event instructions, whereas in the binary event compiler output COFF file, the jump distance "K" is specified in terms of actual bytes. The compiler takes care of performing the mapping between these two ways of specifying the event. The Loop KF event 686 is used to synchronize the Event queue to an external input for acquisition of a light frame. A sequence of event instructions incorporating a scrub frame are placed in the Loop KF loop with the event waiting for the flag F from the real time bus 379. Once radiation generation system 109 is ready, the real time bus 379 changes state to F, which causes the Event queue to leave the Loop KF loop and proceed on to the next event which is a data frame. Together, the X-ray On and data frame realize a light frame, which is in lock step with the previous detector scrub operations. The Loop KF event is used to generate an infinite loop for debugging of detector operation. The loops are made sensitive to a flag from host computer 114 indicating that execution is completed.

Figure 56:
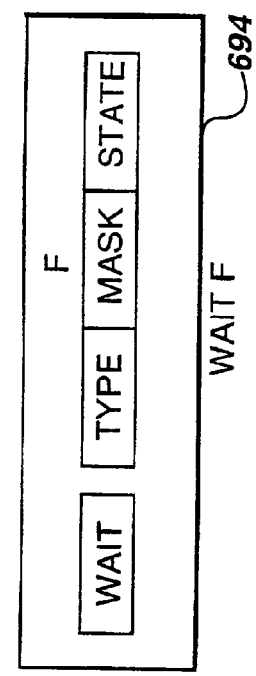
FIG. 56 is a block diagram of a Wait F event.

FIG. 56 is a block diagram of Wait F event 694, which is a binary format. FIG. 56 shows the order of bytes for the Wait F event 694 in EAB memory 474. This order is reversed in the Perl script ("TYPE,MASK,STATE" becomes "STATE,MASK,TYPE") due to the differences in Endian ordering. The Wait F event 694 pauses execution of the queue until the flag F is received. The exact nature of the flag is determined as indicated above using the TYPE, MASK and STATE fields. Type is used to indicate the origin of the flag (TYPE "00"=RT Bus, TYPE "01"=Host Flag). Mask is used to select which bits are to be tested, and STATE holds the corresponding expected states for the test to pass. For example, in order to turn on bit 0 on the RT bus, the following TYPE, MASK, STATE construction is used: ("00, 01,01"). Note that it is possible to turn on any bit independently of any others such that the real time bus 379 does not need to be read in order to change a given bit; the previous state are left unchanged as necessary. The real time bus 379 is read by host computer 114 when using the DFNReadRTBState( ) function call. A Perl Script example follows:

Wait(0x0A0F01);

In this example, execution is paused at the Wait statement until the pattern "XA" is received from the computer application. In this case, because the MASK is "0F," the lower nibble of bits of the incoming Host Flag will be tested. In the case of mammography, the operator holds down both a "Prepa" and a "Graphe" button in radiation generation system 109 to initiate an x-ray exposure, with Graphe actually applying voltage to the x-ray tube. A Wait F event in the X queue is optionally made to look for a signal indicating that the Graphe button on the operator console has been pressed. The Graphe button is interfaced using the real time bus 379 and is represented by a single bit which is tested against for state effectively corresponding to a flag. Once this flag is received, executions would move on to the next event instruction, which would be a Flag F command to radiation generation system 109 calling for radiation generation system 109 to be turned on. The Wait F event is used to synchronize the Event queue operation to host computer 114. A Wait F event is used to stop execution until the host computer 114 signals that it is ready to proceed. For example, using a Wait F in an image loop, an operator optionally steps through a series of precisely timed image acquisitions with a keyboard press on host computer 114 used to tell host computer 114 to proceed to the next frame in the sequence. After each keyboard key press, host computer 114 signals the event queue in EAB memory 474 with Flfag F.

Figure 57:
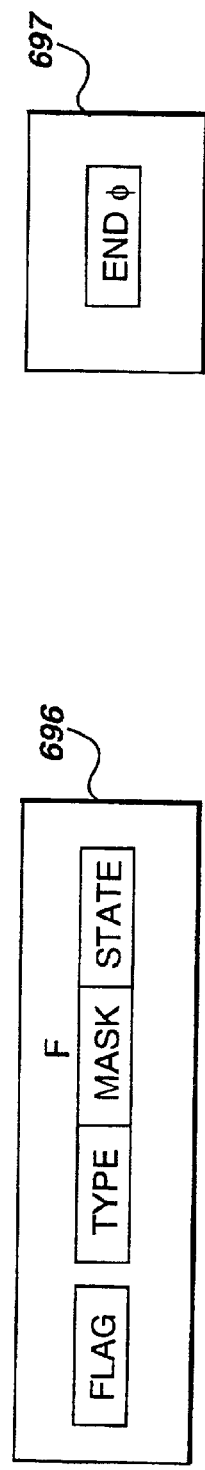
FIG. 57 is a block diagram of a Flag F event.

FIG. 57 is a block diagram of Flag F event 696, which is in a binary format. FIG. 57 shows the order of bytes in EAB memory 474. This order is reversed in the Perl script ("TYPE,MASK,STATE" becomes "STATE,MASK,TYPE") due to the differences in Endian ordering. This event instruction generates the flag F. The exact nature of the flag is determined as indicated. TYPE is used to indicate whether the flag will be applied to the real time bus 379 (TYPE= "00") or will generate an interrupt to host computer 114 (TYPE="01"). MASK is used to select which bits are to be controlled, and STATE holds the corresponding levels for each bit. Flags on the real time bus 379 remain until cleared by a subsequent event. Flags sent to host computer 114 cause a single interrupt to be generated and cause the flag value (STATExMASK) to be transmitted to the computer application. A Perl Script example follows:

Flag(0xB1F100);

In this example, a real time bus flag (TYPE="00") is generated. Since the MASK is "F1" the upper four bits are all changed to the state specified "B", while of the lower four bits, the least significant bit is changed. The Flag F event is used to generate the X-Ray on signal for turning on radiation generation system 109. This is done by selecting the appropriate bit on the real time bus 379 and then setting it to the desired level. This bit can later be cleared using another Flag F event. The Flag F event is used for computer-synchronized image acquisition to generate a flag to host computer 114 indicating that the Graphe button has been detected by a previous Wait F event. Host computer 114 optionally uses this information to signal image acquisition status.

Figure 58:
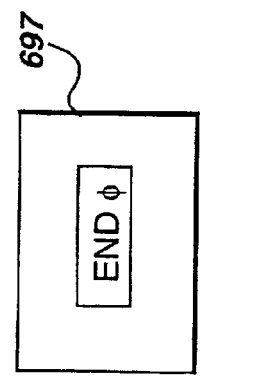
FIG. 58 is a block diagram of an End Q event.

FIG. 58 is a block diagram of End Q event 697. This event constitutes the end of the event sequence. When this event is reached, detector framing node 304 passes from Run mode to Normal mode, and notifies host computer 114 that execution is complete. ENDQ event 697 is inserted automatically by the event compiler and is not present in the Perl script.

Examples of typical event sequences, which may be implemented, are set forth below. They are intended to demonstrate the flexibility of the architecture proposed herein. Each example includes an event graph illustrating the sequence execution in time. The graph is accompanied by a representation of the Event queue for the sequence.

Figure 59:
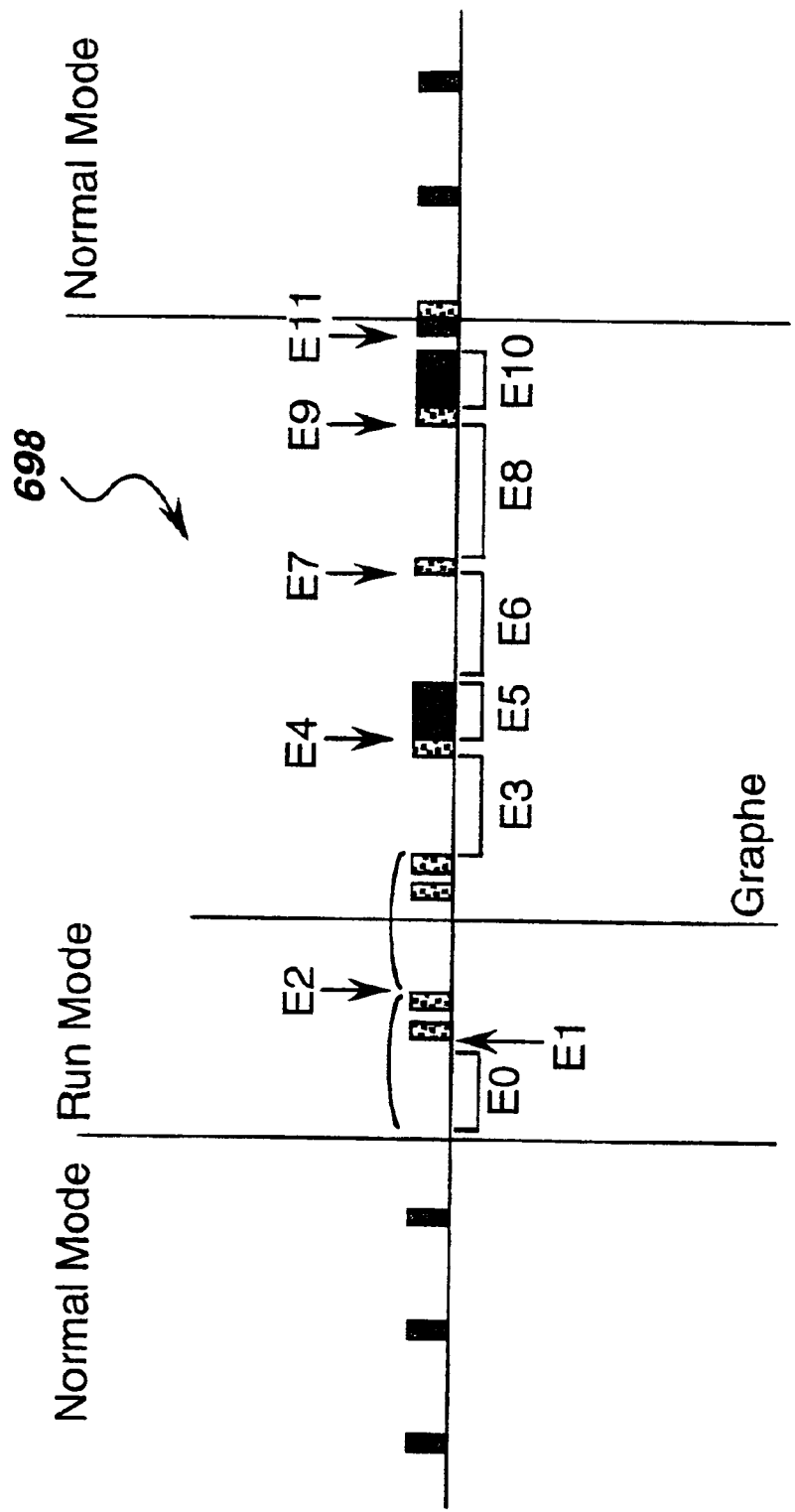
FIG. 59 is an event graph for a mammography sequence.

FIG. 59 is an event graph 698 for a mammography sequence. Image acquisition for mammography provides a good example of an event sequence controlled by external events. Present is an example of a typical mammography digital x-ray acquisition based on radiation generation system 109. The tester system has access to the Graphe push button as a signal on the real-time bus 379 indicating that voltage is applied to the x-ray tube. X-ray On time in this simple example is set manually by the user as part of the technique set at the console (i.e. mAs). The tester has control over the beginning of the x-ray exposure through the real-time bus but does not control the on-time directly. It is up to the application code to set up the Event queue correctly to allow for the expected delay due to the given mAs setting.

Figure 60:
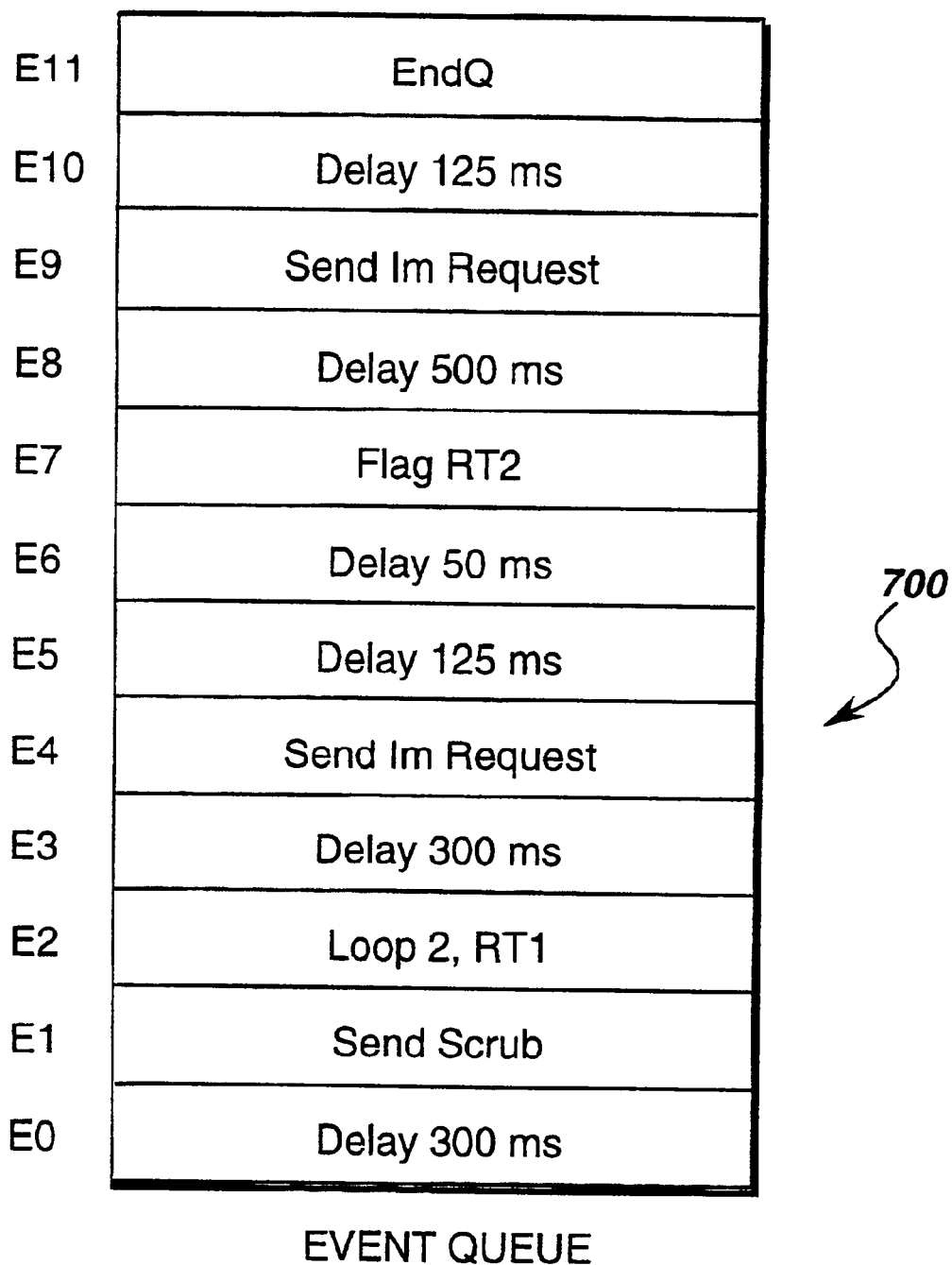
FIG. 60 is a block diagram of an event queue.

FIG. 60 is a block diagram of event queue 700. The start of the sequence is initiated by host computer 114 using the Begin Sequence command on computer communication bus 302 once the queues have been properly setup. At this point the detector framing node 304 leaves Normal mode, and begins sequence execution. The Event queue begins by looping on scrub frames and waits for the Graphe button to be pressed (RT1). As illustrated in the graphs, this is accomplished using events E0–E2, where E1 is a Send event for a Scrub, and E2 is a LoopKF event. The control event E2 takes as defining arguments the flag RT1 which will end the loop as well as the distance K to jump back to the event which begins the loop. In this case K=2 since the loop contains two events. RT1 is a flag from real time bus 379 defined by specifying which signal to monitor (for the Graphe press) and the state to look for (high or low). Once Graphe is pressed, the Event queue detects this change and leaves the scrub loop because image acquisition will begin.

The next group of events in the sequence initiate the offset or dark frame acquisition and then provide the synchronization between the start of the light frame and the start of the x-ray exposure. These events correspond to E3–E10. E4 is a Send event which sends an Image Request to detector framing node 304. Note that the readout delay for the image request is accounted for using the Delay event E5. Once E5 completes execution, data has been stored locally on the DFN in a frame buffer. The completed acquisition triggers direct memory access of this frame buffer to host computer 114 over computer communication bus 302. X-ray exposure is phased relative to the start of the light frame; E6 provides this time delay. Following the delay, E7 sends the X-ray On signal by changing the value of the flag RT2 corresponding to the X-ray On signal on the real time bus 379 to radiation generation system 109. As mentioned previously, the current mammography test system does not have the facility for setting the duration of the X-ray On time. Therefore, this X-ray On signal tells the radiation generation system 109 when to begin exposure, and X-ray Off is not used. The sequence ends when E11 terminates the queue. The EndQ event moves DFN from Run mode back to Normal mode to idle and scrub the panel.

FIG. 61 is an event graph of a Gated Cardiac Sequence 702. Image acquisition of a gated cardiac sequence provides a slightly different example of an externally controlled event sequence. It is assumed that a trigger signal on the real-time bus provides the gate to control when images are acquired during a frame sequence. Such a gating signal might be provided by a heart monitor to synchronize light image acquisition with certain phases of heart activity.

Figure 62:
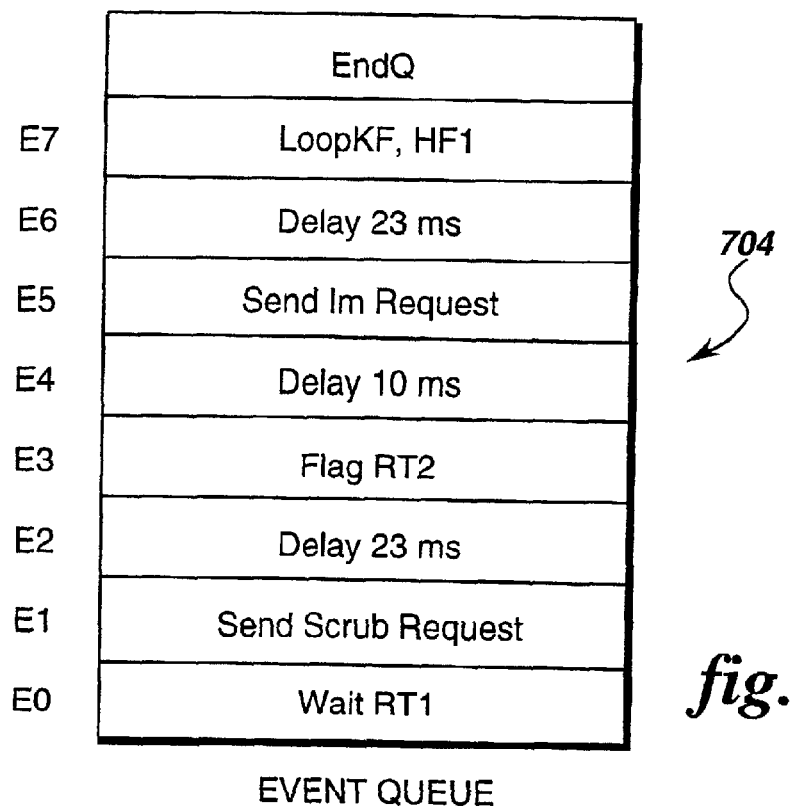
FIG. 62 is a block diagram of an event queue.

FIG. 62 is a block diagram of event queue 704. As in the mammography digital x-ray case, the start of the sequence is initiated by host computer 114 using the Begin Sequence command on computer communication bus 302.

At the start of the sequence, the WaitF event E0 pauses sequence execution until a heart beat is detected on real time bus inputs (RT1). When the beat arrives, detector framing node 304 is scrubbed once (E1–E2) to begin the panel integration time. The x-ray is then turned on at E3. Assuming that the generator turns off automatically after 10 ms, E4 waits for this period to complete. E5–E6 complete the integration period and readout detector framing node 304. The entire construct of E0–E6 is looped using E7 which waits for Host Flag HF1 from the computer application telling the sequence to exit with the EndQ, E8.

The sequence runs continuously and synchronizes with the heart beat until computer application tells it to exit. Alternately with two layers of nested looping it would be possible to scrub the panel at a set rate until the heart beat was detected. One loop would scrub the panel, and the second loop would repeat the entire construct (scrubbing+ single image acquire) until the computer application signaled done.

DFN Autoscrub Feature

Figure 63:
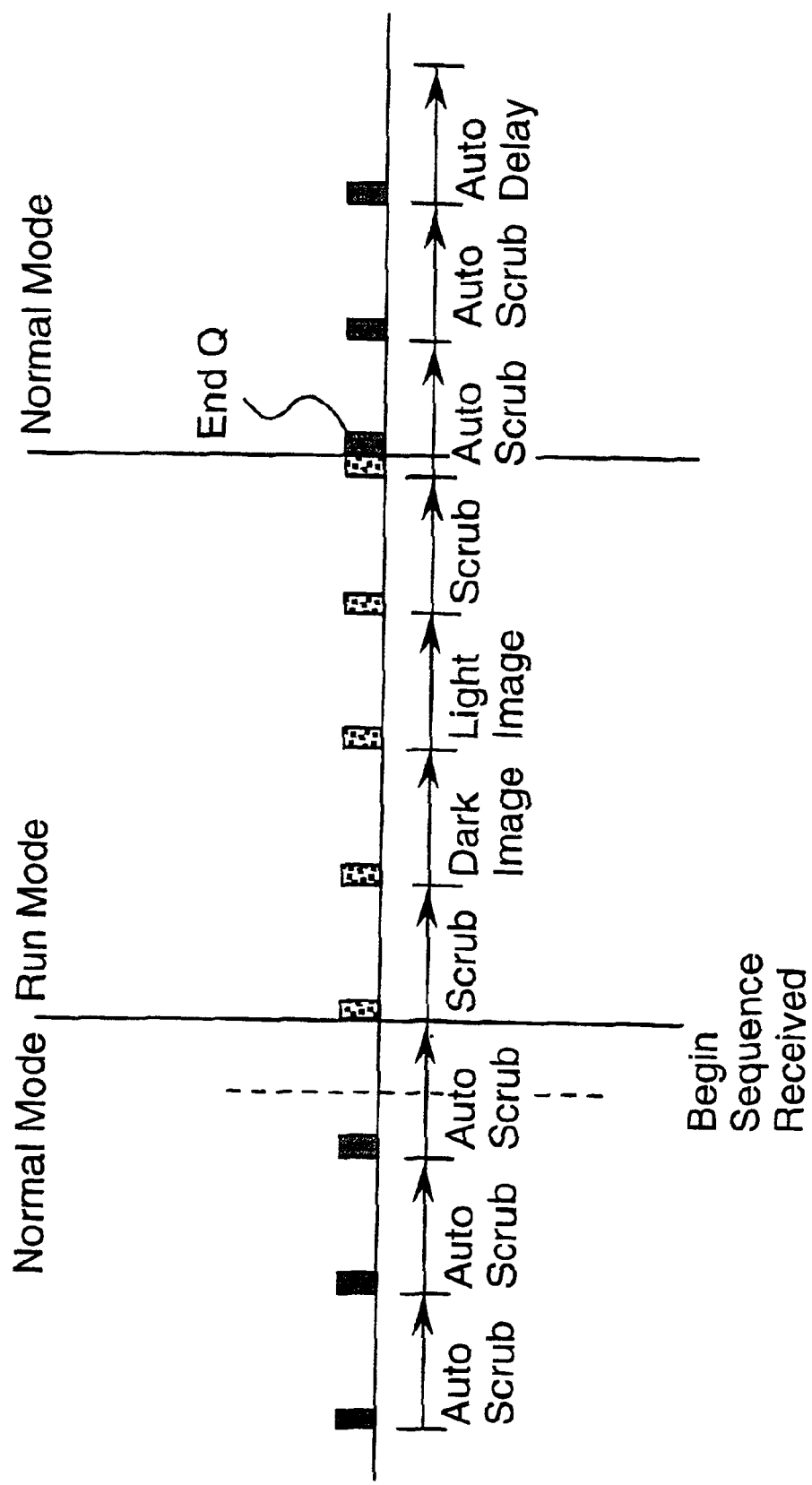
FIG. 63 is an event graph of an autoscrub sequence.

FIG. 63 is an event graph of autoscrub sequence 706. In addition to image requests sent during Event Sequence execution, detector framing node 304 is able to send Scrub requests automatically at a user programmed rate while in DFN Normal mode. To use the Autoscrub feature, the user application first sets up the desired rate to scrub at. This is done using, e.g. a DLL function call DFNSetAutoscrubDelay( ) (defined generally below), which takes as its argument the scrub frame time in 2 $\mu$sec counts. The user application also turns on an autoscrub feature when it is intended to be used with a function call.

Detector Equilibrium

The image detection system 112 is scanned at a constant rate while images are not being acquired in order to prevent degradation in image quality or damage to flat panel detector 116. Detector controlled firmware, i.e. firmware controlled by detector control board 124, is designed to enter an autoscrub mode when sitting idle for a long period of time. In typical operation however, flat panel detector 116 is scrubbed continuously when images are not being acquired. For this reason, detector framing node 304 is designed to scrub flat panel detector 116 while in Normal mode if the user turns on this feature.

Timing Transitions

In order to prevent image artifacts from occurring, a seamless transition is provided from a detector framing node idle state to image acquisition. A detector framing node autoscrub feature scrubs detector framing node 304 at the user set rate until a BeginSequence request is received. To maintain strict timing, the Event Queue waits until the frame time for the last scrub completes before beginning execution of the event sequence. Therefore, a perfect transition occurs if the first event in the queue is either a detector scrub or an image request. On termination of the event sequence, the event queue immediately begins autoscrub by sending a detector scrub command when the EndQ is encountered. Therefore, a perfect transition on termination occurs, if the last two events in the queue (excepting the EndQ) are a scrub (or image request) followed by a delay time which is identical to the programmed delay in the DFN autoscrub frame time register.

Configuration and Use

Bus Driver Configuration

Real time bus 379 is bi-directional. Control of the direction of each channel on the bus is accessible to the user using the DFNSetRTBDirection( ) DLL function call (set forth in greater detail below). On power-up, all real time bus channels start out as inputs. Even though the Event Sequence may drive a channel high, in reality, the channel will continue to be in a high-impedance state until its driver is turned on by the user application. Therefore, the direction of all real time bus channels are set prior to the beginning of the event sequence.

Setting the Default State

Detector framing node 304 maintains a default state for the real time bus drivers. This feature is designed to return the bus to a "safe" condition in the event that a system error occurs. The default state is also set using the DFNSetRTBDirection( ) DLL function call (set forth below). The user application sets the value of the default state prior to the beginning of the event sequence.

Queue Variables—Real-Time Sequence Control

Queue Variables provide communication between the computer application and the Event Sequence. They are used to change parameters on the fly and can also be used to setup a generic frame template before beginning an image sequence. This second application removes the requirement for repeated compilation of Perl scripts when changing parameters such as frame time or Common Electrode Voltage between acquisitions.

Queue variables act as ASCII "keys" identifying numbers in the Perl script which are changed by the user application. The user application uses DLL function calls to pass values for the given keys down to detector framing node 304. These values are written to an area in EAB memory 474 which is separate from the event instructions themselves and is referred to as "Queue Variable Space". When the Event Queue reaches an instruction in the queue which has a Queue Variable in its argument, the queue reads an address which points it to the current value of the Queue Variable in Queue Variable space. The Queue then processes the instruction using the current value of the Queue Variable. The user program can change this value at any time before or during Queue execution since detector framing node 304 prevents the Queue from reading Queue Variable values while they are being written. When a Queue Variable is changed by host computer 114, the value of the Queue Variable is updated immediately in EAB memory 474, however the effect of this updated value appears when the particular event instruction, which uses the particular Queue Variable, is reached by the Event Queue.

Queue Variables—Real-Time Sequence Control

Queue variables provide communication between a host application and an event sequence. Queue variables are optionally used to change parameters on the fly, such as during image acquisition, and are optionally used to setup a generic frame template before beginning an image sequence. The use of a generic template removes the requirement for repeated compilation of Perl scripts when changing parameters such as frame time or Common Electrode Voltage between acquisitions.

Queue variables act as ASCII "keys" identifying numbers in the Perl script which can be changed by the user application. The user application uses DLL function calls to pass updated values for given keys down to DFN 304. These values are written to an area in EAB memory 474, which is separate from the Event instructions, and is referred to as "Queue Variable Space." When the Event Queue reaches an instruction in the queue having a Queue Variable in its argument, the queue reads an address, which points to the current value of the Queue Variable in Queue Variable space. The Queue then processes the instruction using the current value of the Queue Variable. The user program optionally changes this value at any time before or during Queue execution. Conflicts are avoided since DFN 304 prevents the Queue from reading Queue Variable values while they are being written. When a Queue Variable is changed by the host, the variable value in EAB memory 474 is updated immediately, however the effect of this updated value appears when the event instruction, which uses the particular Queue Variable, is reached by the Event Queue.

Perl Script Queue Variables Scope, Definition and Use

All arguments to event instructions defined in a Standard Event set (with exception of loop jump distance K) are optionally parameterized using Queue Variables. For example, a Queue variable is optionally defined for the N value of a LoopKN event. Thus, the user application may optionally change the number of repetitions in a frame sequence without recompiling the respective COFF file. By defining a Queue Variable for the Send event, the user optionally parameterizes all detector parameters, since these are set using detector commands initiated by the Send event. Similarly, frame time can be parameterized by defining a Queue variable for the Delay event in a frame.

Defining and using Queue Variables

In the Perl script, Queue variables are defined in the preamble to frames as well as at the top level of the hierarchy. They are given a default value, which is the value that will be loaded into their memory location when the COFF file is written to EAB memory 474. The default value can be defined either at the frame level or at the hierarchy level for additional flexibility.

FIG. 64 illustrates a top level Queue variable definition format. FIG. 65 illustrates a frame level Queue variable definition format. In this example, the Queue Variable delay_qv is defined to parameterize a Delay event instruction. Queue Variables are not typed, however they need to be assigned defaults. An assigned default is performed for delay_qv at the frame level, where it is set to a default of 20 msec. An assigned default is also performed at a top level, where it is set to 10 msec. As with Queue Parameters, top level definitions take precedence with the frame level default being used in the event that a top level default is not assigned. As with the Queue Parameters, the function call for the frame as well as the compile_init call are passed for the list of Queue Variables (\% qv) to be activated. Once the defaults have been the defined, the Queue Variable is used by simply replacing the number in the event instruction argument with the name of the variable. Single quotes are used for the variable to be recognized.

Using Queue Variables in User Application

In order for the user application to update the values of Queue Variables on DFN 304, the user application needs a reference to the Queue Variable location in EAB memory 474. This reference is provided in the form of an ASCII key, which is the same as the name of the Queue Variable as it is defined in the Perl script. A table mapping the ASCII keys to their respective memory locations in DFN memory is stored in the COFF file upon compilation. This table is called the Queue Variable Symbol Table, and is passed to the DLL when the COFF file is read. The DLL uses this table to look up memory locations when provided with ASCII keys for Queue Variables.

Changing a Queue Variable using DFNChangeQueueVariable( )

FIG. 66 is a format of a function call having defined ASCII names. The user application updates values of Queue Variables in DFN memory using the DFNChangeQueueVariable( ) DLL function call. As illustrated in FIG. 66, the format of this function call provides that SymName is the ASCII name of the Queue Variable, which is identical to the name defined in the Perl script, and sndBuf is the value of the Queue Variable, which will be written into DFN memory. BuffSize is the number of bytes which will be written, and debug provides the DLL developer with feedback on success of the call.

Queue Variables correspond to the arguments of event instructions, and since these have different sizes depending on the type of event, the user specifies the number of bytes to be written using Bufsize.

Integrated Queue Variables Example

When using Queue Variables, the source code of both the user application and the Event Sequence are planned together so that the system functions as an integrated whole.

FIG. 67 is an example application explaining source code for a C++ user application. The illustrated Queue Variables example involves an event queue looping indefinitely on an image capture, the frame time of which is determined by a variable that is modified by the host application in real-time. The source code for sections of the user application and the event sequence together implement the above behavior.

FIG. 68 is an example application explaining a Perl script event sequence. In the Perl script, the image acquisition includes an image request, Send($image_cmd), followed by a delay, which incorporates both the integration time and the readout time: Delay(delay_qv). This delay is parameterized using the queue variable delay_qv. Note that delay_qv is initialized to 20000 counts of the 2 $\mu$sec event clock amounting to 40 msec of delay2. Also, there is a distinction between Queue Variables, which use single quotes, and Perl variables, which use a "$" prefix. The LoopKF statement is used to loop on image acquisition until a host flag (0xAAFF01) is received from the user application telling the queue to stop. During this period, the user application optionally changes the frame time at any point by updating delay_qv.

Since the user application and the event sequence run asynchronously with respect to each other, the exact moment that the queue variable is changed is unknown. The exact moment when the value is used, however, is precisely defined because this is the point when the Delay instruction is next evaluated. If the queue variable change is to be synchronized with the event queue execution, this can be accomplished using host flags. The event queue optionally notifies the user application a short time in advance of the point where the variable needs to be updated so that the host will have enough time to make the change.

Figure 69:
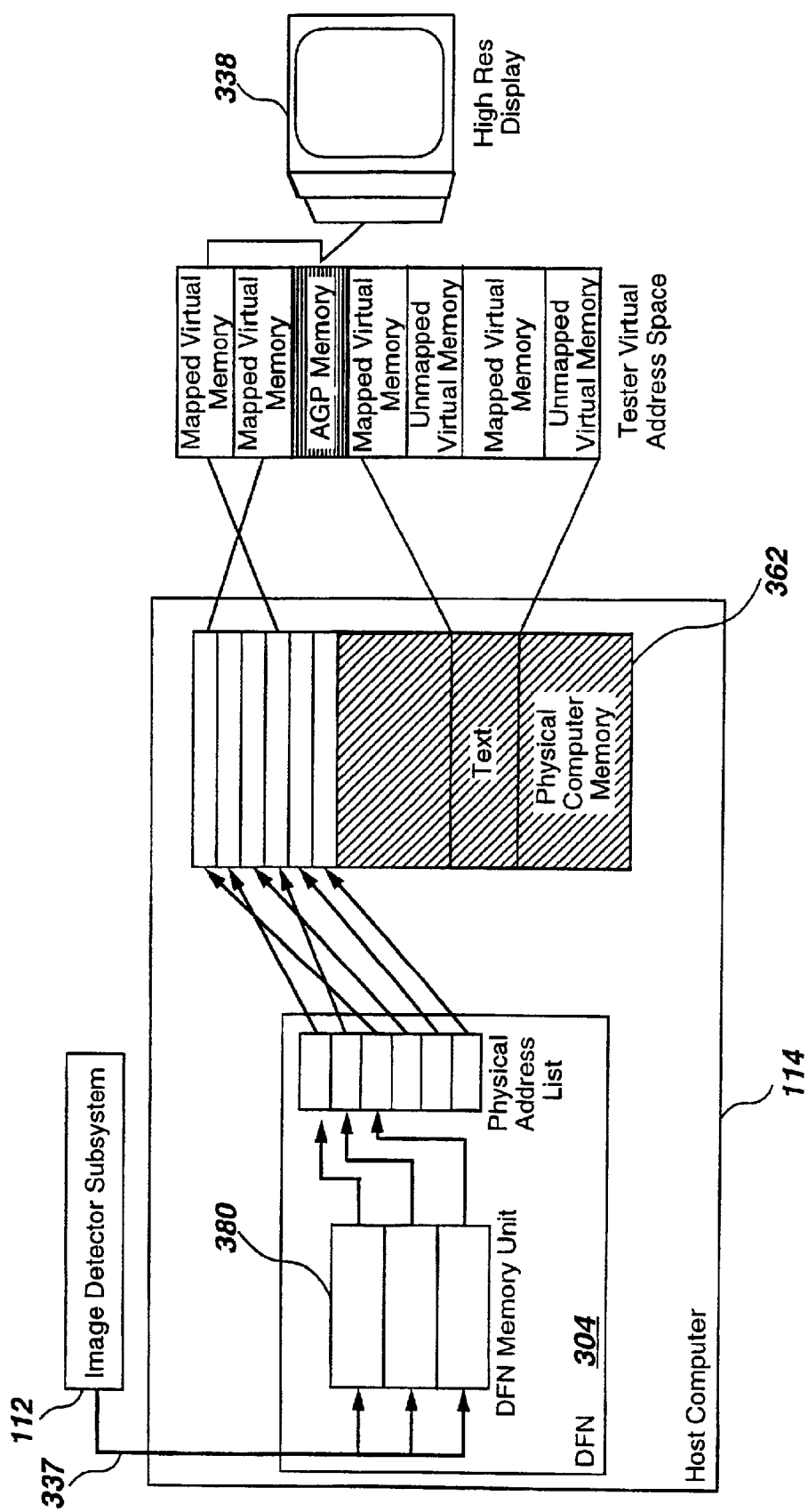
FIG. 69 is a block diagram of a memory map architecture.

On the host application side, the host begins by starting a HF.bin coff file running. This file contains the compiled code for frame_type1. In the simplified example of FIG. 69, the host application then proceeds to update the queue variable with a value for the delay. Alternatively, the user application waits for a host flag to tell that the sequence has begun running. The user application then polls the keyboard or takes input from a GUI telling it whether the particular variable should be incremented or decremented based on an operator request at the time.

Alternately, the user application takes input from the user prior to running the sequence and updates the queue variable right before issuing the BeginSequence. This is useful, for example, when running a series of tests in which the format of the acquisition is the same but the frame time changed each time the test is run. Using queue variables in this case allows the user application to make changes to the frame time without having to recompile the COFF file.

For complex testing using a C++ program to generate sophisticated variations in acquisition parameters, the user application optionally runs repeatedly synchronized with the event queue. Each time through the loop on the user application side various acquisition parameters are updated. For example, the frame time is optionally varied from 20 msec to 100 msec in 100 $\mu$sec increments, while after each set of frames, the average pixel level is calculated and used to set the Common Electrode voltage for the next image or image group. On the Event Queue side, after each image or group of images, the queue then notifies the host that it was done and waits until the host is ready for the next image acquisition before continuing. When the acquisition is completed, the host then aborts the sequence to exit the loop.

Image Acquisition

A performance goal of image acquisition is to acquire and display images in real-time. For 1 k×1 k cardiac/surgical digital x-ray images, acquisition and display rate is 30 frames per second. However, for recorded images, a different rate is optionally used. A display rate of 30 frames per second displays a flicker with a 60 MHz PC. Typically, a review work station will run at 70 MHz. This avoids vertical blanking of the display. For 2 k×2 k fluoro-radiography digital x-ray images, the acquisition and display rate is 7.5 frames per second. The acquisition and display rate for other image sizes (regions of interest) or other panels may be different.

The choice of operating system influences design of system architecture. The more involved the operating system is in the acquisition of an image the more likely the operating system is to drop an image. Failing to display a small number of frames in a 30 frame per second sequence could go unnoticed. A similar failure at the 7.5 frame per second fluoro-radiography rate would be more noticeable (particularly with a moving phantom), but would be acceptable.

The acquisition process minimizes the involvement of host computer 114. The available memory is partitioned into a section managed by the operating system and a second section is managed independently of the operating system. Logistically, an option is applied to the boot configuration (boot.ini) that limits the operating system to the lower 256 MBytes (TBD) of physical memory.

The driver for DFN 304 manages the physical memory above this boundary. At the start of an acquisition, the driver divides the available physical memory into 2 MByte blocks. However, for radiography digital x-ray, multiple 2 MByte blocks are used to make a single image. A list of physical addresses is passed by the DFN driver to the acquisition card. As each image arrives, DFN 304 copies the image to the next physical address on this list and interrupts host computer 114. At some time host computer 114 services this interrupt. An unlikely scenario would be for DFN 304 to copy an image and interrupt host computer 114 more than once before host computer 114 serviced the interrupt. Host computer 114 can detect this situation because DFN 304 has a register that allows host computer 114 to determine how many images have been transferred.

The device driver for DFN 304 maintains a list of available image buffers. Each time the computer application is ready to process an image, the driver passes an image address to the computer application. The WINDOWS NT® operating system provides services that allow the driver to map these image buffers outside of the region managed by the operating system. The driver has an option that will let it reuse these buffers after host computer 114 has displayed their contents. If the computer application determines that it is not keeping up with the input image stream, it can programmatically skip the display of one or more image buffers.

Figure 70:
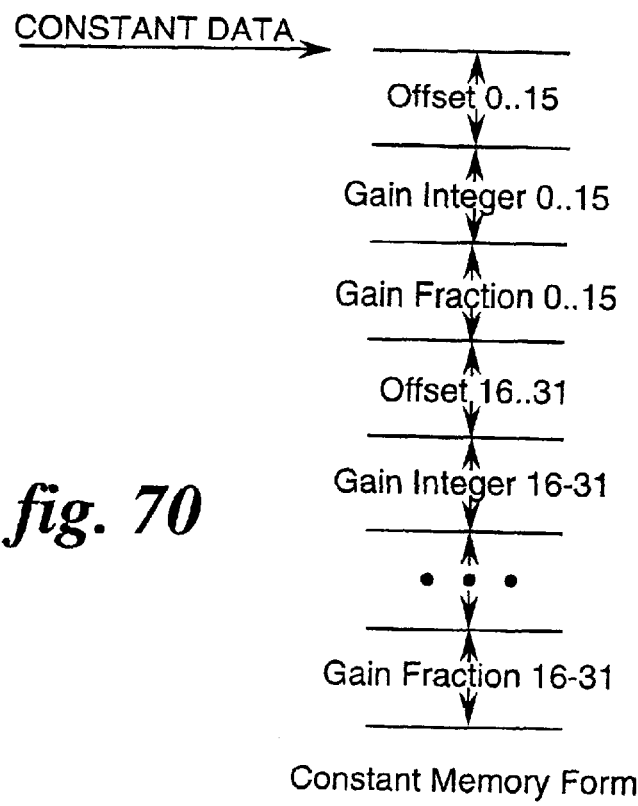
FIG. 70 is a schematic diagram of a constant memory format organizing constant data.

FIG. 70 is a block diagram of a memory map architecture shared between DFN 304 and computer RAM 334 of host computer 114. As illustrated, the physical computer memory 362 in host computer 114 includes mapped virtual memory, AGP memory, and unmapped virtual memory. The mapped virtual memory is displayed on high resolution display 338. More than one 2 MByte buffer may be used to store a single image. One image is displayed at a time with a cache of mapped frames.

In continuous display mode, an application has allocated some number, "N," image buffers in DFN memory unit 380. At any given time the last "N" images are saved in these buffers. If the computer application programmatically skips one or more of these last "N" images, the image data is still available. The other possible operating mode is that the computer application acquire "N" images. In either scenario none of the "N" images that the computer application wanted to keep has been lost, even if the application did not display the image. These buffers are not mapped. There are unavoidable latencies in any data acquisition system. DFN 304 has 10 MBytes of buffer memory to help absorb latency. Buffering, together with careful system design minimizes the possibility of dropped frames.

There are a number of advantages to this image acquisition strategy: host computer 114 is not directly tied to acquisition of individual frames. The image buffers are physically contiguous such that DFN 304 does not manage multiple memory extents. An extent is a physically contiguous block of memory. A 2 MByte cardiac image therefore has 512 memory pages, with a page being 4096 Bytes on PENTIUM® class processors. There can be as many as 512 extents in this image if no two memory pages are physically contiguous.

The computer application does not address the operation of paging individual memory pages by the operating system from an image. This paging activity affects the time used to process individual images. Image files can be quite large. According to an operative embodiment wherein the operating system is WINDOWS NT®, a 2 GByte virtual address space is provided. According to an alternative embodiment, WINDOWS NT SERVER, ENTERPRISE EDITION®, has a 3 GByte virtual address space. During operation, a few images are included in virtual address space at any given time.

According to an operative embodiment, a WINDOWS NT® driver directly manages DMA. In this case, a computer application passes the virtual address of a buffer to the driver. The driver locks the individual pages of this buffer in memory and builds a list of physical addresses. The resulting list is similar to a scatter-gather list. The operating system provides routines to perform DMA using the list of physical addresses that the driver has created. In this case, host computer 114 initiates DMA rather than initiation by DFN 304. This approach is also not preferred because the computer application contends with paging of the image buffers and all the image buffers are subject to the limitation on available virtual address space. Host computer 114 is involved in each DMA. Buffering on DFN 304 permits latency caused by host computer 114. If host processor 115 is too busy to respond to a DMA done interrupt, it is not going to be able to perform the image processing and display. This technique is optionally used to manage image acquisition.

The action of detector framing node 304 for image transfer removes host processor 115 from image acquisitions. With detector framing node 304, hard-real time requirements are satisfied, such as capturing every image in a sequence, without requiring use of a real-time operating system. Detector framing node 304 does not perform scatter-gather DMA because the physical address of each buffer is aligned on a host memory page boundary and because each buffer is physically contiguous.

Conventional systems request one or more images from an image acquisition system. Typically, each request is for a single image, but an application may have multiple requests outstanding. Limitations of the host operating system normally prevent an application from queuing requests for an entire sequence. Modern high performance devices, like those used for image acquisition, traditionally use DMA to transfer data to or from host memory. DMA is a relatively complicated procedure to set up. Host processor 115 becomes involved at several different times to complete the transfer request. The traditional host operating system processes each transfer request individually. If the operating system supports virtual memory, the operating system makes sure that none of the memory pages in the target address range get swapped to disk while the transfer is pending. Different operating systems describe this operation in distinct fashions. Under embodiments of WINDOWS NT® and WINDOWS 2000®, pages are optionally locked. There is also an additional probe operation to guarantee that the target pages are accessible. Other operating systems perform similar tests. Neglecting this detail creates security problems and the use of a probe and lock operation is relatively expensive.

A device driver that functions as an extension of an operating system is responsible for communicating with the image acquisition hardware. The operating system normally probes and locks pages before passing the request to the driver. Alternatively, the driver performs the above bookkeeping when the driver receives a transfer request. The embodiment of WINDOWS NT® supports both techniques. The device driver then allocates resources needed to set up DMA.

Applications typically work with virtual memory addresses. These addresses require access to a memory management unit ("MMU") of a host processor. The use of the MMU is not available during DMA. However, the device that controls the transfers works with physical addresses. Even though the target addresses are virtually contiguous, they are not physically contiguous. In fact the physical addresses may be very fragmented. Each range of these fragmented physical addresses is called a "memory extent" or simply "extent." The driver passes a list of extents to the acquisition device. The list of extents frequently consumes a number of very limited resources. Thus, the driver may not be able to describe the entire image transfer in a single request. Furthermore, the DMA hardware interrupts the host processor each time a transfer having one or more extents has completed.

In the best case scenario using conventional memory management techniques, the host processor is involved in initiating the transfer and in completing the transfer. It is common that the code that completes the transfer actually initiates the next request. The host processor is involved once per transfer. In the worst case scenario, the transfer is split into a number of requests due to resource limitations. Non-real time operating systems cannot bound the interrupt latency (the time used to respond to an interrupt). If the host processor running a non-real time operating system responds too slowly to an interrupt, it will loose image data.

Detector framing node 304 completely removes host processor 115 from the acquisition scenario. Prior to beginning image acquisition, the device driver on host processor 115 passes a list of physical addresses to detector framing node 304. These addresses are outside of the memory that the host operating system manages. Each address in this list describes a reasonably large physically contiguous block of memory (e.g. enough to hold an entire image). The detector framing node 304 treats this address list as a circular queue. When an image becomes available, detector framing node 304 removes an address and initiates DMA to host computer 114. When the transfer completes, the detector framing node 304 sends an interrupt to host processor 115. Host processor 115 does not have to respond to this interrupt in a fixed time window.

When the next image is available, the detector framing node removes the next address from the address list and initiates another DMA, even if host processor 115 has not responded to the first interrupt. Because the interrupt request remains asserted until host processor 115 services the interrupt, the second transfer will not cause a second interrupt. Detector framing node 304 maintains state information such that the device driver on host processor 115 determines how many images have been transferred. The list of physical memory addresses that the device driver passes to detector framing node 304 has N entries. The device driver requests that the detector framing node 304 stop after acquiring N images, or the device driver optionally requests the detector framing node 304 to acquire images continuously. In the latter case, the last N images are saved on the host computer 114 (assuming that N or more images are acquired).

Application software running on host processor 115 optionally requests successive images. The application can display, archive, or otherwise process the images. If host processor 115 is not keeping up with the incoming image sequence, host processor 115 can ignore one or more images. Whether host processor 115 processes each image or not, images will not be lost outside of a requested save window (i.e., capture and save N images, capture images continuously and save the last N images).

Image Processing

A task based operating system running in imaging system 100 meets processing requirements to perform offset, gain, and bad pixel correction as well as supporting window-level operations for contrast management. To complete the image processing within the available time, a Pentium class MMX instruction set is utilized. These instructions permit host processor 115 to operate on four 16-bit values simultaneously. More than four operations may actually be performed at a time because host processor 115 is super-scalar. Host processor 115 is capable of issuing two MMX instructions in a single clock. Performance is sustained when host processor 115 and computer RAM 334 are integrated such that host processor 115 can actually can issue two instructions per clock.

Memory is accessed systematically so that most data comes from the cache and host processor 115 does not wait for a relatively slow memory read to complete. By processing each image in its natural order (i.e. in the order pixels are stored in memory) and observing the recommended 32-byte alignment of all data structures, performance is improved.

Each PENTIUM® class processor has on chip (L1) data cache and on chip instruction cache. In addition to the on chip cache, each PENTIUM® class processor has a secondary (L2) cache. Data and instructions flow from memory to L2 cache to L1 cache. Performance is optimized by operating out of L1 cache and the lesser performance is found operating out of memory.

Processing algorithms are very compact; managing the instruction cache is not significantly involved. The L1 data cache is 4-way, set associative. The unified L2-cache is 4 way, set associative. The lowest five bits of a virtual address specify an offset into a cache line. The next 7 bits of the address specify the cache line. The processor manages the cache ways with a pseudo least-recently-used (algorithm). Each time host processor 115 fetches a different cache line from memory, host processor 115 displaces the "oldest" of the four candidate lines. Fixed binary arithmetic is used having ten bit integer and 15 bit fraction.

FIG. 70 is a schematic diagram of a constant memory format organizing constant data (offset, gain integer, gain fraction). The input image has a page alignment. This data organization has another beneficial side effect on the generated code. The compiler tries to keep frequently used addresses in a limited number of index registers. If separate arrays for the input data arrays are used, as well another register to hold the address of the corrected image, the compiler runs out of index registers. If these three arrays are allocated contiguously but not interspersed as in the previous list, the compiler can use one register to point to the base address, but it requires large offsets to get to the individual components (gain integer, gain fraction, offset). These large offsets affect the capability to decode >1 nsec/clock. A lack of instructions eventually starves host processor 115.

The high data rates and large volume of data associated with digital imaging makes it difficult to monitor a digital x-ray detector in image detection system 112 in real-time. However, imaging system 100 provides a number of monitoring and trace points. These features are useful, as well as flexible and configurable. Capturing a large volume of system diagnostic information degrades system throughput to the point where it is not suitable for its intended application. Failure to provide access to certain data, however, can make diagnosing problems difficult. Further, one cannot predict features and capabilities of different detectors or ways in which one can use existing technology. The problem becomes more difficult if one performs image acquisition on a non real-time computer. As set forth below, monitoring of arbitrary detector functions are provided in a completely configurable manner on a non real-time acquisition computer.

One or more events control x-ray image acquisition. X-ray image acquisition events may produce zero or more digital radioscopic images. Some of events control image detection system 112, while others control radiation generation system 109 and synchronize with the external environment. The events are pre-computed and the results are downloaded as resulting byte-code into detector framing node 304. The detector framing node 304 controls both radiation generation system 109 and image detection system 112. The detector framing node 304 executes detector and x-ray events on a 2 $\mu$sec clock. Each detector command contains a bit flag designating whether detector framing node 304 traces the command. Additionally there is a frame parameter register to control generation of this information. Any spontaneous detector acts generate a response log entry.

During image read-out, response log entries include start of image (SOFN1), start of packet (SOFN2), and end of image (SOFN3). Any event queue optionally sends its start time, event name, and argument to response log 737. A loop command also optionally generates a response log entry for each iteration. DMA completion provides a response log entry that includes a time stamp, an ordinal image number for both the sequence and buffer position, DMA packet size, and the computer memory address of the transfer.

The ability to trace the acquisition at each detector command provides flexibility as set forth below. An engineer enables tracing on a command by command basis and as appropriate for the problem attempting to be solved. In normal operation, tracing is minimized or eliminated to avoid hurting system performance. Each trace is called a response log entry. A response log entry is 32 Bytes in length and includes a time stamp, the two command words sent to the detector framing node 304, two command acknowledgments received from the detector framing node 304, an image tag, and acquisition started event.

The resolution of the time stamp is equal to the rate at which DFN 304 interprets byte code. Host computer 114 provides DFN 304 with the physical addresses for two separate PC buffers in computer RAM 334. Each PC buffer is page aligned, physically contiguous, and an integer multiple of 32 Bytes in length. By making each PC buffer contiguous, computer memory management details are hidden from DFN 304 and bookkeeping procedures that DFN 304 performs are greatly simplified. DFN 304 accesses a selected PC buffer with a simple direct master DMA cycle.

When the one of the two PC buffers is full, DFN 304 switches to the other buffer and interrupts host processor 115. The host processor 115 empties the first selected PC buffer before the second buffer PC fills. The host processor 115 can configure the size of this selected PC buffer. In normal operation, host processor 115 will make the selected buffer large enough so that there is very little overhead in servicing response-log buffer-full interrupts. Since the 16 MByte/sec rate at which the DFN 304 can fill response log buffers is significantly less than the rate at which the host computer 114 can copy data from this selected PC buffer, it is very unlikely that host processor 115 cannot keep up. In the event that DFN 304 fills up the second PC buffer before host processor 115 empties the first PC buffer, DFN 304 stops writing response log entries and generates an error.

Under some circumstances, a computer application might not want to wait for a large response log buffer to fill. In this case, DFN 304 is able to switch response log buffers on command. Registers on DFN 304 indicate the amount of data in each PC buffer and indicate the currently active PC buffer. There is a potential race condition that occurs if the computer application requests a buffer switch as DFN 304 initiates filling a PC buffer. This problem is avoided by ignoring requests to switch when the current response log buffer is empty.

Figure 71:
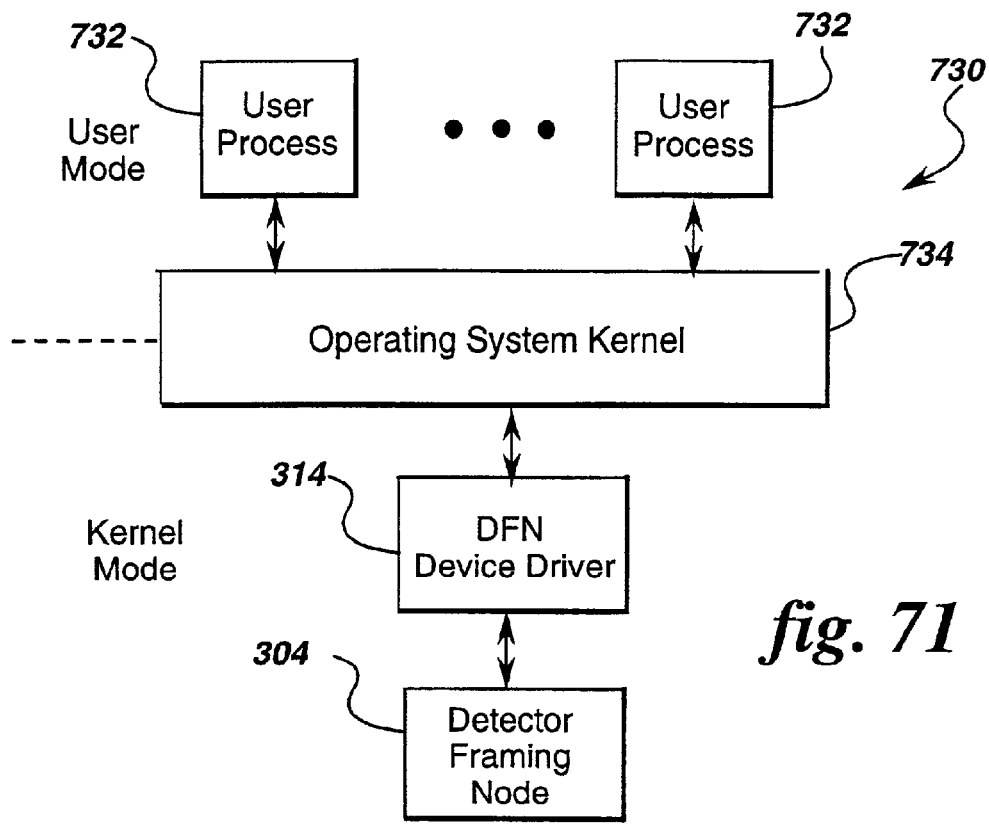
FIG. 71 is a block diagram of an operating system kernel and DFN driver interface.

FIG. 71 is a block diagram of operating system and driver interface 730. The DFN device driver 314 is described for design and function a WINDOWS® platform operating system. In particular, and according to an operative embodiment, DFN device driver 314 is designed to run on the operating system of WINDOWS NT 4.0®, SP5. The operating system does not let user programs directly access hardware. Device driver 334 is a kernel-mode program that provides an interface to access hardware and also controls DFN hardware interactions with the operating system.

As illustrated, interface 730 includes a plurality of user interfaces 732, which interfaces with operating system kernel 734. Operating system kernel 734 interfaces with device driver 334, which in turn interfaces with detector framing node 304. When DFN 304 receives an image from image detection system 112, it transfers the data to computer RAM 334 by DMA. Normally, operating system kernel 734 controls all memory on host computer 114. Memory may be fragmented or organized in a way such that performance of DMA operations by DFN 304 become exceedingly complex. DFN 304 uses DMA to input an image into a contiguous memory buffer in computer RAM 334.

To maintain large, contiguous memory buffers that DFN 304 can use for images, the upper part of computer RAM 334 is "taken away" from operating system kernel 734 by a boot-time parameter called MAXMEM. Memory below MAXMEM is managed by operating system kernel 734 and memory above MAXMEM is managed by the DFN device driver 334. For example, in a system with 512 MByte of RAM, MAXMEM may be set to 128 MByte. Addresses from 0–128 MByte are controlled by operating system kernel 734 and hold the operating system, device drivers (including DFN device driver 334), and user programs. Addresses from 128–512 MByte, which operating system kernel 734 does not manage, are used by the DFN device driver 334 and the DFN hardware. Registry values help DFN device driver 334 configure this space.

Organization of Memory Above MAXMEM

The DFN device driver 334 and DFN 304 use the space above MAXMEM for three things: 1) response log buffers, 2) a list of physical addresses DFN 304 will transfer images to during acquisition, and 3) detector images. By its design, DFN 304 is able to map a section of computer RAM 334 into its address space. This "shared DFN window" is limited to 2 MByte. DFN 304 writes response log entries to this space. DFN 304 also reads a list of physical memory addresses from this space which detector images are transferred to. The list of physical addresses points to buffers which lie above MAXMEM and which are also outside of the 2 MByte shared DFN window.

Figure 72:
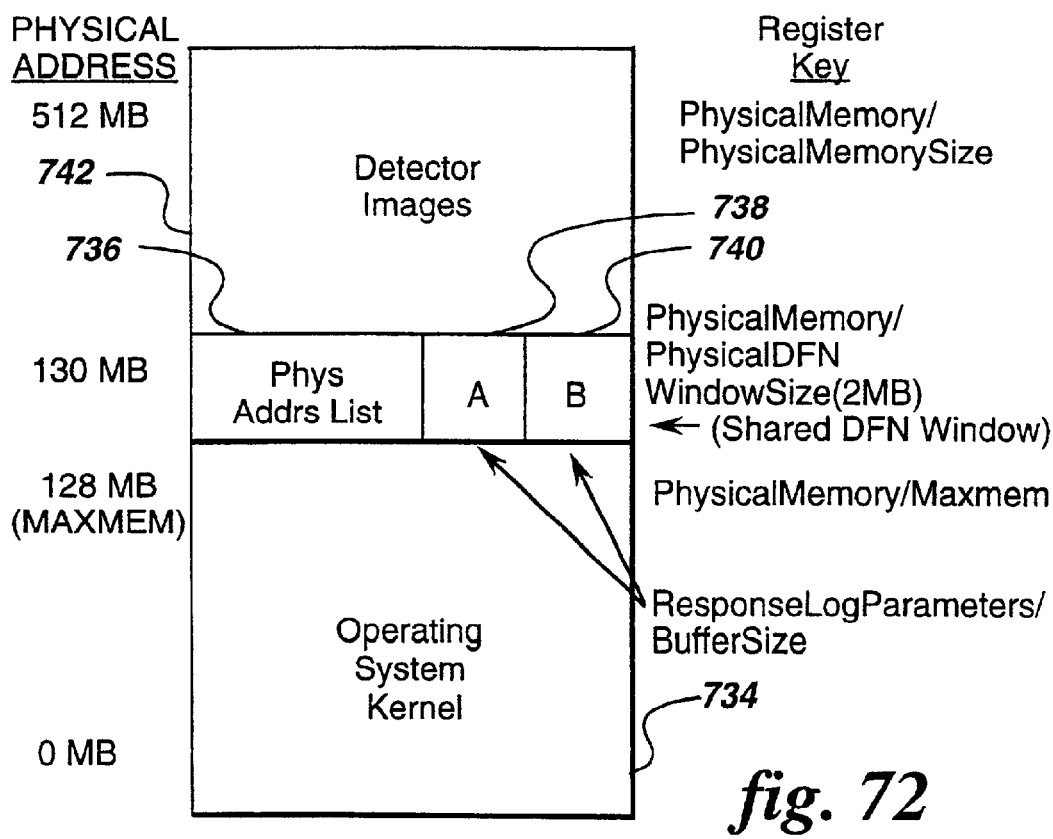
FIG. 72 is a block diagram showing a memory configuration of PC RAM.

FIG. 72 is a block diagram showing the memory configuration of computer RAM 334. This arrangement is used by the DFN device driver 334. As illustrated, operating system kernel 734 lies between 0 and 128 MByte. The physical address list 736, response log buffer A, and response log buffer B lie between 128 and 130 MByte, and detector images are located between 130 and 512 MByte. The list of physical addresses can have no more than 65,536 (64K) 4-byte addresses in it (for a total of 256 KB) and the buffer holding this list is on a 256 KB physical address boundary. The response log buffers start on a 4 KByte physical address boundary and are an integral number of response log entries in size (32 Bytes/response log entry). Each response log buffer is not larger than 262,144 Bytes or 8192 response log entries.

Physical Addresses List

During acquisition, detector images, also called "frames," are read. Each image goes into a buffer in the "Detector Images" memory range of FIG. 72. The collection of images is called a "sequence" and has a unique identifier. More than one sequence can be in memory at a time, although one can be "current" at a time.

Before acquisition begins, the user tells DFN device driver 334 to allocate a sequence of some number of frames. DFN device driver 334 creates a list of addresses, one per frame, in the detector Images area. This list is given to DFN 304 in the Physical Address List area 736 of the shared DFN window.

Figure 73:
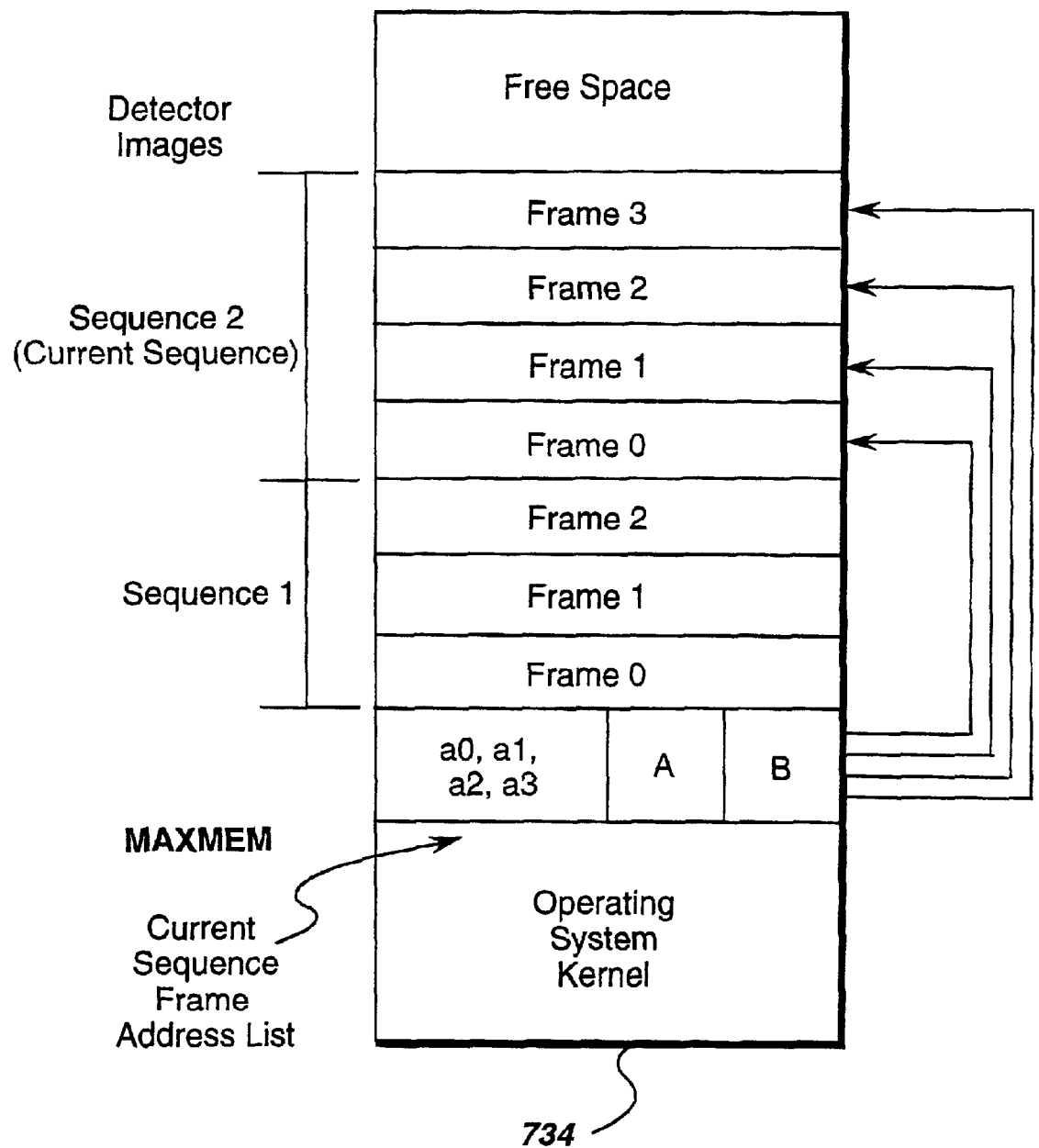
FIG. 73 is a block diagram showing how PC RAM looks for two allocated sequences.

FIG. 73 is a block diagram showing how computer RAM 334 looks for two allocated sequences, i.e. one of which is current and available to take data. As images arrive on DFN 304 from image detection system 112, the firmware walks this list of addresses and performs DMA of the image from DFN 304 to computer RAM 334. The user can request a pointer (called a "map request") to these buffers which it uses to access the image for display, calculations, archive, etc.

Converting the physical address to a virtual address suitable for use by a user program, i.e., mapping, consumes WINDOWS NT® resources called page table entries ("PTEs"). This is a limited resource, which means that a program can use a certain amount before an error occurs. If an unlimited number of simultaneous maps were allowed, DFN device driver 334 would use all system PTEs and WINDOWS NT® would crash. To address this, 30 MByte of data is allowed to be mapped at once. This is independent of detector size. So, for cardiac/surgical digital x-ray, having a 2 MByte image size, 15 images can be mapped at once. For radiography digital x-ray, having an 8 MByte image size, 3 images can be mapped at once. The registry key that controls PTE consumption is PhysicalMemory/MaximumPageTableEntries. One page table entry is used for each page of memory mapped. A page of memory in WINDOWS NT® is 4 KByte. Therefore, for 30 MByte of memory, 30 MByte/4, KByte=7680=0x1E00 PTEs are needed.

The registry setting can be changed to allow for more data to be mapped. However, setting this number too high may crash the system. If the system crashes, the blue screen will show an error condition of "NO MORE PTEs" and this value is manually lowered by changing the registry key. This section deals with the number of images that can be mapped simultaneously. If a user program tries to map too many images at once, DFN device driver 334 returns an error. The user program then unmaps one or more of its mapped buffers before reissuing a map request. During real-time acquisition, buffers are unmapped in the order they were mapped. This is not true for archive (non-real-time) playback.

If Wrap is disabled for the acquisition, the firmware can transfer up to a set number of buffers. If more images arrive from image detection system 112, an overwrite error is generated by DFN 304. If Wrap is enabled for the acquisition, the list of addresses is treated as a circular queue. When a buffer is mapped and then unmapped, DFN device driver 334 updates a tail pointer to let the firmware know that the user has used the data buffer. The firmware will not overwrite an unused data buffer. If the user code can not map and unmap buffers fast enough, images will arrive faster than they can be consumed, and the firmware will generate an overwrite error. In wrap mode, at most the last "n" buffers will be in memory when acquisition ends, where "n" is the number of frames in the sequence.

Response Log Buffers

DFN 304 optionally generates response log ("RL") entries that user programs can use to detect events in image detection system 112 along with associated timing. The RL entries are stored with image data to give a record of the test and to help interpret image detection system 112 data. At startup, the DFN device driver 304 gives the DFN firmware two buffer addresses and a buffer size which will hold RL entries. These buffers lie in the shared DFN window, are each the same size, and are an integral number of RL entries big. An RL entry is 32 Bytes.

During operation, RL entries are written by the firmware into RL buffer A 738. When the buffer fills up, an interrupt is sent to DFN device driver 334 and the firmware writes further entries to RL buffer B 740. DFN device driver 334 will dispose of the data in buffer A 738 (based on directions from the user mode program described below) and mark it as empty. When the firmware fills RL buffer B 740, a buffer full interrupt is sent to DFN device driver 334 and the firmware flips back to filling RL buffer A. Again, DFN device driver 334 disposes of the data in buffer B and marks the buffer as empty. DFN device driver 334 disposes of the data in a full RL buffer and mark it as empty before the firmware fills the alternate buffer and flips back to the full one. If it does not, an overwrite error is generated by the card.

It is up to the user program to handle RL buffers. When the system first boots, the firmware and DFN device driver 334 are running and RL entries may be occurring. On a buffer full interrupt, DFN device driver 334 interrupt handler just marks the buffer as empty, effectively throwing away the data.

User programs that want to keep the RL data put DFN device driver 334 in an "RL save" mode. Then the user program gives DFN device driver 334 a pointer to a buffer that will get the contents of the full RL buffer. For example, during acquisition, user programs would keep RL data. DFN device driver 334 knows not to throw a full RL buffer away. The user program issues an RL read request. If a full RL Buffer exists (res. buffer A 738), the data is copied from the A buffer into the user buffer and then RL A 738 is marked as empty. If no full RL buffer exists, the read is marked as pending. Later, when an RL buffer (A) full interrupt occurs, DFN device driver 334 finds the pending read request. The data of Buffer A is copied into the user buffer and then A 738 is marked as empty.

If DFN device driver 334 is in an "RL save" mode and an RL buffer (A) full interrupt occurs with no outstanding user read request, the data is just left in the RL buffer until the user code reads it. If the user code does not try to read RL buffer A before RL buffer B fills up, an overwrite error is generated by the card.

Detector Images

Detector images are written to memory above MAXMEM and also outside the 2 MByte DFN window. The DFN device driver 334 handles management of this area. Initially, the full region is free. As sequences are allocated, detector-sized buffers are used to hold images. Individual frames or entire sequences can be deleted during playback, which returns the memory to the free list. If a user program tries to allocate a sequence and there is not enough memory, an error is returned by DFN device driver 334. The user either deletes frames or sequences to free up enough space. If no sequences are allocated, the user either adds more RAM to the system (and increase the PhysicalMemory/PhysicalMemorySize registry key) or reduces MAXMEM (and decrease the PhysicalMemory/Maxmem registry key). Reducing MAXMEM will affect WINDOWS NT® performance. Whenever the registry is modified, the system is rebooted so that DFN device driver 334 uses the proper values.

Programming DFN 304

DFN 304 controls image detection system 112 and acquires images from it over the image detection bus 377 to image detection system 112. A series of commands can be combined into an Event Queue program that is run by DFN 304 firmware. These commands are combined into a program called a sequence that is compiled into a common object file format ("COFF") file. The COFF file is loaded onto DFN 304 and a Begin Sequence command is issued to start it running. Several types of data are generated by a COFF file, set forth below.

The main result of a sequence is typically a set of x-ray images from image detection system 112. The x-ray images are DMA transferred from DFN 304 to computer RAM 334 as set forth above. When an image transfer completes, DFN device driver 334 receives a "DMA-done" interrupt. If the user code has previously issued a map request, the address of this arrived image is returned. The user code can display the image or do calculations on the data. When finished, the user code unmaps the image and asks for the next one. Unmapping an image does not delete it from computer RAM 334. An image will be destroyed during acquisition if it is overwritten in wrap mode or if a user explicitly deletes it during playback. A user program does not have to map images as they are being acquired. If there are enough frames in the sequence to hold all of the images generated by the COFF file, no errors will occur and the data will be in computer RAM 334. It can be mapped later during playback.

Response Logs

The DFN firmware generates response log ("RL") entries during acquisition. RL entries hold information regarding images, DMA operations, the real-time bus, firmware state transitions, and errors. Some classes of RL entries are systematically generated while other classes are selectively turned on and off.

When an RL buffer fills, an "RL-buffer-full" interrupt is sent to DFN device driver 334. If the user code has previously issued a read request, the contents of the RL buffer are copied to a user memory buffer, which was supplied as an argument to DFN device driver 334. The user code can store this buffer in a memory list until acquisition completes, write it to disk, or try to parse through it while acquisition is running. The user code then issues another RL read request to wait for the next full RL buffer.

Response log buffers are different from detector images in that they are copied out of the memory above MAXMEM into user space. Images are left in the memory above MAXMEM and are simply mapped into user virtual address space. Therefore, the user is responsible for storing RL buffers or keeping them in memory.

If the user cannot issue RL reads fast enough, an error occurs as described above. It may not be possible to write RL buffers to disk or to parse through them while data is being taken since this may take too much time.

Host Flags

A COFF file may need to notify or synchronize with the user. In this case, host flags are used perform the notification. User programs issue host flag read requests to see these flags. If a host flag has occurred, the host flag is returned on the read request. Otherwise, the read request is left pending until a host flag occurs or until image acquisition completes.

Two different types of host flags are possible: notify and wait. A notify host flag is used to tell a user that an event has happened or a point has been reached in the COFF file. An interrupt is generated and the driver records an 8-bit number associated with the host flag. If a host flag read is pending, this number is returned to the user. Otherwise, the number is stored until a read is issued. No further action is used with a notify host flag.

A wait host flag also tells the user that an event has happened or that a point has been reached in the COFF file, but the event queue is waiting for a response from the user. As with the notify flag, a wait flag generates an interrupt and the driver records an 8-bit number associated with the flag. The number is returned to the user via the host flag read request. The user then replies to the event queue using the same 8-bit number. Wait flags tell the user that some initialization process is finished. The user may, for example, then need to perform an action, such as perform an action on the image detection system 112 or position a target in some way. The queue does not continue until the user replies with the 8-bit wait host flag pattern. Accordingly, the queue and the user synchronize operations.

Errors

A variety of potential errors can happen during operation of DFN 304. Broadly, these errors are related to host flags, event queue, response logs, images (including acquisition, storage, and DMA), and fiber channel. More than one of each type of error class can occur at once. For example, if the fiber channel cable is disconnected, a bad receiver data, CRC, and sync loss errors could happen. A single return code is used to inform a user of such error(s). The user then asks the driver for a bitmask that gives a complete (extended) list. Errors of a particular class are returned on calls relating to that class. For example, the user is told that a host flag extended error happened on the Read and Set Host Flags calls to the driver. The software then handles data types and error processing in modular threads.

Acquisition of Data with Radioscopic Imaging System

Referring again to FIG. 15, a user controls imaging system 100 by writing a computer program, in the C language or equivalent, to control the system and acquire data. The user application loads a binary file, called a common object file format ("COFF") file, into the EP EAB memory 474 using the acquisition DLL 313 and the DFN device driver 314. This binary file is created by a software program called event compiler 408. The binary file is used to generate the event queue. The event queue controls the x-ray generator and the acquisition of data from image detection system 112 over image detection bus 377.

Referring to FIG. 16, the event compiler 408 takes a Perl script as its input. Data from an Excel user interface 339 can alternatively be used to generate the Perl script with translator 331. Event simulator 407 and high resolution display 338 for event simulator 407 optionally receive the output from event compiler 408 for purposes of testing. User API 330 is a C program that accesses four libraries: 1) acquisition DLL 313; 2) display library 335 3) image process library 336; and 4) archive library 337. All libraries are optionally DLL libraries. Thus, the user application optionally links the libraries and does not recompile when recompiling the application program.

The user acquires images in several modes, which are controlled partly by the event queue (determined by binary file and Perl script 333) and partly by the user application program that uses the acquisition DIL 313, the DFN device driver 314, and the other libraries. The user can acquire single frames, multiple frames or can acquire frames continuously. This latter mode (called "fluoroscopy" or "wrap") is optionally used with a cardiac digital x-ray panel, where x-ray generation unit 203 fires at 30 frames/sec and data streams to DFN 304 and computer RAM 334 continuously. Since computer memory 334 is limited to, e.g. 1 GByte, computer memory 334 can hold 500 (16 seconds) of the 2 MByte frames. Hence, in this mode computer memory 334 is treated as a circular buffer and the last 16 seconds of data is retained in computer memory 334.

Driver Operating Scenario

By way of example, a user program that tests panels would need to make a series of calls to DFN device driver 314. This section gives a example of a data acquisition scenario and associated function calls.

1. The user first generates a COFF file that contains a series of commands to be executed on DFN event queue. This file is reused each time an acquisition is done.

2. The DFN 304 and image detection bus 377 are reset (IOCTL_DFN_RESET, IOCTL_DFN_RESET_FC).

3. The frame and ROI sizes are read (IOCTL_DFN_GET_ALLOCATION_FRAME_SIZE, IOCTL_DFN_GET_ALLOCATION_ROI_SIZE). If necessary, the frame and desired ROI sizes are set (IOCTL_DFN_SET_ALLOCATION_FRAME_SIZE, IOCTL_DFN_SET_ALLOCATION_ROI_SIZE).

4. The user allocates a sequence with the desired number of frames (IOCTL_DFN_ALLOCATE_IMAGE_BUFFERS).

5. The user makes the allocated sequence the current one (IOCTL_DFN_SET_CURRENT_SEQUENCE).

6. If desired, the user enables wrap mode on the sequence (IOCTL_DFN_SET_SEQUENCE_WRAP).

7. The COFF file is opened using the COFF file library routines.

8. The DFN 304 is put in NORMAL (or TEST) mode (IOCTL_DFN_SET_MODE).

9. The card is programmed with the COFF file (IOCTL_DFN_PROGRAM_DFN_CARD).

10. The programming can optionally be verified (IOCTL_DFN_VERIFY_DFN_CARD_PROGRAM).

11. The DFN 304 is told to start COFF file execution (IOCTL_DFN_BEGIN_ACQ_SEQUENCE).

12. Data acquisition has begun at this point.
   a. In a separate thread, the user code can request map and unmap of image buffers (IOCTL_DFN_MAP_BUFFER, IOCTL_DFN_UNMAP_BUFFER). Note that mapping of buffers is done in ordinal order starting with 0. Unmap calls are also done in ordinal order starting with 0.
   b. In another separate thread, the user code reads response log data (IOCTL_DFN_GET_RESPONSE_LOG) providing a buffer large enough to hold one full RL buffer (IOCTL_DFN_GET_RL_BUFFER_SIZE).
   c. In another separate thread, the user optionally posts host flag reads in case any are generated by the COFF file (IOCTL_DFN_GET_HOST_FLAGS).
   d. If the user wants to end the acquisition early, the queue can be stopped (IOCTL_DFN_ABORT_SEQUENCE).

14. When a COFF file completes, the original BEGIN_ACQ_SEQUENCE call will return with success. The card is in NORMAL (or TEST) mode.

15. The user can return the card to DIAGNOSTIC mode. The sequence size is read (IOCTL_DFN_QUERY_SEQUENCE_SIZE). Images can be mapped, viewed and/or archived, and then unmapped nonsequentially now that the system is not in real-time acquisition mode.

16. Unwanted frames can be deleted (IOCTL_DFN_DELETE_FRAME, IOCTL_DFN_IS_FRAME_PRESENT). The sequence can be deleted from memory (IOCTL_DFN_DEALLOCATE_IMAGE_BUFFERS).

The following are function calls which may be made by a computer application to the acquisition DLL 313 to control detector framing node 304. Each DLL function call has an associated description.

DFNOpenSystem
Connect to DFN Driver and setup for image acquisition.
DFNCloseSystem
Clean up any loose threads and close the DFN driver connection.
DFNOpenSequence
Open the specified Event Sequence file and allocate image buffers.
DFNCloseSequence
Deallocate image buffers in PC memory.
DFNOpenArchiveSequence
Allocate image buffers but fill PC memory from previous archive.
DFNBeginSequence
Load and run specified Event Sequence COFF file.
DFNBeginSequenceNoMapping
BeginSequence without image mapping.
DFNBeginSequenceNoMappingNoLog
BeginSequence with no response log entries and no buffer maps.
DFNBeginSequenceNoLog
BeginSequence with no response log entries recorded.
DFNWaitForSystemIdle
Block until the end of the currently executing event sequence.
DFNWaitTimeoutForSystemIdle
WaitForSystemIdle until specified timeout has expired.
DFNAbortSequence
Terminate current sequence executing on DFN 304.
DFNDeleteSequence
Free-up allocated image buffers for the specified sequence.
DFNGetSequenceName
Return ASCII name of the sequence based on sequence ID.
DFNRenameSequence
Change the name of the sequence based on the sequence ID.
DFNGetSequenceLengthAllocated
Return number of image buffers allocated for the given sequence.
DFNGetSequenceLengthAcquired
Return actual number of images acquired for the given sequence.
DFNGetSequenceFrameSize
Return the actual frame size used for the given sequence ID.
DFNGetBeginSequenceTimeStamp
Return date and time when the given sequence was begun.
DFNGetCurrentSequenceID
Return the ID of the sequence currently selected.
DFNFindSequenceID
Return sequence ID corresponding to the ASCII string name.
DFNGetBeginSequenceTime
Return exact time (in seconds) that given sequence was started.
DFNSetArchiveSequenceTime
Set start time for previously archived sequence that is reloaded.
DFNGetExtendedErrorInformation
Returns extended error information for reported driver errors.
DFNHardReset
Unimplemented on DFN 304.
DFNSoftReset
Perform a state reset on DFN 304.
DFNDetectorHardwarePresentSpecification
Turn on special driver mode to test DLL without DFN 304 present.
DFNGetBoardVersionInfo
Return DFN board revision, serial number, and firmware revisions.
DFNGetDriverAndDLLVersions
Return software revision strings for DLL and Driver.
DFNSelfTest
Request that DFN 304 perform a hardware Built In Self Test.
DFNSendDetectorCommand
Send the specified Fiber Channel command to the detector.
DFNResetFC
Reset the Fiber Channel chip-set directly.
DFNAccessLocalBus
Read or Write to DFN local bus 384 directly.
DFNGetResponseLogSizeForSequence
Return number of response logs entries for given sequence ID.
DFNGetResponseLogForSequence
Return all response log entries for the given sequence ID.
DFNGetResponseLogSizeForFrame
Return number of response log entries for the given frame.

DFNBeginResponseLogChitchat
Start recording response log entries in Diagnostic Mode.
DFNEndResponseLogChitchat
Stop recording response log entries in Diagnostic Mode.
DFNForceRLBufferFlip
Force driver to return current active RL buffer and switch buffers.
DFNGetResponseLogForFrame
Return all response log entries for the given frame.
DFNGetResponseLogOfRunningSequence
Return specified section of currently active RL buffer.
DFNOpenSequentialPlaybackSequence
Open previously acquired sequence for sequential playback.
DFNOpenRandomPlaybackSequence
Select a sequence for random access using GetSpecificFrame.
DFNGetSpecificFrame
Return specified frame when in Random Playback Mode.
DFNGetNextFrame
Return most recent image and update the frame pointer.
DFNDeleteFrame
Remove specified frame from memory.
DFNIsFramePresent
Return whether or not specified frame exists in memory.
DFNGetFreeFrameCount
Return number of available empty frames in memory.
DFNGetSequenceFrameRange
Return Min. and Max. frame numbers still present in memory.
DFNSetWrapMode
Turn on/off wrapping of the circular image buffer.
DFNIsWrapModeSet
Check if Wrap mode is on or off.
DFNIsWordSwapModeSet
Returns state of WordSwap bit: 1=words swapped, 0=not swapped.
DFNImageWordSwap
Turn WordSwap on or off for mammography digital x-ray acquisition.
DFNSetROI
Unimplemented on DFN.
DFNGetAllocationROI
Unimplemented on DFN.
DFNGetSequenceROI
Unimplemented on DFN
DFNGetAllocationFrameSize
Return the frame size used to allocate memory for next acquisition.
DFNSetFrameSize
Set the detector frame size for use by the DFN during acquisition.
DFNImageReorder
Turn image reordering on/off. Applies to radiography digital x-ray panel 228 and cardiac/surgical digital x-ray panel 182.
DFNIsReorderModeSet
Check whether image reorder is turned on or off.
The following are EAB memory 474 (Event Queue) memory read/write function calls.
DFNLoadEvents
Download COFF file event instructions to DFN 304 directly.
DFNGetEventsFromEAB
Return Event Queue data from DFN EAB memory.
DFNGetEABMemSizes
Return the size in bytes of the DFN EAB(Event Queue) memory.

DFNWriteEABMemory
Write to specific address in DFN EAB memory.
DFNReadEABMemory
Read from a specific address in DFN EAB memory.
DFNSetAutoscrubDelay
Set the delay between autoscrub commands in $\mu$sec counts.
DFNGetAutoscrubDelay
Return the currently programmed autoscrub delay from the DFN.
DFNEnableAutoscrub
Turn on DFN-controlled autoscrub function.
DFNDisableAutoscrub
Turn off DFN-controlled autoscrub function.
DFNReadRTBState
Return snapshot of current state of real time bus lines.
DFNSetRTBDirection
Set direction of the real time bus lines independently.
DFNSetRTBLine
Force high or low values onto the real time bus lines independently.
The following are Host Flag Function Calls.
DFNGetNextHostFlag
Wait for next Host Flag from DFN Event Queue.
DFNGetNextHostFlagTimeout
GetNextHostFlag with timeout if Host Flag is not received.
DFNSetWaitTypeHostFlag
Signal DFN 304 using specified Host Flag.
The following are Queue Variable Function Calls.
DFNChangeQueueVariable
Change queue variable at specified address to specified value.
DFNReadQueueVariable
Returns the current value of queue variable at specified address.
The following are DFN Driver Function Calls.
IOCTL_DFN_GET_EXT_ERROR_INFO
Returns extended error information for DFN errors.
IOCTL_DFN_CLR_EXT_ERROR_INFO
Clears bits in the driver copies of the hardware error registers on DFN 304.
IOCTL_DFN_BEGIN_RL_CHITCHAT_MODE
Begin recording response log data for asynchronous detector communication.
IOCTL_DFN_END_RL_CHITCHAT_MODE
End recording response log data for asynchronous detector communication.
IOCTL_DFN_GET_RL_BUFFER_SIZE
Returns the size in bytes of a response log buffer.
IOCTL_DFN_GET_RESPONSE_LOG
Returns the next available full response log buffer.
IOCTL_DFN_FORCE_RL_BUFFER_FLIP
Causes DFN 304 to switch its current RL destination buffer.
IOCTL_DFN_GET_RL_CLASS_ENABLE_MASK
Returns the response log class entry mask showing which class(es) are currently reported.
IOCTL_DFN_SET_RL_CLASS_ENABLE_MASK
Modify the response log class entry mask which determines which classes are recorded.
IOCTL_DFN_ABORT_RLREAD_REQUESTS
Clears all response log read requests.
IOCTL_DFN_GET_FRAME_SIZE
Returns the frame size for a sequence.
IOCTL_DFN_GET_ALLOCATION_FRAME_SIZE
Returns the frame size that will be used in the next sequence allocation.

IOCTL_DFN_SET_ALLOCATION_FRAME_SIZE
Sets the frame size for future sequences.
IOCTL_DFN_GET_ROI_SIZE
Returns the ROI size for a sequence.
IOCTL_DFN_GET_ALLOCATION_ROI_SIZE
Returns the ROI size that will be used in the next sequence allocation.
IOCTL_DFN_SET_ALLOCATION_ROI_SIZE
Sets the ROI size for future sequences.
IOCTL_DFN_ALLOCATE_IMAGE_BUFFERS
Attempts creation of an image sequence with specified number of buffers.
IOCTL_DFN_SET_CURRENT_SEQUENCE
Makes the sequence corresponding to the sequence identifier the current sequence.
IOCTL_DFN_DEALLOCATE_IMAGE_BUFFERS
Frees all image buffers and sequence information associated with an allocated sequence.
IOCTL_DFN_SET_IMAGE_REORDER
Forces reordering on a sequence regardless of registry default.
IOCTL_DFN_CLR_IMAGE_REORDER
Forces no reordering on a sequence regardless of registry default.
IOCTL_DFN_QUERY_SEQUENCE_SIZE
Returns number of frames in the sequence and other information of the sequence.
IOCTL_DFN_DELETE_FRAME
Deletes frame specified by the ordinal frame number from the current sequence.
IOCTL_DFN_IS_FRAME_PRESENT
Reports whether specified frame number is present in the current sequence.
IOCTL_DFN_GET_FREE_FRAME_CNT
Returns the number of frames of specified size available in free memory.
IOCTL_DFN_MARK_ARCHIVE_SEQUENCE
Force immediate map request completion when filling a sequence from an archive.
IOCTL_DFN_SET_SEQUENCE_WRAP
Define a sequence to be operable in wrap mode.
IOCTL_DFN_GET_CURRENT_SEQUENCE_ID
Returns the sequence identifier of the current sequence.
IOCTL_DFN_MAP_BUFFER
Returns an address for the image buffer specified in the current sequence.
IOCTL_DFN_UNMAP_BUFFER
Unmaps the specified image buffer in the current sequence.
IOCTL_DFN_DELETE_ALL_SEQUENCES
Deletes all sequences allocated by the driver.
IOCTL_DFN_SET_DETECTOR_WORDSWAP
Forces pixel word swapping on a sequence regardless of the default.
IOCTL_DFN_CLR_DETECTOR_WORDSWAP
Forces no pixel word swapping on a sequence regardless of the default.
IOCTL_DFN_RESET
Resets the DFN board firmware.
IOCTL_DFN_RESET_FC
Resets the Fiber Channel hardware.
IOCTL_DFN_GET_VERSION_INFO
Returns DFN 304 version and S/N, as well as firmware revision numbers for EP 374 and DAP 372.
IOCTL_DFN_GET_EAB_MEM_SIZES
Returns the size of EAB memory and of the individual queue areas within it.
IOCTL_DFN_WRITE_EAB_MEMORY
Data can be written to EAB memory 474 with this command.
IOCTL_DFN_READ_EAB_MEMORY
Data can be read from the EAB memory on EP 374 with this command.
IOCTL_DFN_PROGRAM_DFN_CARD
Programs EAB memory 474 with code from the user generated COFF file.
IOCTL_DFN_VERIFY_DFN_CARD_PROGRAM
Returns the code in EAB memory 474 that was programmed previously.
IOCTL_DFN_GET_GEN_DATA_CFG
Returns configuration settings for the Test Image Generator circuit on DFN 304.
IOCTL_DFN_SET_GEN_DATA_CFG
Sets specified configuration settings for the Test Image Generator on DFN 304.
IOCTL_DFN_BEGIN_ACQ_SEQUENCE
Starts the event queue and begins data acquisition.
IOCTL_DFN_ABORT_SEQUENCE
Stops the currently running DFN acquisition before an EndQ is received.
IOCTL_DFN_SET_AUTOSCRUB_DELAY
Sets the delay between consecutive autoscrub requests in 2 μsec clock ticks.
IOCTL_DFN_GET_AUTOSCRUB_DELAY
Returns the delay between consecutive autoscrub requests in 2 μsec clock ticks.
IOCTL_DFN_ENABLE_AUTOSCRUB
Turns on the autoscrub circuit on DFN 304.
IOCTL_DFN DISABLE AUTOSCRUB
Turns off the autoscrub circuit on DFN 304.
IOCTL_DFN_CONFIG_RTB
Sets the default state and driver direction for the real time bus on DFN 304.
IOCTL_DFN_READ_RTB
Returns the current state of the real time bus lines including the default and direction settings.
IOCTL_DFN_WRITE_RTB
Writes data to the real time bus 379 in the State/Mask format used by the Event Queue.
IOCTL_DFN_GET_MODE
Returns the current state (Normal, Run, Diagnostic) of EP state machine.
IOCTL_DFN_SET_MODE
Sets the current state (Normal, Run, Diagnostic) of EP state machine.
IOCTL_DFN_GET_HOST_FLAGS
Reads host flags from the event queue.
IOCTL_DFN_SET_WAIT_HOST_FLAG
Block while waiting for the specified Host Flag from the event queue.
IOCTL_DFN CLR_ALL_HOST_FLAGS
Clears any outstanding Host Flags or Host Flag requests.
IOCTL_DFN_ACCESS_LOCAL_BUS
Read or write the DFN local bus is while the card is in Diagnostic mode.
IOCTL_DFN_SEND_DETECTOR_CMD
Send commands directly to the detector while in Diagnostic mode.
IOCTL_DFN_SEND_DFN_CMD
Bypass the driver to Execute a DFN command directly in Diagnostic mode.
IOCTL_DFN_SET_TRACE_LEVEL
Sets the debug trace level which controls printing of trace messages by the kernel debugger.

IOCTL_DFN_GET_TRACE_LEVEL
Returns the debug trace level controlling printing of trace messages by the kernel debugger.
IOCTL_DFN_BUGCHECK
Force a system crash in order to generate a crash dump for analysis.
IOCTL_DFN_SET_BREAK_FLAG
Causes driver checked version to break on entry to every function.
IOCTL_DFN_CLEAR_BREAK_FLAG
Causes driver checked version to NOT break on entry to every function.
IOCTL_DFN_DUMP_HEAP_LIST
Dumps information of free memory heap and sequence memory usage to an output file.
IOCTL_DFN_SET_LEDS
Turns DFN LEDs on or off independently according to the specified state.
IOCTL_DFN_GET_BASE_ADDRESSES
Returns kernel virtual addresses so user application can access DFN memory space directly.
IOCTL_DFN_FREE_BASE_ADDRESSES
Releases the specified kernel virtual addresses.
IOCTL_DFN_DUMP_DFN_MEMORY
Writes a section of DFN memory to a file.
IOCTL_DFN_MAP_PHYS_ADDR
Maps a physical address to a user virtual address; used to access RAM above MAXMEM.
IOCTL_DFN_UNMAP_PHYS_ADDR
Release the specified user virtual address.
IOCTL_DFN_READ_DFN_ADDR
Attempts to read the DFN board at the offset given in the input argument.
IOCTL_DFN_WRITE_DFN_ADDR
Attempts to write a value to the DFN board at the offset given in the input argument.
IOCTL_DFN_GET_FC_LOOPBACK
Returns the state of Fiber Channel loopback; 0=loopback disabled, 1=loopback enabled.
IOCTL_DFN_SET_FC_LOOPBACK
Enables or disables Fiber Channel loopback; 0=loopback disabled, 1=loopback enabled.

As this invention may be embodied in several forms without departing from the spirit or principal characteristics thereof, the present embodiments are therefore illustrative and not restrictive. Those skilled in the art will appreciate that changes may be made to these embodiments without departing from the principles and spirit of the invention. Accordingly, the scope of the invention is defined by the appended claims rather than by the description preceding them, and all changes that fall within the metes and bounds of the claims, or equivalents of such metes and bounds thereof, are therefore intended to be embraced by the claims.

What is claimed:

1. A detector framing node receiving image data and communicating a portion of the image data to a host computer, comprising:
    an image detection interface to receive image data in the form of at least one image frame having
    a predetermined sequence of event instructions constructed off-line;
    a control unit to select a predetermined portion of the image data received on execution of the predetermined sequence, for storage; and
    a memory unit to store the predetermined portion in response to the selection by said control unit.

2. The detector framing node according to claim 1, wherein the rate of communication between said image detection interface and said memory unit is greater than or equal to the rate of reception of the image data by said image detection interface.

3. The detector framing node according to claim 1, wherein said control unit is programmable to receive the image data from a selected flat panel detector of a plurality of different flat panel detectors.

4. The detector framing node according to claim 3, wherein said control unit communicates the received image data to a host memory of the host computer independent of an operating system run by the host computer.

5. The detector framing node according to claim 4, wherein the host computer runs a non-real time operating system, and the detector framing node continues to receive and store the image data from the selected flat panel detector during a lapse in communication with the host memory.

6. The detector framing node according to claim 3, wherein the received image data is radioscopic image data and the selected flat panel detector includes an amorphous silicon photo-diode array outputting the radioscopic image data in response to detection of a radiographic image.

7. The detector framing node according to claim 1, wherein a plurality of image frames are received continuously by said image detection interface.

8. The detector framing node according to claim 7, wherein each image frame is at least a 1024×1024 array of 16 bit words of image data received at a rate of at least 30 frames/sec, or is at least a 2048×2048 array of 16 bit words of image data received at a rate of at least 7.5 frames/sec.

9. The detector framing nods according to claim 1, further comprising:
    a computer communication interface to communicate the image data stored in said memory unit to a host memory of the host computer,
    wherein the image data is stored in the memory unit according to a first order and output to the host memory of the host computer according to a second order.

10. The detector framing node according to claim 9, wherein said detector framing node transfers the received data to the host memory as indicated by a list of physical addresses stored in registers in said detector framing node.

11. The detector framing node according to claim 1, wherein said image detection interface (376) receives the real time data at a rate of at least 60 Mbytes/sec.

12. The detector framing node according to claim 1, wherein the detector framing node is a PCI card and the host computer runs a non-real time operating system.

13. The detector framing node according to claim 1, wherein the detector framing node is a PCI card and the host computer runs a real time operating system.

14. The detector framing node according to claim 1, wherein the detector framing node is a PCI card and the host computer runs a task based operating system.

15. An imaging system, comprising:
    at least one host processor to execute operations with a host operating system;
    a host memory to store image data;
    a computer communication bus connecting said at least one host processor with said host memory;
    an image detection interface to receive image data in the form of at least one image frame having a predetermined sequence of event instructions constructed off-line, from an image detection bus;
    a detector memory unit to store the image data received by said image detection interface; and
    a computer communication interface to communicate the stored image data from said detector memory unit to said host memory along said computer communication bus.

16. The system according to claim 15, further comprising:
a detector control unit to control communication of the image data between said image detection interface and said detector memory unit independently from the host operating system.

17. The system according to claim 16, wherein said detector control unit is programmable to receive the image data from a selected flat panel detector of a plurality of different flat panel detectors.

18. The system according to claim 17, wherein said detector control unit communicates the received image data to said host memory independent of the host operating system.

19. The system according to claim 15, wherein the image data is received by said image detection interface as an image frame, and the detector memory unit stores a predetermined portion of the image frame.

20. The system according to claim 19, wherein said detector memory unit only stores the predetermined portion from each image frame received by said image detection interface.

21. The system according to claim 15, wherein the rate of storage of the image data into said detector memory unit is greater than or equal to a rate of reception of the image data by said image detection interface.

22. The system according to claim 15, wherein the host operating system is a non-real time operating system, and said image detection interface continues to receive and store the image data from the image detection system during a lapse in communication with said host memory.

23. The system according to claim 15, wherein the image frames are received continuously by said image detection interface.

24. The system according to claim 15, wherein each image frame is at least a 1024×1024 array of 16 bit words of image data received at a rate of at least 30 frames/sec, or is at least a 2048×2048 array of 16 bit words of image data received at a rate of at least 7.5 frames/sec.

25. The system according to claim 15, wherein the image data is stored in said detector memory unit (380) according to a first order and output to said host memory according to a second order.

26. The system according to claim 15, wherein said computer communication interface transfers the image data to said host memory as indicated by a list of physical addresses stored in a plurality of registers.

27. The system according to claim 15, wherein said image detection interface receives the image data at a rate of at least 60 Mbytes/sec.

28. The system according to claim 15, wherein said image detection interface, said detector memory unit, and said computer communication interface are disposed on a PCI card and the host operating system is a non-real time operating system.

29. The system according to claim 15, wherein said image detection interface, said detector memory unit, and said computer communication interface are disposed on a PCI card and the host operating system is a real time operating system.

30. The system according to claim 15, wherein said image detection interface, said detector memory unit, and said computer communication interface are disposed on a PCI card and the host operating system is a task based operating system.

31. The system according to claim 15, wherein the received image data is radioscopic image data and the image detection bus receives the image data from a flat panel detector.

32. The system according to claim 31, wherein the flat panel detector is selected from a plurality of flat panel detectors having different image data output format.

33. The system according to claim 15, wherein the image data is radioscopic image data (318) received by said image detection interface at a rate of at least 1 Gbit/sec.

34. An imaging system, comprising:
a host computer comprising at least one host processor to and a host memory connected to the at least one host processor with a computer communication bus; and
a card connected to the computer communication bus to receive image data in the form of at least one image frame having a predetermined sequence of event instructions constructed off-line, from an image detection bus from an image detection bus at a first clock frequency and to communicate the received image data to the host memory through the computer communication bus at a second clock frequency different than the first clock frequency.

35. The system according to claim 34, wherein said card selectably receives at least a 1024×1024 array of 16 bit words of image data at a rate of at least 30 frames/sec or at least a 2048×2048 array of 16 bit words of image data at a rate of at least 7.5 frames/sec.

36. The system according to claim 34, wherein the image detection bus receives the image data at a rate of at least 60 Mbytes/sec.

37. The system according to claim 34, wherein said card communicates the image data to the host memory along the computer communication bus at a data rate of at least 33 MHz.

38. The system according to claim 37, wherein the computer communication bus is a PCI bus.

39. A detector framing node to receive image data in the form of at least one image frame having a predetermined sequence of event instructions constructed off-line, forming an image of predetermined size and to communicate the received image data with a host computer having at least one host processor and a host memory, comprising:
an image detection interface to receive the image data; in the form of at least one image frame having a predetermined sequence of event instructions constructed off-line, forming an image of predetermined size and to communicate the received image data with a host computer having at least one host processor and a host memory;
a plurality of frame buffer memory units, each having a corresponding predetermined data storage capacity; and
a control unit to select a predetermined portion of the image for storage into a selected frame buffer memory unit of said plurality of frame butter memory units.

40. The detector framing node according to claim 39, wherein said control unit is programmable to receive the image data from a selected flat panel detector of a plurality of different flat panel detectors (116), wherein each of the different flat panel detector outputs a corresponding differently sized image.

41. The detector framing node according to claim 39, wherein said control unit communicates the received image data to the host memory of the host computer independent of a host operating system.

42. The detector framing node according to claim 39, wherein the rate of storage of the image data (316) into said plurality of frame buffer memory units is a rate greater than or equal to a rate of reception of the image data by said image detection interface.

43. The detector framing node according to claim 39, wherein each image frame is at least a 1024×1024 array of 16 bit words of image data received at a rate of at least 30 frames/sec.

44. The detector framing node according to claim 39, wherein the image data is stored in said detector memory unit according to a first order and output to said host memory according to a second order.

45. The detector framing node according to claim 39, wherein the image detection bus receives the image data at a rate of at least 60 Mbytes/sec.

46. The detector framing node according to claim 39, wherein said card communicates the image data to the host memory along the computer communication bus at a data rate of at least 33 MHz.

47. The detector framing node according to claim 39, wherein the portion of the image selected by said control unit is less than or equal to the predetermined storage capacity of each of the plurality of frame buffer memory units.

* * * * *

UNITED STATES PATENT AND TRADEMARK OFFICE
CERTIFICATE OF CORRECTION

PATENT NO.         : 6,901,159 B2
APPLICATION NO. : 09/774552
DATED              : May 31, 2005
INVENTOR(S)        : Baertsch et al.

It is certified that error appears in the above-identified patent and that said Letters Patent is hereby corrected as shown below:

In Column 53, Line 43, delete "FUiLL" and insert -- FULL --, therefor.

In Column 53, Line 51, delete "FLL)" and insert -- FULL) --, therefor.

In Column 62, Line 19, delete "Flfag" and insert -- Flag --, therefor.

In Column 70, Line 4, delete "Modem" and insert -- Modern --, therefor.

In Column 78, Line 31, delete "DIL" and insert -- DLL --, therefor.

In Column 86, Line 29, in Claim 9, delete "nods" and insert -- node --, therefor.

In Column 88, Line 5, in Claim 33, delete "(318)" and insert -- (316) --, therefor.

In Column 88, Line 8, in Claim 34, after "host processor" delete "to".

In Column 88, Line 15, in Claim 34, delete "from an image detection bus" before "at a first".

In Column 88, Line 52, in Claim 39, delete "butter" and insert -- buffer --, therefor.

Signed and Sealed this

Twenty-eighth Day of July, 2009

JOHN DOLL
*Acting Director of the United States Patent and Trademark Office*